(12) United States Patent
Sooknanan et al.

(10) Patent No.: US 7,947,436 B2
(45) Date of Patent: May 24, 2011

(54) POLYNUCLEOTIDES AND POLYPEPTIDE SEQUENCES INVOLVED IN THE PROCESS OF BONE REMODELING

(75) Inventors: Roy Rabindranauth Sooknanan, Beaconsfield (CA); Gilles Bernard Tremblay, La Prairie (CA); Mario Filion, Longueuil (CA)

(73) Assignee: Alethia Biotherapeutics Inc., Montreal (CA)

( * ) Notice: Subject to any disclaimer, the term of this patent is extended or adjusted under 35 U.S.C. 154(b) by 187 days.

(21) Appl. No.: 11/792,932

(22) PCT Filed: Dec. 13, 2005

(86) PCT No.: PCT/CA2005/001917
§ 371 (c)(1),
(2), (4) Date: Feb. 25, 2008

(87) PCT Pub. No.: WO2006/063462
PCT Pub. Date: Jun. 22, 2006

(65) Prior Publication Data
US 2009/0004206 A1    Jan. 1, 2009

Related U.S. Application Data

(60) Provisional application No. 60/634,981, filed on Dec. 13, 2004.

(51) Int. Cl.
G01N 33/48    (2006.01)
G01N 33/53    (2006.01)

(52) U.S. Cl. .................. 435/4; 435/6; 435/7.1; 435/7.2; 435/7.21

(58) Field of Classification Search .................. None
See application file for complete search history.

(56) References Cited

U.S. PATENT DOCUMENTS

| | | | |
|---|---|---|---|
| 5,742,127 A | 4/1998 | Ahn | |
| 5,981,830 A | 11/1999 | Wu | |
| 6,203,979 B1 | 3/2001 | Bandman | |
| 6,420,157 B1 | 7/2002 | Darrow | |
| 6,426,199 B1 | 7/2002 | Darrow | |
| 6,451,555 B1 | 9/2002 | Duffy | |
| 6,458,564 B1 | 10/2002 | Darrow | |
| 6,479,274 B1 | 11/2002 | Antalis | |
| 6,482,630 B2 | 11/2002 | Gan | |
| 6,485,957 B1 | 11/2002 | Darrow | |
| 6,498,024 B1 | 12/2002 | Malek et al. | |
| 6,514,741 B1 | 2/2003 | Presnell | |
| 6,617,434 B1 | 9/2003 | Duffy | |
| 6,977,170 B2 | 12/2005 | Chan | |
| 7,049,420 B2 | 5/2006 | Xiao | |
| 7,060,810 B2 | 6/2006 | Xiao | |
| 7,211,425 B2 | 5/2007 | Uemura | |
| 2003/0003530 A1 | 1/2003 | Ashkenazi | |
| 2003/0027144 A1 | 2/2003 | Underwood | |
| 2003/0036061 A1 | 2/2003 | Ashkenazi | |
| 2003/0049645 A1 | 3/2003 | Mu | |
| 2003/0077647 A1 | 4/2003 | Weich | |
| 2003/0096340 A1 | 5/2003 | Ashkenazi | |
| 2003/0124706 A1 | 7/2003 | Yang | |
| 2003/0186297 A1 | 10/2003 | Choi | |
| 2003/0207348 A1 | 11/2003 | Shimkets | |
| 2004/0001801 A1 | 1/2004 | Madison | |
| 2004/0043930 A1 | 3/2004 | Anderson | |
| 2004/0048255 A1 | 3/2004 | Chan | |
| 2004/0126777 A1 | 7/2004 | Bhatt | |
| 2005/0026169 A1 | 2/2005 | Cargill | |
| 2005/0153333 A1 | 7/2005 | Sooknanan | |
| 2005/0176030 A1 | 8/2005 | Gan | |
| 2005/0255114 A1 | 11/2005 | Labat | |
| 2005/0272054 A1 | 12/2005 | Cargill | |
| 2005/0287546 A1 | 12/2005 | Plowman | |
| 2006/0084066 A1 | 4/2006 | Sah | |
| 2006/0154293 A1 | 7/2006 | Xiao | |
| 2006/0188903 A1 | 8/2006 | Rancourt | |
| 2007/0042945 A1 | 2/2007 | Bodary | |
| 2007/0093443 A1 | 4/2007 | Madison | |
| 2007/0166756 A1* | 7/2007 | Shimkets et al. ................. 435/6 |
| 2007/0224201 A1 | 9/2007 | Wu | |
| 2008/0152663 A1 | 6/2008 | Cannon | |

FOREIGN PATENT DOCUMENTS

| | | |
|---|---|---|
| EP | 1132477 | 9/2001 |
| EP | 1792912 | 4/2006 |
| WO | WO9914328 | 3/1999 |
| WO | WO0029448 | 5/2000 |
| WO | WO0037640 | 6/2000 |
| WO | WO0112788 | 2/2001 |
| WO | WO0146443 | 6/2001 |
| WO | WO0198503 | 12/2001 |
| WO | WO02055704 | 7/2002 |
| WO | WO02064839 | 8/2002 |

(Continued)

OTHER PUBLICATIONS

Nishi et al. (203, J. Biol. Chem. 278:46396-46402).*
Ko et al. (2000, Development 127:1737-1749).*
Yuan et al. (1999, Cancer Research 59:3215-3221).*
Smith et al. (2002, Gene 297:169-177).*
Nishi et al. (2002, Nature Reviews 3:94-102).*
Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Agrawal et al. "RNA interference: biology, mechanism, and applications" Microbiol. Mol. Biol. Rev. 67(4): 657-685 (2003).

(Continued)

Primary Examiner — Elizabeth C. Kemmerer
(74) Attorney, Agent, or Firm — Choate, Hall & Stewart LLP; Fangli Chen

(57) ABSTRACT

This invention relates, in part, to unique and newly identified genetic polynucleotides involved in the process of bone remodeling; variants and derivatives of the polynucleotides and corresponding polypeptides; uses of polynucleotides, polypeptides, variants and derivatives; and methods and compositions for the amelioration of symptoms caused by bone remodeling disorders. Disclosed in particular are, the isolation and identification of polynucleotides, polypeptides, variants and derivatives involved in osteoclast activity, validation of the identified polynucleotides for their potential as therapeutic targets and use of the polynucleotides, polypeptides, variants and derivatives for the amelioration of disease states and research purposes.

31 Claims, 85 Drawing Sheets

FOREIGN PATENT DOCUMENTS

| WO | WO02068647 | 9/2002 |
| WO | WO02095007 | 11/2002 |
| WO | WO03063688 | 8/2003 |
| WO | WO2004009803 | 1/2004 |
| WO | WO2004023973 | 3/2004 |
| WO | WO2004033636 | 4/2004 |
| WO | WO2004053068 | 6/2004 |
| WO | WO 2004/076639 A2 | 9/2004 |
| WO | WO 2004/076639 A3 | 9/2004 |
| WO | WO2004093804 | 11/2004 |
| WO | WO2005083125 | 9/2005 |
| WO | WO2005119262 | 12/2005 |
| WO | WO2007073478 | 6/2007 |
| WO | WO 2008/016356 A2 * | 2/2008 |

OTHER PUBLICATIONS

Baron "Anatomy and Biology of Bone Matrix and Cellular Elements" In: Primer on the Metabolic Bone Diseases and Disorders of Mineral Metabolism, Fifth Edition, American Society for Bone and Mineral Research, Washington DC, pp. 1-8 (2003).
Boyle et al. "Osteoclast differentiation and activation" Nature 423(6937): 337-342 (2003).
Brummelkamp et al. "A system for stable expression of short interfering RNAs in mammalian cells" Science 296(5567): 550-553 (2002).
de Vernejoul "Dynamics of bone remodeling: Biochemical and pathophysiological basis" Eur J Clin Chem Clin Biochem 34: 729-734 (1996).
Elbashir et al. "Duplexes of 21-nucleotide RNAs mediate RNA interference in cultured mammalian cells" Nature 411(6836): 494-498 (2001).
Frost "Dymanics of Bone Remodeling" In: Bone Biodynamics, Little, Brown and Company, Boston, MA, USA, pp. 315-333 (1964).
Gee et al. "Potential therapeutic usefulness of intermolecular triplex DNA" In: Huber BE, Cancer Therapy in the Twenty-First Century, vol. I: Molecular and Immunologic Approaches, Futura Publishing Co., Mt. Kisco N.Y., pp. 163-177 (1994).
GenBank Accession No. M32599.1, Mouse glyceraldehyde-3-phosphate dehydrogenase mRNA, complete cds.
Hannon "RNA interference" Nature 418(6894): 244-251 (2002).
Janssen et al. "LAB: a new membrane-associated adaptor molecule in B cell activation" Nat Immunol 4(2): 117-123 (2003).
Jilka et al. "Increased Osteoclast Development After Esgtrogen Loss: Mediation by Interleukin-6" Science 257: 88-91 (1992).
Kawai et al. "Functional annotation of a full-length mouse cDNA collection" Nature 409(6821): 685-690 (2001).
Kawaida et al. "Jun dimerization protein 2 (JDP2), a member of the AP-1 family of transcription factor, mediates osteoclast differentiation induced by RANKL" J Exp Med 197(8): 1029-1035 (2003).
Lee et al. "Stable gene silencing in human monocytic cell lines using lentiviral-delivered small interference RNA. Silencing of the p110α isoform of phosphoinositide 3-kinase reveals differential regulation of adherence induced by 1α,25-dihydroxycholecalciferol and bacterial lipopolysaccharide" J Biol Chem 279(10): 9379-9388 (2004).
Morello et al. "cDNA cloning, characterization and chromosome mapping of Crtap encoding the mouse cartilage associated protein" Matrix Biology 18(3): 319-324 (1999).
NCBI Reference Sequence: NM_007388.3, *Mus musculus* acid phosphatase 5, tartrate resistant (Acp5), transcript variant 3, mRNA.
NCBI Reference Sequence: NM_013599.2, *Mus musculus* matrix metallopeptidase 9 (Mmp9), mRNA.
Netzel-Arnett et al. "Membrane anchored serine proteases: A rapidly expanding group of cell surface proteolytic enzymes with potential roles in cancer" Cancer Metastasis Reviews 22(2-3): 237-258 (2003).
Poli et al. "Interleukin-6 deficient mice are protected from bone loss caused by estrogen depletion" EMBO J. 13: 1189-1196 (1994).
Rubinson et al. "A lentivirus-based system to functionally silence genes in primary mammalian cells, stem cells and transgenic mice by RNA interference" Nature Genetics 33(3): 401-406 (2003).
Shan et al. "TSP50, a possible protease in human testes, is activated in breast cancer epithelial cells" Cancer Research 62(1): 290-294 (2002).
Smith et al. "Mutations in ATP6N1B, encoding a new kidney vacuolar proton pump 116-kD subunit, cause recessive distal renal tubular acidosis with preserved hearing" Nature Genetics 26(1): 71-75 (2000).
Smith et al. "Vacuolar H+-ATPase d2 subunit: molecular characterization, developmental regulation, and localization to specialized proton pumps in kidney and bone" J Am Soc Nephrol 16(5): 1245-1256 (2005).
Srivastava et al. "Estrogen Blocks M-CSF Gene Expression and Osteoclast Formation by Regulating Phosphorylation of Egr-1 and Its Interaction with Sp-1" J. Clin. Invest. 102: 1850-1859 (1998).
Stehberger et al. "Localization and regulation of the ATP6V0A4 (a4) vacuolar H+-ATPase subunit defective in an inherited form of distal renal tubular acidosis" J Am Soc Nephrol 14(12): 3027-3038 (2003).
Strausberg et al. "Generation and initial analysis of more than 15,000 full-length human and mouse cDNA sequences" Proc Natl Acad Sci U S A 99(26): 16899-16903 (2002).
Tonachini et al. "cDNA cloning, characterization and chromosome mapping of the gene encoding human cartilage associated protein (CRTAP)" Cytogenet Cell Genet 87(3-4): 191-194 (1999).
Ko, M.S.H., et al.: "Large-Scale cDNA Analysis Reveals Phased Gene Expression Patterns During Preimplantation Mouse Development", Development, vol. 127, pp. 1737-1749, 2000.
Nishi, T., et al.: "Expression and Function of the Mouse V-ATPased Subunit Isoforms", The Journal of Biological Chemistry, vol. 278(47), pp. 46396-46402, 2003.
Nishi, T., et al.: "The Vacuolar (H+)-Atpases-Nature's Most Versatile Proton Pumps", Nature Reviews, vol. 3, pp. 94-102, 2002.
The Riken Genome Exploration Research Group Phase II Team and the Fantom Consortium, "Functional Annotation of a Full-Length Mouse cDNA Collection", Nature, vol. 409, pp. 685-690, 2001.
Smith, A. N., et al.: "Molecular Cloning and Characrerization fo Novel Tissue-Specific Isoforms of the Human Vacuolar H+-ATPase C, G and d Subunits, and Their Evaluation in Autosomal Recessive Distal Renal Tubular Acidosis", Gene, vol. 207, pp. 169-177, 2002.
Yuan, L., et al.: "Isolation of a Novel Gene, *TSP50*, by a Hypomethylated DNA Fragment I Human Breast Cancer", Cancer Research, vol. 59, pp. 3215-3221, 1999.
Albrecht et al. (2003) Structural Modeling of Ataxin-3 Reveals Distant Homology to Adaptins, Proteins 50(2):355-370.
Ishida et al. (2002) Large Scale Gene Expression Analysis of Osteoclastogenesis in Vitro and Elucidation of NFAT2 as a Key Regulator, J. Biol. Chem. 277(43):41147-41156.
Kawaida et al. (2003) Jun Dimerization Protein 2 (JDP2), a Member of the AP-1 Family of Transcription Factor, Mediates Osteoclast Differentiation Induced by RANKL, J. Exp. Med. 197(8):1029-1035.
Nomura et al. (1994) Prediction of the Coding Sequences of Unidentified Human Genes. I. The Coding Sequences of 40 New Genes (KIAA0001-KIAA0040) Deduced by Analysis of Randomly Sampled cDNA Clones from Human Immature Lyeloid Cell Line KG-1, DNA Research 1:27-35.
Nomura et al. (1994) Prediction of the Coding Sequences of Unidentified Human genes. II. The Coding Sequences of 40 New Genes (KIAA0041-KIAA0080) Deduced by Analysis of cDNA Clones from Human Cell Line KG-1, DNA Research, Supplement, 1:251-262.
Sooknanan et al. (2004) Identification of Osteoclast-Specific Genes Using Subtractive Transcription Amplification of mRNA (STAR), J. Bone and Miner. Res. 19:S415.
Tremblay et al. (2004) Functional Validation of Osteoclast-Specific Genes in RAW264.7 Cells by RNA Interference, J. of Bone and Miner. Res. 19:S414.
Nobuo Nomura et al., Prediction of the Coding Sequences of Unidentified Human Genes. II. The Coding Sequences of 40 New Genes (KIAA0041-KIAA0080) . . . DNA Res 1994 1: pp. 251-262.
Nobuo Nomura et al., Prediction of the Coding Sequences of Unidentified Human Genes. I. The Coding Sequences of 40 New Genes (KIAA0001-KIAA0040) . . . DNA Res 1994 1: pp. 27-35.

* cited by examiner

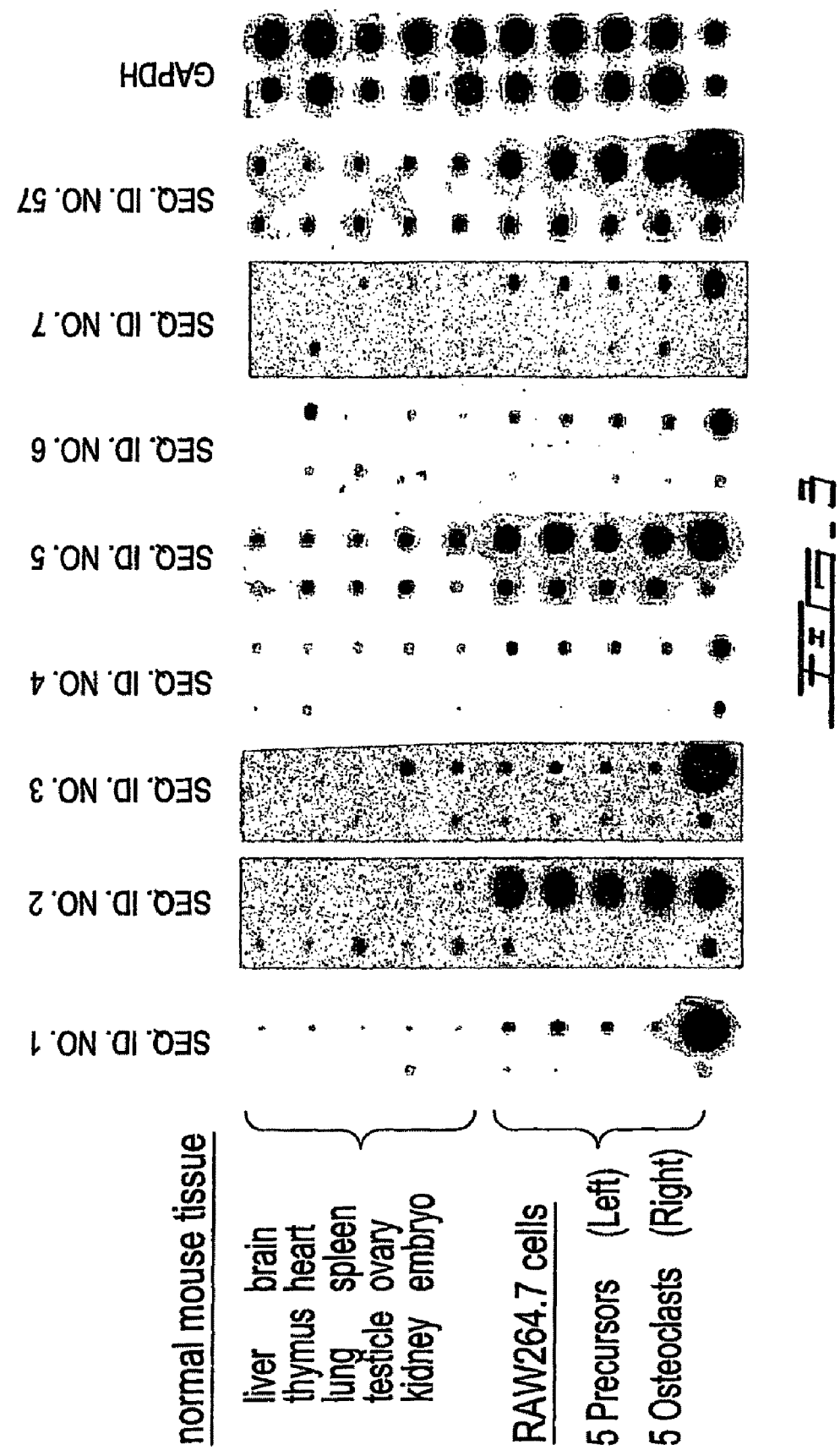

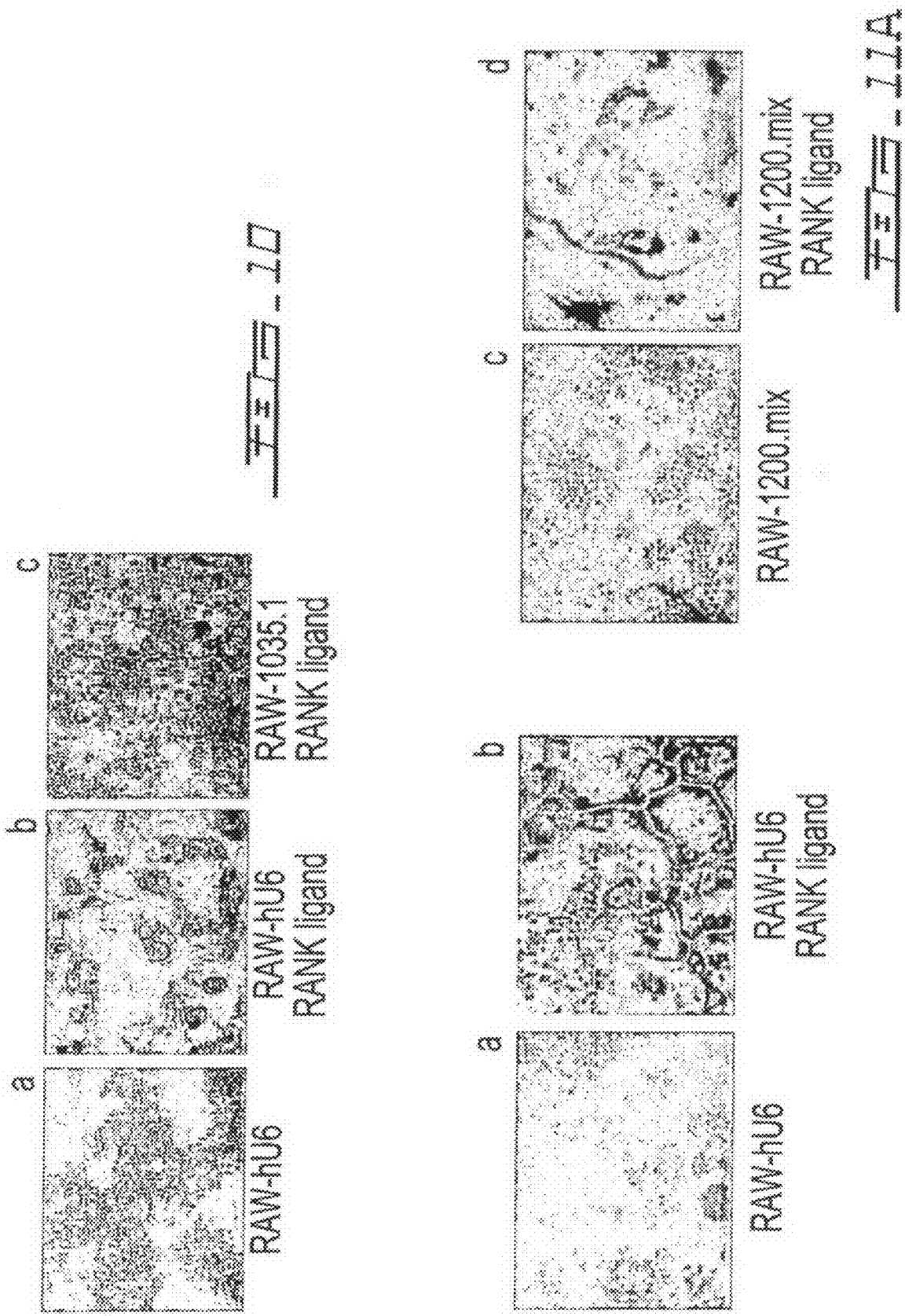

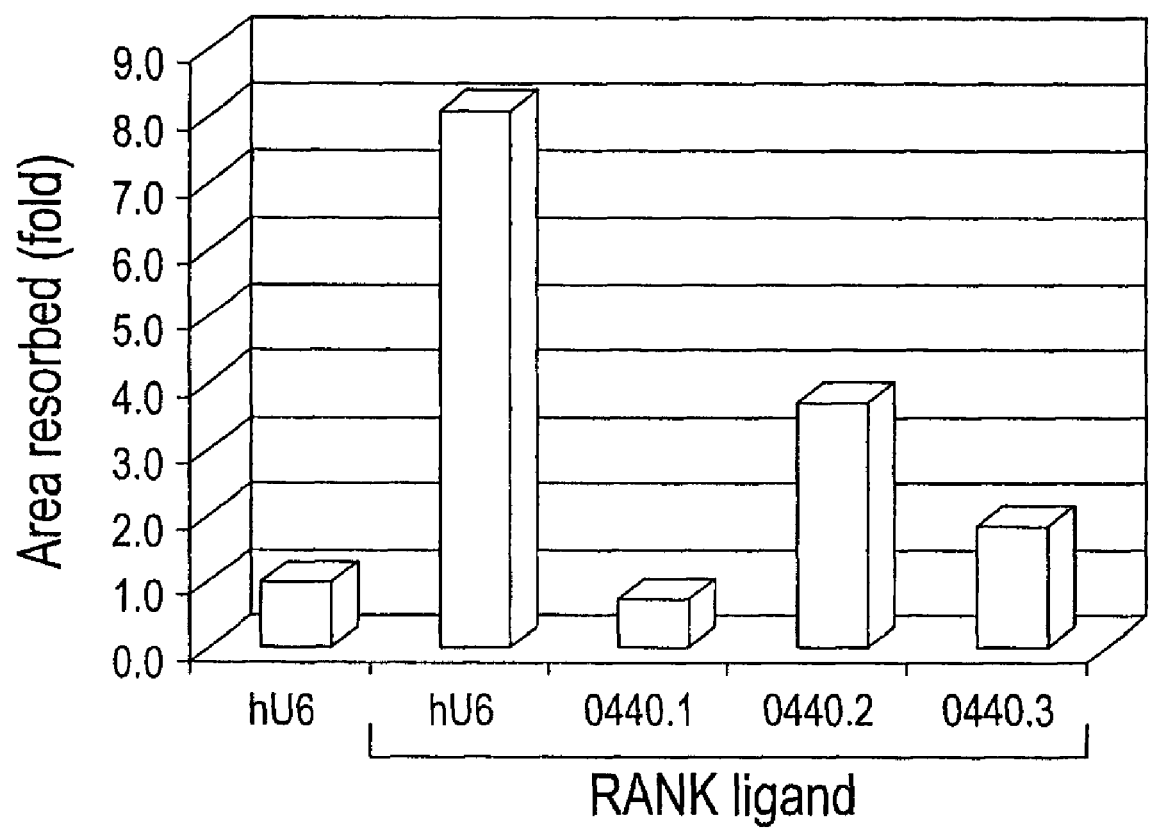
FIG._14B

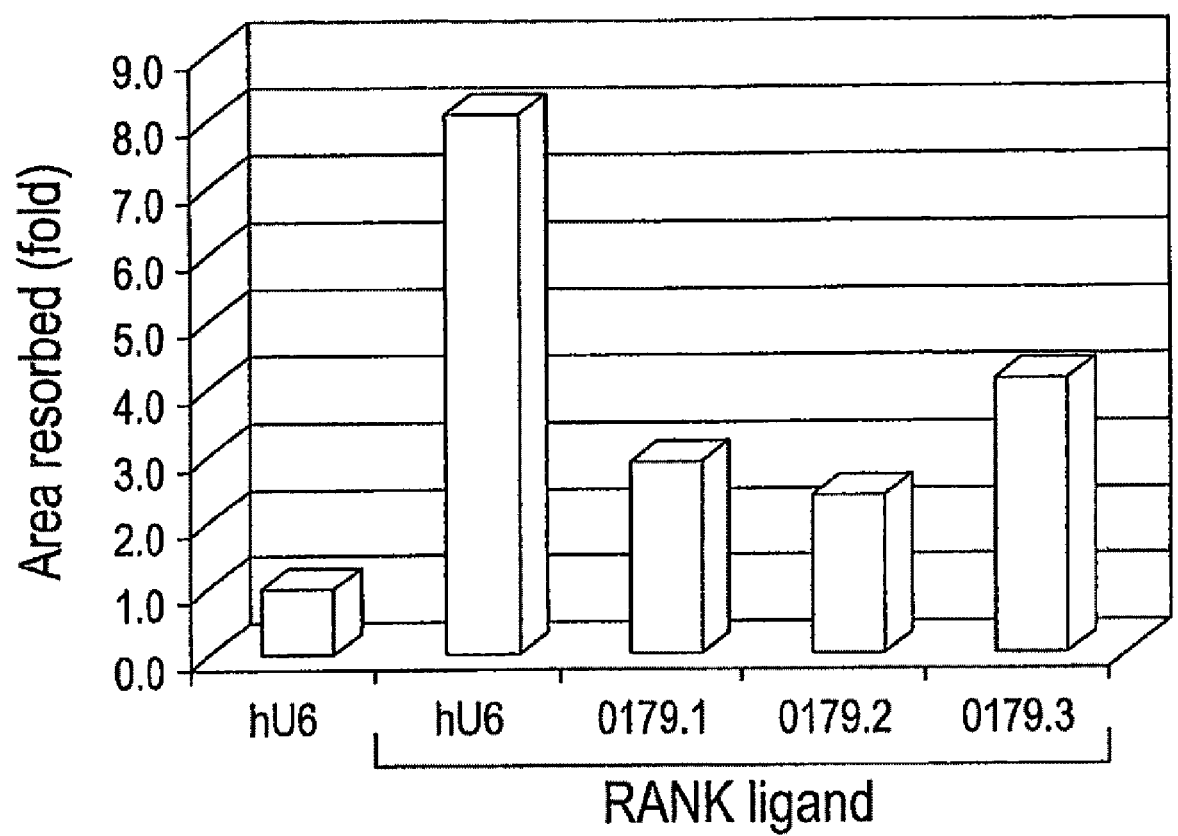
FIG_15B

FIG. 15A

M - DNA ladder
1 - Precursor CD34+ cells } Donor 1
2 - Osteoclasts
3 - Precursor CD34+ cells } Donor 4
4 - Osteoclasts
5 - Positive control (human breast cancer cell line - MDA231)

| NucleotideSequence (5'-3') | ORFs |
|---|---|
| SEQIDNO.:1 | SEQIDNO.:93 |
| GATTGTGGAGGAACCTAGCGGCGCAATGAGCCCTGGTGCGGGCCAGAGGTCCGTGCAGGCCCTCAGGGTCCCCGTG TGCCTGGGGCTTCCCGGCTTCCCGCTCCCGCCCCTTCTCCGGGCACCCTCCTGCTGCTGCTGCTCCTGCCTCGGCCCG GCAGTGAGCGCATCCGCCCCGCCCCGGAGCCCTCCCGGGACGCATCCCGGGACGCTGTCCACCACCCGGACCTTCCAC AGGCTACTTGGCCGCAGGAGCATCCGGACGCTGTCCACCACCCGGACCTTCCAC GAGGCATCTGTCCCTGCAGGCAGGCTTCGCCTTCTCGGCAAGCCAGACTAACCAGACCAGACGGCTCCACGAACTCA CAGACCATGGCTCCACTGAAACGTGGGGGACTCTCGGCATGATGGACACTACTGGTCCGTTCTTAAGACGGTTCATTC CAGCAACCTCCCCTTCTGTGCTCCTCCGCAGAGCCAGACCCTACTCTCAGGGACCCAGAAGCCATGACTCGGCGGTGGC CCTGATGGTCAGCGTGCAGGCTAATGGCTCACACATCTGTGCTGGGATCCTTATCGCTTCCAGTGGGTGCTGACCGTG GCCATTGCTTGAGCCAGAACCATGTTAACTACATAGTGAGGGCGGGAGCCGTGATTAATCAGACGGCAGGAACCAG CTCAGATGTGCCGGTCCATCGAGTCATCAAGCTCAAGTCAAGTCGGGGCTCAAGTGGGGCTCAAGTGGTTGGCCTGGCCTGGAT ATGACATCGGCCTTTCTGGAGGACAGTTCTCTCTGCAGTGGAGCTACAGTGTGGCCCATCTGCCTGCCTGGCCTGGAT TACGTGGTGGAGGACAGTTCTCTCTGCAGTGGAGCTACAGTGTGGCCCATCTGCCTGCCTGGCCTGGAT GTCCCTCCAGGAGGAAGTCTATCCTGACAGCAGCAAGAAAATGTGATCATTCTACCACAAGTTCTGTCTATGAGATAACTGGC CTCTGGTTCGGATCATCAACCCTCAGATGGCACATGTGGTACCTGGTGGGAATGATGAGCTGGGACGGCTCAGTGGGGAGCCCCTGGCTCC GAGCCCCTGGTCTGCTCTTCAGATGCCATATCCTACTACAGGCCCTGATCTGGAGTCTGGGGAGTTGGGGCCTGCCAGGCTGCAAGAGAGGA GGCCCCACCCATCTTTCTGCAGGTCTCCTGGCTTTCTGTTCCTCCTCATCCTTCTGCGGGTGCTCAGCCTGTGACACTGTCTCT CAGCCCCATCCAGGACCTTGCTGCCAAAGAAATCTGTAAGAAGAAGTTCTAGCCAAGTGTCACCCACTGGGCCGTTCACAGAG CCTTCCTCCCCTCCTCCTAAGTGCTGTGTGCCTCAGCGTTGGGGTGGCGCTGCCGGAGCGCGGGAGGAGCTAGACAGAGATTA AACACTTCTTTTCCTC | MEPWCGAEVRGQGPQGPRVPGAS RSRSRALLLLLLLLLLLPRRPA GERIRPRPPRHAHPRPPLTRWR PSTGYLAAGASPGTLSTTVPTGP GVSCGSRGICPSGRLRLPRQAQT NQTTTAPPNSQTMAPLKTVGTLG MMDTTGSVLKTVHSSNLPFCGSS HEPDPTLRDPEAMTRRWPWMVSV QANGSHICAGILIASQWVLTVAH CLSQNHVNYIVRAGSPWINQTAG TSSDVPVHRVIINHGYQPRRYWS WVGRAHDIGLLKLKWGLKYSKYV WPICLPLGLDYVVEDSSLCTVTGW GYPRANGIWPQFSLQEKEVSIL NSKKCDHFYHKFSRISSLVRIIN PQMICASDNNREEFCYEITGEPL VCSSDGTWYLVGMMSWGPGCKKS EAPPIFLQVSYYRPWIWDRLSGE PLALPAPSRTLLLAFLLLLLLLG TL |
| SEQIDNO.:2 | SEQIDNO.:94 |
| ACACTTTCCCGGACCAGGGCCAGTGTTCAGTTGCTATCCAGGACTCGGAGCCACTTCAGCCTGAGCAGTATGCTTGAGAC TGCAGAGCTGTACTTCAATGTGGACCATGGCTACCTGGAGGGCTTGGTTGAGGATGCAAAGCCTCCTAACTCAGC AGGACTATGTCAACCTAGTGCAGTGTGAGACCTTGAGAATTCATCTCCAGACCACGACTATGCAACTTC CTGGCTAATGAAACAAATCCTCTCACTGTTTCCAAAATTGACACGGAGATGAGGAAGAAGCTCTGCAGAGAGTTTGACTA TTTCCGGAATCATTCCTTGAGCCCCTGAGCACATTTCTCACCTACATGACATGCAGTATGATAGACAATATAATTC TACTTATGAATGGGGCCTTGCAAAAGAAATCTGTAAGAAGAAGTTCTAGCCAAGTGTCACCCACTGGGCCGTTCACAGAG ATGGAAGCTGTCAACATTGAGAAACACTCTTGATGAACTATATTGAATTGCGCAATAAACTATACAAGTCTTACCTTG TCAAGATTGTATGTCAAGGATCACGGTGATGTCACAGCAGACGTTATGTGTCCCATTCTTGAGTTTGAGGCCGAC | MLETABLYFNVDHGYLBGLVRGC KASLLTQQDYVNLVQCETLEDLK IHLQTTDYGNFLANETNPLITVSK IDTEMRKKLCREFDYFRNHSLEP LSTFLTYMTCSYMIDNIILLMNG ALQKKSVKEVLAKCHPLGRFTEM BAVNIAETPSDLFKAVLVBTPLA PFFQDCMSENTLDELNIBLLRNK LYKSYLEAFYKFCKDHGDVTADV |

FIG. 22

| NucleotideSequence (5'-3') | ORFs |
|---|---|
| AGACGCGCTTTAATCATCACTCTGAACTCATTGGCACTGAACTGAACTAAGCAAAGAAGACAGGGAGACCCTCTTCCCCACCTG<br>CGGCAGGCTCTATCCAGAGGGTTGCGTTGCGGTTGTTGTTAGCTCAAGCTGAAGACTTTGAGCAGATGAAGAGAGTGGCAGATAATT<br>ATGGAGTTTACAAGCCTTTGTTTGACGCTGTCGGTGGCAGTGGGGGAAGACACTGAAGACGTTTCTATGAGAGAG<br>GTACAGATGAATGAAATATCGTGCTGGCATTCAACAGGCAACTCATTATGTGTTTTATGCTATGTAAAGTGAAGGAGCAAGA<br>GATGAGAAATATCGTGTGGATAGCAGAATCATCATCATGTTGCCATGAATCTCACAGAGGCATCGAACAGCTACAATCCAATTTAT<br>AAGCCAGTGTACAGAAGATCATACATCACCACCTTTCCAACAACAGCCCAGTCGTTTTTCACATTTGACTTCCTGCTCACTGGCCTCATACGTTCATTTT<br>TATATAAAGTAAGTACATACCACCTTTCCAACAAGCCCAGTCGTTTTTCACATTTGACTTCCTGCTCACTGGCCTCATACGTTCATTTT<br>TGCCTTTCTTGTTTCCAACAAGCCCAGTCGTTTTTCACATTTGACTTCCTGCTCACTGGCCTCATACGTTCATTTT<br>CATTGACCCTGTGGCACTTTTTGATTCTCATTTGGTCAGACTAAAATCATACGTAATCAGGTTCTTCACGAGTTCTTTT<br>CCGTTCTCTCCCCAAGCTCAAACACTGCTTTGCTTTGAAGACACGTTCCCTCTTCCCCAAGACTTTTGAGAAAGATAGATTCC<br>GTGGGTAGCTAACATACACCATGCTTGGTGAGACAGTTCCCTCTTCCCCAAGACTTTTGAGAAAGATAGATTCC<br>CCAAATGCAAGCATTGTTAAATTTATTACTAACGCACACATAGAGACAGAGAGAGAGAAATAGATAGAGAC<br>AGAGACAGACAGAAGGATGAAATAACTTATATCAGAGATGTAGAGATACAGCATGGTGCTACATAAAGTGAAACAATGCAGAGTT<br>TCCAACTAATTGTACTTTATTCCTTCAGAAGATGTAGAGATACAGCATGGTGCTACATAAAGTGAAACAATGCAGAGTT<br>GCTCAGAAAAAGAAAATAGCAAAATAAATCTGTCAGTCAGATGATGACTCAGCAGGAACTGCAAAACTACAAGATCATCTTAATCCTTTACTTACTATGC<br>TGCTCTGCTTCACAAATAAATCTGTCAGTCAGATGATGACTCAGCAGGAACTGCAAAACTACAAGATCATCTTAATCCTTTACTTACTATGC<br>GATTCCTGGAATCTCACATATGGAAGGAGGAACTGCAAAAGAATTTTAAAGAAGCCAAGTGCCTACTCCTCTCAAAACCCTTCCTTTC<br>ACCCCACCACTACACTGTATGTAGAATAGTATGCATAAGAAGAAGCCAAGTGCCTACTCCTCTCAAACCCTTCCTTTC<br>CTATATACACATGCTATGTAGAATAGTATGCATAAGAAGAAGCCAAGTGCCTACTCCTCTCAAACCCTTCCTTTC<br>TAACAAAATAATAGTTTGTTGAACTAAGAAAAGCCAAGTGCCTACTCCTCTCAAACCCTTCCTTTC<br>CTCCTGCCAACCAACACCTTCTCAACCACTTAGACTGTTTGTGGCAGCAACCAACCAAACAAGTAACTAATACAGAAAACTGATACTGCCATTGCTACAA<br>TAAACTGTTGTTTCAGTGATTTTGGGGATTTAAAAAAAAAAAAAAAAAA | MCPILEFEADRRALAITLLNSFGT<br>ELSKEDRETLFPTCGRLYPEGLR<br>LLAQAEDFEQMKRVADNYGVYKP<br>LFDAVGGSGGKTLEDVFYEREVQ<br>MNVLAFNRQLHYGVFYAYVLKE<br>QEMRNIVWIAECISQRHRTKINS<br>YIPIL |
| SEQIDNO.3 | SEQIDNO.:95 |
| CCCGGCCTCCCTTCCTAGGCCCTGCCCGCGTCCTCGCCCTCTGCTCGGGGCTTCGTTGCGTTCGTGGGCCACGCGCGATGGGGCCC<br>CGCAGCCCCTGCGGCGTTCCGGTTGTCTGCGGTGTGCTGCGGTCCGGATGGCCCCCCCGCTCCCGCGGGCGCAGTAGCAGCGCTA<br>CAGCTTCCGCAACTTCCCGCGGACGAGCTGATGCCGCTCGAGTGCCTCGGCTGACCAGTACAGCGGCG<br>AGCACTGGGCCCGAGAGCGTGGGCTACCTGGAGGTGAGCCGCGCCGTCTGCGCTGCGCCGACAGCGAGGCCTTCTGC<br>CACCGCAACTGCAGCGCGGCGCCAGTGCCTCAAGCAGGCCCTGCGCAGGCCCTGCCAGCCCAGCCGCTCAG<br>CGTGCTGCGCGGACTTTCAGCAGCGCGAGCCCTACAAGTTTCTGCAGTTCGCCAATGACCTCCCGAAGCC<br>TGCTGCGGGACTTTCAGCAGCGCGAGCCCTACAAGTTTCTGCAGTTCGCCAATGACCTCCCGAAGCC<br>ATCGCTGCGGCTCACACTTCCTGAAGCATCCAGATGACGAGAGATGAAGAGAGAAACATGGAGTATTATAAGAGCTT | MGPRSPAAALLVLLCVGCAPTPG<br>RGQYERYSFRNFPRDELMPLESA<br>YRHALDQYSGEHWAESVGYLEVS<br>LRLHRLLRDSEAFCHRNCSAATP<br>APAPAGPASHAELRLFGSVLRRA<br>QCLKRCKQGLPAFRQSQPSRSVL<br>ADFQQREPYKFLQFAYFKANDLP<br>KAIAAAHTYLIKHPDDEMKRNM |

Fig. 23

| NucleotideSequence (5'-3') | ORFs |
|---|---|
| GCCTGAGAGCCGAGGACCACATTAAAGACTTGGAAACCAAGTCGTACGAGAGCCTGTTTGTCCGTGCGTGCGGGCCTACA ACGGGGAGAACTGGAGAACGTCCATTTCCGACATGAGTCTCGCGCTTCCGACTTCCTACGAGTGCCTG GCTGCCTGCGAGGGTCGCGGGAGATCAAGGACTTCAAGGACTTCTACCTGTCCATAGACAGATCACTAGTGAAGTTCT GGAGTGTAAGATTCGTTGTGAGGAGACCCTCACCCGAGTCTATCCCGTGGAGAAATTGTGCGACCATGT ACCACTATTACAGTTTGCGTATTACAAGTTGAATGATCGCAAGAAGAATGCAGCCCGTGTGCCGTCAGCTACCTGCTCTTT GACCAGAGTGACAGGGTCATGCAACAGAACCTGTGTACTATCAGTGAGACGCTCCAGAAGGAACTGTACGACTTCGTCAGGAGCA CTTCCAGCCAGACCCGAAGCAGTTCAGTTCTTCATTGTGAGATATGTGGAGTATGTGGAGACGGAAGAGTCTGCCTAGTCCACA ACCTAATGATGACGATGAGGAGAGGTTGTGGACTGTGTGCCTGACTGTTGTTGATACCTCAGTATTCACGCTTGTC GGGGCTAAGGACTCTCTCCCGAGTCCTCGACTCCCCTGTTCCTGTGGTTGTTGATACCTCAGTATTCACGCTTGTC AGTAAGAAGGAAGCCACCATCTCTCCCTACCAAGTCAAGCCTGACTTCGTGGACTTCCCCTGTTCCATCTAGTGTCCTCCTCAAAGTCAC TTCATGGTTACACGTCTTCATGCCGTCTTCCCTACCAAGTGTCTCCCATGTTCAGAAAGACAGTCTTCTGTGGTCTGCTTTCTCATCCCGGA GTTCGTCTCCCCTCGATCCCATGTCTGAGAAAGACAGTCTTCTGTGGTCTGCTTTCTCATCCCGGA AGAAAATCAGTATTATTTTTAAGTAAGAAACACTAAAAGATGATAAATATATTTGGAGAATTAAAAAAAAAAAAAA AAAAA | EYYKSLPGAEDHIKDLETKSYES LFVRAVRAYNGENWRTSISDMEL ALPDFLKAFYECLAACEGSREIK DFKDFYLSIADHYEVLECKIRC EETLTPVIGGYPVBKFVATMYH LQFAYYKLNDLKNAAPCAVSYLL FDQSDRVMQQNLVYYQYHRDKWG LSDEHFQPRPEAVQFFNVTTLQK ELYDFAQEHLMDDDEGEVVEYVD DLLETEESA |
| SEQIDNO.4 | SEQIDNO.:96 |
| GACTCGGCCTCCGGGAGACAAAGGGCCCTGTCGTCGCCGGCCCCCGAGCTGTTCCGGGCAGCTGTTCCGGGCCATGGGCCAGGACAGACCGTCG CGCCGGTCCCAGAGCCAGGCTCCCAGAGCTACACAGGCTACACAGGCTAGCTGGACACTGGACACTCAAAGCCAGACAGAGAACCCCCACCCCTC TCTGGACTGACGCAGATGAAGAGCTCAGAGAGCTAGAGGTCCAGACAGAGGAACTGACTGTGTGCCCCTGAAGTGACCTCCCTGTCAGCCTGACCATGAAGC GAGCTGACCTTCAAAGTGACAGCAGCTTGGCTGCCTTCAACGCGAGTTGCAGCTTCAGCTTCCTGTACAAGCGTGGTGGC TCAACGAGCGACAGGCTGGCCACCGGCTTTCGTCCCGGTGACAACCTCCGGCAATATCCTCTTACTTGCAGAAGGCAGCCGCGA CGTGGGACCGGCCTGCATCCTGTCGTCACGGTGAGCTGGTCCGGTGAGCTGGATGCCGGGAGGAGTTCGCTTCGCAGTGCGCT GCCGCTGGGGCCAGCTTCCACTATCCGCTTGGTGGTGCCGTACGTGCTGGCGCCGTTTGACCAGCAGCCAGCCAGCAACTGGCTGCCATGCGGAGTCGAAGGCGAAGCCGTCC CGGCGCAGCTTCACCCGCCAACCGCGAGCCCTTGTTTGACCAGCAGCCAGCAACTGGCTGCCAAGGAGAACGGCTGGTAGTGTGAGCACGCTGC CCGAGCAGCCCTTCGGTAGCCCTCAGCGCGCCTTAGGGACCAGCAGGTGCAGGACTCAGCAGCCAGTGGCGCGGAGGCCAGGCTGG GCATCCTTCGCCCAGCTTAGAGTCCCCTGGCATCGTAGCGCGATATGCCCTGGCATCGTAGCGCGATATGTCCGTTCCGCTGAGAATGCCTGTTTGCAGAAGAATCTGAACCTGAGGTGCTTC CCTAGCCAGCTTAGAGTCCCCTGGCATCGATCGTGATCTCCGTTCCGCTGAGAATGCCTGTTTGCAGAAGAATCTGAACCTGAGGTGCTTC GTGGGGTGTAAGGTATTACATGTATTCCGTTCCGCTGAGAATGCCTGTTTGCAGAAGAATCTGAACCTGAGGTGCTTC TGACTCAGGAGACGCTGTCCCCTGGTCAGGAGAAGGACTGGTCCCCTGGTCAGGATCACTTACTTCTCAGAGGACACTTACTTCTCAGAGGAATTCGAACTTGAACCTGAGGTGCTTC TAGAGCCCAAGGAGCTGTTTCAGAGAACTCCGCGCCTGTGTGACCTTGACCGTGTGTCCGCGTGTGACAGCCCCGAAGCTGACAGCTGGCCACA GGCCCATGGGCCCAGGTTACCTGGTCCTCTCAAGGATCTAAAGCTTGAACCTGAGGATCTAAAGCTTGAACCTGAAGCTGTCTGGGCTCTGT | MKLNERSLAFYATCDAPVDNAGF LYKRGGRGTGSHRRWFVLRGNIL FYFEAEGSREPLGVILLEGCTVE LVDAREEFAFAVRFAGGRSRPYV LAADSQAALEGWVKALSRASFHY LRLVVRELEQLAAMREGSPANA LPANPSPVLTQRPKENGWVWSI LPEQPSVAPQRPPPLPPRRASA ANGPLASFAQLHARYGLEVQALR DQWRGGQAGLASLEVPWHPGSAE TQTQDQPALRGHSGCKVLHVFRS VEWPVCNPGSQGT |

FIG. 24

| NucleotideSequence (5'-3') | ORFs |
|---|---|
| GGGCCTACACCAGTAGGTGGAAATGTGGACTTGAACTGGATAGGTCCCCAGGCTCCTGGCCTGGAACCAGCTAAGTCAG<br>GACTGTGTCCAGCTTTGTCAGTTCACCTGGAGAGACAGAAGCAGGGCCCTCGACTGATTCCGACGACTGTCCTGGCCAGCTTC<br>CTCCCAGTTTCACCTGGAGGAGACAGGGCCTCCCAGACTGGCTTCTCATGCCTGTCTCTCCTCCTCAGGCCACTGTCCTAGC<br>CACTGCAGTGACCAGTGCCCCCACCTGGGTTCTGTTTACAGTTCCTCCTCCTGGGGTCTGGCCAGTGTGCCCCTGACTGCA<br>CAGGACAGCCGGCCCCCACCTGGGTCTGTTTACAGTTCCTCCTCCTGGGGGTGTGGGGGACACTGGGTGCTTCTGTCTG<br>TCCTATGAACACAGATTTCACCCTGGCTCTTGCCTCTCGCTGCCTCAGGGCCACTTGGCTCCACCCTGCCACTTTTGTTGGCTGCAAGGGTGGCATTG<br>TCGCCAGGGCCTCCTTGGCTCTCGCTGCCTCAGGGCCCACTTGGCTCTCACCCTGCCACTTTTGTTGGCTGCAAGGGTGGCATTG<br>CTGTCTTCCACCAGTGAAGTTAAGTAGTCAGTCTCACAAACCTCTAAAGGTACGGCAGGAGGTGGGAGACAAGGCAGAGTTGTTCC<br>TCTCCAGGAGCCAGCCCTCGACAGTGGTGCCTCTGGGACTTGGTCTGTCTCCTCAACTCTCCCACTGGAGTCATACGGCTGAGGT<br>GTAGACTCTAGTCTGGGACGGCTTACAACTCTAAAGGTACGGCAGGAGGTGGGAGACAAGGCAGAGTTGTTCC<br>CTCTCCAAAGCACAAGGTGAACACCAGCTGATTCTGGGCTAGGAGAGAGTTATCAATCATGGACAGGGTATGAGGGCCA<br>AAATAAAAGCCCGGTCG<br>SEQIDNO.5 | SEQIDNO.:97<br>MREIVHIQAGQCGNQIGTKFWEV<br>LSDEHGIDQAGGYVGDSALQLER<br>ISVYYNBSSSKKYVPRAALVDLE<br>PGTMDSVRSGPFGQLFRPDNFIF<br>GQTGAGNNWAKGHYTEGAELVDS<br>VLDVVRKECEHCDCLQGFQLTHS<br>LGGGTGSGMGTLLLISKIRBEYPD<br>RIMNTFSVMPSPKVSDTVVBPYN<br>ATLSVHQLVENTDETYCIDNEAL<br>YDICFRTLKLITPTYGDLNHLVS<br>ATMSGVTTSLRFPGQLNADIRKL<br>AVNMVPFPRLHFFMPGFAPLTAR<br>GSQQYRALTVPELTQQMFDAKNM<br>MAACDPRHGRYLTVATVFRGPMS<br>MKEVDBQMLAIQNKNSSYFVEWI<br>PNNVKVAVCDIPPRGLKMASTFI<br>GNSTAIQELFKRISEQFSAMFRR<br>KAFLHWFTGEGMDEMFTEAESN |
| CAGGCGCCCGAGCGCAGACGCGCCCGCCATGAGGGAGATTGTGCACATCCAGGCTGCGGGCCAGTGCGGGAACCAGATCGGTAC<br>CAAGTTTTGGGAAGTGCTCAGTGATCAGTGATGAGCACGGCATCGACCAGGCCGGAGGCTACGTGGGCGACTCAGCGCTGCAGCTGG<br>AGAGGATCAGCGTCTACTACAATGAGTCATCCTCTAAGAAGTACGTTCCGCCGTGCGCCCTGGTGGACTTGGAGCCCGGC<br>ACCATGGACAGTGTGAGGTCTGGGTTCACTACACGGAAGTTCTCCGGCTGCAACTTCATCTTCGGACAGACGGGTGCCGG<br>AAACAACTGGGCCAAGGGTCACTACACGGAGGCTGAGCTTGGTGCTGATGTGGTGCGCAAGGAGTGTG<br>AGCATTGCGACTGTCTTCAGGGCTTCCAGTTGACTCACAGGCGGCTCCACCACCGGCATCAGCCGTCACCAAGGTCTCAGAC<br>ATCAGCAAGATCCGAGAGGAGTACCCGGACATTATGAACACCTTCAGCGTCATGCCGTCACCCAAGGTCTCAGACAC<br>CGTGGTGGAGCCCTACAACGCCACATTGTCAGTGCACCAGCTGGTAGAGAACACCGACGAGACCTACTGCATCGACAACG<br>AGGCCCTCTATGACATCTGCTTCCGCACGCTCAAGCTGATCACCCCCACGTACGGGGACCTCAACCACTTGGTATCCGCC<br>ACCATGAGCGGTGTCACCACATCACTGCGTTCCCTGGCGTTCCCCGGCTTTGCCCCCTCACAGCCCGGCAGTACCGTGCCCTGA<br>GCCATTCCACGTCTCCACTTCTCATGCCCGCTGAGCTCCAGAGATGCTGGCGCACGATCCCGAGCAGTTCTCCGCCATGTTCCGCGC<br>CAGTGCCTGAGCTCACACAGCAGATGTTCGATGCCAAGAACATGTTCATGATGGCGACGTGCCCGAGCATCCCGAGCAGTTCTCCGCCATGTTCCGCGC<br>ACCCGCTGAGCTCACACAGCAGATGTTCGATGCCAAGAACATGATGGCGCGATGTTGCGCGATGAGAGCAGTTCCATGCCAAGCAGCTTGA<br>CAGCTACTTTGTGGAGTGGATCCCCAACATGTCAAGGAGCTATTCAAGGTCATGGCGCGATGAGCAGTTCTCCGCCATGTTCCGCGC<br>CAGCTACTTTGTGGAGTGGATCCCCAACATGTCAAGGAGCTATTCAAGAGACTCATTGAGGTGGAGCATGAGGCCTGAAGATGCCT<br>CCACCTTCATTGGCAATAGCACTGCTATCCAGGAGCTATTCAAGGAGCATTGAGCGAGAGTCTCGGCCATGTTCCGCGC<br>AAGGCCTTCCTGCACTGGTTCACCGGTGAGGGCATGGACGAGATGTTCACCGAGGCCGAGAGTAACATGAATGACCT<br>GGTGTCCGAGTACCAGCAGTACCAGGACGCCACGGTCAATGATGGGGAAGAGGGCATTTGAAGACGAAGAAGAGA<br>TCAACGAATAGGGAGCCATAAGATGCTACAGTGAACGTCTGCTCTTTCTTAGCTTGACTTGATGGTGTGGAATGGTGCCCTG | |

FIG. 25

| NucleotideSequence (5'-3') | ORFs |
|---|---|
| GTCTAAGCATGTCACTGGCCCCTCTCAAACCAAATGCACCACTGTTCTCCAGTTACCTGGAACAGTCCCAGCAGACC AGGGAGATCTCATATAGGAACCCTGAAAGCAAAGTAGGGGCTCACACAGAAAGTGACCACCTTTGTTAAG CCCCCTTCCACCCCATCAGAGTTAGAATAGGGATTTGTTTTTCATCCTCGGTGATAAACTAAAACCACAGTGCTG CCTTAAGTGAATGCACACTATGAAAAAAAAAAAAAAAAAAAAAAAAAATGCTAAACCTGAAAAAAAAAAAA AAAAAAAAAAAAAAAAAAAAAAAAAAAAAAAAAAAA SEQIDNO. 6 | MNDLVSEYQQYQDATVNDGEEAF EDEDEEEINE SEQIDNO.:98 |
| GGCCTGCTTGTCCGCGCGTGGGCCAGTGGCGGCCCGCAAGCTCCAGGTGGCCGGCCGTCGGGAGACGAACAGTCCCCGCC GGGCCAGGCAGGGGAAGGAGCCCGGGACTGGCCTCACGTGACAGCAGGAGGTCGCTGCGCGGGAGACGCGGTCAGCCCGGTGGGC CAAGGCTGCACCGGGCAGGGCGAGGCAAGGCGTCCGCCACCCTCGCGGCCACCCTCCCCGCGGGCGCCTCCTCCGCCAGTCCGCTGGC TGCCGTTCCCCTTCCGCGGCTATCCCCGGAGCCCCGCGGAGCTTCGGAGGGCCCGAGCTCCTCACGCCCTCCGATCCTCGCTAGCTCTTGGCATTGG GGCTTTCTCCGCCACCCAACCCGGTCTTCGGAGCTCTTCGGTGTGTTGATTCGACGAAATGAAGAGCAAGGAGCGATGT GACCCCTTCGGTTCTGCCCTCTCGCATTGGAGCCCTAGTTGGCATCTCAGAGAGGAGAATCTCAGAGAAAACACGGCCAGGAAAGCGTGGTG TTTCTTTTTTTCAAAGGGGTTGGGGTGAAAGTGTTGGCTAAATAACTAAGCTTTCCAACCTTTCTCCCAGTGACAAGCATAAATCATGAACACAGAGAA AGTTAGATTTTTTTTTGTCCCTTTGTCTCAAGAACTGAATTCCAATCATCATCCAGGAGGATGAGAGCGAGTGTTTAGCGGCTC TAAATGGTGAACCTAAATCGAAATGAATAAATCTACCATGATGCGTGCCATGCCACAGCAGCCAGGAGACAAGCCAAAGCTGAATCCTCGGACTTCC TGCCTGGAACGCGCCAACGCCTTCACGCGGGAAATGGAAATGCTGGAAGCATTGCACCCGGAGATTTCCAGAGGCTGTCTCCGAACACTATGGTGACGCCCAC CCAAGCAGCGCAACGCCTTCACGCGGGAAATGGAAATGCTGGAAGCATTGCACCCGGAGATTTCCAGAGGCTGTCTCCGAACACTATGGTGACGCCCAC AGGACAGCAACGCCTTCACGCGGGAAATGGAAATGCTGGAAGCATTGCACCCGGAGATTTCCAGAGGCTGTCTCCGAACACTATGGTGACGCCCAC AAGAAGAGACATGCTGGAATGGAAATGCTGGAACTATGAATGTCTTACTAATGTCATGGGCTTCAAACAAGGTCATATGGCTATGAAGCTGT TGGTGGGGACAAGCGAAGGGAACTGGGTGTCATTGCCTCAAAAGACACACTGGATCTGTGTTCGTGAGGTGGGGAGGGCCTACTACAAC TCTGCTGGGGGTCCAACTCAAGTTGCCTCAAAAGACACACTGGATCTGTGTTCGTGAGGTGGGGAGGGCCTACTACAAC CTTGACTCCAAACTGAACTCCTACTGTGTACCCAGACCCTTTGAGCTGATTGGAGGCAGAAGTGGAAGCCATCAGAGCTGGAGGGCCGACGTGTGACAGTTGT TAAAAACTGTGAACTCCTACTGTCTCAACCCTCCAGACCTCTTTGAGCTGCATGGGCTGACTGTCAGTGACACTTCCCCAAACATCTCATTG TTGACCCCTCTTTGTCTCAGATTTGCCAGTGCAATAGACAGATTGCCAGTGTCTATTCCAGTGCATTACAGGTGTGATGCCAAGAAGGCGTC GGTTTCCCCTTCAGATTTGCCAGTGCAATAGACAGATTGCCAGTGTCTATTCCAGTGCATTACAGGCTCTGTGGTAGTGTCACTGATCTTCAGG GAAGAAGGTAGGAGCTGGGTATTTCTCCCTTTCCCATAAGGCTCTATTTGATACAGGCTCTGTGGTAGTGTCACTGATCTTCAGG CTTTGAGGGGGCTGGGTATTTCTCCCTTTCCCATAAGGCTCTATTTGATACAGGCTCTGTGGTAGTGTCACTGATCTTCAGG CTTACGGAAAGGCCGCCCTCACCTGCAGTGTCAGTGCACCATGGGCGTCGACCTGGACCTGAGAGCCTCTTCTTGTCCCTTTAAACCCAGCCAGCCTTT CAAGACTCCAGCAGCTCTTATAAGAGGCTCTGCTATTCCAAAATAGGTGAATTGCACATCATTCTAGCACAGTGGTGAAAGATATGCC | MSCVPWKGDKAKAESSDLPQAAP PQIYHEKQRRELCALHALNNVFQ DSNAFTRETLQEIFQRLSPNTMV TPHKKSMLGNGNYDVNVIMAALQ TKGYEAVWWDKRRDVGVIALTNV MGFIMNLPSSLCWGPLKLPLKRQ HWICVRBVGGAYNLDSKLKMPE WIGGESBLRKFLKYHLRGKNCEL LLVVPEEVEAHQSWRADV |

| NucleotideSequence (5'-3') | ORFs |
|---|---|
| ATGTCAGGGGGTTCCCTGTCTCAGAGCATTATGTGTACTAACTGTAGCAGAGGAATGGGTGTGGGTAACCTGGAATCG CTTTGGTTCTTAGTGGCTCCAGTTTGTTGTTCTGATCTTTCATTCCTGCGGGACCTTGTGCGTCGGTGATAGGAAATAA AACTGCCCCCCTCACCAAACACCAATAAACCCTGTGAGTGTGAGAAAAAAAAAAAAAAA | |
| SEQIDNO.57 | SEQIDNO.:100 |
| GCGGGAGGGACACTCGGCGGCCGCGACGGGGCGCTGGCGCAGCGGACGCTGCAGCGGCGCGCGGGGCTGGCGCCG CGGCGGCTCCCGGGCCGGGACGGGCCCTGGGCAGCGGCGGCAGCGCGGAGTGGGCACCGCGCCTGCAGCAGGTTCT GGGCCGGGCCGCGCCGCCTCCGCAGCCGCTTCTGCAGGCTCTCGGCCGCTCGCAGCCCCCTGCCAGGGCTCGGCAC GGGCAGATCCCAGAATCCCAGACCCTTCAGTGACCGGAGCTCGGCGGATCCGCCGCCCCCTGCCAGGGCTCGGCA GACCACAGAGGAGCTGAAATACGCTGAAATCCGCAACATTGGGGGCGATGAGTGAAGAGAGCGAAGAAAGGCGCC TGGGCAAGACAGGCCCCAACCCGTGAAGACGTAGAGAGTGAAGATGAGTTTCTGCAGAGGAGTCAGAGCGGCTGAGCTCAT GTCGCTGCAGCCAGATGCCGGAACAAGAACAAGAGAGAGCTGAAGCTGAAGACGCACAGATAGCGTCAGGAGAAGACGAACCGCCACCGCC CCACCTGCATCGTGCGCAGACAGATAGCGTCAGGACGAACGCCCGAGTCCGAAAGGCAACCACTGCTGGAGCAGCTGGACAAGAAG TGACTGAAGGCCTGGAGGAGCATCAGAGGAGGAAGAGGAGCTTAGCATAACTGACCTCCAGCTGCTGGCTCTTTTTGAAA CAGAGGGGCCCTCGCCGCGCACGTGACAAGTCTATGTGAAGAGCGGACAAACTCAGAGGACGGACTTGAGAAACAGAGGT CTCAGCCCTCCTGCCGCGCAAGAGCGGACTTGAAGAGAGCGGACTTGAAGAGAGCACCTGACCTCCAGCGTTGACCCGCAGA TAGGGCGTCTCCCAAGAATCGACTGGAATCCAGTGAGCGGAGACACAGTGACACAGCCCAGCTGCCAAACACAGGCCAGGTTGTGCAAACACAGTG CTCCTTTGGCCTCTCTGCCAAGAACTCAGCATAGACTGCAATCCACCTCCCCAAGCCCCAGCCCCTGCCAAGCCCAGCGGAAGGGGGTGCACTGT TGGCCCGCGATGGAACTCAGCATAGACTGCAATCCACCTCCCCAAGCCCCAGCCCCTGCCAAGCCCAGTGGAAGGGGGTGCACTGT GGGCTGCAATGCCCAGCTGCGCTCGGCGGCAGACCGGGCCCTTGGCTGCGGCACAGACTGGCGGGACACGTTTTTATACTTTTCTTTTTTTTT TGTTTACAGACTGGCTGTCCTGGCGGGCCTTCCAACTGCCACACGTTTTTATACTTTTCTTTTTTTTTT TTTAATATTTTACAAAAAAAGATTTTATACAAGCAATATATATATATATATATATATATGATTCTA TAATCACTCGATGTGACACAGTACAAATATGCTATGCTCGTTATGGACATCCACCCAGTTAAGGCCATTGTAATTC CTAAGTACTGTAGGCTCTGGGTGTTGGGGGGTGGCCAGGCGGGTGAGTACATTTCCATCCTTGTAACCCTTGTAGTA CCCAGTCCTGTATCGTTCAGTAAACATTGCTCTTAATTACCCAAAAAAAAAAAAAAAAAAAAAAA | MMPGQIPDPSVTAGSLPGLGPLIT GLPSSALTTEELKYADIRNIGAM IAPLHFLEVLGKRPQPVKSELD EEEERRKRRREKNKVAAARCRNK KKERTEFLQRESERLELMNAELK TQIEELKLERQQLILMLNRHRPT CIVRTDSVRTPESEGNPLLEQLD KK |

FIG. 29

| NucleotideSequence (5'-3') | ORFs |
|---|---|
| SEQIDNO.9<br><br>CCGGTCAGAGACCTCTCCTGCGCACCTTGCGCAAGAATCACCCCCCAGAATCAACGAGTCAACCCTTCT<br>CACTGCGGAAGAGACCTCAAGGGTCAGGGGTGGCAAGATCAAGCTGCTGACACACCCTGGACCACTCCACTGCCCCTGGTT<br>CCACCATCACCACTTACCTCTACCAGCTGCCTTAGTGACCATCCAGACATCCTGTCCACTGCCAGCTCTGAGACCCTGTCCG<br>CCCTGTCGCTCACTACCTTCACTACCCTGCTTCCCCGACGATGGAGACTGCACTGCCAGTCCTGGCCTCCCAGTGCCCCA<br>TGGGCCCGACTGAGGAGACTGACAACTTCATCAGTGAGGGGCAGCAGCCCTGAGCCCCTGGTCTCTAGATCAGGACCCCCT<br>CTGGCTGTGGCCACTGACAACTTCATCAGTGGTGTGTGAATTCCCCACAAGGGTGGCTAGGGAGCCCCTGAACCGGCACATAGCC<br>CAACAATAATCCCCCTGCTGTGTGGAGCAGAGACCCCTTCACCGCCCCCATCAGCTCCCCGGAGCCGGAGGAGGGCTGCCC<br>TTCCCCGGCCAGCAGCCCTGCCTTGGCCCGTTCAGCTTTGCCTTTCATCATGTGCCCCCCAGCTGTTGCCCGCTA<br>TGCCCTGGCTGCTGCCTGGCCCAGTCTTCTCTGCCACCGAGGCATCATGCCAAGCACCACCCAGCCTGCAGC<br>CCGCAACTTGAACTGTGAGGCGGGCACGCTCTTAGCACTGAGCGCTGACCCCCTCAGGCTTCCAACCCTGTAAGGACAG<br>TGCCTGGGGCACGCTCTTAGCACTGAGCCTGACTAGTCTTCTCCATTGGATCACCGAACTAGACACAGCATTGTGACACA<br>TGCACTTGCTGGACAATGCAGCCCAGATGGGCTGACTAGTCTTTCTCCATTGGATCACCGAACTAGACACAGCATTGTGACACA<br>TGGACAGAGACACTCCTAGCCAAAGTATATTCAATAAAACTGCCTGGCTGGACTCTTTTCTGGAAGTCATCCTCCACTCAGCG<br>CAGGACTAACACGTGCAAAGTATTTAAAAATATTCAATAAAACTGCCTGGCTGGACTCTTTTCTGGAAGTCATCCTCCACTCAGCG<br>GAGCGCCCTCCCTGACGTTCAGTTCTAGTTGTGAGCAGTTCAAGCAAGCAGCAGTCGTTCATGCCCGAGAGTGAGG<br>CCCAAGAGAATCCAGTTCTAGTTGTGAGCAGTCAAGCAAGCAGCAGCCTAGGTTAAGGATGTAGGTCACAAGGTCTTGTTCAAGTGTC<br>GAGTGCTGGAGGAATAGCAGTCTTAAAAATTGGCAGCCGTAGGTTAAGGATGTAGGTCACAAGGTCTTGTTCAAGTGTC<br>TGAAAAATAAAGCATCATGACAGT<br>GAGCT | SEQIDNO.:102<br><br>MTILPKKKPPPPDADPANEPPP<br>PGPLPPAPRRGAGVGVGGGTG<br>VGGGERDRDSGVVGARPRASPP<br>PQGPLPGPPGALHRWALAVPPG<br>AVAGPRPQQASPPPCGGPGGPG<br>GGPGDALGATTAGVGAAGVVVG<br>VGGTVGVGGCCSGPGHSKRRRQ<br>APGVGAVGGASPEREEVGAGYN<br>SEDEYEAAAARIEAMDPATVEQ<br>QEHWFEKALRDKKGFIIKQMKE<br>DGACLFRAVADQVYGDQDMHEV<br>VRKHCMDYLMKNADYFSNYVTE<br>DFTYIYINRKRKNNCHGNHIEMQ |

FIG. 30

| NucleotideSequence (5'-3') | ORFs |
|---|---|
| TGAAGAACGCTGATTACTTCTCAACTATGTCACAGAGACTTCACCACCTATATCAACCGGAAGCGGAAAAACAACTGC CATGGCAACCACATTGAAATGCAGGCTATGCAGATGATGTACAACCGTCCTGTGTGGAGTGTATCAATATAGCACAGAACC TATCAACACATTCCATGCGGATCCATCAAATGAAGATGAACCATCCGTGTCAGCTACCACCGGAATATCCACTATAATT CAGTGGTGAATCCTAACAAGGCCACTATTGGTGTGGGGCTGGCTCCGTCATTTAAGCAGGGTTTGCAGAGCAGTCC CTGATGAAGAATGCCATAAAGACATCAGAAGAGTCATGGATTGCTGAGAATCTTACCTTCAGTGGCTGAGCAGCTACAGA CTGGGAGGCCACAAATGAGGCCATAGAGGAGCAGGTGGCTCGAGAATCTTACCTTCAGTGGCTGAGGGATCAGCAGAAAC AGGCCCGCCAGGTCCGGGGACCCAGCAGCCCACGTGGTCCCCAGGCACTGTTCAGCCTGCCACATGCCAGTTCAGCCTCCAGT GGCTGGAGAATGGACTAGTCGGTCCCCAGGCACTGTTCAGCCTGCCAGCCTCCAGCACCCTGAACTGCATGCCGA GCTAGGCATTAAGCCCCCTTCCAGCAGCGGGGGTGATCGGCCACCTCTCCGTCTCTTGTGTCCCTCCTACCCGCTCTTCTGGAGTGCCGGGCCCTCATC GTCAGTTCTCAGCAGGGCGTCCCCCTCGCCCTTGGTCTGCCCTTTGGTCTGCCCTTGTGTCTGAATGATTGGGACAGATGATTGGGACAGATCGGGACAGCAGTCCCA CAGCAGATGTCCCCCTCTGCCTTTGGTCTGAATGATTGGGACGATGAGAGCCACCCCAAACTTCTTTGCTTTCTCCATCATCCCT ACAGGAATACCTAGACAGTATGAAGAAAAACAAAGTGCACAGAGAGCCACCCCAAACTTCTTTGCTTTCTCCATCATCCCT ACTGGACATCATTCCCGATCCCCACTCCTGCCTTTGATGCCACCCAAACTTCTTTGCTTTCTCCATCATCCCT TTCTTTTGTTTCCTCTTTTCTTTTTTTTCCACTTCTGCCAGTGTCTCTGCAAGTCGCTAAGAGGCCCACAGACAGATCAGCATTCCACAGGGGACTCT GCCACCACATTGGTCTCTGCAAGTCGCTAAGAGGCCCACAGACAGATCAGCATTCCACAGGGGACTCT GGAAAGGTGCGGAAGTAGGCAAGAGGCCCACAGACAGATCAGCATTCCACAGGGGACTCT AGACAAGGAAGTCTTCTGCTCACCCTTCCTTAAAGATCAGATAAACTTGTCATCCCTTCCCAGCAATGATGACAGGAAA ATGGAAGTGGCAAGTTTTCCTTCTAGTATCCGAAGAATCTGAGCCTTCAATGTAAAATTTTCTTAATTGCT TTATTTCACAAAAAAAAAAAAAAAA SEQIDNO.10 | AMAEMYNRPVEVYQYSTEPINT FHGIHQNEDEPIRVSYHRNIHY NSVVNPNKATIGVGLGLPSF KPGFAEQSLMKNAIKTSEESWI EQQMLEDKKRATDWEATNEAIE EQVARESYLQWLRDQEKQARQV RGPSQPRKASATCSSATAAASS GLEEWTSRSPRQRSSASSPEHP ELHAELGIKPPSPGTVLALAKP PSPCAPGTSSQPSAGGDRATSP LVSLYPALECRALIQQMSPSAF GLNDWDDEILASVLAVSQQEY LDSMKKNKVHREPPPDKS |
| ATTTTATATGTGAGGCTTCAGTTGGTGTTGATAGAAGTTGCCCTCGACTGTGCAAATTGACATAACTATCAGGGGCAG TTGGGCATAGCTCCGCCAGCAGAGCCTGCAGTGAAGATGCAGCTCATGTGGAGTGTGGCAGCACGGA CCGACATCAGCATCACTCCTCCACAGAAGATGCAGCTCATGTGGAGTGTAAGGTCAAAAAGGTCTG CAGAGACAAGAAGTCTTCACCTAGAGCAACATCTTTGCAAGTAAGGACCTTGATAGATTGAGGAATCAT GTGAAAAAGACAAGGCCTGATGGCAGGCGGGCACAGGCAGTAGCATTGGTAGATCGGTGGCGAGGCT GCCTTAATGTATATTAAACGATGCTCTGTGTGTCTTCCCAAACACAAGCCTGTCTTGACCAGCGTGCTTCGTATGTGCTGCTCCACGTTCCAGTCACC AGTCCGTGAGTAGTCCTTCCTTTGTATCACACCAGTGTTTTAAAGTTGTGTTCGTATGCTGCTCCACGTTCCAGTCACC TTCCATGCCAGGGACTGCTGCCGTGTCAGCTGCCGTGCAAGCCGGGAGCGCCTTCCCGCCATCAGTAGTTACTCAGTGTCTGGAACTCTAATGGCAATAACTCTAAATGCATAATATGCATATGTGGGA AAATGACCCCAGATGCGGAAATACAGGTTTACAGCCAGATGTGGGTGATAGCCCTTCAGTGATAGCCCTTCTCTGTCCCTTCACT GAGGGGAAAGTGGAAATTGGAAATACAGGTTTACAGCCAGATGTGGGTGATAGCCCTTCAGTGATAGCCCTTCTCTGTCCCTTCACT GACCTAGAAGGATTTGAGCTGCTGCAGCTTTAGACAGAAAATGTCCACATTGCTGACTGTGGCCATAAATATGCTTT SEQIDNO.:103 | FICEASVGVDRSCPLTVQIDIT IRGQLGLAPPSRACTVKMQLMV LAVECGSTDRQISTPPQLRQPS PAATQLIVSAKRSAETRSLHLE QHLGTSLQVRTLID |

Fig. 31

| NucleotideSequence (5'-3') | ORFs |
|---|---|
| AGTACTGCTTGCTGATGTATAAATCTGTAATAGTACTATATGTAATTATTTCTTTTGACTTTATTCAAA ATGTATATTTTCTGATTATTATCATGAGCTATAAAGCAAAAAGATCAATATCTGATATTCTCCAAATAATAAATTTCA AGATTCATTGAAAAAAAAAAAAAA | |
| SEQIDNO.11 | SEQIDNO.:104 |
| CGACAAGAGGTAATCCTCCAGGCTCGTGATAGCACAGTGTTATCACAGATAACAGTAAGATGGCTCCTGTCCTCAGTGAA GTAACTTAGAAACCATCACTCAGAGCAAGTCTTCTGCGAGGACGCTGGGCGACCTCGTCCGCAAGCTCGGGGAGAAGATC CTTCCTGAGATCATCCCCATCCTGAGAAGGACTAAGTCGCAGAAGAGCGACGAGAGTCCCTTGTGCACGGCGTGTGCATCGGGCT CAGCGAGATCATGAAGTCCACCAGCCGTGACGTGCTCTTCTCTGAGTCCTGTGCCACGGCCAAGGAAGGCGC TGTGTGATCCCCTGAGGAGGTCCGGAGGCCAGCCAAGACCTTTGAGCAGCTGTCGAATTTGCCTGACGGTCTGAAGCA TTGGAGGACATCTCCCGTTCCTACTGAAGCGGTGGTGCCCTATCGGTGCCCAAGCTGACACAGCTGATCTCTCTCTCTCCAACGTCATGTTGAGAGGCGAGATGGCCAACTGTCAGGCTGTGTTGGAAGCTCTCCAAGCCCTAAGCCCAAGCTGACACTG AAGGAGAAGCTTGGGACTCCAGACGAGCCAGCTCCAGCTCGTGTTTGGAAGATCATCGAGAGATTCTGGAAAATCTCCAATCTCTCAGGGATGGGCCCAGCAGATCAGGGATCTGTGGAGGCAGGCGGCTGATCAGCTGTTCACAATCGCGCCTCTG ATCCGCTCTTCAATGACTCAGCCCTGGCTCTCTGTCCCTGTTCCTCTCCAGTGCCCTGATGAACTCCACAGACTGGAAATTCCCGTTTTCAAGACCAGGAAATCCGCTCCATCCTCCAGTGGCGTCAGCTTACAGCTGACCTTCCATCCAGCTCCCTCCCTCGGTGGGAAGGGAGTAACTTCATCCGCCCAGAGCTGACTGGACAGGGACAGCCGGCTTGGGCAACCACCTTCACCAAAGCCCTTGCAGTGGTCCCTGAGGGCCGCTCTGGGTGATCGGGCGTGAGGCTATAGCCTCGCCAAAGATCCGAAGCTCCCAGCGACAGCCTGTGCAGGCAGATACAGCAATGACTTCGAGGATTCGAGGATTCGAGCATGGCTTCCTCATGAAGTTCTACATGTGACATCACCACTCAGCTCGGAGCTCATGGAGCCAGTGCCCTCCCCATCGCCATGAGTGGGATGCTGCATTGGCAGGCAGATACAGCAATGACTTCGAGGATTCGAGGATTCGAGCATGGCTTCCTCATGAAGTTCTACATGTGACATCACCACTCAGCTCGGAGCTCATGGAGCCAGTGCCCTCCCCATCGCCATGAGTGGGATGCTGCATTGGCAGGCAGATACAGCAATGACTTCGAGGATTCGAGGATTCGAGCATGGCTTCCTCATGAAGTTCTACATGTGACATCACCACTCAGCTCGGAGCTCATGGAGCCAGTGCCCTCCCCATCGCCATGAGTGGGATGCTGCATTGGCAGGCAGATACAGCAATGACTTCGAGGATTCGAGGATTCGAGCATGGCTTCCTCATGAAGTTCTACATGTGACATCACCACTCAGCTCGGAGCTCATGGAGCCAGTGCCCTCCCCATCGCCATGAGTGGGATGCTGCATTGGCAGGCAGATACAG | MKSTSRDAVLFFSESLVPTARK ALCDPLEEVREAAAKTFEQLHS TIGHQALEDILPFLLKQLDDEE VSEFALDGLKQVMAVKSRVVLP YLVPKLTTPPVNTRVLAFLSSV AGDALTRHIGVILPAVMLALKE KLGTPDEQLEMANCQAVILSVE DDTGHRIIIEDLLEATRSPEVG MRQAAAIILNMYCSRSKADYSS HLRSLVSGLIRLFNDSSPVVLE ESWDALNAITKKLDAGNQLALI EELHKEIRFIGNECKGEHVPGF CLPKRGVTSILPVLRBGVLTGS PEQKEEAAKGLGLVIRLTSADA LRPSVVSITGPLIRILGTGSTG L |

Fig. 32

| NucleotideSequence (5'-3') | ORFs |
|---|---|
| SEQIDNO.12<br><br>GAAGACCCCGCAGAGAGCACGTTGTTCTCGGCCTCTCCCGAGCTAGGCCAGCCATGGCGGCGGTAAAGACCCTAAATCC<br>GAAGGCCGAGGTGGCCCGGGCCCAGGCAGCGGCCCTGGCCGTGAACATCAGCGCGCGGGCCTGCAGGATGTTCTGAGGA<br>CAACTTGGGGCCTAAGGGCCACCATGAAATGCAAATTCAACACCCACGCCTTGTATCTGGTGCTGGAGACATCAAACTTACTAAAGATGGCAATGTG<br>CTGCTTCATGAAATGCAAATTCAACACCCACGCCTTGTATCTGGTGCTTTGATAGCAAAAGTGGCTACAGCCCAGATGCAGATACTGG<br>CGATGGCACTACATCCAATGTCCTCATCATCGGGGAGGTGCTCAAACAGGCGGACCTGTACATTTCTGAAGTCTTCACC<br>CAAGAATAATAACTGAAGGTTTTGAAGCGGCAAAAGAAAGGCACTCCAATTTCTGAACAAGTCAAAGTAAGCAAAGAG<br>ATGCAGAGAGAAACACTCATCGATGTGGCCAGACATCTCGCGACTAAAGTTCATGCCTTCTGAACTTGCAGATGTCTTGAC<br>AGAGGCTGTAGTGGACTCCATCTTGGCCATTCGAAGATACAAGCTTAATCAGAGGCCTTGTTTTGGATCATGGAGCTCGGCATCCTGATATGAAG<br>TGAAGCATAAATCTGAGACAGATACAAGCTTAATCAGAGGCCTTGTTTTGGATCATGGAGCTCGGCATCCTGATATGAAG<br>AAGAGTGGAAAATGCTACATCCTCACGTGCAACTGTCTTAGAGTATGAGAAAACAGAAGTGAATTCTGGTTTTT<br>TTACAAGAGTGCAGAAGAGAGAAGTCTGGTGACTCAGATAAGGATTTGTCGTTATTAATCAAAAGGGATTGACCCCTTTCCTTA<br>AGCTGAAAAAGAAAGTCTGGTGACTCAGATAAGGATTTGTCGTTATTAATCAAAAGGGATTGACCCCTTTCCTTA<br>GATGCCCTTGCGAAAGAAGGATCTAGCCTCGCAGAGACATGAGAGACATGCAGGAGAGGCTGACACTTGCTGTGTGG<br>TGGGATAGCTCCTGAATTCCTTATTGAAGTGTAACAATCCCCGTTCGCTGACTGGTTAAAGACCAAATAAGCAC<br>GTGAGGAAGTTCACCTTATTGAAGTGTAACAATCCCCGTTCTGCTGACTGGTTAAAGACCAAATAAGCAC<br>ACACTGACTCAAATCAAGGATGCAATAAGAGATGGCTTGAGGGCTGTCAAAAATGCTATTGATGATGGCTGTGTCCC<br>AGGTGCGGGTCAGTAGAAGTGGCACTGGCAGAAGTCTGATTAAATACAAGCCCAGTGTGAAGGGCCAGGGCGCAGCTTG<br>GAGTCCAGGCATTGCAGATGCCTTGCTCATCATTCCCAAGGTTCTTGCCCAAATCTGGTTTTGACCTTGACGAAACA<br>TTAGTTAAAGTTCAAGCTGAGATCGAACATTCAGAATCGGGCCAGCTGTGTGGATCGTTAGGGTGCACAGGTGAGCCGATGGTGGC<br>CGCAGAGATGGGGTGTGTGGGATAACTACTGTGGAAGCAGCTGCTACACTCCTGTGAGGGTTGAGGCCTGTCATCGAAGAAGCAGGTTGAGGGGTTGAGGGGTTGATGCCACCACATTC<br>TCCTGGTCGACCGAGATCATGCGAGCTTCAAGCTTGTCCAAGTCGAGCTTCAAGCTTGTCCAAGTCTGATTTGGAAAAAATTTTCTCTTCCTGAGTATCTGAAGACTCAAAGCAGTCTT<br>GGGAATGGTTATTTTGTCCAAGCTTGTAAATTATACTGTAAAAATTTTATTTTTGCCTTGAGTATCTGAAGACTCAAAGCAGTCTT<br>TTTGACACCTATTCAAATTATACTGTAAAAATTTTATTTTTGCCTTGAGTATCTGAAGACTCAAAGCAGTCTT | SEQIDNO.:105<br><br>MAAVKTLNPKAEVARAQAALAV<br>NISAARGLQDVLRTNLGPKGTM<br>KMLVSGAGDIKLTKDGNVLIHE<br>MQIQHPTASLIAKVATAQDDIT<br>GDGTTSNVLIIGELLKQADLYI<br>SEGLHPRIITEGFEAAKEKALQ<br>FLEQVKVSKEMDRETLIDVARI<br>SLRTKVHAELADVLTRAVVDSI<br>LAIRKKDEPIDLFMVEIMEMKH<br>KSETDTSLIRGLVLDHGARHPD<br>MKKRVENAYILTCNVSLEYEKI<br>EVNSGFFYKSAEERBKLVKAER<br>KPIEDRVKKIIELKKKVCGDSD<br>KGFVVINQKGIDPFSLDALAKE<br>GIVALRAKRRNMERLTLACGG<br>IALNSFDDLNPDCLGHAGLV<br>YEYTLGEEKFTFIEKCNNPRSV<br>TLLVKGPNKHTLTQIKDAIRDG<br>LRAVKNAIDDGCVVPGAGAVEV<br>ALAEALIKYKPSVKGRAQLGVQ<br>AFADALLIIPKVLAQNSGFDLQ<br>BTLVKVQAEHSESGQLVGVDLS<br>TGEPMVAAEMGVWDNYCVKKQL |

FIG. 33

| NucleotideSequence (5'-3') | ORFs |
|---|---|
| TTTCAACCCACTGAACAGATGTTTTAGCTACACCGATACAAAATTACATAATAAGATAAGCATGTTGTCTACCCTGT TCCATAAGTGTCTTCTTGAAAGTTGTAATGGTTTTCTCCTAAATAAGCATGTGACACATGCCTGTAAGCCTAGCCCTT TGGAAAATAGTCCGGAATTTCTATGCCAACTCAGGCTACAGGAGACCCCAGGTGCGAAAGAATAATTGTGTGATGTATT TGAAATTATCCAGCCAACTCCCTGTTAAACATGTAAGATCCTTGCCAGTGTAAAACATCTGGGTAATTTATGGGTTGC ATAATGTCTAATAAATACTTAAAAGAGTG | LHSCTVIATNILLVDEIMRAGM SSLKG |
| SEQIDNO.13 | SEQIDNO..:106 |
| CAACCTCCTCCAGTGGCCAGTTGTGCGCCCTGGGACTTACTACAGCTGGGCATGGCAGACTCTGCACAGTGCCAACAC TGGTATACCTGGTCACAGTGGCTGCGGCTTCCTGGGGAACATATTGTTCGGATGCTGCTGGAACGGAGCCCAGGCTC CGGGAGCTGGCTGTCTTTGACCTGCACCTGAGTTCTTGGCTGGCAGGAGCTGAAAGCAGGCCTGTGCAGTGACTGCCAT CCAGGGGGATGTGACTCAGGCCCATGAGTGGCAGCAGCCATGTCGATCATCCATACAGCTGGGTTGG TGGATGTGTTTGGGAAGGCCAGTCCAAAGACCATCCACAAAGTCAACGTGCAGGGCACACAGAATGTGATTGATGCTGT GTGCAGACTGGCACTCAGTACCTGGTCTACACGAGCAGCATGGAAGTGGTGGGCCACACTCAAGGGCCACCCTTCTA CAGGTGAGCTCAGCCCCACTTAATCTTAGAGCCCATTCCCTCCAGCAGTCAGTAAAGCCCTTGCGACCCACAGTGGTCAT CCAATGAAGATACCCCATATGAGGAAGGTCAATGGAGGGCTACCCTGGTGACATGCCCCTGCACCCACGGGGCATTTATGGTGAAGTCAT CAGTCATGAGAGAGACTTCATACTACCAGGGACTCGCGTTTGGAGGCTCTTATTCGGGCCGTCCAGCTTCTGTGAGCA CGGTCGGGCTCTATGTTGGTAAGGACAGGAGGACAGCAGGGCTCGAGGAGTGGCTCGAGGAGTGGCAGAGTCACGCGTACG CCTGGCTCCACGCGAGCTCAGGCAGATAAGAACATGGCGTAGTTATGATGAGCAACAGAGGAGCGAACAGTCTCCAGAGAAGGGAGAA CAGTTGGGAGGGCTGACATAAGAGCTAGTGGCCAAGGAGAGTGGGCCGCCCAGCTTCTCTCCCTCCCCCCTGCTG AGCATCTACACGAGCAGTGGATCCAAGTAGAGTTGCTTGATGCACATACTGGTGGCCCGGAGCTGAGCAGTCAGCAGTGTA ATTAATCAGACAGTGGCACATGTTCTTGATGCACATACTGGTGGCCCGGAGCTGAGCAGCGGCTGAGCAGGCGGGCTCGG GCAGCAAATGTTGCTTGATGCACATACTTATAAAGCTCACCTTATAAAGCTGAGTTTCTGAGTCCCTGCTCTTGACTGA TTTCTGCTATGATAAGTCACCTGCTGCCCTACTGCTGCTCAGTGAGTGTCTGTGCAGTGGCTGCTCCGC TAGGCGCCCCACCACTGCTGCTACACCCCTGCTAGAATCCCGACACCCACCTTTACTGTCAGTACCAACAA CCACTGGTCTGTACAAGCCATTTGGCTACAAGCCCCTCTTCTCATGGGAAGAGCAGGACCCGACCATTCAGTGGGTGCAGGCGA GGCACAGCCGGCATTTCAGCTCGGTGAGTGGCTGCCTTTGAGCAGCCCTGGCACATACTCAGTTCCGTGAGCCCCAAAT TGGAGGGTTCAGCTCGGTGATGGCAGCCAGGGGCAGGGCTGCCTTTGAAGATGAAGACTCTGCTCCAGTTCCGTGCCACATCATGACTCCGTGATGTGGACCCTGCCA CATCTTAACTACACAGATCCAGGCCTGACTCCAGGTAGTTGCAGGTAGTTGGCAAAACTGATTTCTTGCTCTGTGGTCTCCATTTTGAATGGTCTCACCTTCTCAGCTACCTCTTCAGCTACCTCTCCATTTCAGACCTGCTC TTTGGTGCCAACTGCCCTGTCTCCAGGCCTGCCAGGCCTGCCAGTATGTCCAGAGATCTTACGCTGCTGTCTGCTGTCCGTGCTTACGCGTCCAGTCCAGAGATCTTACGCTGCTGCTGCTGTCCGTGCTTAATAGTTTCACCATTTTTAAGTGGTTATATGTGATCTCTTTTAAGTGTATCCTCTTTAGACATTTATCTTTTAAT | MADSAQVPTLVYLVTGGCGFLG EHIVRMLLEREPRLRELRVFDL HLSSWLEELKAGPVQVTAIQGD VTQAHEVAAAMSGSHVIHTAG LVDVFGKASPKTIHKVNVQGTQ NVIDACVQTGTQYLVYTSSMEV VGENIKGHPFYR |

Fig. 34

| NucleotideSequence (5'-3') | ORFs |
|---|---|
| TTGCTTTAAAGAAATCTGAAGAATCAATGATTTCCATGTCTTGCCTCTCCTAACAAATTCACCTATGACATTGTTAGC TTCCTCCCCTAGGATGCCAACCTGTATCTGGCCAAGCCTAGAATAAAATCCTTTCCAAAAAAAAAAAAAA | |
| SEQIDNO.14 | SEQIDNO.:107 |
| CCAAGATGGCGGCGACAGCAGCCGTGTCTTGGTGTCCTCCGGCCGCTTGGGCTGGAGGCTCCTGCAGCTGCGGCTGCGCCTGCCC GTGGCCCGCTGCCGACCAGCTCTGTGCCACTGCGTCGTGGCCCGAGTTTCCGTCCACCCCAGGTACACAG GCAGCCTCCCCACTCTCTCTCCAGCAGCATTCTGAGACACAGGGGCCCGAGTTTCCGTCCACCCCAGGTACACAG ACCAGAGTGGAGAGGAGGAGACTATGAGGCAGCAGTACACAGCAGCCCAGTCCTTGGGTCTCTCCAGCGAGCAGCCAGCAT GTGCCTGCCCATGGCTGGACTGCAGAGCTGATTCTTCACTTTGTGACCCAGTGCAATGCTCGCCAGCAGTGCTGAAGAGG GTTGGGAGCGATGGCAGTGAAGCTGGGCCAGGCAGGAAGACAGAACCAGTTCCTGAGGGATGCAGTGGAAACCAGACTG AGCAGAAGCTGGTGCAACTCCCTACATTGAGCACTGGCCCGGACCATCCTCCTGACCATCCCTCCTCCACAACATCCCACCAGCCT GAACTTGCTCACCAGCATGGTGGATGACATTGAGGCCCTGGAGCATCCACCAGTTAACTGGTACACCCGCC GTGCAGTGCTGGCTGGCATCTGGCAAAACCGGATTAATGATGACAACAGAGCTGTGATGACATGGGCCACAGAGGCACT CGCTTCCTGGAAAACTGATGGGTGCAGCGACTGATAGATGAAGGCTTTGACAAGATGAAGGCTCTAAACCAGCTGCTAAACCAGCTGAAGTCCACGGAGAGAGGAACC GGTGCAAGGACTGATGGGTGCAGCGACTGATAGATGAAGGCTTTGACAAGATGTGCCACCCATTGAACAGGATGTTAATGAGAACA GTGTGCTGGAGGAGCAGCAGTAGATCGTATGAACAGCCACAAGGCTGGAAATCACAACAAGGCTCTGCGCCGTTCTGAGCGTGTGTTTGATCATGTCTGAACTGG GCCACTTCTTCAGTTCCAGTTCCAGCCTGGCCTCCAGCGATGTGCAGAGGCTCGATCTGGTGTTGATCATGTCTGAGGCT CACATCCAAGGTTTCAAACCACACAAACCTTGGCACTGAGTAACTCGTCGTATCAGAGACTGCTACAGCAAGATTGAG AGAATGCTCTCTAGGAGCTGGCATGGTGACCTATGGTAGAGAATTACAAGCTCGTCTTGAGCTAGCACTACAGAGTGTGATCCTGTCAAATCCCTGA AGATCAGAGGCAGGCTTGTCTTTGTAGAGAATTACAAGCTCGTCTTGAGCTAGCACTACAGAGTGTGATCCTGTCAAATCCCTGA GAAATATTCTTAGGGCTCCACAACCAAGGTCCGGAGCCAACATAGTGGAGCTCTTCCCCAGCACAGGGCAGACAGTG CTCACAAACATTTGCCACTGCCATTGCCCTCTGGATCCCTCAGAAAGTCTGCCTCCCTAGGAAAGCTGCCTTTTTGACAG TCGTGCTGAGCCTGAGCCTGGCACTCACAGACCATGCACCTTCAGGATGCATTAGTGTATTAGAATCTGTAAAAATAAAT ATGTTTGAAACAAAACAAAAAAAAAAAAAAAA | MAATAAVSGVLGRLGWRLLQLR CLPVARCRPALVPRAPHTAVGF RSSEEQKQQPPHSSQQHSETQ GPEFSRPPPRYTDQSGEEEDY ESEEQLQHRILTAALEPVPAHG WTAEAIAEGAQSLGLSSAAASM PGSDGSELILHFVTQCNARLNQ VLEEEQKLVQLGQAEKRKTDQF LRDAVETRLRMLIPYIEHWPRA LSILLLPHNIPPSLNLLTSMVD DMWHYAGDQSTDFNWYTRRAVL AGIYNTTELVMMQDSSPDFEDT WRFLENRINDAMNMGHTAKQVK STGEALVQGLMGAAVTLKNLIG LNQRR |
| SEQIDNO.15 | SEQIDNO.:108 |
| CCGGGGCAGGTCTAGAATTCAGCGGCCGCTGAATTCTATCCAGCGGTCGGTGCCTCGCCGCGTGTGTCCCGGTGCC GGGGGACCTGTGTCAGTTCAGCGGCTTCTGAGATCACACAGCTGCCAGGCCGTGCCAGGCCAATTCTTGGCTT TGATTTTTATTATTACTATTATTTTGCGTTCAGCTTTCGGGAAACCCTCGTGATGTTGTAGGATAAAGGAAATGACA CTTTGAGGAACTGGAGAGAACATACACGCGTTGGGTTTGAAGAGAGGAAACCGTCTCCGCTTCCTTAGCTTGCTCCCTCT | MDMFPLITWVFLALYFSGHEVRS QDDPPCGGRPNSKDAGYITSPG YPQDYPSHQNCEWIVYAPEPNQ KIVLNFNPHFELEKHDCKYDFI |

| NucleotideSequence (5'-3') | ORFs |
|---|---|
| SEQIDNO.16<br>TGGCAAAGAAAGAGCTGGCTGTACACCCTAGATCCCATTCTGATCACCATCATCGCCATGAGCTCGCTGGGGTCCTGC<br>TGGGGGCCACCTGTGCGGGCCCTCCTCCTTTACTGCACCTGCTCCTGTTCGGTCTGAGTTCGAGGAGCTGCACACTG<br>GAGAACTACAACTTGAGCTCTACAAGGCCTCAAGACACAAGGTCAATCATCAGAAGTGCTGCTCGAGGCATG<br>ACCGATTGTCTCGATCGCTTCTGCGCGTTCATTCTGACGAGAGGGCTAGCGAAGATTACAGTTTTGTTTGT<br>TTGTTTTCCCTTGGAAACTGAAGGGAGATGCAGCTCGGCTAGAACATGAAGCAGTCATCGGATCAAGAGCATAG<br>GGCCAGTCTAGGAGGAGAGATGCAGCTCGGCTAGAACATCGAGTTCGCCTGCCTGCTAAAATCCAGCTGCCTCAACCTTAC<br>GAACCCGGCCCCGAATTCCGGCTGTCAACATGGATGACACAAGCATACATGTCCTTCTAATTAATGATCACTATAATCTCCTGTGTG<br>GACTCTGTTGCGTGGTGCTTTGCTTGCTAGACATGGAAACATTTGAAACCATTTGCATTGTGAGTGCAGATCCATGTGGGGCTAGTGCAGCAATGAAACA<br>CAGAATTCAGAAATAGACCTGTGTCTTTTATGGGAAATACAGATAAAAATGCCACTGGATGCTGTGAAACATGAAACACACAAATTCAAGAATG<br>TTCCCAACACAGTGTACACTTGCAACCTTGTTTTGGATTTCTCATACACCAAGACTGTGAAACACCAAGAATTCAAGAATG<br>TGTTCAGTGGGTATGAGTGATATGTATGTGTATGTGTATGTGTGTATGTGTTGTGTGTGTGTGTATGTGTGTGTGTGTTAAGT<br>TATGTATGTATGTGTATGCATTTGTCTATATGTGTGTGTTAGTGCTTGTGTGTATAAGTACCTGTGTTGTTGTGCTTGTGTATGTG<br>CATGTATGTGTATGTGTGTTTGTCTGTCTCTTTGATATGTGTTGTTTGCTTGTGTAAATAGTACCGGTGTGTATATGT<br>CTGTGTGTGTGTGTATGTGTTATAGAAAGACAGTCTGAGATGTCTTCCTCAATACCTCCACTTATATCTTGGATAGACAAAAG<br>GTTAGTATGTTTTATAGAAGAAGACAGTCTGAGATGTCTTCCTCAATACCTCCACTTATATCTTGGATAGACAAAAG<br>TAATGACAAAAAATTGCTGGTGTGTATGGAAAGGGGACACATATCCAGATGGATGAGAAGTGTAAACTGTGCAGTC<br>ACTGTGGACATCAATATGCAGTTCTTCACAAATGTAGATATAAAGCTACTATAGTTATACCC | KEKSWLYTLDPILITIIAMSSL<br>GVLLGATCAGLLLYCTCSYSGL<br>SSRSCTTLENYNFELYDGLKHK<br>VKINHQKCCSEA |
| SEQIDNO.:16<br>GGGGAGGCGCGGCGGCAGAGCAGGGGCCCGGCCAGGCAGCGCTGCGCGGGCACGAGTTGGCCAGCAA<br>GCTGAGCCGGAGGCTGCAGATGGAGGGCGAAGGCGGAGGCGGACGGCAGCAGCCGTCAACGGGCCGGCGGCGG<br>CGGCGGCCGAGGCTCCCGACGAGACTTCGGCGGACGGCAGCCGCGACGACGAGCTGAGCGCCAAGCTGCTGCGCGC<br>GCGGACCTCAACCAGGGCATCGGCGAGCCACAGTCGCCCAGCCGGTCTTCAACCCTACACCGAGTTCAAGGAGTT<br>CTCCAGGAAGCAGATCAAAGACATGGAGAAGATGTTCAAGCAGTATGATGCCGGATGGCTTCATCGACCTGATGG<br>AGCTGAAACTCATGATGGAGAAGCTTGGGCTCCAAGGCACACTTCGGCCTCAAGCAGAGTATGATCCAGGACGAG<br>GATTCGACAGCAAACTCAGCTTCGCCCGCTGTCCGAGATCGATGTCTCCACAGAGATCAAAGCTGAGAAGGAAGACAGGAG<br>CGGCTTGCACGTTCACCGTCCCCCGCTGTCCGAGATCGATGTCTCCACAGAGATCAAAGCTGAGAAGGAAGACAGGCT<br>CCAAGGTACAGGCCATCAACGTTCGGCGAAAGCGGGCTTTAAGGAGCTGCAGTCCACGTTCAAGTTGCAGTTCAAGTAGTTATACCC<br>GAGGAGGTGAAGCAGCGGGAAAGCGGGCTTTAAGGAGCTGCAGTCCACGTTCAAGTTGCAGTTCAAGTAGAGCAGGCT | SEQIDNO.:109<br>MATDELASKLSRRLQMEGRGB<br>ATEQPGLNGAAAAAAAPDET<br>AQALGSADDELSAKLLRRADLN<br>QGIGEPQSPSRRVFNPYTEFKE<br>FSRKQIKDMEKMFKQYDAGRDG<br>FIDLMELKIMMEKLGAPQTHIG<br>LKSMIQFVDEDFDSKLSFREFL<br>LIFRKAAAGELQEDSGLHVLAR<br>LSEIDVSTEGVKGAKNFFEAKV<br>QAINVSSRFEEIKAEQEERKK |

FIG. 37

| NucleotideSequence (5'-3') | ORFs |
|---|---|
| CCCTGCCCCGTGTGCGGTCTGGGGCACGGGTGGGTACAGGGATCTGTGGGAGACTAGTCCTGCTCTCTGT GCCCGGACCACTACTAAAAACCGCAAACGATATGTGACCCGCAGCCCGATCTCATTCAGGAGTCTCCTGCTGCGTTGTCCCTGCCC TGCCCTCTCCTGCGGTTCATGCGGCTGTGATGCCAGCCAGCATCCTCTGCCACCCTGCCCTTGGTGTCTTGTTCTCTG GCCACTTGCTGCCTGCTCAGCCAACTTCACGCCCTAGCCCATTCAGCCCATTCAGCCCTTGTCAGCCCTACTTTCTCCACCCACC CAACTCCCTTAACTATAGGCCCGCCCTGCCCATGTCCAGAGAGTGAGACTCTTCTATTAGTGAGGAGATCCA GGCCCCATCTCTGATGGAAGTGGAGACTGTTCAATGGGGCCCAGCCAGGGTGAAGGCTGTGAATCTGCTCACTCACAGGCT GGCCCTAGCACTCTAAGCTGATTTGGGGATGTGACTGATAGGGTTCCGAGGGAGGCAGGGCAGAAATGTCACCCTCTGACGGCCT ACACTCTGCCAGGCATGCTCAGGGGTCCAAGGGCTGAGGGTCCAAGGGGCTGTGAGAGAGGGGTGGGGTCCCTAAGGATTGGCCTTTCAGGGTGG ACCCCCGCAGCAAGCTGAGGTCTGACTTGCCTTGACTCCCCAAGGAGAGGTTGTCACCAGCCTGCTGTTATGTGCACTGGGACTCGCATGGGGA CCTTTCACACTCTCCTTGGGTTTGTCACCAGCTGCCGTTCCTCCATGTGCTTGCTCACGTGTGTGATGCGTGCGT CTCCCAGCCACAGTGAAACCCGTGACGTCACCCAGTCTAAGTACACAATGCCCGTTATGCAAATGTTCAGCGTGTC TGCTGTGTTGTGAAGCTCGATAACTCTTTATTTACTACAATGTCCCCAGAGTCCCTGGGACCCCTGTGGGACTTGCAAAGG ACTGCTTGTGAAGCTCGATAACTCTTTATTTACTACAATCGGAGGGCCAAGCCCAGCTCCTTGCCTGTGGCCTTG TTTATTTTTCGGTCTTAGAACCTATGAAGATGTTTATACAGAATGAATATAAAAATAAATTCCATTGCAATATATAA GCTTGCGTTGCCCTCAGTACCTCCAAAATGAGATAAAATTCTATATTCTTATGTGTTGTGTTTGTTGACCTGGGAGAGCTCTGTCCCTT GGTTCCCCCTCAGTACCTCCAAAATGAGATAAAATTCTATATTCTTATGTGTTGTGTTTGTTGACCTGGGAGAGCTCTGTCCCTT TAACTAAATGAGATAGAAAAATTCTATATTCTTATGTGTTGTGTTTGTTGACCTGGGAGAGCTCTGTCCCTT CAGGATGAGGTCGCTGGATCTGGGCCGTCACATCGGGTCGATCAGGAGTCTGGGAGGAAGGCACTCTGCTGGGAAGAGTGGACAGGAT AGCAATCTACAAACACTCCTGATCTAAGCACTACCTGTATTAAACTCATTTCATCCTTAAAGG | QAEEVKQRKAAFKELQSTFK |
| SEQIDNO.17 | SEQIDNO.:110 |
| CCCACGCGTCCGGCCAGCAGCAGCAGAGTCAGAAGAAGGCGGTCCGATCGTGCTGTGCTCGAGGTGGCTTCTGAGCGTTCC TGTCCCTTCGCCCCGCTACCTTCCTTGGGTTCCCACCATGCCGATGTACCAGGAAACATTCCGAGCCTTCTTTGCAAGCCCTT GAATCTCGCCAAGATCAGAATGTTGAAAACGCTTGTATGAGTTGAAGGCAGCAGCCCACACAGTTGAAATGATTCACAC CCCAGATGCAAGACTTGGACGTAACCAACATCCTGAAGCTGATGAGCCCACAACTTTAGCCACAACACATTGGACTTGA ATTCCGTGCTTGGAAAGACTATGGGCGCTGAAAAGACATTGTGATCAAGGATTATGGGCGCTGCACACACTGTCCCCTG CTTGTGCTGCAGGCTGTCTTCGGTGAAACGCTACAGGGTCCCTGCTACAAGCAGCAGCTAGCAATCGTCTGTCAAGAATGTGCC CGAGAATCTTGTCAAGTGCTCCGGGAGCAGGCAGGAAGCAGTGAAGCTTCACTCAGCCTCACACTCACTCTGATTT GGAAGAATGTGCCAAGACAGACATGTGTTGGCCCAAGAAGATGAAGCGTGAATGCCTCACCCTCATCGAATGCCATGTT TTCCGTTCTTCTCTGTTTGGCCAGAAGGCACCAGCCAGATGAAGCAGCATAATGCTCGTCACCCTGTTTCCGCTCAGACACAGCCCATGTT TCAGCTTCGAGAAGGCAGCAGTGGGCAGTGAAGACATAAAGAAAAGCGGCCCCGCTCTGCTGCTGCTCCAGCGACTGGGAGCAGTGCTGGGC TGGTTTGAAATGAGCTGAGTCACTGTGGCAGATGTGGTCGTCAGTGTGGTCGTCTGTCAGACTGGGGCAGCA | MPMYQETSEPSLQALESRQDDI LKRLYELKAAVDGLSKMIHTPD ADLDVTNILQADEPTTLATNTL DINSVLGKDYGALKDIVINANP ASPPLSLLVLHRLLCERYRVLS TVHTHSSVKNVPENLVKCFGEQ ARKQSRHEYQLGFTLIWKNVPK TQMKFSVQIMCPIBGEGNIARF LFSLFGQKHNAVTLTLIDSWVD IAMPQLREGSSKEKAAVFRSMN SALGRSPWLVGNELIVADVVLW |

FIG. 3B

| NucleotideSequence (5'-3') | ORFs |
|---|---|
| CCCACCAATGTGCAGCGGTGGCTTAAGTCCTGTGAAACCTGGCCCCCTTCAGCACTGCCCCTTCAGCTCCTTAAGTGAAT<br>TCGAGCAGCTTGTCTTGCAGGGTTCAACAGAAGAATGGTACGGCTTCCAGTCTGTTGTCAGAAAGGACTTGTCCAATAA<br>AGTACCATATCATCTAAAAAAAAAAAAAAAAAAA | SVLQQTGGSSGAAPTNVQRWLK<br>SCENLAPFSTALQLLK |
| SEQIDNO.18 | SEQIDNO.:111 |
| TTCGGAGAGGGCCCGCTATAAAGGCCTGTTGTTTGCTCAGGTCCGATGTTCGCGAGCGTGCCCGAGCGTGCTGTTTGCTCTCGTGT<br>GGGGAGGCTGGGGTGCAGAATTTCTGAAGTGAAAGGAGGAGTCTGCACCTGTCTCTGTGTGGTAGATGATGAAAGATA<br>TTGACATGGGAAAAGAATATATCCCAGCCCTGGGTACAGGGACAAGAGCGTGTACCAGGCAACAC<br>AGAGACCCCGAGGAACCAGGTTCCGTGGAGAACAAGATCGTTGGAAATGCCAAGATGTCTCGAAACAGCAGCCCGAGTTGA<br>GGGGCTTTCCCTGGATATCTCTGTGCATTCTCGGAGCACCACCAAGCACTACCAAGCAGGAAAATACCACCATG<br>GTTTAAGTGTCCTGAAGCCCTTCCGGACCACTACCAAGCTGGTTCACAAGAAGGGGAGCTGTTAATGAGGATGTGTGGCCTTGTC<br>ACCTTTTCATGGCTCTCTCCTCCTGGCCCGAGTGGTTCACAAGAAGGGGAGCTGTTAATGAGGATGTGTGGCCTTGTC<br>CAAGTATGAGTCTTCTGCAAGTGAACTGCAAGTAGAGGACTGTGCCAAGAAGAGACTGTGAATGAAGTTGGGCCAGACG<br>CTGCTTCCCTGGCAGGGTTGTGTGGATCTTCTGCCGACCAGGCTCATCCTGTCCATCGTGTCCTGATGATCACGCAG<br>CTGGCTGGCTTCAGTGAGCCTTCAGTGGCCTTCCTCCTCGGCGGTCTTGGTCGGCTCGTCAGAGTCTAACCTGCAGTG<br>CAGCTTGTTGTTAGTGCTGGGCCCTTGCGGGGGGCCATTGCTCAACATTTGCTCCAACATGGGCAGCACCCACCACCTG<br>ACCGAACCCGGTGTCAGTGTCCGCTTGCGGGGGGCCATTGCTCAACATTGCTCTAACCTGCAGCCGTTGGCAGCCTGCT<br>AAATCCCTGGGTGAGCTCATCAACATTGCTCTGGGCATATCTTGGCCATCTGTCAACCTTGGGCCTTCCTGGATCAG<br>GGCTGGAGGACCGTGTTGTTCCTCTTTATCCAGAAGATGAATGAAGTTCGTGTCCACTAATTCATTAAATGTATGCCTGGGTCAAAGCGTT<br>CGGTTTTTATCCTCTTTATCCAGAAGATGAATGAAGTTCTTACCTACATTAAATTCATTAAATGTATGCCTGGGTCAAAGCGTT<br>ACAGATGACCCGTGTCCAGAAGAAATCCGAGCAGACCGAGCAAGGACTCGGATATTGGAGAAAAGCCGGTACTTTCAGAGACATCACTGTTG<br>TTCTCAGTGTGTGCAAAAATCCGAGCAGACCGAGCAAGCGATCGGATATTGGAGAAAAGCCGGTACTTTCAGAGACATCACTGTTG<br>GAGTGGCTCCTATTGTGTGGCTAGTGATCGCCAGTGGTGACGTTCCGTTCACAGGAACGTTCCGTTCCATCGACTGCG<br>GCAAGGCCTTCACAGTGGCTGTCTTCAATTCATGACTTGTTCTTTGAAAGTAACACCATTCTCAGTGAAGTCCCT<br>CTCTGAAGCATGACATCGGCTGTGAACAGATTTAAGACAGATTTTGAGAGTGTTCACATGGAAGAGGTTCACATGATAAAGAACAAACGG<br>CCAGTCCTCACATCAAGATGACAAGATAGAGATGAAAAATGCCACCTTGGCATGGGACTCCTCCACTCCAGTATACAGAACTCGCCC<br>AAGCTGACCCCCAAATGACAAAGACAAGAGGCTACCAGGGACACACCTCCTCCTGGACGGGCAAGAAGCGGCCAACACTGA<br>GCACCAGGCCGTGCTGCAGAACAGAAGGACTCGGACGAGCCGCCAGCCGGCCCAGCCGGCCCAGCCGCAACACTGA<br>GCAAGCAGATCCACACAGGGAGCCTGCGCCTGCAGAAAAACCTCTCCGTTCCAGCCTAGAAATTGAAGAGGGCAAACTG<br>GTTGGAATCTCGCGGACTGTGGGAGACCTTTGCTTAGTTGCCAGATGACTCACACATTGACTTAGGCCAGATGACGCTTTGGAGGG<br>CAGCATTGCCCTCAGTGGGACCTTTGCTTAGTTGCTCAGATCTCAATGCCCTGGATTCTCAATGCCACTCTGAGAGACAACATTC<br>TCTTTGGGAAGGAATTTGATGAAGAGAGATACAACTCAGTGCTGAATAGCTGCGCCTGACTTGGCCATTCTC<br>CCCAACAGCCACCTGACTGAGATTGGAGAGCCGAGGAGCCAACCTGAGTGGTGACAGCGCCAGAGAATCAGCCTTGCTAG | MKDIDMGKEYIIPSPGYRSDRD<br>RSAVPGQHRDPEEPRFRRTRSL<br>ECQDALETAARVEGLSLDISVH<br>SHLQILDEEHSKGKYHHGLSVL<br>KPFRTTTKHQHPVDNAGLFSYM<br>TFSWLSPLARVVHKKGELLMED<br>VWPLSKYESSDVNSRRLERLWQ<br>EELNEVGPDAASLRRVWIFCR<br>TRLLLSIVCLMITQLAGFSGPA<br>FVVKHLLEYTQATESNLQYSLL<br>LVLGLLLTEVVRSWSLALTWAL<br>NYRTGVRLRGAILTMAFKKILK<br>LKNIKEKSLGELINICSNDGQR<br>MFEAAAVGSLLAGGPVVAILGM<br>IYNVIILGPTGFLGSAVPILFY<br>PAMMFVSRLTAYFRRKCVAA<br>TDDRVQKMNEVLTYIKFIKMYA<br>WVKAFSQCVQKIREERRILEK<br>AGYFQSITVGVAPIVVIASVV<br>TFSVHMTLGFHLTAAQAFTVVT<br>VFNSMTFALKVTPFSVKSLSEA<br>SVAVDRFKSLFLMEEVHMIKNK<br>PASPHIKIEMKNATLAWDSSHS<br>SIQNSPKLTPKMKDKRATRGK<br>KEKSRQLQHTEHQAVLAEQKGH<br>LLLDSDERPSPEEEGKQIHTG<br>SLRLQRTLYNIDLEIEEGKLVG<br>ICGSVGSGKTSLVSALLGQMTL |

| Nucleotide Sequence (5'-3') | ORFs |
|---|---|
| AGCCTTGTACAGTGATGATAGAAGCATCTACATCCTGGATGACCCCCTCAGTGCCTTAGATGCCCATGTGGGCAACACATCT | LEGSIAVSGTFAYVAQQAWILN |
| TCAACAGTGCTATCCGGAAGCGCCTCAAGTCTTAAGACGGTTCTGTTTGTTACACCAGTTACAGTATCTGGTCGATTGT | ATLRDNILFGKEFDEERYNSVL |
| GATGAGGTGATCTTCATGAAGGAAGGCTGTATCACAGAGAGACACCCCCAGTTGAGATTAATTGAACTTAAATGGGATTA | NSCCLRPDLAILPNSDLTEIGE |
| CGCTACGATTTTAATAACCTGTTGCTGGAGAGAGACACTGTGGAGATTAATTGAAAAAGAAGCTACTGGTTCAC | RGANLSGGQRQRISLARALY |
| AAAAATCACAAGACAAGGGCCTAAGCAAGGTTCAGTGAACCAGGGTCAGTGAAGTCGGTGAAGTCGGTCAGCTTGTG | SDRSIYILDDPLSALDAHVGNH |
| CAGGTGGAGGAGAAAAGGCAAGGTTCGTGTGCCTTGCATCCAGGCTCTACATCCAGGCTGCAGGCTGCAGGGGCCCCTTGGC | IFNSAIRKRLKSKTVLFVTHQL |
| TTTCCTGGTCATCATGGTCCTCTTCATGCTGAATGTGGGCAGCAGAGAAGCTTCGTGAGTGAACAGAGAAGCTTCGTGAGTGACAGCCACTGGTGGCTTAGCTACTGATCA | QYLVDCDEVIFMKEGCITERGT |
| AGCAAGGAAGCGGGAACAGCACAGTGTATCAAGGGAACAGAGAAGCTTCGTGAGTGACAGCCATTGAAGGACAACCCCTTCATG | HEELMNLNGDYATIFNNLLGE |
| CAGTACTACGCCAGCATCTACGCCCTCTACCGGCTCATGGCCAGTCATGAGCTATTCCGAAGATCCTTAGAGCTTGAAAGCCATTGAAGGAGTTGTCTTCGTCAA | TPPVEINSKKEATGSQKSQDKG |
| GGGCACACTGAGAGCCTCCTCCGGCTCCATGATGAGCTATTCCGAAGATCCTTAGAGCTCCCATGAAGTTTTTGATA | PKPGSVKKEKAVKSEEGQLVQV |
| CTACCCCACAGAAGAGGATTCAACAGGTTTTCAAAGACATGGATGAAGATGCTTCAAGGCTGAG | EEKGQGSVPWSVYWYIQAAGG |
| ATGTTTATTCAGAATGTAATCCTCGTGTTCTCTTCGTGTTGGAATGATTGCTGAGCTCTCCAGGGTCTTCCTGGCCGGT | PLAFLVIMVLFMLNVGSTAPST |
| GGGCCTCTCCTCTCCTCATCCTCTTCACTTCCCACATTGTCTCCAGGTCCTCGATTCGTGAGCTAAAGCGGTTGACAATA | WWLSYWIKQGSGNSTVYQGNRS |
| TCACGCAGTTCCCTTCCCTCCCCACATCACGTCTAGCATTCAGGGCCTGAGCCACCATCCATGCCTACACAAAGGCAG | FVSDSMKDNPFMQYYASIYALS |
| GAGTTTTTACACAGGTATCAGGAGCTCCTGGATGACAACCAGGCTCCCTTTTCCTGTTCACCTGTGCAATGAGGTGGCT | MAVMLILKAIRGVVFVKGTLRA |
| GCCAGTGCGGCTGGACATCATCAGCATTCAGCATTCCGGGCCTTGATTACCAGCACTGGCCGATGATTGTCCAGGCATGGCCAGATCCC | SSRLHDELFRRILRSPMKFFDT |
| TTTCAGCCTATGCGGGGCTTGCACTTCCGTGGAGACACTCGTGCCATTCCTACGCTGTGGAGACACTTCCGTGGAGACTATTCCAGTTCACCGTCAGACTGGCATCG | TPTGRILNRFSKDMDEVDVRLP |
| GAGACAGAAGCACGGTTCACTTCCGTGGAGACACTCGTGCCATTCCTACGCTGTAATTGGACTATTCCAGTTCACCGTCAGACTGGCATCG | FQAEMFIQNVILVFFCVGMIAG |
| CAAGAACAAGGCTCCTCCCCATGACTGGGCCCCAGGAGGAGAAGTAACCTTTGAGAATGCAGAAATGAGAATACCGGAGAA | VFPWFLVAVGPLLILFSLLHIV |
| ATCTCCCTCTGCTTCCTTAAGAAAGTGTCCTTCACCATCCATGGTCCTCGTGGAGCTATCTGGAGCCTCATCAAGATTGATGAGCCACTGTCA | SRVLIRELKRLDNITQSPFL |
| GGGAAGTCCTCTTTGGGATGCCGATGCCGGGATGCCCCTGCCTGGCCGACCTCGAAGCAAACTGGCCATCATTCCTCAGGAGCCAGTGCTTGTTCAGTGGCACTGTCA | SHITSSIQGLATIHAYNKRQEP |
| CAGTGACATCGCCCTGGCCGACCCTTTCAACCAGTACACGGAAGACACCAGATCTGGAGTCAGCAGCGCACATGAAGGAATGT | LHRYQELLDDNQAPFLFTCAM |
| GATCAAACCTGGACCTACCTCTGAAACTTGAGTCTGCGTCACTGTAGAGATTCGAAGTAATGAAGAACGGGACAACTTCTCTGTTGGGAACGGCAGCTGTT | RWLAVRLDLISIALITTTGLMI |
| ATTGCCCAGCCAGTCACTACCTCCAGCAAGCCCCTGCGTCACTGTAGAGATTCGAAGTAATGAAGAACGGGACAACTTCTCTGTTGGGAACGGCAGCTGTT | VLMHGQIPSAYAGLAISYAVQL |
| GTGCATAGCAAGACCCCCTGCGTCACTGTAAGATTCTGAATTTAAGATGCCCATGCCATGGACACAGAGACAG | TGLFQFTVRLASETEARFTSVE |
| ACTTACTGATCCAGGAGACCATCCGGAAGCATTTGCCACCATGCTGACACCATGGGACACTTCCCCGTCCTTCTGTCTAATGA | RINHYIKTLSLEAPARIKNKAP |
| CTGGCCTCTGACACAGATTCTATGCCATGTTGCTGCAGAGAACAAGGTGGCTGGAGTTTGACACCATGGGACACTTCCCCGTCCTTCTGTCTAATGA | PHDWPQEGEVTFENAEMRYREN |
| CAGTTCAAGATTCTATGCCATGTTGCTGCAGAGAACAAGGTGGCTGTCAAGGGCTGAGTCGCTGTGCAAGTCCCCGTCCTTCTGTCTAATGA | LPLVLKKVSFTIKPKEKIGIVG |
| CTCTTCCTCAGAGCATTGCCATTCTCTTCCTGGTTGGGCCCCATCCTGCTCCTGCTGAAACTTCGCCTTTCCAGTTT | RTGSGKSSLGMALPRLVELSGG |
| TATCTCTCACACAACCATTCAGGATTAGCTGCGTCACTGTAAGATTCTGAATTTAAGGAAAGTCATATTTGATTATTGTATTATTCC | CIKIDGIRISDIGLADLRSKLA |
| CTATTCACTTAAATGAAATTAGTTTTTGTTCTTAAATGCACTCTATATGTAGCTATGTCTATATATAATTCGTACATAGCCTATATTTACAGTAAAATG | IIPQEPVLFSGTVRSNLDPFNQ |
| CAGTGGCCTATAATGAAGCTTTATATGTAGCTCTGCTTCCGTCTTCCTGTGTCAGCTGCTGCTGCTGCTGCTGCTTATGTTAGAGCAGTGGGCAAAGC | YTEDQIWDALERTHMKECIAQL |
| TAAGCGGCCCGGAATTCTCAGGGCTCCCAGTGTTCCATGCTTCAGGTTCCTGAGGCTGCGCCACAGGCGCGCACCAGAGTGTGCAGTTCCTG | PLKLESEVMENGDNFSVGERQL |
| CAGCCCCCACCCCAGTCTGCTCCTCCCAGTGTTCCATGCTTCAGGTTCCTGAGGCTGCGCCACAGAGTGTGCAGTTCCCTG | LCIARALLRHCKLILDEATAA |

| NucleotideSequence (5'-3') | ORFs |
|---|---|
| GCCAGCTGTTCCCAGCCCAGGGTCCACTGCTGCTGTGTTGTAGGTGGCATTTTCATTTGCTGACCCCAAGGCTCCAGAG<br>CTCAGCAACAGGGCTCAGGATGGTGGGTCCGTTCTTCCTCACTTAGTCCTCTGCAAAGTCTGCACCCACCCCTCAG<br>CAGCTCTTGCTAATCAGTGTCTCACACTGGTGTCACCCCCTTGTGCTCTGTAGAAGACCTACCTCAGGTTGCTGATTGC<br>TGTGTGGTTTGGTGCGCTCTTGCAGACCCCCTTGTGCTCTGTAGCTTGGGTGGGTGTTGCCACTGTCACC<br>AGTCGAGTGGTCAGCGTCGCATGTCGTGACCAACTAGACATTCGTGCCCTTAGCATGTTGCTAAATACCTTATAAAAG<br>CAAAAATATGAAAAAGTGAATAAAATTATTTTGATTTGT | MDTETDLLIQETIREAFADCTM<br>LTIAHRLHTVLGSDRIMVLA<br>QGQVVEFDTPSVLLSNDSSRFY<br>AMFAAAENKVAVKG |
| SEQIDNO.19 | SEQIDNO.:112 |
| CTGGAGAGGAGCGCGTCCTGACGGGACTACGTTTCCCGGCATGCGCTGAACAGCTACCGTCGTGCCCTGCTTCTCCTAGA<br>CCGCTTGCCCGGGTTCTAGAGACACCGCCCTCTAGGAGGCGGGCGGAGGAGAGTCGAGGCGGAGCTGATGGCTGCGCTGAAA<br>GCGGGGCGGGGTGCAAACTGGAGCCTTCGGGCATGCGGGCCTTTGGGCGCCATCTCTGGAGGAAGCCTCCCAGTCCGG<br>TCCTGACCTCCGGGCTCTGCCAGTCCGAACTCCGATCTCTGATGACTTATGGACCCCCAGTCTCCCGG<br>CCCAGGTGCCTCAGGCTCGAGGGGTTCCTTGCATACGGGCAGATCTGACGTTCTAGGACCGTCGGGCACGATTGAATGTG<br>GGGACTTCAGGCTCAGCTGCCAGTGGTGCAGTGCTGCTGTTGTGGGGTCTCGGGCTCTGCGGTCCGTGTTCCTGCTCCG<br>CGCAGGAGGTGCAGTGGTGCGAGCCAGTACAATTCATGCAGATGTGTGTGGAGAAGACACAGCCCCTGCTGGTCTATATCGAG<br>CACCCACTTCCTCCCGGAGCCACCCTTCTCCGGCGTGAAGTCCCCATCTCAAACGGATCAGGATTCGTAGTGGCTTCAGATGGGCT<br>ATCCTAGACCGGCCAACGCCCACGTGGTGGCTAGCAGACATTGCCACACTGAGGATTCAAACCAAGGAGCCTCCTCCACACTGCCCTC<br>CATGGTTACCACAGCTGTGGATCCCGTAGCACATTGCCACACTGAGGATTCAAACCAAGGAGCCTCCTCCACACTGCCCTC<br>GGCCGCTCTGCTGATGTCCGGCAAGGGAGTTTGTTGTTCCATGGAAGCCCCTTTGCACTGCAGAACACGATCACATC<br>TGGTATTGTCAGCTCTGCTGCCAGGGACCTCTGGGACTCCCTGGTTAACCTGGATGGGGAGGTGATTGGAGGTGAACACCATGAAGGTG<br>CAGCTATTGATTTTGGGAAATTCGTGCCATCCTTCTCAAAACAACGTGGAATACATTCAGACCGATG<br>ACAGCAGTGGAATCTCCTTTGCCATCCGTCCAGGTGGTCCTCGATGCGCGGGAAGAATCCCTTATTGAACTACAGC<br>TGGAACCAGTGGGTCCCAGCGCCGCTACATGTTCAGTGATGATGAGCTGGAGTGATGCAGCCTCCCAGCATCCTTATTGAACTACAGC<br>TCCGTGAGCCAAGCTTCCCTGATGTTCAGCATGGTGTCCTCATTCATAAAGTTATCCTGGGCTCCCCGCACACAGGGCT<br>GGTTCGCGGCCTGGTGATGTGATCTTTGGCCATTGGGGAGAAATGCACAAAATGCTGAAGATGTTATGAAGCTGTTCG<br>AACCAATCACAGCTGGCAGTGCAGTGCGATCAGAGACACTGATCTTATATGTGACCCCGAGGTCACAGAAT<br>GAATGACTGGACCGGCAAGAGTGTGAACCTGCGGAGGCAAGTCCCCTGATCCAGTCGTCATCAGTCCTGGCTCCTGGAAGAACACAT<br>GGGTAGAGGAGGAGTCAGTGAACCTGCGGAGGCAAGTCCCCTGATCCAGTCGTCATCAGTCCTGGCTCCTGGAAGAACACAT<br>TTTATATAAAATAAAATTATACCTAGCAAAAAAAAAAAAAAA | MAALKAGRGANWSLRAWRALGG<br>IFWRKPPLLAPDLRALLTSGTP<br>DSQIWMTYGTPSLPAQVPEGFL<br>ASRADLTSRTPDLWARLNVGTS<br>GSSDQEARRSPGSRREWLAVA<br>VGAGGAVVLLLWGWRGLSTVL<br>AAVPAPPPTSPRSQYNFIADVV<br>EKTAPAVVIEILDRHPFSGRE<br>VPISNGSGFVVASDGLIVTNAH<br>VVADRRRVRVRLPSGDTYEAMV<br>TAVDPVADIATLRIQTKEPPPI<br>LPLGRSADVRQGEFVVAMGSPF<br>ALQNTITSGIVSSAQRPARDLG<br>LPQNNVEYIQTDAAIDFGNSGG<br>PLVNLDGEVIGVNTMKVTAGIS<br>FAIPSDRLREFLHRGEKKNSWF<br>GTSGSQRRYIGVMMLTLTPSIL<br>IBLQLREPSFPDVQHGVLIHKV<br>ILGSPAHRAGLRPGDVILAIGE<br>KLAQNAEDVYEAVRTQSQLAVR<br>IRRGSETLILYVTPEVTE |
| SEQIDNO.20 | SEQIDNO.:113 |

FIG. 41

| NucleotideSequence (5'-3') | ORFs |
|---|---|
| GGAATTCCTAGCATGTTGGGTGTTATGTAGTCAAAGGAGGCATTATGAGCTGTACCCCAGGGACTTCCTGATCCTTA CATGTATAAATAGCAAGACCGGGCCAGGAACAGCAAGCAGTCTGAAGGCCAGCTGCTGCCACTAGAAGATGAAGC CTTTCATACTGCCCTCTCCTTCATTCTTACAAGGCACAGACATGCCAGATCACAACATGGGCCCCAGACAACAGAGACA AAAGAAGTCCAGAGCAGTCTGAAGGCACAGACAAGGCCTTGAAGCACAGTCATGGGCTTTCAAGACTCTTCAGA TTGCTGCCTGTCCTCTATAACTCACGGATTCAGTGTTCCAGGTCTGTCCAACCCCAGTGTGGGTGTTCAGAGAT CGGGCATCATCTTATCACGAAGAGGGGGTTCAGGTCTGTCCAGTGATCGGAGAGAAGGGTGTGAACTGCCAGCTACT AGATTGGAGCAGCAAAACTCACACACGACCACCTAAGTGGCTCTAAGTGTTTATTTTTATAGTATATAACATTTTTTCTGT TCTCTTGGTCTTCCCCAGTGACCATATCTGGCTTGTCACAGAGGGAACTGCTCTGTGCCAACCCAGTCATGCTGAAAACTCAGAT TCCACTTTAAAGTGGCATATCTGGCTTGTCACAGAGGGAACTGCTCTGTGCCAACCCAGTCATGCTGAAAACTCAGAT GCCTGGAAGGTCTGAAGCTGACTCACATGACTACACATAATATTTGATTGAGATAAATGGGCAAGCTGTGAGAGATGGC TTGGTGGTTAAGAGCACTGCTGCTCAACCAGAGGACCTGGTTCAATTTCCACTTAGATGGCAGCTCAAACTATCTATAA TTCCAATTCACAAAGAAAACTGATTGCCCTATTTGCCTTTAGTTAGTAGTATTTACAGTATTCTTTATAAATTCACCTT GACATGACCATCTTGAGCTACAGCCATCCTAACTGCCTCAGAATCACTCAAGTCTTGCACTTTCGGTTCCCAGCGAT TTTAAGTGGATAAACTGTGAGAGTGTCTGTGGGACTTTGGAATGTGTCTGGTTCTGATAGTCACTTATGGCAACCAGG TACATTCAACTAGAATGAAAATAAATTCTGCCTTAGCCACCAGTAGTATGTCTGTGTTGTAAGGACCCAGCTGATTTTCCCA CCACCCCCTCCATCTGTAAGCCACTAATAAAGTGCATCTATGCAGCCACCACAAAAAAA | MKPFHTALSFLILTTALGIWAQ ITHATETKEVQSSLKAQQGLEI EMFHMGFQDSSDCCLSYNSRIQ CSRFIGYFPTSGGCTRPGIIFI SKRGFQVCANPSDRRVQRCIER LEQNSQPRTYKQ |
| SEQIDNO.21 | |
| CCCGAGTGTCGCTGCCTCCTCCTGTCTGCCTTGGTTAGGGGACATCCCGGGAGGAGCGAAAAGCCCAGCTGGCCGGGCCGGTG GACCAGCGAGCGGCGCAGCTGTGCGCAGACTGTGCGCGGCGGGAGGCGCGGGCGAGGCGGGAAGACAAAAACCCACCCTGTTCCTCTCCGGCCCC ACGCGGGATCATGTACCAGGATTATCCGGAAGTTCCGGGAACCTTTGACACCTCGTCCGGGAGAGAAGTTCGGAGATTACGCGCG AGTCCTACTCCAGCGGTGGCGGCAGGACCTGCTGAGCCTGCTGGTGCTCGGGCAGCAGGCGGCTCGGGCAGTCCTTCATCCATCC ATCAACGCCACCATCCACCAGTCCTACAGTCCCTTGGGGCCACAGTGATCAGTGTACAGCCCTCGGGCCACATGGCTCCATGTCGATCAATGGCTCTGAGGAGTGATCA ACGTCACATCGGTACCACCGTGGGGGCCGCAGAACCGTCCAGCAGCTGTCTCCGGAGCTGCAGAAGGAGAAGCTGCAGGCGGAGACCGA AGACCATGGTAGCCACCGTGGGGCCGCAGAACCGTCCAGCAGCTGTCTCCGGAGCTGCAGAAGGAGAAGCTGCAGGCGGAGACCGA AGGGAGAGAAACAAGCTAGCTGCAGAAGAGATTGCTGGAGCTGGAGCTGCAGAAGGAGAAGGAGAAGCTCCGGGCTGCAGAAGCTAGAGTTCATGT TGGTGGCTCACGGCCCCGTGTGCCAAATCAGCCCCGAGGAAGCGCCAGATCGCCCCCGAAGAGAGACAGCAGCCCCTCTTCCTCAGCAGGAT GGTACGGGCAGTGCCAGTCGCTGTCATCAAGCCCATCACTCCCGGGGTGTTTCTACGGGAAGAGCCTCTGCACACCC GGACAAGACCCAGCGCCTCGGCCGCTGCTGTCATCAAGCCCATCACTCCGGCACTTCAAACCTTGTCTTCAACCCCAATGTCCTGAGCAG CCATCGTGGTGACCTGCACGGCCTCCACGCCTGCACCTCGAGATCCTGCTCCAAGGCTCCACCGGAGAGCAGTAGCACGTGGGGACCAGTCATCAGACTC GAGTCGCCTTCGTCGCCCCTCAGATCCTGCTCCAAGGCTCCACCGCCTGTAACCCTGTCCTCTGTGAGGAATCCTCATCCATCATTACC CTTGAACTCCCCACACTTCTAGCCTGTAACCCTGTCCTCTGTGAGGAATCCTCATCCATCATTACC | MYQDYPGNFDTSSRGSSGSPAH AESYSSGGGQQKFRVDMPGSG SAFIPTINAITTSQDLQMVQP TVITSMSNPYPRSHPYSPLPGL ASVPGHMALPRPGVIKTIGTTV GRRRRDEQLSPEEEEKRRIRRE RNKLAAAKCRNRRRELTEKLQA ETEELEEEKSGLQKEIAELQKE KEKLEFMLVAHGPVCKISPEER RSPPTSGLQSLRGTGSAVGPVV VKQEPPEEDSPSSSAGMDKTQR SVLKPISLAGGFYGEEPLHTP IVVTSTPAITPGTSNLVFTYPN VLEQESPSSPSESCSKAHRRSS |
| | SEQIDNO.:114 |

| NucleotideSequence (5'→3') | ORFs |
|---|---|
| ACACCCTTCCCAGGGACCAGCACCTTTAAGCACTCCAGGGCCTTGAGGGAATAAGGCCCCTGGCTCTGGGACCCACC<br>CGGTGGGACTTAGTGGTGAGACACTGGTTGATCTCTTAGAAGCCCTGGACACGCCCTCCCTCATTCATCTTGCAAGCGA<br>AGCGAATCCTTTTCTTGAGAAGCCTGCCCCGCCCCTCTTCTGAAGCCCCTGGAGCTGGAGCTGGAGATCGGAGCCTACCC<br>CACCCCCCCCTCTTCTGAAGCCCCTGCCCCGCCCAAGCATGCCAGTGCCCGGATGGTTTCTGTCCTTTGTTCTGTCTGAA<br>GTGGACAGTATCCTTTCCTGCCCCGCCAAGCATGCCAGTGCCATTCATCGGGTGGTCCAGATAGTAAAGCGCTTTATTTCGGAGCT<br>TCCCTCTGGGTTTTATAAGATTTGCCATGACATTCATCGGGTGGTCCAGATAGTAAAGCGCTTTATTTCGGAGCT<br>GGGGAAGCAGATGACTCTTCCACTGGGGCGCAAGGGGCACCCACTGTGTCCGAAGGGCAGTCAAAGTGCAATATATT<br>GAAACTTCCCTCCTACACACCAGTGCGCTGTGGTTACAGACCGGTGGTCACATCTCTTTGAGGATGGCTTGGCTGGAAGACAGGG<br>CTGGGATGCGCCAAGACCTTTCCTCCCCGGTCTGGTTTGCCAAACGTCTAATTACCAAGCCAGGATTGTGCAACAAAGCCAC<br>TGTGAGTGCGACAACAGGGGCACAGGTTGGGTTGCCAAACGTCTAATTACCAAGCCAGGATTGTGCAACAAAGCCAC<br>ATGGCTGTCCTAGTGAGCTTCCTTTCTTACCTGTCGTTAGAAGCTCCAAGGCTCAGCTGGCGCTGCTCATCCCCAACT<br>CTCTCTAGACTTGGAAGCACTCCTTCCTAGAAGCCACACATCACTCCAAGGCTCAGCTGGGCGCTGCTCATCCCCAACT<br>CTCATAGTGACATCACCTGTGGATATTTAATGAGTGCGGGTCGCGGTAGAGATGTTTCTGCAGCGCAG<br>CAGCCCCAGGTACCTAGCCTCCCCTGGCTGTCTCCCTGTCAGTGAGATGCAGGAGCCGCCTCCTAACCCAGCAGGCCTCT<br>GCTACTGATGAATCCAGTGGGTTCCTTTCATATTCTCCTGGCCAACTCCAGAGTGTCTTGAGTGTCTATTCGGTTCTATTGGTTCTATTC<br>CCCTGGGAGTCGTTGGCTGTGGTCCCACCAGTTTGTTGTAGGCTTTGAGTGTCTATTCGGTTCTATTGAGTGCCTTCTC<br>CTTTCCACTACAGAAGAACCATCACTCCATGGGTGTCCCAGCCTGTCCAAGGCACACAGTGGATGTGCCTTCTC<br>TCCCTTGTCCCCACTCCATGTTGACACAAGTATGACAAGTATGGAAGCCTGGTTAGAACTTGTTTCTAGTGCTAATGCTCTGA<br>CCTAGTATTCCATTGGAGATCACTGTCCAGCCATTCAAGCATTAAAGCCCCTTGTTATTCGAGTCAAGCTTATCCCCATTTTGAGAG<br>AGAAGGGGTACCTTCACAGACGTGGGAAGCATGCTCAGCTGCCCCCAAGTTCCATAACAGCATGCCATAACACCAGGACAC<br>AGGGACCATGTGGGAAGCATGCTCAGCTGCCCCCAAGTTCCATAACAGCATGCCATAACACCAGGACAC<br>AGATAATCTCAATGTGTCTTTTCCTGTATGCCTTCAGAGCCTAACTCTGCTGCTCTAACCGAGCCTTGGTCTCTGGTCTCTAGGGCAGG<br>GGAGTGCTCCACAAGGTGTTGCTCAGTTGAGAAGCTTTATCGCCTCAGACAAGTCGGAGCCAGCAGCGGAGCCTAGAG<br>GAGTGGGCAGTCTCAGTTGAGAAGCTTTATCGCCTCAGACAAGTCGGAGCCAGCAGCGGAGCCTAGAG<br>GAAATGAAGCTGGCGCCCCTGTTCTGCCTTTTCCAAAGCCCCCTTGCAAGCAGCCCTTGAAACCCTCCCATAGCAGGCC<br>TGGGACTTGGTACCCTGGTTGGACACTGCTAAATGGGCCTCTGAGTCTGCCCATAGCATGATCAACCCAGTCACAGGCC<br>GGCCAGAAGCACAGCAGTTGGGGAGGCTAAATGGGCCTCTGAGTCTCAGTTTCATCTGTGTCTTGCTTGTGCATCGG<br>TTGGCTTTCTGATCCACTGTCCAAGTTGGGTCACAAACATGTCACTCATGAGGGTGAGGGCAATCCTTAAACAGCTAGACTTC<br>TCCTTCCGATCCCACTGTCCAAGTTGGGTCACAAACATGTCACTCATGAGGGTGAGGGCAATCCTTAAACAGCTAGACATGG<br>CTTGTCCTCCTGCCTGCCCAGTCAGGGAGCAGCTGACTGAACAGTCCTCTGGGTTAATACAGGGGCCAATCCTTAAACAGCTAGACATGG<br>GCTGTCATGAACTTGGGCTGGACTGTGAGACTGTTCTGTGGAACAGTCCTCTGGCTGGCTAGCACAGCTACGGACACTGGAA<br>AGTTTTGTCGTGGCACCAGGCTTCTTAGGAAATTGGGAGCTAACAATGGGAGCAACTGTTCCGTGGGGAAGTTTAGGAGCT<br>GAGTAGAGCCCAGGTGAAGCTTAGGAAATTGGGAGCTAACAATGTGCCAGTCAGTCAGCACAAGTCAAAGCCAACAGGAAGCAGAACC | SSGDQSSDSLNSPTLLAL |

| NucleotideSequence (5'-3') | ORFs |
|---|---|
| TGTAGCTTTCTCTGGCATTAGGGAGGAGAGAACCCTGTTGTTCTTCCACTTAACTCCTGCTGTTGAAGAGGGGCAGGCACGTTC GAAGCTTCTGGATTCATTTTCCTCCACTTCTGAGAGACCAAAAGTGTTCCTTGAGATGTCACCATTGTCTTTCACA GTGACTTCCTTCCCTGAGCAAACATTCATGTGGCTTCGCTGGGAGGAAGAGTTCATTCCTTCTAGAAGGCCCCAGGTTAAATAA ATGAGGCACTTTCTATTATCCTCTTTAAGATAGGACTCCCAGGTGGGAGACTCCTCAGACTCTGCCCTATCTGCCTCCTCAAGACTCAT AAACACTTGGGGTAAGAGGGCTTTCTCAGAAGATTGTGACCAATAGGATATGTGCTGTATAACTTCTTTTAAACTGTAAGTAAA CCACAGCAGCATCGCCCATCCAGGCTCCTCATCCTCTCCTCAGACTCCTCAGACTCTGGCTCTGGTCTCCTCAGTGCTGCTGAAG GGGCCACCTTAGTTCTCATAGAAATTGTGACCAATAGGATATGTGCTGTATAACTTCTTTTAAACTGTAAGTAAA GGGTCTTGCAGCTTTGTGCTTGTGTTATCTTAGCATTTATCTTCAAACCAGCATCTCACTATTTATTGACAGTGGTGTGT GTGTGTGTGTGTGTGTCTGCGTGCACAGTAAGCCAGTACCTCACACATGTCGTGTGTGTTCATGTGTGTGCATGCTT GTGTCTTTCCACAGCTTTTTTTTTTTTTTTTAAGGATCATCACCAGTACTCACAACATGTCAGGAGGAGCTGGGTCAGATTTGACAGAG TGGCCACGCCTCACCAAATGTCTGTAATGACTACTCACAACATGTCAGGAGGAGCTGGGTCAGATTTGACAGAG GGTATGGGAAGGGAGAAAGAGATAGCATTAAAGTACATTTATTATTTAAATGTTACATTTCTTGTGTGTT CCAAGCCTGAATAAATGATCTCTATTTGTCATTCGTGTTTCCACCTTGACTTGTGCTGCTGTATAAACTGTATTAAAAAGGC GACTAGGATAATGATCTCTATTTGTCATTCCTGTGGGACAGTGGCTACTGAGAAATCTACATTGTAAGAAGACAATGAA GACCCTGGCCCCTGTCTCTCAAAACTTAACTTCTCTGTATGATTTTTTTTAAAAAAATATTCATTTATTTACTTG TGGTTACTTGATTTTGAGGAAGAGAGTAGGACCCAAGCTTGTACAAACGGCTCCCAAAGCTTTATTGGCTCCCCGAGGGGTGCTCCTGAAGCGCCTAGTTGAGGGGTCGCTCTGCTCGAAGCATCTGTGGTGGTGTGCTATGGAGGAAAGA ATATCGTATTTGAGGAACGTGAGGCAAATGGGTTGTACAAACGGCTCCCAAAGCTTTATTGGCTCCCCGAGGGGTGCTCCTGAAGCGCCTAGTTGAGGGGT TTGCTATTAGATCCTGAGGCAAATTAACGGTTGTACAAACGGCCTAGTAGAGTATCTCGCTCTAGTTGAACTCTCCAGGCAGACTCTTAT TTTTGTCCCTACTTTTGTATAGTTTTAAATTAATGACACAAGCCTACACAGATTTGCACTAAGAAAAGCTTGGTAGGAGCTTGGTAGGAGCTTGGTAGGAGCTTGGTAGGAGCTTGCTGCTATGGAGGAAAGA GCTCAGAAATCTTTGTATGTGACACAAGCCTACACAGATTTGCACTAAGAAAAGCTTGGTAGGAGCATCTGTGGTGGTGTGCTATGGAGGAAAGA CTGTGTACTGTATGTGACACAAGCCTACACAGATTTGCACTAAGAAAAGCTTGGTAGGAGCATCTGTGGTGGTGTGCTATGGAGGAAAGA ACATATTAAAAACTTATTTCTCCCTCGGTTTGTTCTCCGTTTATGTTTTGTTTTGTTTTGTTTTGTTTAGCTTTCCTACTT CCACTGAGTAGCATTTTGTAGAATAAATTAATCAAGACAAAAAAAAAAAAAAAAAAAAAAA | |
| SEQIDNO.22 | SEQIDNO.:115 |
| GGTTTCACCCGGCTGGGGCTGTGGCCCTAGTGCCCTGGGTGTGCGGCCCGGCCGCCCTGACAGCAGCGTCGCGGAGCCG GCTACCCCGACCTTGGGGCACTGCGAGAGCTTGGTGGTGGCAGAGCGACATCGCCGCCTGGCGAATGGAGGCGGGAGCCGA ATGGTCCTCCGGCCCGTGTCAAGAGCTTGGGACTGTTGGGGCGTAGTGTTCGAAGATGAGAGCAAGGGCTGCTCAAGCGGCGAGACA GTGCCGGGCACGTGCTGCTGAGGCGGGAGAGCCAGAGCGCAGGGCTGCTGAGGCCCTGAGGCCGCTGAGCCCTGCCAC CTCTGCCTGGGGCCCGAGCGCTGGAGTCTGGGGGCTGCCATCGGTGGGGCCATCGGTGAAGTGCAGCCTCCTCAGAAGTGGAATACT TGAACCTGCGGTTGAGTTCGGTCTGCTGAGGCCTGGTGAAGTGTCACCTTGTTACCAACCAGGAAAACACGAGTTTCCC TTTCGCTTTCAGCTTCGGTTCGAATCTGAACCTTTGGCAACATCGTTACTGGGAAGTATTCAGTACTGTGAGGGC | MGGEAGANGPRGRVKSLGLVFE DESKGCYSSGETVAGHVLLEAA EPVALRGLRLEAQGRATSAWGP SAGARVCIGGGSPAASSEVEYL NLRLSLLEAPAGEGVTLLQPGK HEFPFRFQLRSEPLATSFTGKY |

FIG. 44

| NucleotideSequence (5'-3') | ORFs |
|---|---|
| TGTTTTGGAACGACCCCAAGTTCCAGATCAGAGCGTCAGACGAGAGCTCCAGGTTGTCAGTCACGTGATGTCAACACAC CGCCCTTATTGACTCCTATGCTGAAGACGCAGGAGAAATGGTTGGCTGTTGGCTTTCACCTCTGGTCCTGTGTCACTG AGCGTCAAGATCAGAAGGGCTACTGTAACGGAGAAGCTATCCTATCCAGAAATAGAAAATGTTCATCTCG GCTGGTTGTTCCCAAGGCAGCAGCCATATTCCAAACCCAGACGACTTGGTTCTGGGAGTACGGACACCTGAGTACTACTGGAGATCCGACACAGG TTGCCAATGTTCGAGGAAACCACATTGGTTCTGGGAGTGCTGGAGATGCTGAAGATCCCACCTGTC ACCCCATCCATCCTGGATTGCTCATCATCAGAGTGGACTACTCCTTAGCTGTAATCCAAGCTTCTTGAATCATTAAAAA TACAT | GSIQYCVRAVLERPQVPDQSVR RELQVVSHVDVNTPPLLTPMLK TQEKMVGCWLFTSGPVSLSVKI ERKGYCNGEAIPIYAEIENCSS RLVVPKAAIFQTQTYLASGKTK TVRHMVANVRGNHIGSGSTDTW NGKMLKIPPVTPSILDCCIIRV D

| NucleotideSequence (5'-3') | ORFs |
|---|---|
| ATGGTTAGGGGTGGAGGACCTGTGATGAGTGCAGCTCCAATCGCAGCAAAAGGACGAAGTCCTTCGCC<br>ACCTGCCAGCAGAAGACGCTGCAAGCCCCGGCCGCGCAGTAGCCTCTCCTGCTGCAGTCCGACA<br>GAGTTTCAGATCCAAATCCGGAGGAAGCAGCAGGGCACTTGCACTTCTCCCCACTTCTCCCCGACCTC<br>CTCTGGAGGCCCCGGAGGAAGGAGCCCCAAGCCCACTGCTATCCTTCTCCCCACTCTCCCCGCGACA<br>GAGACTCCCACAGAAGGAGCCCCAAGCCCACTTGCCAAGTGTCGGTCGCCTCACTCGCGGATTCAGGCGGA<br>TCCGATGCTGGCGAGTGGGCCACTTGCCAAGTGTCGGTCGCCTCACTCGCGGATTCAGGCGGA<br>CTGCCTTCCCTCGGGTGCGTTCGCCTCCCGCTCCCCGCTGGACGTCTGCGAAAAAGAAGATA<br>AAAGAGTACCTGGAGCGAACACCATGACTTCCTTCAGCCGCTACACCTTGGGTTTCTAGAGGTGGACAG<br>ACAGAGGCGGGAGCCGACGCGGGAGACCGGGGAAACCGCGGGAGCCAGACAGCGGGCTCAGCGTGGGCTGGCGCGGCG<br>GCCGGGACGGTCAGCACTTCGGACACTTCGGGACAGAGCGACTGCCCGGGGAAGGAGGAGCCGCGCGAGCGCGCGCTGGGCCGCG<br>CTGCCTCCACAATGCACCGTTCCGCCGGCGATTCACCGCCGCGAAGGAGCTGGCTGCCAATATAAAGTCTGCTCTTCCGCTCAGAAGA<br>CGGCGCCAGCTTGGCGATTCACCGCCGCGAAGGAGCTGGCTGCCAATATAAAGTCTGCTCTTCCGCTCAGAAGA<br>CGGAGGGAAGCCAGACAGAAAGGGAGCTGGCTGCCAATATAAAGTCTGCTCTTCCGCAATGGTAGAAAGGA<br>TACGAAATGCTCCCAGAGACAATGTGAGAAGATCCCCTCAGAATGGTACCGAGCTCATATCGTGAAGGAACCT<br>GAAGTAAGGAAAGATCCGTCGAATGCAACGCCCTTGCAAGACTACTCTCCCAACCTCCCAGAAGTACTCTCCCAACCTC<br>GTGCTATTCGTGAAGACCTGGCAGGCAGATCTCTAAGAGAAACAGCATCATCGACTGAATGACAGCTGAAACGTGCAGGGGAGC<br>CCATCTCCATTTGTACACTCGGATCTCTAAGAGAAACAGCATCATCGACTGAATGACAGCTGAAACGTGCAGGGGAGC<br>AGTCCATTGTACACTCGGATCTCTAAGAGAAACAGCATCATCGACTGAATGACAGCTGAAACGTGCAGGGGAGC<br>CGGGAGCGGCCGTCAGAGTCTCCGCCGGCCAACAGTTGACAACAAACAGCGGCAAAGCACGTACGGCAGAATCAT<br>CTCTCTTGGAGCCAACGCGGACTTGACAACAAACAGTTGACAACAAACAGCGGCAAAGCACGTACGGCAGAATCAT<br>TAGAACCCACAGAAGCCCCGGCCCGACACCGGCCGTGGCGATGCCCCC | MVRGGGPVMSAASNRSKRTKVL<br>RHLPAEDAASARGAAVASLLLQ<br>SRQSFRSKSIGLALLFPSPRSP<br>AFDLLWRPGGRKQGTLPLLRKG<br>RRGGDRDSHRRSPKPCILLPTP<br>RPHIRAGPMLASGPLAKVSVLI<br>PGAGIQAGLPSLRVRSPPAPLP<br>AWTSAEKEDKRVPGANTMISFS<br>RYTLGFLEVDRQRAGADGGPGN<br>RGAGSRRARRVRAGRSAPRTAP<br>CARSRAAAQRWARAASTMHRSA<br>GGRRRGNPAQLLLGPRASLAIH<br>RRRSRALLPLPPKQEGRKGKPD<br>RKGAGCQYKVCLPLCPPIRNAP<br>RDNVRRPAIFCASGNGRKEK |
| SEQIDNO.25 | SEQIDNO.:118 |
| CCTCGATTCAGTTTTGGTGAAATGCGCGCCATTCTACTTCTCTCTTTGCTCACACTCGCGATTCTGCC<br>CCCGCAAGAGTACTCTGGGGACGTCCTATCGCTGGAGAGAGCCGTTCGCATCCTGAACCTGTTGGCGCTGCTG<br>GGCCGCGTCACCTGGCTAGCAGCTTGGGCCAGCTCCGCAGCTAACTTTCCTGACGCTACTGAAGAGTCTGCTCCTC<br>TGTGTTCTTTCCAGTGCTGTTGTTCGATCCAGTTTTCTGGTGGTCTCCAGCGAAGCGACAAAGCCGTTGTGAGTG<br>GGATGGCCCGGCACCCGGTAGTGTCTTAATGATGATGTGTCTTTGTCAAGAACTCTGAGAGAAATGAAGAGAGTCCTCAGCAATGATGTT<br>GGCTTCTCGTGGTTCCCAGAGCCTGCCAGGTCATTCACCAGTGGAACCTGGCTGCTGTGTTCTGAACATGCC<br>CAGAGCCCTGTGTCTGCCAGGTGAACCTGCGTCACCTAACGTCAGGACCTCTTGATGAAGACGTGAAGAGATGTCTTCCT<br>GTGTAGAGATGTCGACTGACTGAGAACCTGCACTTAAGTGAGACCTTAAGTGAGGATGAGAGAGGCCAGCTCT<br>CTTTGCTACCTTGGCTGAATTGCTCTACAGAGTGCTGAATTGCTCTACAGAGTGAGGCGGTTTGACCTTGAACCTTCTCAAGAGGATCTTGAAGACTCTTCAAGAGGATCTTGAAGACAGACAGACAAAGCA | MAQSPVSAEVIHQVEECLDEDE<br>KEMMLFLCRDVTENLAAPNVRD<br>LLDSLSERGQLSFATLAELLYR<br>VRRFDLLKRILKTDKATVEDHL<br>RRNPHLVSDYRVLLMEIGESLD<br>QNDVSSLVFLIRDYTGRGKIAK<br>DKSFLDLVIELEKLNLIASDQL<br>NLLEKCLKNIHRIDLNTKIQKY |

FIG. 46

| NucleotideSequence (5'-3') | ORFs |
|---|---|
| ACCGTGGAGGACCACCTGCGCAGAAACCCTCACCTGGTTTCTGCTGATGAGATTGTGTGAGAGCTT<br>AGATCAGAACGATGTATCCTCCTTAGTTTTCCTTACAAGGATTACACAGGCAGAGGCAAGATAGCCAAGGACAAGAGTT<br>TCTTGGATCTGTGATTGAATTGGAGAAACTGAATCTAATTGCTTCAGAAACTGAATTGTTAGAAAAATGCCTGAAG<br>AACATCCACAGAATAGACTTGAACACAAAGATCCAGAAGTACACCCAGTCCAGCCAAGGAGCAAGATCAAATATGAATAC<br>TCTCCAGGCTTCGCTCCCAAAATTGAGTATCAAGTATAACTCAAGGCTCCAGAATGGGCGAAGTAAAGAGCCAAGATTTG<br>TGGAATACCGTGACAGTCAAAGAACACTGGTGAAGACATCCATCCAGGAATCTGCTTGATCATTGATTGTATTGGCAACGACATAAACCCAGATTGTTC<br>GAAGAGACTTACAGGATGCAGAGCAAGCCCCTAGGAATCTGCTTGATCATTGATTGTATTGGCAACGACATAAACCCAGATTGTTC<br>TCAAGAGACCCTCACTTCCCTGGCTATCATATCAAGACTTTCTGTTTCCAAGTCACATGACATAACCCAGATTGTTC<br>GCCGATATGCAAGTATGGCCAACATCAAGACTATGACAGCTTTGCATGTGTTCTCGGTGAGCCTAGGAGGCTCCCAAAGC<br>ATGATGGGCAGAGAGATCAAGTTCACTCAGGGTTCTCCCTTGGATCATGTCAAGAACATGTTCAAGAACATGTTCACGGGGAAGATAGCAGCCTGGAGG<br>TCTCAGAGGGAAGCCATCAATAAAAAATGTGGACTCTAAGCCCCTCGAACCCAGACACTGCACAACTCACCCAGAAGCTGATATC<br>TAGATGGGCCATCAATAAAAAATGTGGACTCTAAGCCCCTCGAACCCAGACACTGCACAACTCACCCAGAAGCTGATATC<br>TTTTGGAGCCTGTGCACAGCAGAACGTATCTCACTTGGAAGAAGCCTCATCCTCTGTCTATCTCGAGAAGCTCTC<br>CCAGCAGCTGAAGCTGAAGCAAGGCAGGAGACGCCCACTCGTGGACCTCGAGCCTCAGCCTGTGAACTCATGGACAAAGTGTATGCGCTCCTACGTGA<br>GTGGTGTTTCGTCTAAGGAGAGAAATACAGCCTGGTATATCATCCAGGTGCGCGGCTTGGCGGTTACGCCTGCTCT<br>GAACCCCAGACCGTTGGTGTTCTTCGCCGTGAGTCCTGCCCTAGGGTTCTCCTGTGCCTAGAGCATGAGCCGTAACCCTGTGCCTGGAA<br>GCTGCTTCTGCACTCCCGCCGCGTCCTTTACCTCTCTAAACTTCCCTACTTACATTCCTTAGTCGGATGTTTCCTTAGTCTACCAAGTTATT<br>ACGTCTCACTCCCGCCGCGTCCTTTACCTCTCTAAACTTCCCTACTTACATTCCTTAGTCGGATGTTTCATGCGACTG<br>TGGAGAACAGTAAGACATAAACCTATTGTTTGTTTTGTTTCAAGATTTGACACTCAAGTTAACTTCATTAAGTACCCATTTAAGAGTAACTTGAGACTTAACTTGAGACTTCACA<br>GTATGGGGTTGTATAGTGTATAGTGCACATCTAATCATTCATTTGTTTTGTTTCAAGATTTGACACTCAAGTTAACTTCATTAAGTACCCATTTCTTCAAGACTTTCACA<br>GGTAAATTGTTCTATGGCACAGACATAAACCTATTGTTTGTTTTGTTTCAAGATTTGACACTCAAGTTAACTTCATTATGTCATTTATGTCTGTTTAATA<br>TTGGCCACCAATTCTGTGACCCAGCCTGACCCAGCATGACAGAGGGCTCCCGAGATGGGTCTTGCCCTGGTTGTAGTGGCTTTGGGAGAGCAGTCTGACCTCACCAGGATCAGG<br>TCTACAGTCTAATGCTTTGAAGGATGGCTTCGGTGAAGGAGAATGAGCCCTACTCCTGAAGGTTGTAGTGCTTGCCCTGGTTGTCAGGAGAGCAGTCTGACCTCACC<br>CAGCTGTGCAGTGGCTTCGGTGAAGGAGAATGAGCCCTACTCCTGAAGGTTGTAGTGCTTGCCCTGGTTGCTCAGGATCAGG<br>TGCCTGGGCAGCAGCACAGTAGAGCCAGCCCAAGAACAACAGTGAGTGGGGAGCTTGCCCTGGTTGCTCAGAAGCCCTGTG<br>AACAGGAGGGATGACCAACTTGGGGCTTTGAGGTGGCCCCAGCATCCATACTCGTGAACTGCCAGAGCCTGTG<br>AAGGGGCGGTCCAGTATTTATAGTGCACCAGAAGCCAGAGCCGTGACCATGGAGGACCAATGCACAAACAGGGTATCTGAGAAGGGTCCCG<br>TGAGGGTCCAGTATTTATAGTGCACCAGAAGCCAGAGCCGTGACCATGCACAAACAGGGTATCTGAGAAGGAACAATGACCCATTGCACTGAGTAAAGATGTA<br>AGTGAATGAGTGAAGATGTGTGGCACCAGAAATACTGAGGGACACACACAAGCTTTATGGAGATGTTTGTTTGTTTG<br>TTTGTTTTGTTTTGTTTCTTTGCAGGAGAACAGATTGCAAGGCGAGATAAGGAAGCTGGAGACATGAGTGGGG<br>TTGGGTGCATGATAGTAGAATTCACAAAGAATCAAAAAAAAAAAAAAAAAAAA | TQSSQGARSMNTLQASLPKLS<br>IKYNSRLQNGRSKEPRFVEYRD<br>SQRTLVKTSIQESGAFLPPHIR<br>EETYRMQSKPLGICLIIDCIGN<br>DTKYLQETFTSLGYHIQLFLFP<br>KSHDITQIVRRYASMAQHQDYD<br>SFACVLVSLGGSQSMMGRDQVH<br>SGFSLDHVKNMFTGDTCPSL<br>RGKPKLFFIQNYESLGSQLEDS<br>SLEVDGPSIKNVDSKPLQPRHC<br>TTHPEADIFWSLCTADVSHLEK<br>PSSSSSVYLQKLSQQLKQGRRR<br>PLVDLHVELMDKVYAWNSGVSS<br>KEKYSLSLQHTLRKKLILAPT |
| SEQIDNO.26 | SEQIDNO.:119 |

FIG. 47

| NucleotideSequence (5'-3') | ORFs |
|---|---|
| CCTTTGAACAACTTTGTTGATGAGAGCTCTCCAGGATTGCCTATAGAAGAAGCTTTGGATGAGTGCATGGAAGCGTAGC TCTGGAGAGACGCTGAGGCAGCAGCAGGCGGCTCAAGACTTCAAGGTTTCAAGACTTCTCAGAGACTTCAGAGACTTACTCAGTCAGTGCCTATAGAAGGGCAGAGTGGAAAGTCGCCGCAGGGCTGACGATGA AACAGAGACAACATTCTCAAGGTTTCAAGACTTACTCAGTCAGTGCCTGTCCCATCGGATCAAGTGACACTGGAGAACTAG CTGAAATGCCACCACCTCAGTCAGATCTGCAGTCAGTTGCTAACTTTAATGACAGCAGCAGCATTGAAGTAGCCAACAGCCCAGC CCTTCCTCCACAGACCACAGTGCCTCCCGCTCAGTTGCTAACTTTAATGACAGCAGCAGCATTGAAGTAGCCAACAGCCCAGC ATTCCCGCAGCCCTCCCGGAAGGAGCATGGAATTTGCTAACTTGCAGCAGAATCACTTAATAGGGCCGGGCTTTCCTATGGC AATACCTGGCTCCATTGCCTCCAGGCCACCACAGTGCCTGAACCTTTATACACAACATCCAGAACCATCAAACACGCTGTCAGAGCC CTACCTCCATTGCCTCCAGGCCACCACAGTGCCTGAACCTTGTCTGTTCTTCGCTTCTCCCAGCCTTGTGTGAAGAGAGCAAGCGTCCCCAAGACAGCCTG ATTTCACCACTGTCACCAAAGAAGAATCGAGGGCCACAGCAACCCACCTGCCTTCAACTTCCCGGCCCAGCCTTGTGTGAAGAGAGCAAGCGTCCCCAAGACAGCCTG GCCCCTTGTACCAAAGAAGAATCGAGGGCCACAGCAACCCACCTGCCTTCAACTTCCCGGCCCAGCCTTGTGTGAAGAGAGCAAGCGTCCCCAAGACAGCCTG GCTCAGGGCAAAGAATCGAGGGCCACAGCAACCCACCTGCCTTCAACTTCCCGGCCCCAGCCTCTGGGCCAACAGCACCAC CTCATCTGCCCCCTACCAGAGAACATTCCGTGCAATGGATCCAGCAGGACGAGTCAGCCCAGAGAGTTGATAGCTCCACCA AGACTGTCAAACCCCTGAGGATCAGTCAGGATCGAAGCGCTGAAGCCCAACAGAATCGAGAGTCCTTCAACTACTCGATGTGCAG CACCTTGGCCAGTTCCCACCCCTCCATGCCAACAAGCAGAATCGCGGGGCCAGGCCGCCAAGCCCAGGCGCCAATGAGGAGGCCAAGA AGGAGACAAGCGACCCGCCATGTCCCCGATCAGTCAGTAGCGCTCCAGGAGCTCTGGGCAGCAGCCCGGGCAGCAATGAGGAGGCCAAGA AAGTGACCCCGCTCCATTACGTTCGGTCCCTGCTCAGCCCGCTCAGCCTGCGCCTCAGTCTGCAGCGGTTCCTGTCGCAGGATATGCGGCGGGCCAGTGGCGGCTCCTACTTC GTGCAGCAGCCCTCCATTTTGATGTGATGAGTCAGAATTTGACAGTCAGATTTGACAGTTGCAGAATAAATATTTTAAATTTGAAAAAAAAAA TATTTGCATTTTTGATGTGATGAGTCAGAATTTGACAGTCAGATTTGACAGTTGCAGAATAAATATTTTAAATTTGAAAAAAAAAA AAAAAAAAAAAA SEQIDNO.27 | MPPPQSRLLQYRQVQPRSPPAV PSPPSSTDHSSQFANFNDSSRD IEVANSPAFPQRLPPQLFGSPF SLPSEHLAPPLKYLAPEGAWN FANLQQNHLIGPGFPYGLPPLP PRPPQNPFIHIQNHQHAAGQEP FHPLSSRTVSASSLPSLEEYEP RGPGRPLYQRRISSSSAQPCVE EASAPQDSLAQGKESQGHSNPP AFNFPAPESWANTTSSAPYQNI PCNGSSRTSQPRELIAPPKTVK PPEDQLKPESGEVSSSFNYSML QHLGQFPPLMPNKQIAESANCS SQQSPAGSKPAMSYASALRAPP KPRPPPEQAKKGSDPLSLLQEL SLGSSPGSNGFYSYFK |
| CGGCGCGTTGAGGGGCCGGGTGAAAGGTCACAGCGCGGCGGCGGCTCGGCTGCGGCAGCTGCGGCGGGAGCCGAGTG TCCCGAGTGCACGTGTGCAGCCAAAGAGGGCGGCAGCGGCGGCCAGATTTCCCCGGGAGCCTCAGGGCC TGGCTTGGCTTCTCAGCCAAAAGACGGCTGTGCGGCCTGTGGGGTTGAGCTCTGAGCTCAGGGCCGTGGTCTGAGCTCAGGGCG ACGAGGACGAGCGTTGCGCCGCTGTAACGACGGCCTGCAGCAGATGAAAGGCCGGATGCAGCTGAGCTGGAG ATGTGACGCCACCAATATTAAACAGTGAAGAGACTTGAACCAGTTCATCTTTCAGTCAGCTGTAGTTCAATGATAAATTCTAC AAGGATGTGCTAGAGGTTGGCGAGCTAGCAAGACTTTACATGATGACACTAGGAGTGCCTTGCACCTTACCGAAGACTAGAGAAG GGATCATTCACAGAATCAAAAGACTTTACATGATGACACTAGGAGTGCCTTGCACCTTACCGAAGACTAGAGAATAGGAA CTAAAATGTTAAATCATCATGTCTAAACATCTGTGAGAAGGATGGCCACTTTGAGATTATCGAGCAAAGAAGAACATCTGAAGAGGATAGA AATGAGTCAGCGATTGACTTTTACCGAAGTTTGGCTTTGAGATTATCGAGCAAAGAAGAACATCTGAAGAGAACAGAGAAGACAACT GCCTGCAGACGCCATGTGCTTCAGAAAAACCTTGCATCTCGTCAGAAGTGCATCCATTGCGCCAAATAAAAGAAAGACCCATTGGTTCCCTTCC GAACAAATCACAAATGAACTTTCTTGCACTTGCTCTGTTCGCCAAATAAAAGAAAGACCCATTGGTTCCCTTCC SEQIDNO.:120 | MKGRIELGDVTPHNIKQLKRLN QVIFPVSYNDKFYKDVLEVGEL AKLAYFNDIAVGAVCCRVDHSQ NQKRLYIMTLGCLAPYRLGIG TKMLNHVLNICEKDGTFDNIYL HVQISNESAIDFYRKFGFEIIB TKKNYYKRIBPADAHVLQKNLK VPSGQNAETQKTDN |

| Nucleotide Sequence (5'-3') | ORFs |
|---|---|
| GTTACATCTAAAATAAACTTATGTGATGTTCTGGTAGTGATCTGTCTGTAACTGTGTCATGAAATCATTATTGTGCTGAATT TTACAGTCTGCAACTATGTCATTGTGTGTACTGAAGACCTCTGGACTGTGATCCATCCATATTCACTAGGCCTAATTTAAACTCATG AATAATCAAAGTATGCTAATTCAGACCTCTGGAATTGGGAAAGACACCAGGCAATAAATCTGAATTTAATCTAGTGA AAAAAGATCCCCAGGAAATGCCTTATTCGCATATTCTGATCTATTACTTTTTGAAATATAGAACTTTAGGCTTTATTCTAGTG AGTATGAACTGTAAATGTGCATATTCTGATCTATTACTTTTTGTAGTGAAGATTTTAGTTGAGTGAGTGGATTTTATGTT AAGTACTTCGAAATTTTTGACAGTGTGTTAATTATCTAGTGACATAACAGATTGTGTATCCTATA ACAAAGGATGCCTTTGTCTTATTGTAGACAGTGTGTGACATAACCAGTTAGGCTGTGACATAACTTATATCAGCCAAGGCTGCAA ATTGATGAAGGCTTAACAAAGCCTAGTATGTTGTTGGATAGGATATTTGTTAAATTTACGAACATTCAGTGAACTCATTTACTGTCCTCAACA ATTCAAGACATATGAGTTAAGTATGAGTTAAAACATGTTGATACT | |
| SEQIDNO.:28 | |
| GGCAAAGGCGCGCGTTCTCTGCTCTGCGCCCCGGGGCCGGAGAAGGCATCATGTCAGACAACGAGGACAATTTCGACGGCGA CGACTTTGATGACGTTGAGGAGGACGAAGGACTTGACGACTTGGAAAAATGCTGAGGAGGAGGCCAGGAGTATGCGAGA TTCTCCCATCGGTGAGCGAGCGACCACAGGCCAACCAGAGCGGATCACCTCCTTACAGTCAAGTATGAGCGTGCCCGA GTGCTGGGGGCACCCGGCTCTTCAGATCGCGATGTGCCCCGGTGATGGTGGAGCTGGAGGGGAGACAGACCCTTTGCT CATCGCCATGAAGGAACTCAAGGCGCGAAGATCCCATGATCATTCGCCGTCACCACGACTTATCAGCCAGCTATGAGGACT GGGGGCGTGGAGCAGCTTATCATCAGCGACTTGAGCGCGGGCGTCGGCCTTGCTGGGCACCCTCTGTG CCCGTTTATATGTGTAAATAATAAACCTCACCCCTTTCCAAAAAAAAAAAAAAAAA | SEQIDNO.:121<br><br>MSDNEDNFDGDFDDVEEDEGL DDLENAEEGQENVEILPSGER PQANQKRITTPYMTKYERARVL GTRALQIAMCAPVMVELEGETD PLLIAMKELKARKIPIIRRYL PDGSYEDWGVDELIISD |
| SEQIDNO.:29 | |
| CCACGCGCTTCCGCGGACGCGCGTGGGCGGGCCGGGCACAGGAGAGCTCTCCGGCACCTCCGGAAAGCCACCTCGGCCTCCCCCGCC CGGGCTCCCAGCGCGCGGCCCAGCTCGACCTTCAGCAGCGACCTGCTCCTGCCGAGGAGCCGAGCCGAGCCCGGTCG CGGGGGCGGGAGCGGAGCGTGCGTCGGTTCGACAGGCTGCACAGGTCGCGAGGAGGAGCGGCCCAAGTATGCCGGAGACAGAC CCTGCAGAACCACCAGCAGCCCACTGGAGCCCTTCCTGATCGGTGAGCGGTGAGCCCAGAAGCAGGTGGTGATCCTGAGCCAG CCGTTTGTGCTAAGATCGTCCAGTCTGACCTCAGAATGAGTGGATTACCACCAGAAGCAATTCAACTTGATCCCTATATGGCCAG GATAGCTTCTACCGAGTCCTCACCTCAAAAACACTCAAAGGAAAATCACCCGAAGGAAATCACCGTCCAGATCCCCGTATACGACTTTG CTTTGACAACGAACTCATCTTCAAAGAGGAGACGTCACCATCTACCCGCGCTGCTCTTCGAAGGATCCTAGCCCTTGCTATAT TCTCCCACTCACGGAAAGAGGAGACCTGTTCCAGATGAAGCTTTTTGTGGGACACAGATGCGGATACCGCGGATACCTCGTCTTCTCGCCGAGTATT TCCCAGGAGGTCCGAGACCTGTTCCAGATGAAGCTTTTTGTGGGACACAGATGCGGATACCGCGCTTCCGCCGAGTATT | SEQIDNO.:122<br><br>MAGDSEQTLQNHQQPNGGEPFL IGVSGGTASGKSSVCAKIVQLL GQNEVDYHQKQVILSQDSFYR VLTSEQKAKALKGFNFDHPDA FDNELIFKTLKEITBGKTVQIP VYDFVSHSRKETVTIYPADVV LFEGILAFYSQEVRDLFQMKLF VDTDADTRLSRRVLRDISERGR |

FIG. 50

| NucleotideSequence (5'-3') | ORFs |
|---|---|
| GAGGGACATCAGCGAAAGAGGGAGGAGGACCTTGAGCAGCAGATTTTATCACAGTACATTACGTTTGTGAAGCCTGCCTTTGAGG<br>AATTCTGCTTGCCAACAAAGAAGAAATACGCCGATGTGATCATTCCTAGAGGTGCCGACAATCTCGTGCCATCAACCTCATC<br>GTGCAACACATCCAGGACATCCTCAAGCGGGGCTCTCCAAGCGGCAGACGAACGGCTATCTCAACGGCTACACCCCTTC<br>CCGCAAGAGGCAGGCGTCAGAGTCCAGAGAGGCTCAGGCTCTGTGTCTTCCCTTTCTGATTCCCTTTTGTCTTTCCCTGCCCTTTTCATT<br>TCCAAGACACAGGAGGGGTCGAGAGGTCGAGAGGCTCTGTTCCCTTCGTGTCAGATCGCCTCCTGGAACAGCAAATCTTGATGGAACTTGACCCTG<br>CCACGGAGATGAAATGCCTTGATTCCCTTCGTGCCTTTTGTACTTTGTAATCTGATTCCCTTCGAAAAATTACTGTATTTAAGAAAACA<br>AGCTTAAGTGACAAACTGTGCCAACTAGTACTGTGGTGATGCCTAATTATGAACCCAACGTGTAACCAGTTATAATACACA<br>CATACATACGTCTATATAAAAAAAAAAAAAAAA<br>SEQIDNO.30 | DLEQILSQYITFVKPAFEFCL<br>PTKKYADVIIPRGADNLVAINL<br>IVQHIQDILNGGLSKRQTNGYL<br>NGYTPSRKRQASESSSRPH |
| CTGCGCTCCGCCGCGCGGAGTAGAATGAACTGTAACAAAACAAGCCCGAGCCTTTGTATCTGCTTAAAGGGGCCGCGGCCA<br>CTTCCCTCCGGTCCCCTCACCCCCGCCGTCTCAGGGCTCCCGGCAACTAGCTTGGAGAAGGCTTGGAAAGGCCGCGTTCCC<br>TCGCGCTGAGGAGCGGAGCGCCGGCGGGAGCAGGCCGGCTCGGGAGCGGGTGTGTGCGGAACGCCGGAGCGGAGCACCGGAGCGCAAACAAAG<br>CGGCGCCGGAGTGGACTCTGGTCCCGGGAGCGTCTTCAGGGCTCGTCAGCGAAAGTTTGTTTTATGATGGCTTGAGAGCGCGAGAGAGTCGGG<br>CTCGGGGAGCCTCGAGTAGCTCGTCCCGTGCCAGGAGCGGCTCTCCGGAGCCCGAGCCCCGAATTGAATTTGTTTTCGAGGAGGG<br>GGGGGCCACCGTCGTCTCGTTTTAGCAGTTTTCTTTCTTCTTCTTCTTGAATTTCTTTTCCCCGTTCACGAGTCACCGTGAAGCGGG<br>GCTGTAACTCATCATGTCGAAAGTGATCCAGAAGAAGATCCAGAAGAACCACTGGACTGGGACTTTCCGTTCCCGTTCACGAGTCACCGTGAAGCGGG<br>GACCCCAGGAGGGCGAGCTGGGGGGCTTCCGCCCCGGAGCATGGCCGAAGTGGGACTGGGCCGAAGGTGAGCTGCTGCGTGAGGTGCAGGGGT<br>GCCGAGCGCGGCGGGGGCTTCGCCCCGGCTATGACGTGCTGCGGAGACCTACCCACGGCCATGGCCTTGCAAGGAGGCCGTCAAAGCCGTCA<br>CCGGGTGTCCGGCTGTCCGGCTTGCCCCGGCTATGACGTGCTGCGGAGACCTACGCCATGGCCTTGCAAGGAGGCCGTCAAAGCCGTCAAAGCCGTCA<br>GACAAGGAGGAAGGCTCAACAGGACCAACCTCAGGACGACCTACCGCCACACATTTCCTCAACAACGGTTCCAGAGAAGGAAGATCATGAGCTC<br>CAGCAGACCATAGGAGCAACCTCAGGTCGCCTTGCCTGCCTTGGACCTGGACCGGAGCGGGACCCCCGTGTTGGAAGTCGGCACTCAGCAGAAGGAAGATCGGACTATG<br>CGTGGATTACAGCTTTCTGACTGTGAAGAGTTCTTGGAACCTCCCAAACCTTCGACCACCCAAACCTCCCAATGGAAAGTGATGCCTACAAATGCAAAATGTCGGCATAGTCCACC<br>AAGGAAACTATTATGGGACACACCCAAACCTCCCTAAGCGACACCAGTGAACAAAGTCCTACAAATGCAAATGTCCAACAGTCCACC<br>CTGCAGTCTGCTCCAAACAGTCGACCGTCCCTGAATAGTCGCCTTCACGGACCTTACGGCACACTCGGACCAGGACGAGCACTC<br>GGAGATGAGGAGGAGGAGGGCGCTCCCACTCGTGAATAGTAGCATCCTCGCTGCTCCCATCGACCCCTTTCAAGAAATGGAGAAGT<br>TCCAAGAAGCAACGCTCCCACTCGTGAATAGTAGCATCCTCGCTGCTCCCATCAGACCCCTTTCTCAGAAGTTCCTCAG<br>TACCTACCCTCTTTCTGCAGACCACACGAAAAACAACACCCGTGTGAACTAGAGACATCATGGTTAGACCCCTCGGTGCCTGAACAAACAGCAGCCTCTGAAG<br>CTATTTCATAGACGATGAAGGGGTACACACCGAGGAGCTGGACAGTGAACTAGCAATGAAACCGCCAATATGAAAACGCCAATATGAAAACGCCAAACG<br>AATGTGAAGATGATGAAGGGGTACACACCGAGGAGCTGGACAGTGAACTAGACGCAATATGAAAACGCCAATATGAAAACG<br>GACCCTGTCTACGGTGTCTACTATGTAGACCACATCAACAGGAGACGCAATATGAAAACGCCAGAAGATTGAA<br>GAAGAAACAGCTTGAACAGCAGCAACAGCAGCAACAACAGCAGCCCTCAGCCCTCAGCCGCCAGAAGATGAGGAGGACATGAGGATCATGCAT<br>SEQIDNO.:123 | MSKVIQKKNHWTGRVHECTVKR<br>GPQGELGVTVLGGAEHGFPYV<br>GAVAAAEAAGLPGGGEGPKLAE<br>GRILLEVQGVRVSGLPRYDVLG<br>VIDSCKEAVTFKAVRQGGRLNK<br>DLRHFLNQRFQKGSPDHELQQI<br>IRDNLYRHAVPCTTRSPRRGEV<br>PGVDYSFLTVKEFLDLEQSGTL<br>LEVGTYEGNYYGTPKPPSQPVS<br>GKVITTDALHSLQSGSKQSTPK<br>RTKSYNDMQNAGIVHPENEEEE<br>DVPEMNSSFTADSGDQDEHTLQ<br>EATLPPVNSSILAAPITDPSQK<br>FPQYLPLSAEDNLGPLPENWEM<br>AYTENGEVYFIDHNTKITSWLD<br>PRCLNKQQKPLEECEDDEGVHT<br>EELDSELELPAGWEKIEDPVYG<br>VYYVDHINRKTQYENPVLRAKR<br>KKQLEQQQQQQPQPPQPEEWT<br>EDHASVVPPVAPSHPPSNPEPA<br>RETPLQGKPFFTRNPSELKGKF<br>IHTKLRKSSRGFGFTVVGGDEP |

FIG. 51

| Nucleotide Sequence (5'-3') | ORFs |
|---|---|
| CTGTGTGCCTCCTGTTGCTCCTTCCCATCCCCGAGCAATCCGAGCCAGGGAAACTCCACTTCAGGGCCAAACCT<br>TTTTTACAAGAAACCCCTCTGAAGCTGAAAGGCAAGTTCATTCACACGAGAAAGCAGCCGAGGCTTTGGCTT<br>CACGGTGGTTGGAGGAGACAGGGGATGTAATTGTGAGTGTTCAGATCAAGAGCCTCGTCCTGATGGTCCTGATG<br>GCAAGATGGAGACAGGGGATGTAATTGTGAGTGTTCAGATCAAGAGCCTCGTCCTGATGGTCCTGATG<br>ATCTTCCAGTCCATTCCATTGGTGCCAGTGGTGACCTGAGTTATCATTGCCTTTTGACCCGATGA<br>CCCTAATACAAGTTTAGTGACCTCGGTGCCCATTTTGACAAAGAACCAATTATTGTAAATGACAAGAGACCTACGATT<br>CACCAGCCGAGCCACAGTAGTAAAACAGGCAAAGTCAGGAGCATGAAGGACGCCAGGCAGGCCCTGATGTGGCT<br>TCCAACAGCTCTCATGGTTACCCCAACGACAGTCTCCTTGGCTTCCCATAGCCACCCAGCCAGAGCTAATACTGT<br>TCACATAGTCAAAGGGCCAATGGGATTGGCTTTACGATCGCAGAAGCCCGGTGGGGTGCCAAAGAGTGAAACAGA<br>TTGTTGACAGTCCACGCTGCAGAGCCTCAAAGAAGGGATCTTATCGTGGAGGTGAATAAGAAGAACGTGCAGGCCCTG<br>ACGCACAATCAAGTCGTGGATATGCCAAAGTCCCACTGCAAGGAAAGACAGCCAGATAGCTCCCAGCACCAGCGTCTCCAGCC<br>ACCAGTTCCCAAGAAGAGCCCAAAGTCGCCACTGCAAGGAAAGACAGCCAGATAGCTCCCAGCACCAGCGTCTCCAGCC<br>ACCGGAGCCTGCACACTGCGTTCCCGAGCCATACAGGTGCTCCCAGTACTCACTCGCAGGAGCATGTATGAAACCG<br>GATCAGAACCGACAGTCTCGGGAGAACAGGACATCTCTGAGAAAAAGCCAGATCCTTTTAAATCTGGGCCAGTTGGATTTGACACAGACGGCCCGTTGAGGTCTGGAGAT<br>ACTTCCAGATTACCAGGAACCCATTTATATCGTCACATGTAATTGGGACACCAGTCCTCACACTGGTCTCTTGCCGTCCCAAAGCACACGCCAGCAGAATCGCACGG<br>GAATTAATCTGTGTGATGGGATGGAAATTGGTCTTTGCCGTCCCAAAGCACACGCCAGCAGAATCGCACGG<br>CCTCATCACACCAGTAGCCAGTAGCCAGCTCGGCCAGTCAACCAGCAGCGGCAGCACCAGTCAACCAGCAGCGGCCAGCACCAGCCAGTCAACCAGCAGCGGCAGCACCAGCCAGAACTCTCTG<br>AACACTGTGAGCTCTGGCAGCGACAACTTCGAGTCTCCAAATGCTGAGTCCTGACTAATGCTGACAAGCAGCAGGGGCACAACCTTCAGCAGGGACACAACCTTCAGCAGGGACACAACCTTCAGCAGGGACACAACCTTCAGGCTTCCGTGAGCGCTGT<br>GCTCCAGCCCTATGATGTGGAGATTCGGCGTCCTCAAATGCTGAGTCCTGACTAATGCTGACAAGCAGATTCTCAGTTGAGTTCAAGG<br>CCGAAGCGGGACAACTTCAGCAGGGACACAACCTTCAGCAGGGACACAACCTTCAGGCTTCCGTGAGCGCTGT<br>CATGCCCCCTCAGCAGGAGCAAGATTTCTACACTGTGAAATTGGAAAGAGGGCCAAGGATTGGCTTTAGTCTTCAG<br>ACCGCCAGGCTGCAATATAACATGGAATTCAGAGATCTTTATGTTCTGCCTTGGCAGAGATGTCCTGCAGAAAGATGTGGAAGATGAGG<br>GGGGCCAGGCTGCAATATAACATGGAATTCAGAGATCAATGTGAGAACACTCTCGGGCCATAGAACTGATCAAGAA<br>ATTGGCGATGAAATTCAGAGATCAATGTGAGAACACTCTCGGGCCATAGAACTGATCAAGAA | DEFLQIKSLVLDGPAALDGKME<br>TGDVIVSVNDTCVLGHTHAQVV<br>KIFQSIPIGASVDLELCRGYPL<br>PFDPDDPNTSLVTSVAILDKEP<br>IIVNGQETYDSPASHSSKTGKV<br>SSMKDARPSSPADVASNSSHGY<br>PNDTVSLASSIATQPELITVHI<br>VKGPMGFGFTIADSPGGQRV<br>KQIVDSPRCRGLKEGDLIVEVN<br>KKNVQALTHNQVVDMLIECPKG<br>SEVTLLVQRGLPVPKKSPKSP<br>LERKDSQNSSQHSVSSHRSLHT<br>ASPSHGIQVLPEYLPADAPAPD<br>QTDSSGQKKPDPPKIWAQSRSM<br>YENRLPDYQEQDIFLWRKETGF<br>GFRILGGNEPGEPIYIGHIVPL<br>GAADTDGRLRSGDELICVDGTP<br>VIGKSHQLVVQLMQQAAKQGHV<br>NLITVRRKVVFAVPKAENEVPSP<br>ASSHHSSNQPASLTEEKRTPQG<br>SQNSLNTVSSGSGSTSGIGSGG<br>GGGSGVVSAVLQPYDVEIRRGE<br>NEGFGFVIVSSVSRPEAGTTFE<br>SSNATLLTNAEKIATITTTHAP<br>SQQGTQETRTTTKPKQDSQFEF<br>KGPQAAQEQDFYTVELERGAKG<br>FGFSLRGGREYNMDLYVLRLAE<br>DGPAERCGKMRIGDEILEINGE<br>TTKNMKHSRAIELIK |
| SEQIDNO.:31 | SEQIDNO.:124 |
| GGAAATCCTGGAAGGATTTATATCTCCTCCTGTGGTTCTGTGGGAAGGACTCGTGCCGAATTCGGCACGAGTGGAGCT<br>GGCCTGAACTTTTGGACCTTGGTCTTCCAGTAGGAAATCAGTCTCTCAAGGCCTCCAAGCCTGAGAAAAGG | MASKPEKRVASSVFITLAPPRR |

FIG. 52

| Nucleotide Sequence (5'-3') | ORFs |
|---|---|
| GTGGCCTCCTCTGTCTTCATCACCCTGGCACCGCCAGCGCCGAGATGTAGCCGTGAGTGAGGAAGTGGGCCAGGCAGCTTG TGAAGCCAGACGCGCTCGGCCCCTGGAGATGCTTCCACAAAGACACCTGGGCCGCAGTGGGCAGGAGCCCAAGACCT GGACGCCCCTCTGGCAAGACCAATGCCTCACTCTCTGGAGACCTCAGCTCTCCAGCTCTCCAATGAGAGGATGCTCTCCCACCT CCTTCCCTGAATGAGGAGGAGACCTAGACCTGCTCATTCCCGCCTCTCCGCCTCTCGACTTGGAGCAACTGCACCTGCCCCCGC GCCTCCTGTCTTCTTACCAGGGAAGTCGTCTGTCGCCCAGACCCTGGTACCGATGTCTGTGGTTTCTGTCACAGCCTGTCTCCTCT CACAGGCTCCATCATCAGACCTGTCACACTTCCAGAGAGAGGATCTTCTACGGATGTCTACGGCCCAGTCTTGCCTCACCTGTCCCAGTTGGCTG CCAGAAGAGCCTGTCACACTTCCAGAGAGAGGCAGTACCACGCCCAGTCTTCACCTGTCCACCGCCAGTTGGCTG AGAGCTGGCTGTTGAGGCCATGAAGGAATGGGGCGCCCCCGTGTGCTACCAGGATACTCTGAGAAGTGTGGCAAGTGC GACAGAGATTCTACCAGAAGGAATGGGGCGCCCCCGTGTGCTACCAGGATACTCTGAGAAGTGTGGCAAGTGC GGAGAGGTGGTCCAAGAGCACGTGATCCGGGCCTTCCACCTGCTTCACCTGCGTGACCTGTGC CGGCTGCATCAGCGACGAGAGCTTTGCGCTGACAGCCAGAACCAGTGTACTGTGGCTGATTCTACAGGAAATTTG CCCCGTGTGCAGCCAGAACACTGGCTGAGAATCATCCCCGAGACGGAAGGACGCCTTCAAAATCGAGTGCATGGAAGG ATTTCCACGAGAACTGTTACCGCGCTGCAAGCCCTGTCACCTGAAGCGGAGTGCCTGCTGTCTGGTTGTGCTGCTGAACCTACCGACCAGAGCTGCTACCC GCCTTCCCTGACTTGGTTCCCCTCCTGACTTTCTTGAGACAGAGGCTTGGGCTTCACTGGGCACCAGCACACTGC TCAGCCCATAGTGTCTAAATGCACAGCAGCCTTGAGACAGGCCCTCACCACCAGCCCTCCCATCTCTAGTGCTGCC AGACTTTCTACCTCCTTCATTGACCAGGTCTCAGGATGATAACCTGTTCTCTGAAGTGCCACTCCAGCATGCTTAGCGCCACTGTCCAAAAGTATTTTTTGAGAATAT AAGTGTCTAGATTGTAGACATGATAGCTAAGTTGTTTGAGACTAAGCTAAGTTGTTTGAGACTACACACCCTTTAATCCAGACACACCCTTTAATCCAGCACTTGGATTTGGGGGGAGAGAAATCTTTGAATTTTTCTCTTTTTCT CTAGTCTGATCTACTACGGGTAAAATCAGTAGACCAGGTTCATTTCCAGCATCCCTGGTTCAGGGCTGCGAAGATGCTCGGTGATGAAGAGCGAGCT CCTTGCTCCTCCTTGCGGAGAGCTGGCGCCCCTTCCTTGGAACCTTGGAAACCTTAATGCAAAACATCAATTTAATCCTGTCTAATGCAAAACATCAATTTAATCTCAGTACTCTGTCCAGAGCCCAGAGACA | DVAVSEEVGQAACEARRARPWE MLPTKTPGAAVGRSPKTWIPSG KTNASLSGVTPQLSNGGCSLPP PSLNEEDLDLPPPPPSAYLP LPEEPPVLPGKSLISDLEQLH LPPPPPPQAPSKGSSVHPP PGHARPSEELPPPEBPVTLP BREVSTDVCGFCHKPVSPRELA VEAMKRQYHAQCFTCRTCRRQL AGQRFYQKDGRPLCEPCYQDTL EKCGKCGEVVQEHVIRALGKAF HPPCFTCVTCARCISDESFALD SQNQVYCVADFYRKFAPVCSIC ENPIIPRDGKDAFKIECMGRNF HENCYRCEDCSVLLSVBPTDQG CYPLNDHLFCKPCHLKRSAAGC C |
| SEQIDNO.:32 | SEQIDNO.:125 |
| GACACTTCCTGTCACCCGGGGCTTTGGGAAGCTTGAACTTCCAGTAAAACCAGCTTCCCGAAGAATGGACTCCATGCGGAC CATGGCCTTTTCCCTTTGTAATCTCGCCAGCCGTGCCAGCCTGGAACTGCACTTTGACATCTTACACTGAATGCAGAAGAAGACTCA GCTCTACCTCAGCCTTAAGGCTCCAGCTTGCCGGGTCCAGCTGCCGAGCCGCAGATAGCTGTCATTTCTCTGGCTGATGA GAGGCCACATCAGGATGCTTCCTTGTCCAAAAGATGCTTCATTGATGCCAGGATCGGGCACATCAGGAGGATCCATAGAAGGC CCCAAGTGCAGGATCCAGGTCAGGTCAACTGAAGCTGTCCATTGAATGCCAGGATCGGGTCTGCTGCCGCACATCATGAGAAGGC AAAGGCCCTGATGAGCAGGGAGCCTGCATCTGCGATCCCTATGTGAAGGTTTCTTTGATCCCAGGAAGACAGCCAGCTCCC | MERPHQDASLSKKDACTQTYPP RRRIRHAQVQDAGQLKLSIDAQ DRVLLPHIIBGKGLMSREPGIC DPYVKVSLIPEDSQLPCQTTQI IPDCRDPAFHEHFFPVPBEGD |

| Nucleotide Sequence (5'-3') | ORFs |
|---|---|
| SEQ ID NO.: 33<br><br>CTGAGAACTCCCGTTTTTGCTTTCTGTAGGCTTCTAAGGAGCAGCAGCCGGTGGCCAGGACCAAGTGTAGCTCAGCAA<br>CCTTTACAGAGACAACATGAAAGGAATCTTGCCCAGTCCAGTAATGAGAGCTGGGTTCCACTCCCATGCTCTGGCTAGG<br>TAGCTCACCCTTTCTAACTGTAGAGACCCAGCAGGACACAGAATCTCAAGGCTGTGGATTGGAAGGACGAGGCCATATGC<br>TAGAGAGTATTTGTCGGGTTAGTACCTTAAGGACGATTCTGTGCTCTTTGAGTTGCTAAAAATGAGCCATGCTGAGTTATCAGTCTAAC<br>ACCTGAGTCTTAAGTACCTTAAGGACGAGTGCATGTCCAGGAATCAGCTAACACCCAGCCAGCAAAGATTGGCTTGGTTCAAGGGTTGTGTA<br>ATGGTGGCCCAGGAGAGTGCATGTCCAGGAATCAGCTAACACCCAGCCAGCAAAGATTGGCTTGGTTCAAGGGTTGTGTA<br>AGGGAATGGGGTGACTCTGCAGCCAGTGATCAGCCCACGGGTAAATCGAAGCGGGTCTGTGCAGACAGCACACTTTG<br>GCACCACACTGCTGATTCTCTGCATCTGGACGAGCCGTTCTCTCCCTGATCAGCAGACCTCTGGGCACGTGAACATAACA<br>ATTTCACTTGATTCTCTGCATCTGGACGAGCCGTTCTCTCCCTGATCAGCAGACCTCTGGGCACGTGAAATCAGCTA<br>CCCACCCCGGGACGAGCCGTTCTCTCCCTGATCAGCAGACCTTCTCGGCTAGCTCCTGGCCCGACCTGTGAGCGCACCAT<br>TGGCTGATGGGAAGAGAAGGAAGGTACTCCTGCAAGTCAACAATTAATTGGTCGTCGTGGAGCTCTCAGCGTGCCCT<br>GGCCATCTTGCTTCATAATCAATGACAATTAATTGGTCGTCGTGGAGCTCTCAGCGTGCCCT<br>CGGTCTTCAGTCACCCCAGCTGTTCAAGAGGAGGAGCTCAGCGGCCTCAGCGTGCCCTCGAGAGTCATAATCACGGAACC<br>ACGCCGGCCCCCCTGCCACATAAATCACGCTAAGAAGCACACGCACTTTCTTGTCTGAAAGGCCATCTGTGAGATTGAATA<br>TGGTGTCCGGCCCCTTGAGTCTCCTACCCGTTCTGAGGAGCTGGGATCCCATTCTGTGTCTCCCACTCTGAGTCCTTGAAGCTCATCT<br>CAAAGTGCCTCTTTGAGTCTCCTACCCGTTCTGAGGAGCTGGGATCCCATTCTGTGTCTCCCACTCTGAGTCCTTGAAGCTCATCT<br>CTCATAGAAGCCCTCATTGCCTGAGTCCTTTGGCCCTTTGGGAGCTGGAATTATACAGACCTTCTGAGAATGGTGATTCT<br>TATTTGTACATGTCTTATTATTATTACTATTATTATTAATAATTATTATTTAAAATAAAAAAAAAAATAAA | SEQ ID NO.:126<br><br>MSVRFSATSMKEVLAPEASEFD<br>EWEPEGIATLGGPVTAIIPTWQ<br>ALTTLDLSHNSICEIDESVKLI<br>PKIEYLDLSYNGLRVVDNLQHL<br>YNLVHLDLSYNKLSSLEGVHTK<br>LGNVKTLNLAGMFLESLSGLHK<br>LYSLVNVDLRDNRIEQLDEVKS<br>IGSLPCLERLTLLNNPLSIIPD<br>YRTKVLSQFGERASEICLDDVA<br>TTEKELDTVEVLKAIQKAKDVK<br>SKLSNTEKKAGEDFRLPPAPCI |

FIG. 55

| NucleotideSequence (5'-3') | ORFs |
|---|---|
| GCTGAAGGCAATTCAGAAAGCCAAAGATGTCAAGTCCAAACTGAGAACTGAGAAAACAGAGAAAAGAAGGCTGGTGAGGACTTCCGGC | RPGGSPPAAPASASLPQPILSN |
| TCCCGCCTGCACCCTGCATCAGACCCGGCGGCTCCAAACTCCCCGCCTCAGCTCCCTCGAGCCTCCCTCAGCCTCCGATCCTC | QGIMFVQBEALASSLSSTDSLP |
| TCCAACCAAGGTATCATGTTTGTACAGGAAGAGAGGGCCCTGGCCAGCAGCCTCTCATCCACGGATAGTCTGCCACCCGAGGA | PEDHRPIARACSDLESIPAGQ |
| CCACCGGCCCATTGCCCGAGCCTGCTCGACTCCTTGGAATCTATCCTGCAGGACAGTGGCCTCTGATGATCTGAGGG | VASDLRDVPGAVGGVSPDHAE |
| ATGTGCCAGGAGCTGTTGCGGGCGTGAGCCGTGAGCCCAGAGGTTCAGGTGCTGTGCCTCAGCCACACTGATCCGCCA | PEVQVVPGSGQIIFLPFTCIGY |
| ATCTTCCTGCAACGGCAACTCCCTGCTTGCATTGCCTCTGGATTGAGGCTTGAGAACTCTGAAATGGAGGCCCAACAGGC | TATNQDFIQRLSTLIRQAIERQ |
| GGCCATTGAACGGCAACTCCCTGCTTGCATTGCCTCTGGATTGAGGCTTGAGAACTCTGAAATGGAGGCGCAACAGGC | LPAWIEAANQREEAHGEQGBEE |
| AAGAAGAGAAGAGAGGAAGAGGAGATGTTGCTGAGAACGCGCCAGACGCAGCAGGAGAAGAGGAG | BEEEEEEDVAENRYFEMGPPDA |
| GGGAGTGGCCAGGGAGAGAAGAGGATGAGGAGGAAGAGGAGCGCCTGGCTCTGAGGTGAGCCCT | EEEEGSGQGEEDEEDEDERAEE |
| GGGCGCGATGAGGACTTCCGTGCCTGACTTCGCTGAGCACATCCGCATCCTCAAGGTGCTCTGTGCTTCTGATCCACGTGCAAGGCA | ERLALEWALGADEDFLLEHIRI |
| GCATCCGCCAGTTCGCTGCCTGCTTGTCTGCTCATCCCGTCGTTTGTCTTCTGCGTCGATCGAGACTCAAGA | LKVLWCFLIHVQGSIRQFAACL |
| GGCCAGCAGCCAGCACATCCTCATCCCGTCGTTTGTCTTCTGCGTCGATGCGACCTCACGGAGTTTGGCTTCCT | VLIDFGIAVFEIPHQESRGSSQ |
| CATGCCCGAGCTGTGTCTGCTGCTCAAGGTGCGGCACAGTGAGAACACGCTCTCATCATCTCGGATGCTGCCAACTTAC | HILSSLRFVFCFPHGDLTEFGF |
| ACGAGTTCCATGCGACTTACGGTTCTTGCGCCAGCTGCGTGCAGGGCCCATGGCCCCATCCTCAGGAGCGCAGCAGC | LMPELCIVLKVRHSENTLFIIS |
| CACCACCACCCCGTTCCCTGAGCTCTGGTCTACAAGCGCATGGTCCAGAATCGCATTATCAGGCAATATCGAAT | DAANLHEFHADLRSCFAPQHMA |
| CTGCTTCCCTGTGCACGCGTGTGCTCGGCAGTGAAAGCGCTCTGCCGGCCGCTCCTGCGTCCCATCCC | MLCSPILYGSHTTLQEFLRQLL |
| GGGCCAGTGCACGCTGTGCTCACATCCCAGCATCTCAACGTCAAGCCCGACTTCAACCCCCATGCCAAATCGAGGCCCACAA | TFYKVAGGSQERSQGCFPVYLV |
| TACTGGCTGCTGCCCAACCGCAACACAGCTTCAAGCTTACAGGCCATGTCGAGTCGCTGCCATCCGAGTCCAGTGCACCC | YSDKRMVQTPAGDYSGNIEWAS |
| CTGCCCGCAACCGAGGGGGTGCCTTCGCTGATGGCCATGCGTCGAGTCGACTCAGCTGCTTCGTTCTTGTTCGTCTTGTGCTG | CTLCSAVRRSCCAPSEAVKSAA |
| AGCCAGCCCGAGCTGTGCCTTCGCTGATGGCCATGCGTCGAGTCGACTCAGCTGCTTCGTTCTTGTTCGTCTTGTGCTG | IPYWLLLTSQHLNVIKADFNPM |
| CCCACCAGAGAATCCTTCAGCTAAGCCCAGAAATCAGCTCTACACATCAGCTGCGCCCGCTCGAGACTGTGTCATCTC | PNRGTHNCRNRNSFKLSRVPLS |
| CAAGAATCCTTCCGGCTCCGGCTCAGTCCCACCAACAGCTTCAGTGCCAGCCCGCCTGCTACAGGAGAGACCCCAG | TVLLDPTRSCTQPRGAFADGHV |
| CAGACGCTCCGGCTCCAGTGCAGTCCCACCAACAGCTTCAGTGCCAGCCCGGCTTGGCTCCAGATCTGGCT | LELLVGYRFVTAIFVLPHEKPH |
| CCTGTACAGAGGGCCCCAGCAGGCCTGAGGTCTAACTTCAGCAGAGGCTCAGCCCGAGCAGGAGGCTCCGG | FLRVYNQLRASLQDLKTVVISK |
| GGCTCCAGCAGACAGGCCGGCAGGAGGCTCCAGCCGCAGAGCTCCGGCAAACCAGGCTTCTGCCAACCAGGTTCG | NPSAKPRNQPAKSRASAEQRLQ |
| CCCAGCAGAGACTCCAGCTTCAGCAGCAGAGGCCCGCTCCAGCACGGAGGCTCCAGCAGGGGGTCC | ETPADAPAPAAVPPTASAPAPA |
| GAGGCTCCAGCTTCAGCAGAGGCTCCCGCTCCAGCTCCCCAAACCAGGCTCCTGCTCCAGCAAGAAGTCCCTGCCAGT | EALAPDLAPVQAPGEDRGLTSA |
| CGCTCCAGCAGGGGGTCTAATCAGTCCACATCGAAGAGAATCAGATCCCTTCTCACTGCCAGTATGCCAATGAGGAGCTGAG | EAPAAAEAPAAAEAPAAAEAPA |
| ACCCAAGTGAGCGGGCCTAATCAGTCCACATCGAAGAGAATCAGATCCCTTCTCACTGCCAGTATGCCAATGAGGAGCTGAG | AAEAPAAAEAPAAAEAPAPAEA |
| CACATTGCCCCTGTGGTCATCAGTGTGTTCTACAGACCCCCGCTACTTCTCGTTGTTGTTGTTCACCTGCAGCTCTAGAGCTGAG | PAAAEAPASAEAPAPNQAPAEA |
| GCAAGCTCCAGCAGAGACTCCAGCAGTGCTGTCTACAGACCCCCGCTACTTCTCGTTGTTGTTGTTCACCTGCAGCTCTAGAAGG | EAPASAEAPAPNQAPAPARGPA |
| CTGTGTACTTCATATGCATGATGTCCACGTTCCTTCCGGCTTGGCCTTCAGTGCTTGTGTTGAAACTGACTTGACCTGCAGCAGCAGCCCT | PARGPAPAGGPAPAPAEA |
| GACTATAACAACAGTCCTTTCCACGTTCCTTCCGGCTTGGCCTTCAGTGCTTGTGTTGAAACTGACTTGACCTGCAGCAGCAGCCCT | LAQAEVPAQYPSERLIQSTSEE |
| TTTCGACCAGTACTTCCGGCTCCGGCTCCTCCCCGACGCAGGTGGTCACGCCTTTGACTCGGACAGCTACCCTGACGC | NQIPSHLPVCPSLQHIARLRGR |

FIG. 56

| NucleotideSequence (5'-3') | ORFs |
|---|---|
| ACTGCTTCCTCCAGCATCTGATGCTTGTGCTGTCCTCCCTGAGCGCACACCCTGCCTGAGCCTGTTGACAAGGACTTC<br>TACTCAGAATTTGGGACAAGAATACAGGGAAAATGGAGAACTATGAGCTGATCATTCCAGCCGCGTCAAGTTCACCTA<br>CCCCAGTGAGGAAGAGGTTGGGACCTGACTTGTCCCACAGAAGATGCTGATCCTGCAAAGAATCCAGCCCTCA<br>GCATCTTACTGTACATCCAGGCCTTCCAGGTGGTCACACCACCTTGGGCGGGGCAGGGCCCCACTGCGCCTAAGACG<br>CTGCTCCTGACCAGCGCCGAGATCTTCCTGGATGAGGACTACATCATCCACTATTGGACGGGTGCTCATGGCTACCCT<br>ACCGCAGAGGGACAGATACCGGCTAGACGATGGCCGCCGGGTCCGGGATTTGGACCTGGGTGCTCATGGCTACTCCT<br>ACCCACACAGCCCCTCACTCTCTGTTTTTGATGACACACAGGGTCATGGGAGTGTCACCCTGCTGACCACTCTTGGG<br>GAGATGCCAGGTGGTCCTGGCAGGGTTGGCCAGGACTACAGTGGCAGGTGTTTGTCCCAGTGCCGAGAGCCG<br>AGAAAAGCTCATCTCACTGCTCGCACGACAGTGGGAAGCTCTTTGTGCAGGAGCTCCTGTGAGCTCACTGGCTAGT<br>GCACGCCATAGCAGCCCTGGCCTCTGCCATGCCGCTCAGCCCATGCCAGTCCTGGTGAAGGCAGGGAAGCGGGCTTCTCGT<br>TCTTTTTAAGGTCTTTCTCCTCTCCCTTGTTCTACATTGTTTTGTCGTGATTGATGCTGTTAGCGTGGGCGTGT<br>GGACCTGATAACCCCACGTCCTTTTCTAGCAGTGTTAAGTCCAGTCCTTCGTTGCTGTTTGCTCATTGTGGGGTGCC<br>GCTGCTAATTACAAAGCTGGTAGCAGAGTTACACAGGCAAGCTCCCACGTTGTGGGCTTTTCAAAATGGAGGCCTCTC<br>AAGTCCAGAGCAGAGAGCCCTATGGGAGTTCCCAGTCCATGGCCTCCAAGAGAGCCAGTACAGGGACCTAGAGCTG<br>CCAGCACCAAGTATAATTCCTGTTGCCTACGTTCTATTCTAATAAAATGGAGTTTGACACCAAAAAAAAAAAAAAAAA<br>CTCGTGCCGAATTCGGCACGAGGAAA | ALIDLFHNSIAEVENEELRHLL<br>WSSVVFYQTPGLEVTACVLSS<br>KAVYFILHDGLRRYFSEPLQDF<br>WHQKNTDYNNSPFHVSQCFVLK<br>LSDLQSVNVGLFDQYFRLTGSS<br>PTQVVTCLTRDSYLTHCFLQHL<br>MLVLSSLERTPSPEPVDKDFYS<br>EFGDKNTGKMENYELIHSSRVK<br>FTYPSEEVGDLTYIVAQKMAD<br>PAKNPALSILLYIQAFQVVTPH<br>LGRGRGPLRPKTLLLTSAEIFL<br>LDEDYIHYPLPEFAKEPPQRDR<br>YRLLDDGRRVRDLDRVLMGYYPY<br>PQALTLVFDDTQGHDLMGSVTL<br>DHFGEMPGGPGRVGQGREVQMQ<br>VFVPSAESREKLISLLARQWEA<br>LCGRELPVELTG |
| SEQIDNO.34 | SEQIDNO.:127 |
| GCGTCAGCTCTGAGCCGACTTTACTGTCCCAGAGCCTTAGACTGCCCGCCGGAGGACGTGGAGGACGAGGCAGCCGCG<br>GGAGAGACAGCTGTGGGGCCCTGGCAGCGACCTCGCGCTCGTGTACCCAGAGCCATCCAATCGGTGTGCGC<br>CCGCCCCCGCCCCCTGCCCGGACGCGGGGCCGGCTCGTGTCTTGTGGTACCCAGAGTCTGCGCACGCTGAGGTGCCCCTGCGC<br>AGTGAGGACCTGGGACTGGGCCTCCAGCTGGCCATGCCAGAGCAAGAAGATTGCAGGATCTGTGCCGG<br>CCGCAGCTTTGGCCGATGTGTGAAACCAGCGCGTTGGATCTTTCATACCGCGTCCAACCTCCAGTTCTGCTTTCGCACGTCCT<br>GAGCTGTGTGAAAGATGTCTCTGATGGCAAAGCCGAGTTTGCTTGTAGCAAGTGCGCTTTCATGCTCGATCGATCTATCGAT<br>AGGCAAAGATGTCTCTGATGGCAAAGCCGAGTTTGCTTGTAGCAAGTGCGCTTTCATGCTCGATCGATCATCTATCGAT<br>TCGATACTGTCATTGCCAGTATGCCAGATAATGATGACTCTGGCGAGGAGAACAAGGCGGGAGTGGGACAGTAGACAT<br>TTCCGGCTTGCCAGATATGAGTACGCTGCTCATGCTCGTCATGCTTCCAAGAGACTTTGCCTATTCGAAGGGCCCGAAACCGACCCAGGAGAGATGTCGGTTGT<br>ATGAGGATCAGATTAACGACTCACACAGCTGTCATGCTGACTATGAAGCCATTTGTAAGGTGCCTGAAAGTGCCCAGAAGTGGCCCACCAGAAGTGGCCCAGAAGTGTTCTATGC<br>GCAGCTCTGCGGGTGCGGATTCGACCATTGTGCACTGAAGAACCGGCATTGTCAGAGGTTGGGCCACCAGACTTAGCAAGCA<br>CCCCTCTAGCAGGTGGTCTACCAGCATTTGCACTGAAGAACCGGCATTGTCAGAGGTTGGGCCACCAGACTTAGCAAGCA<br>CAAAAGTACCCCGAGGCATGGAGAAAGCATGAGGAAGGACACCAGGTTCCTCCGTGAGTCTCTGGATGCTAGTGTCCAG | MKEICRICAREICGNQRRWIFH<br>TASKLNLQVLLSHVLGKDVSRD<br>GKAEFACSKCAFMLDRIYRFDT<br>VIARIEALSLERLQKLLLEKDR<br>LKFCIASMYRKNNDDSGEENKA<br>GSGTVDISGLPDMRYAALLQED<br>FAYSGFECWVENEDQINDSHSC<br>HASEGPGNRPRRCRGCAALRVA<br>DSDYEAICKVPRKVARSISYAP<br>SSRWSTSICTEEPALSEVGPPD<br>LASTKVPPDGESMEEGTPGSSV<br>ESLDASVQASPPQQKDEETERS<br>AKELVKCDYCSDEQAPQHLCNH |

| NucleotideSequence (5'-3') | ORFs |
|---|---|
| GTCAGTAGCAGCAAAGGAAGCAGCTGGAGTCTTCCTACTCCCTGCACGGACCTAGTTCTTGAGCTAACTGAGGTCTTGA AGCATACTGCCACATCTTAAATCATTCCATTTAATTTCCCATTCATACTGCTCTCTTCCCTGGCCTGTCCCTCATTCCTTT ACCCCTTCCATGGGCCAATAAAAGTTTACTCCCCATCTTACCACCCCCGCCACAAGTCCCACGTCATGTCATCAAATGCA TGTGTGTGTATTATTTTTGCCATCCAATCAAATCCTGTTCTTTGAAAGCAATTTTAATCAAATAAAGAATCAAGTATG AGTTTAGGTTTAGAAGAAGTAGAGAGTCCCGTGAGAGTGACTCTGGGAGGGTATAAAAATTTGCCCTGAAGGCCT CAGAACTAGACAGGAGGGTGTGGGCTGAGCTCAGGAGAGCAGAGACCGTTAGTGTTCCAATAAAATTTGCCCTGAAGCCT CTTCAGAGAGTTGACTGTCTAGGGAAAGATCAGAAGTCAGATCAGTGACAGCATGGTCTAGTCCATAAAAGCCTATACAACTC ATGTTCTTCACTGCCTAGGGTTCTTCAAGCCTCAGGCATGCCTTTAGTCAGAACATGACTTTAAAAACCGGTTTCCC AAATCAGAATCCTCTAGATAAAAATCATCTCTATGTGATATTTTCCCACCTCCTTTTTTTATTATTTGGTTTGTT TTTTTGGTATTTATTTGTTTGTTTGAGACTGAGTCTTGCTCTGTGGCCTGGCCTGAAATGCACTGGGTAAACCAGACTGGCA TTGAACTCACAGAGATGAGCCTGCTTCTACTTTGGGTGCTGGAGTTAGAGGCATGGCTGGGATTAGAGCTGTCAGCAT CCCCCTTAAGACAATAGTTTCCAGATCCCCAGATCAGGGGAAGTATAATTCTTGATGTCTCATTAGAGGTGAAGCGG GTGGCGTCCTTCATTGACCTCGCTTCCATTCTAGCATCTTAAATGTAGGTTTTACTCACCCTCTCGCTTTCTTGGAGAGC GTTCAGGTCACTCAGAAGGAGGCCTTAGATCTTCATTTCCTAGTGCTGAAGTCCATGTCAGTAAGACGATGTGAGTGCTCAT GTGGGGAGGTGGTAGATTGTTCATTTCCAGAACCTTTCATTGAGCTTCGTGTAACCTCAGCTGTGAAATCTTCTGATGAAG CTGAGCCCCCTTCCCAGAACCTTCTGCCCAGAGCTACACTGAGCTTTCATTTGACATGGCATGTTGAAGTGGACATGAAGA ACACTACATCCATGTGTATCCAGCTTGACATGCCATGGCATGTTGAAGTGGACATGAAGATCCAGACATTTGAAATCTTCTGATGAAG AACTGATGTGTATCCAGCTTGACATGCCATGGCATGCCTGAGCTTACAACCTTACAACCTTTACAACCTTTAGGGGAAAGG TAGTTCACAAAGATTGATGCCATGGCCATGCCCTTGTCATTGAGCTTACAACCCCATTCTAGTAACCCCATTCTAAGATATCTAA ACTTCATTATTAATATTAAGATATAGATAGAAGATAGAAGCAGACAGACATAAATGAGTTGAGCTATGAGCATGTCAAACAATTAAAG GGCCTGCCTGAACAAACCTTATGTAACAAGCAATTAGGAAATGTGTTACTCAACTTGCTTACTCAACATGTTACTCAACAAGTTCTGCAAAGC ACCAGGCCTGTTAGTGTCATTACAAGGCAATTCTAGTAATCTCTAGGGTTCTGAGGCCTCACAGTGATTATAATAATGAAGTTAATAATTAGT TGCTATTAAGTTTCAACCTCTCAACAGAGTAGGTTGATAGACAAGTAAATAAGAGTTTTGTTATCAATTCCATAAATGTGACTAT GCAACTGCCAACCTCTAACAGAGTAGGTTGATAGACAAGTAAATAAGAGTTTTGTTATCAATTCCATAAATGTGACTAT AAAATCGTACTGACTTTCTGTCCTGAATGCTAGAATGAAGGTGGAGACCTTGCTGTGCTGGAGGAATGCTTGCCC ACAAGCTTGTCAATAATTGACACCTTAGTACCGAACACAGTTCTGATGAATTGTACAGCGTGAGCCACAGGTGATGG TACTATGATTACACGTCATTCATATCATAATTGATTTAATATATTATAATAAATAAACTTAGTTTAAAATAATACAATTAACAAAAAAAA AAAAAAAAAAAAAAAAAAAAA | RSRLNEALQAERQLYSSLVKFH AQPENSERDGTLQVELEGAQVL RTRLEEVLGRSLERLSRLESLA AIGGGELESVQARHKHAF |

| SEQIDNO. 35 | SEQIDNO.:128 |

| NucleotideSequence (5'-3') | ORFs |
|---|---|
| GGCAGCGGAGTGAGCAGCACCCCGGTTCCACTGTGCCGCACCCGACAGCCTGAAGCCAGCATGGAAGGACAGCCTGAGTGCG CCGATCAGCAGTATGAGTGCGTGGCGGAGATCGGCGAAGGCCTATGGGGAAGGTGTTCAAGGCCCCGACCTGAAGAAC GGCGGCCCGCTTCGTGGCTCTGGCCTGGAAGCGCGTGCGAGTGCAGACCAGTGGTGCCATGCCGCTCCACCATCCGCGAGGT GGCGGTGCTGAGGCCACCTGAGACCTTCGAGCACCCCAACGTGGTCAGGTTGTTTGATGTGTGCACAGTGTCACGGACGG ACAGAGAAACCAAGCTTACACTAGTGTTTGAGCATGTTGATCAAGACTTGACCACTTACTTGGACTTTCTTCATTCTCACAGAGTAGT GGCGTACCCACAGAAACCATAAAGGATATGATGTTTCAGCTTCTCCGAGGTCTGAGACAGATAAAGCTGGCTGACTTTGGCCTTGCCCGA GCATCGTGATCGAAACCGCAGAACATTCTGGTGCGACAGCAGTGGACAGAAGTGTACCCAGAAGTCCTGCTCCAGTCCAGC TCTATAGTTTTCAGATGGCCCTTCTGGAGTGTCGTCGGTTGACATATCTTGCTGCATATTCCCAGAGAAATGTTTCGCAGAAACTTTTCGTGAAG TATGCCACCCCTGGATCAACTAGGACAAAATCTTGGACTATCATTGGACTCCCAGGAGAGAAGACTGGCCTAGGACGCTGGCCC TTCCCCGGCAGGCTTTTCATTCAAATCTGCTCAACCCATCGAGAAGTTTGTGACGAACTAGGCAAAGAC CTACTTCTGAAATGCCTGACGTTTAATGCCTAAAAGGATATCCGCCTAAAATCACCCGTACTTCCAAGA TCTGGAGAGATACAAGGACAACCTGAACCTCTCACCTGCCATCCAACTGAAGCTCTGGGAGCTGAACACAGCCTGAGGTT CCACGGGGATGCCCATGAGCTCGTCATCTGAACACATTGGCGGCGTGCCCTAACGCCTCCAGAGCAGTTGA AGATTGCTGGCTGCCAACCTTCGGCTGCCAGCTTCTGGGTGGGCTTCTGCCCTTACCAAGGAAACCACCTAGTTTACTGTT CAGAGATCAATGCAAGGGTGATTGCAGTTGAATGTCAGTTCGTTTCATCCTTGTTGTTTCTAACCTTGAATGCGCAGTGTAGG GAAAACTTCCAGGCCAGCTGAGTTGCTGTGTAAGAGAGAAGAGTAGTCCTCCAGAGTGTCCAAGAAGCTTCAGGAAGTGATTCACAA TGGAGTCTTGTTAGGAGGCGGAATACCATCTAGCTGTTCTCCAACCGGAACCGCAATATTTTTTAAGAGACTTTTAAGCATACATCTTCTATTTACT AAGGTTAGATGCCACACAAAAATGTGTCCCAGGCGAACCGCAATATATATAGGTGAGTGTACCTCAGATAGGTTTTAAAGATAGAGAGCACCTGTT CTTTGAAAGCTGAACTTATTACTTGCACACATTTAAGGAGTGTACCTCAGATAGGTTTAAAGATAGAGAGCACCTGTT CTATAAGTATCTTATTACTTGCAATACAATTCTTCACGTCTTGAGGCTCACCATTCCGAAACCCTAACAGTATCCC TTTCTGGTGTGAGATGTTATCATTTTCTTCACGTCTCTTCCACCAGTCAAGTGCCTTAGGGAATCACTTCCTGCT CTGACTAGAGGCGGAATACCATCTAGCTGTCTCCACCACACCACCTGCCATCGCCATTGTGCTGCCTTGTGTAGTGC GAAGCTCAACACCAGCACTTCAATTCATTTTCCTGCCACTGCCTAGGCTAACGACAGATGCCCAGTGCCCCAATC CCACACCGCTTGCACGCTTACGTCTCTTTCACCGAAATGCTTTGGGCTAGGCTCACATTCCGAAACCCTAACAGTATCCC CTTGTGCCTTTGTAATACAGTCTTCCCCGCGCAGCTGAGGTCACCTAGGCAGTGAAGAGTGCTTGTTCTGTGT ATAGACTACTACCGACTGTCACTGCCTACTTTTAAGTGTATGTTGTCAGTGTAATGTCTGAGGAAATGTCTTT TCCTCTCTTCTAGAGATAACTACTACTGTCATCTCTCTGTCCGCAGGATGTGTTTCTG | MEKDSLSRADQQYECVAEIGEG AYGKVFKARDLKNGGRFVALKR VRVQTSEEGMPLSTIREVAVLR HLETFEHPNVVRLFDVCTVSRT DRETKLTLVFEHVDQDLTTYLD KVPEPGVPTETIKDMMFQLIRG LDFLHSRVVHRDLKPQNILVT SSGQIKLADFGLARIYSFQMAL TSVVVTLWYRAPEVLLQSSYAT PVDLWSVGCIFAEMFRRKPLFR GSSDVDQLGKILDIGLPGEED WPRDVALPRQAFHSKSAQPIEK FVTDIDELGKDLLLKCLTFNPA KRISAYGALNHPYFQDLERYKD NLNSHLPSNQSTSELNTA |
| SEQIDNO.36 | SEQIDNO.:129 |

| NucleotideSequence (5'-3') | ORFs |
|---|---|
| CGACAGGGCGGCGGCGGGGGTGAGTGCGAGGCGAAGCGCAGAGCGCGCAACTCTGAGGAGGCGATGTTAAGTCAG<br>AGTACAAGACAGAAAATGTCCACTGAACGAACTTCATGACAAACCTGTCCACTATTCAGAAAATAGCCCTAGGAA<br>TTCCAGCAAGTGCAACAGTGCCTACACTTCTGTATCGTCAGATATAGGGAAAGCAGAGAAGAGATTGACATTGTTGAA<br>GAAGATGACATTGAGATAGAGATGCGAGTGCCGCGGAGTCTGTGAAGCTCATCATTGGTCGACAAGGAGCCAATATTAA<br>ACAGTTGCGGAAACAGACAGGCGCGCGATTGATGTGACACAGAGGATGTAGGCGATGAGCGAGTGCTGCTTATCAGTG<br>GGTTTCCTGTTCAGGTGTGCAAAGCCAAAGCAGCAATCCATCAGATTCTGACAGAAAACACCCCAGTGTTTGAGCAACTC<br>TCAGTCCCTCAGAGATCTGTGGGCAGAATCATAGGGAGAGGCCGGTGAGACGATTCGTTCTATCGTAAGGCTTCTGAGC<br>CAAAATCACTTGCGACAAAGAATCGATACTGGAGAAAGTTTCAGAAGATGAAGAACTTCAGGAACACAGAAGAAG<br>TGGCAGCAGCTAAGCATCGATACGTCCACGAGAAGCAGCCAATCAGTGTGAGAAGAGGAAGTGAGGTACCTGGGAGCTGTGAGCTGAGAAGCAGCTTT<br>ACCAGAGTCCCACGAAAGCAGCCAATCAGTGTGAGAAGAGGAAGTGAGGTCCTGGTGAGCTGAGAAGCAGCTTT<br>ATGGAAAAAATACCAATTCTAGCATGGACCAGTCACACCCCTGAAGTTCCTCCGCAAAGGACCTGGAGCTGATATGTTG<br>TTGTAGGACCAAAAGAAGGTTCCCAGTCCTGACTTCAGTTTCATGCTGATGAGTACCTAGATAACTTGTCAGATGACCAGTCCAGAG<br>ACGTCCATGTTGAAATTCTCGGATCCCAAATCATTGGTTCCCGCAGCCTGACTTGGATAAACTTGTCAGTGAGATGACCAGC<br>ACACCCTAATCACTTCTCGGATCCGAAGACTGTGTCGCCAGAAATGAACTTGACTGTCGCATGTGAGAAAATGAACTTGGATGAAAATGAAC<br>ACTATGAGAATACTGAGCCCGGGTTCTTGGGAACTTGGAACTTGGAGAAATGAACTTGACTTGTTGACTTTGGAGATAATGGAGA<br>TGGTATCGAGCCCGGGTTCTTGGGAACTTGGACTTCTGTTGACTTTCTGTAGCTGTGAGCAGCCCTGAC<br>TGCCACTAAGGATCTCAGGGCTCTCAGGGCGCGATGGAAGAGAGTCTGTAAGGCTTCTAAGCAATAGAATGCAGTCTGGCAC<br>GGATTGCCCCCCACCAGGTGAAGAGTGGGAAGAGTCTAGATGAGTTTGACAGATCACTCACTGTCTGCTGACTGGAAGC<br>CCCCTGGTGCCCAAGATTTCTAGCTATGTCCAAGATTCTCAACTGGCAGTGAGATTCTCCTGAAGACATGAAGAACATGAAGAAACA<br>TGAGAAGAAACTTGATATGGGCTAGAATTAGTTCGTAAAGGTATGCAGTGATGTTCAAGCATACTCACTGAAAACAAAAAG<br>GAACTGTCCAAATATGTTGAAGGACATGCCCACAGAACATGAGGATTCTTCAGCCCTCTATGTCTCGGTGATGATAAACCTTGA<br>AGCCCTGAAGAGATGGCCACATACCCTGTCCTGCCAGCTGTCCAGCTTGTCAGAAGCTGCCTGCTGTTGCTCTGCGAGAGGAGT<br>AGACGACTTATCAAGCAATCCATGAAGAATCTGGGCTGCAGTGCCTTGGTGGCTGAAGCTAACGAGAGCGATGAGCAGCTTGCCGAGAGCTTCTATGTCCAGTTATCCTTCA<br>CTATGATAGACAGAAAGTAACGACGCAAATGAGAGACGAGATCCATAATCAGGTTCCAGAATCCAAATCAGTTTTGTTTCATTGTTCATCTTTC<br>GATCTACCAGAAGATCCATGAAGTCCTTTACTTGCCGAGGCAAATGAGAGAGCAAAATGAGAGACAGATTCTCCCAGCTTCCTGGTCCTCCCTATCTTTC<br>AATGTTGAATGCTGTATAATTCCCAGCTTCCCATATGAGCCAAGGTTTGGGCACTCAGAAGCAGACGCCAAATGCTCCAGTTTATGCAT<br>GGGCTATGTTTTGAGCCTGTAGTTATAGGAGTATATTGGTGGACTCAGAAGACTGCAGTTATCAGAGAGATAAGGCAAAATCAGCATAA<br>TCAGGTGACTGGTAGTTAAAGCCTCATAAGGGAAGAGTGTACTACCTCTCACCCACAGTTCGCCAGGGTTATTGGAGATGGTCCT<br>CTATATTAAAGCCTCATAAGGGAAGAGTGTACTACCTCTCACCCACAGGTGTTAAGGAAATGTTATTGGAGATGGTCCT<br>CCAGCTATTCTTGTGAACTTCAGTTAAATACAACTAGAAGGGAGAAGTATCTTAGGAAAATGGTAATCAAAATTGGGGAAATGTGTTGCT<br>ATATGTCGTATACACAACTAGAGAGAAACACATATCTAAACACATACTCAGTCACAACGTGGGAGTAGCCTGTGGGTAAAGTCTCTGA<br>AATAAAGTTCTCAAAATTATTGCCAGCACTCACATAACGAAGCATCTTGAGACAAATGTCCTTCCCATACAAGTATTCACA<br>GTAAGCCTTTGGTAGTAATTGCCAGCACTCCACTACTCCCTCAGAACCATAACCAGTTTAGCTATTAGCTATATACAAGTATTCACA<br>CTCTTCCCGTAAGTCACTGCAGAAGTCCAGTCCAGACCATAACCAGTTTAGCTATTAGCTATATACAACCTACTT | MSTERTSWTNLSTIQKIALGLG<br>IPASATVAYILYRRYRESREER<br>LTFVGEDDIEIEMRVPQEAVKL<br>IIGRQGANIKQLRKQTGARIDV<br>DTEDVGDERVLLISGFPVQVCK<br>AKAAIHQILTENTPVFEQLSVP<br>QRSVGRIIGRGETIRSICKAS<br>GAKITCDKESEGTLLLSRLIKI<br>SGTQKEVAAAKHLILEKVSEDE<br>ELRKRIAHSAETRVPRKQPISV<br>RREEVTEPGGAGEAALWKNTNS<br>SMGPATPLEVPLRKGGGDMVV<br>GPKEGSWEKPNDDSFQNSGAQS<br>SPETSMFEIPSPDFSFHADEYL<br>EVYVSSEHPNHFWIQIIGSRS<br>LQLDKLVSEMTQHYENSLPEDL<br>TVHVGDIVAAPLSTNGSWYRAR<br>VLGTLENGNLDLYFVDFGDNGD<br>CALKDLRALRSDFLSLPFQAIE<br>CSLARIAPTGEBWEEEALDEPD<br>RLTHCADWKPLVAKISSYVQTG<br>ISTWPKIYLYDTSDEKKLDIGL<br>ELVRKGYAVELPEDMEENRTVP<br>NMLKDMATETDDSLASILTETK<br>KSPEEMPHTLSCLSLSEAASMS<br>GDDNLEDDLF |

| Nucleotide Sequence (5'-3') | ORFs |
|---|---|
| ACACTGTAAGAGAAGGCCTGTACTAGGGTTCTAGAAGTAGTCTTCACTATAAACTTACTTCTAGTGTCTTTCA TTACTGACAGTAGTGCAAGACACCACTGAGACTTGTGACAGTACTTAGAGAATTAAATACAAAATGCATAGCTTAACGA ACTTTAGGAAACAAGGCAAGTGAACTGGAAATCTAAACTGAACACATGATGCCTTATATAGCTTCTCTAAACTCTA GTATTAGTAGCCATGCCTGGTGTCCCAGACCTATACCCTTTGAGGCTAGTGAGAGTGAAAGTTAAGGCCAT GCCTAAGCAACTTAGTAAGATGCTATCTCAAAAGAGGCTAGGGGTGTAGCTAGTGGTATAGTGTAGCACTGTGTCATT TGCAGCATGCCAAGTTAGCAGAAAGACATCAAGGAGGAGCAGTTTGAGCATCTCTTTACTCTAGAGAACCTAGACAGG CCCCTATTAATGTTCCAGGTTCTGACTGTAGTGAACCATTTAAGTGTGTTCAGCCAGCAGGTGAGTTACTACACAACAG ACTCTGGAGGCCATTTGTCTCTAGTTTCCTCCGGTGTCTCTTTTCCCTGAGTTAGAGACCTGTAGTTAATTGT GTAAAAGCCTATTTAAACCAATTGTGTGGGACTGAAAGATGCTCAAAGTTAAGAACACTGACTGCTCTGTAGAAAA CCCAGGTTCAATTCTCACCACCCACATGGTGACTCACAACATCTTTTAATTCTAGTTCTAGGGGACCTAGTTCTCTT CTAACTTCTAACCAGTATGCATATGGTATACATATACATGTAGGCAAAACATTCATCTACATGTCTAAAATTTGAGA ATAAAATTTTGAAAATAACATATGTACATACCTAAAAAAAAAAAAAAAAAAA SEQIDNO.37 GGCCTCCGGAGCTTTGCTTGTCTTCCGTAGGTCAAGGCGTTGGTTCTCTCTCTCTTTTTTTTAATAAATAAAGTGG AACCTGACTCACGACTCAGAGACGCTATGACTTGCTCAGTTGCTCAGGGTCTCAGGGTCTCCATGGCAACGGAGCCATCCAGAAAG CTGACAGTCCCAACTCAGAACCTTGGAGTCAGAGAAATCACTGTCTTCAAGACACAAGAGAGGCAAAAGTTCTGAGC CAGTATTAAAGGGCACAAAACCGGACTGAAGGGCTGAGGCTCAAGAGATGGCTCAGCGCTTTAACAGGATGCTGTGTTCTTCCAGGGATCCT GGTTGGCTCTCCCAGTAGTGGTACTACATCTGAAGTACAGTTTAACAGGATCTGACCCCTGGGAGCATC ATGTACATATGTGGCTACTGATCCATGCAGGCAAGACACTCATACACTAAAATAAATAAACCTGGCTAAACTTAAAGACT CACCACAATCAAATGTCTAAAATATTAACCTCAGATTGATTATAGCAATTAAAAAACCCAGAAGTGTCTAAGATAACCTGGAAGCTAACT TATCCATAGGAATATTTAACCTCAGATTGATTATAGCAATTAAAAAACCCAGAAGTGTCTAGAAGTGTGAAAGTGTCTGATTAA AGTGACCTCAGGTTCTGAGAACTTATGCAGCATCTTCTGTGGTGATGATGTCGAAATGCATGGTGCATATAATCATCAAGCT CTCAGCCAGGTTGGGATCTGAATTCCTCAGCAGCTCTGGAGCATCATGAGTAAACCAGAGGACGTTAGAAATGGCTAGGAGTATTTCTGAAGGAA GATTCTTTGGATTCTGATTATGGGAGAGAGTGGGAAAAACATGAAAAGTGTTACTCACCAAAGCAACTATGATCTTATTTATTAAA CATGTTGACACAGCATATTATTGTATACACCCTGTATAGGGAGCCTGACCTCTGAGTGAGCTGAGCTGAGTGAGGCAGAGAAA AATAAAGTCTTATGTGGGAGGAAGGGGAACGTTCTGGACGTGGGAACCTGACTCGGGTACATAGTGGGGCGGC CATTGTAGTGGGAAAAGGGGACGTTCTGGACTGTCTTCACTTGAGCTCTGCGGCATTGGTTGCACTTCCAGATAAGTCTTATGCA TGAGCCCAGAATGGGAGGGGTTACACCTTGGGACCTGGCCAACCCAGCTCTCTCTGCTGCCAAAGGAAACC AGCATGAAGGGGACGTTCTGGACGCGGGTGGGTATAAGGGCCACTGTTAGAGGAACAGGCACTCTCCAA GGCAGCAGAGGGTGACTGTCTTCACTTGAGCTCTGCAGTTTCAGAGACTCCTCATTGGTTAGGCTCCCAGATAAGCTTTATGCA ACCTGGGAGAAGCATCACTTCGGTACTCCGGTCTCAGTCGGTACTCCATACGCCCTCACAAAGAAGAAGGATGACTGCTTAAACTTCTG ATGGCCTGTCCCATACTGGTCTCGTCGGTACTCCATACGCCCTCACAAAGAAGAAGGATGACTGCTTAAACTTCTG | SEQIDNO.:130 MRGPELGPETSMEGDVLDTLEA LGYKGPLLEEQALSKAABGGLS SPEFSELCIWLGSQIKSLCNLE ESITSAGRDDLESFQLEISGFL KEMACPYSVLVSGDIKERLTKK DDCLKLLFLSTELQALQILQK KKHKNSQLDKNSEICQEVQAVC DALGVPKSDTSDIPLLLSQVES KVKDILCRVQKNHVGKPLLKVD LSSEQAEKLERINDALSCEYEC RRRMLMKRLDVTVQSFGWSDRA KAKTDNIARIYQPKRYALSPKT TVTLAHLLAAREDLSKIIRTSS GISREKTACAINKVLMGRVPDR GGRPNEIEPPPEMPPWQKRQE GGGRGGWGGGGGGRGGGGGRG GWGGGGWGGGGSGGWGGSG GGGGGRGGFQGRGRGDYGGRGDYG |

FIG. 62

| NucleotideSequence (5'-3') | ORFs |
|---|---|
| TTGTTTTTAAGTACAGAACTTCAAGCTTTACAAATATT | GRGGYGYGRGGYGRGYGDPYGG GGGGGGYRRY |
| SEQIDNO.38 | SEQIDNO.:131 |
| GCCTGCCACCTCTTGTGCAGTCGCTATCTGCTGAGGACTACCTGGTCCACTCCTCCCCTGCTGGAGGTCCACAGAAGG ACCGAGATATGTCCACATGGGACAGGCAGGCAATGAAGTGTATCCTGGCAAGCAATGACTATGATTAGCCAAGCCCAC TGGGCCCAACACTAAGCAAAACTCACGTAGAACTCTTGGCACTGTGTAGAAGCCCCTCTTGGCACAGCCTCTGCAGCACG GTGCCCACCTTGTTACAGTTCTGCACCTCACCATCTGCCCTCAGATAGCCAACTCAGGGAACTAGGACTTCACCGCCCA CAAACAGGATGTGTGGCACCCAACAAACTCCCCTGCAGACCCACTCTTGAGCCAGGCCAGTCCTATGGGCCAAGCTGTAGT GGACATTGTTCCTACCACCACCACCAGAGGTCTTTGAGTCTCACACAGTGAACGGAATGTGGTAACTTCTAGGTGCCCCGCAC ATGTTGGTCTCCTACCACCACACCAGAGGTCTTTGAGTCTCACACAGTGAACGGAATGTGGTAACTTCTAGGTGCCCCGCAC TTAGCCTAGCACCTTTCTTACATGATCTCAAGTTGAACCGACTTCCTTGAATGTCTAGCGTACAGCACAACAGTGCCTCTTTTAAT TTAGGGAATTGGGGCTACTGCTGTTCTGTATGGCCACATCATGCTCTGTCTCCACAAGACTCTCATCGATGTGGTGTGTGATAAATGTATA AGCATGGCAAGGTCTGTTCTGTATGGCTATGCTATATGTTGCATATGCCTATGCCAACTCTGTATATGTTGAAGCAAACTGTGTATAAAGCAAACTGTGTATA CAGTCTTTCTGATGGCTATTAAAGCAAACTGTGTATAAAGCAAACTGTGTATATAAAAAAAAAAAAAAAAAAAAAAAAAA AAAAAAAAAAAAAA | MCGPNANAPQTTVKAHTIEWHC PAGHCWHPTNSPHRPTLEPGQS YGPSLVVCWSLPPHQRSLSLHS ERNVVTSRCPALSLAPFLHDLK LNRLP |
| SEQIDNO.39 | |
| CCACGCGTCCGGGCACACGCCGGTAGGATCTGCCTCCCAGGTGCTGAGATTAGACACCATGCCCGGCCTTTGGTACTTTGT GGTTTGCTGTGTTTGTTTGTTTTGCTTCTTGTCTTGTGCTTCTTGTCTTTACTAACTATCATTGGAGGTTGTCAAAAGCCTCCATGGCCGTGT GTTCCTCTCTCTGCCCTCAGCTAAGCACACAGAAGAGACTCTGCAGAATGCAGACCTTGAGACCTTGAGGCCACAGTTAAACCATGTGGGAAGC CCGTGGTTTCTGTGCTGAGTGGTGTCTGAGCTGATGACAGTGCAGTTGTCCTTAGTTGTCCTTTATTCTTCAGTTGCTCC AGGAACGGCCCCCTCTCAGCAGTCCAGAATTCAAGCAATGCCATGTCCTGCCAAGCACGGTCCCCTGC TCAGCTTTTGTAGGCATCAGCTATTCTGGAGATGGAAGCAGGAGAGTCAGCTGAGCCTGGGATTTGGTACTAGTCTGCAAAAGAGA CTATGACTTCAGCTATTCTGGAGATGGAAGCAGGAGAGTCAGCTGAGCCTGGGATTTGGTACTAGTCTGCAAAAGAGA CCCTGAGAGGGAACCACCAGAGGGCTGTCCAAAGCCCTCACTGGCCAGTAGAAATGGCAAGAACTGAGACCCTTAGAGAACTGAAAGCGGGAAACCACCAGCCATCTGCGGAAACCACCAGCCATCTGCACC AAATCTAGCAGTTTCTAAGTATCCCACTTAGAGATCGCACACACCACTTAGAGATCGCCCTGGACATCTGATGCACATTGTGGCCTTCTGTCAAGAGCACACACTAGATAGCACACTAGATA AAGAGAAGTGTTCACTGACTATCACTACATTAGTTGACACCCACTTAGATGCACATTGTGGCCTTCTGTCAAGAGCACACACTAGATA GTAGCTCACTGACTATCACTACATTAGTTGACACATACTATTCGAGGTGAACAGAGCTCATAATGGAAGTGTAAGGTGTGCGCTGTGT GCACCAAGCACTGCCCAAGTGCACTAGCACTATTCGAGGTGAACAGAGCTCATAATGGAAGTGTAAGGTGTGCGCTGTGT | |

FIG. 69

| Nucleotide Sequence (5'-3') | ORFs |
|---|---|
| AATATTTCTAATAAATATATTTGTTTCTGCCTCAAAAAAAAAAAAAAA | |
| SEQIDNO.:40 | SEQIDNO.:132 |
| CGCTGCTACAGGTCCAAAGTGACGAGGCCAGACGAGACTGAACCAAGACCAAGTCTTTCATTCCTTAGCATATTTATCCC AGTGTGGAAGGCTAGCTCCACCCACGCGGCTCCTTCTCAGCTGCTCAGCACCCTTCATGCGACTGACAGAAAGAAGTATGAGC GCTGCCGGCGGATATAGTTCTCCAGACCCTTTGCCTTGTTACGGCGTGGTTCATACTGCAGGGAC TTTAGAGACAGGGATGCCACTTCGGAACTAAAGGATATGACATTTGACACCTTAAGGAATCGCCCGTCTTTTACGTGTT TCACCGTTCTGGCTACCGACTGTTCCAGCGTCCGAGATTCAACCCATTCTTCAAACCTTCAAACCTTCTGACTTAC CGTTGAAGTTTTGAAAGCTCAAATCACCGCACCATTCAGCTTTTTAACGAGTAAGTAACACAGACGCAGAATTAAG TACCGGGATTTGGGATGTGAAACACCCCCAACACATCAGTATTTTACTGATATTTTCAGACTTAATTAAAAAAAAAAA AAAA | QHRSHARLTEKKYEPLPADIVL QTLLAFALTCYGVVHTAGDFRD RDATSELKDMTFDTLRNRPSFY VFHRSGYRLFQRPDSTHSSNLS ASSSDLPLKF |
| SEQIDNO.:41 | SEQIDNO.:133 |
| CCACGCGTCCGCTTGAAGTCTAGCTTCTCGGGGAAGATAAGGGGAGTCAAAACTCTCAAATCCGGGCGGAGGAGAGCC AGAGGAGGTCACCCAGTGAATGTAAAAGTCGCCGGGGTTTCGGCTCAGCCCGCAGCCTCAGAGCTGAGCCTGCAGCCG CGCAAATCACCCAGTTGAGGCCAGAGAGCGCGCTGCCGCTCAGAGCTGAGCCGCCGCAGCCGGCTGCCGAGCTCCG GAGCGGGACAGCCGTCGGTGCACACCGTGAGGTGAGGAGGAAAGTTTCCCCTCCTTGCTGAGCAGCAGCCTTCAAG AGAGCAGCTGCGGTGAGGTGAGGAGGAAAGTTTGCAAGCTTGAGAGAGGCAGCAGCCCTGAACCGCAATCCGTGAACCA AATCATGGCTGCAGGAAGTCCCCTCCTTCAGGAAACATGCTCTGAATCACCAGTTCCACATTCCCCTGCCTCGTCCATGG ACCTCCTGAGCAGCCAAGTCCCCTCCTTGCTGAGCGTCGCACAGATGCTATCGAAGACGTGTCTATACATGCACTCTTCA CGGAAGAAAAAGGGCCCCTGCTTCAGAAATGCTGCACTCCAAATCTCCCACTCCAAATCTCATCTTCAGGATCCATATCTTCGG GACCCAGGACATATCTGGAATACGGTCAAGACGCCACTGCAAGGGAAAACTTCATCTTCAGGATGCTGAAAAGGAATTG ACCCAACTCTGGAATACGTGAAGTTCTCAAGGACCCTCCTTGGTTCGCGCTCAGCCGGAAACTTGCCTGTGTGACTCAGT GAGGAGGAGCTGCTGCAGCGGATGGGAGCTTCCTGGGTCAGATCCCCGACCCGAGGCTCAGCCCGCGACCTCCCGGGCC AAACCTTGTGCAGCGGATGGGAGCTTTAAGATCAATCCCGGGACCACTTTAAGATCAACGGAGCCTGAGCCTCGTGTGCAGTACCAA GGAAGAACCTCGCTCAGAGCTTTGACTCCATCCAATCAATAGGACAGGAAGCCAGAGCCGGCGTTATGGAGGCCATCAG TGGTGCCATCATCATGAAAGCCAGCCTGGCTGCCCCGGAGCTGGGTGAAGAGGCTGAGCCTGAGAAGGCAGCAGCAGCAGCCAG GAGGCCGGAACACAGCAGGAGGAAGGCCCTAACCCTGCCCCCGAGGGAAAACCTCGAGCTCGGGAAACTCAAAGCCTCAAAGCC GCTCGGGACAGCAGCAGGAAGGCCCTAACCCTGCCCCCGAGGGAAAACCTCGAGTTACCACGTTCACCTGCCTGATCA CGTCCAGGAAGCAGCAGGAAGGCCCTAACCCTGCCCCCGAGGGAAAACCTCGAGTCGGGAGAGTCGGGAGGTCACAGCCTGGGAGAGTCCTGCCCCCC | MAAGKFASLPRNMPVNHQPPLA SSMDILLSSKSPLAERRTDAYQD VSIHGTLPRKKKGPPSIRSCDN AGHSKSPRQSSPLTQDIIQENP LQDRKGENFIFRDPYLLDPTLE YVKFSKERHIMDRTPERLKKEL EEELLLSSEDLRSHAWYHGRIP RQVSENLVQRDGDFLVRDSLSS PGNFVLTCQWKNLAQHPKINRT VLRLSEAYSRVQYQFEMBSFDS IPGLVRCYVGMRPISQQSGAI IFQPINRTVPLWCLEERYGTSP GRGREGSLAEGRPDVVKRLSLT TGSSIQAREHSLPRGNLLRNKE KSGSQPACLDHVQDRKALTLKA HQSESHLPIGCKLPPQSPSMDT SPCPSSPVFRTGSEPTLSPALV |

FIG. 64

| Nucleotide Sequence (5'-3') | ORFs |
|---|---|
| AGTCTCCGAGTATGGACACAAGCCCTTGCCCCAGCTCTCCCGTGTTCAGGACTGGCAGCGAGCCACTCTGAGTCCAGCA CTGGTACGAAGGTTCTTCAGATGCTAGGACAGGGGAGGCGCTTCGGGATCAGACAGCCAGCTGTGCCCAAGCCACC CCCGAAGCCCTGCAAGGTGCCCTTCCTCAAGACTCCCCCATCTCCCTGGCTCACCTCAGAGGCCAACTACTGTG AACTGAACCCTGCTTTTGCTGTGTGTGGGCTGTGACAGGGAGGGAGCCAAGCTTCCATGCAAGCCACGAGATGCTG CTGACAGCCAAACAGAATGGGCACTGCAGTGCAGTGGATCCACTGTGTCAGCAGCGGATGAAGAAGGTCAGGAGGACAAGACCAAGTTTGTGCCACCTCTCATGGAGA CCGTGTCGTCATTCATTCAGACCCAATGCTTTGAGTCCAAGCTTCTTCTCCAGAGAACAAACCCTGAAACGGCCATGCTGA AGCACGCGAAAGAACTGTTCACCAACCACGATGCCAGAGTCCAGGTCATTGCCGCAACCAGCGTCTGAGCTGGACTGCAAGGTTGC TAGGATACTCGAAGTCTCTGAAGACAGAAGAGGCATGGGTGAGCTCTGGTTGGAGCTCGTGGACATTCTTACCTCATG GACGGCAGCTGCCGCTGACATCATCGAGAGGCACAACACGTACCCTCAATAAGATCATCCAGGTGCCGGTGAACTGAAGATGCCATGGGAGACCT GGCACACTGGAGAACCGAGCGGGTACCCTCAATAAGATCATCCAGGTGCCGGTGAACTGAAGATGCCATGGGAGACCT CTATGCTTTCTCTGCCATCATGAGAAGCCCTGAGAGATGCCTCAGATGAGAGAAGCAGTTGAAGCCTTTGACCTGTGACCTTAATGGAACGCCAGGCTGTCACTTTT ACATATGTCCCAGCAGACAGCCATCTGCAGTGGGAAAACAATGACAGGATGAATGTGTATTGTGTGCAGATTCTGCAGAGATTCTGAATCACTTGGCAACAGCCAGTTGACGACAAGTT TGAAGGGACCGACATGTGGAAAACAATGACAGGATGAATGTGTATTGTGTGCAGATTCTGAATCACTTGGCAACAGCCAGTTGACGACAAGTT CTGAGGCTTCTGAGTTCTAACGACCCCTCAGTTGCTAACAGCCCCTCAGTTCTAACAGCCCCTCAGTTGAGAGACAGCCGAGCTGTGAGAACCAGCTGGAG TTAAGGACTGAGTTCTAACCAGATCTCCACACTTCCAACTCAGTGGACCTAGAAACTAGAATAACAGGCCGAGCTGTGAGAACCAGCTGGAG CAACCAGATCTCCACACTTCCAACTCAGTGGACGATAGTAAAATGTAACATATTATTATTAATAAGATAATATTGCCACCATCTTAGTTATTTATTCTGTGTCTGTCAGATAAATGTAAACTAGATAAATGTAAAACATAGAGGCATTTAAAGAGAAAGC GGCCTTGGGGCTACTGGGACACTCCAGTGTCAGGAATGTCTGTCAACTCTAACAGAGCACACATTGTGATGCAACATATTTGTATCAATGCTTTAAATTACTAGTATGTTGCTGTT CTAACATCCACAGGATAGTAAATGTAAACTAGATAAATAACAGGCCATTTAAAGAGAAAGC TAATGAATGGTAATTATTATTAAGATAATATTGCCACCATCTTAGTTATTCCTGTCAGATAAATGAAACTGTAAATAGTTATGAATGAAATATCT GTTTAGTATCATGGCATTTGACCATCTTAGTTATTCCTGTCAGATAAATGAAACTGTAAATAGTTATGAATGAAATATCT ATGAAACATGGAAGAAGGTATCAGTTATATTCTTTGAATATGAAGAAGTATAATGAATGAAACATGGAAGTGA TTTTGTGAAAAAAAAAAAAAAAAAAAA | RRFSSDARTGEALRGSDSQLCP KPPPKPCKVPFLKTPPSPSPWL TSEANYCELNPAFAVGCDRGAK LPMQAHDSHEMLLTAKQNGPSG PRNSGINYMILDGDDQARHWDP LAVQTDEGQEDKTKFVPPLMET VSSFRPNDFESKLLPPENKPLE TAMLKHAKELFTNHDARVLAQH MLSVDCKVARILEVSEDRKRSM GVSSGLELITLPHGRQLRLDII ERHNTMAIGIAVDILGCTGTLE NRAGTLNKIIQVAVBLKDAMGD LYAFSAIMKALEMPQITRLEKT WTALRHHYTQTAILYEKQLKPF SKILHEGRESTYVPASNVSVPL LMPLVTLMERQAVTFEGIDMWE NNDESCEILLNHLATARFMAEA SESYRMNAERILADFQPDEEMT EILRTEFQMRLLWGSKGAEVNQ NERYDKFNQILTALSRKLEPPS GKQAEL |
| SEQIDNO.42 | SEQIDNO.:134 |
| GGCACGAGCTGAGCAGAAGAGAGGTTCTCGCCGCACCTAGCCTTCGCCTGGGCGCCCGATTCTTCTCTTTGCCGCTGGGCCCTCG GCCAGAAGCCACACGGCGACACGGAGCCCCATGGGGTGCGGGGAGCCAGGCCATGGGGTGCGGGGAGCCAGCTGGGGGCAGAGG CCCAGGACGCCGCCGGCCCCAGGCCCCGGCGAGCCGGGCTCAGCCAGGGCACCCCAGGGGTGCCCCTCTTGGTCTGAGCAGTGC GAGTGTGCTAGGGAGCCCACCACCAGACTGGGCGGTGAAACTGGCGTGTGGGCTGGGCGCGGGGGCAG TGCCATGCACAAGCAGCACTGCTTAAGTGCCCGGATGCTATGAGGTGACCCGCGTCCCGCCCCTGCCCGTCTTG AGCCCTCCTGCTACGGGACTGGCAGGTGCCGGAGTGCCCTATGGGCCAAGTGGGGCAATGGGCTAGCTCCGGTTATGA GGCTACAGTCTCGCAGACCCTGCGCCTTCACAGGCCAGGAGGCTACCCCCACCCCTGCCACCAAGCCAAGCTACTCATCCCCACAGG | MHKHQHCCKCPECYEVTRLAAL RRLEPPGYGDWQVPDPYGPSGG NGASSGYGGYSSQTLPSQAGAT PTPRTKAKLIPTGRDVGPVPPK PVPGKSTPKLNGSGPGWPECT CTNRDWYEQASPAPLLVNPEAL |

| NucleotideSequence (5'-3') | ORFs |
|---|---|
| GCATTCCTACCCTGTACTGCGGCTTGCAGCTCTGACGGCTAACGGCTACAGAAGGATCTTATTTATATATAG ATATATATATGTAATTTATATAATATATAGAAATTATTATATATATATATACACTCTTCTATATAATATATATAT ATATTCACATACATTGGACTAGAAATCTATGGAGACGTCCATCAACGTACTATGTTATTAGAGAAATGCTTAATTT TCATATTCCAATGCAATGACATTCTTCTTCAGAGCTAAGTTGTTCCACCTGGTTGGGAAGGGGTTGACAACAGTAGTTGCTATACCAAAGC ACTCGAATTTGGTCATTCTTCAGAGCTGACTAAAGCAGTGCTGCCAACCTACAGCATAAGAAGGGGCTTGG CTGGGAGCTGGAGATTGGGAGACGTGACTAAAGCAGTGCCTATTGTTTATGCCGCCTGATGTGTCTGCAGAGAGTTTCTTTTG GAATGGCTAATGATGCTCCGATGAAATTGCCTATTGTTTATGCCGCCTATGCGACTGTGTCAGCCTGTCAGCCTGTCAGCCTGATTTACTTTA TTCATTTTAAGTGCTGTTAAACCAAAACCATGTTGTGCACATGTTGCCAGTGCTTGTGAGGTTCTGAAGGAGCCAGGCCTGGGATA CTATTTAAGTGAATGCTAGAATCCTATTTGCCAGTCTCAAAGGCTTGTGAGGCAGAGGCTGGTGAGGGCAGAGAGTACAAGCTGGGGCT CAGCGGTAACTTAGGCCTGGCCATCCAGTCAACAGAGGAAAGCAGGGGCCACTGACAGGCATAGGGAGGGTGCTTGCTTCTGCT CGGAGTTACCATGCTGGACTTAGCTAGGGGTTCCTTCACGGGGCCACTGACAGTGAGTTGGATTCTTTCTTTGCAACTG CGGTTGCTGGGACAGTGGAAGAGACCACCAGGCTTGGCCAGCCGTAGCTTACTGTTGAGCTGTGAAATCTTGTTGCTTTTTTTCCCAGAGTCTGATGGC CTCCAATTGCCCTACCCCAGCCCTCACCAACAGCTCGGTAGCTTACTGTTGAGCTGTGAAATCTTGTTGCTTTTTTTCCCAGAGTCTGATGGC GTAAAATTGAGCTGTAGAACTCGCTTACTGTCCTTCCCCTGCTCCTGCAGGGAACATAGAATCAGGAACTCTGTTCACA AGTGACTGGTCTCAGTGATTTCCCTCCCCGATCCAACGTGTCCAGAGCCAACGTGCAGGGAGCTGTGACTCTGGGGCCCCAGAGTTGGGAGCTGGGGAA GGTATCCTACCAGCATAATGACTTGAAGTGACTGTCAGTGAGGCTAACTGTGACTCGTGGGGCCCAGAGTTGGGAGCTGGGGAA TGGGCAGTAGCTACACTGTCAGGCAAAGCAGCAGCTCAGTGCAGCGATAAAGTGACAGATGATTGTGACTCTCCGAGGGGTGAGCGGGAA GTGTTGATTCTCTGATGGTAACTGACAGCAGTGACAGCAGTGTTCCTTCCAAGGAGACACATATTTTAATAAATGATAGTTGCAATG GTAAGCATGATAATAGTTGGTTTACCAGTGTTCCTTCCAAGGAGACACATATTTTAATAAATGATAGTTGCAATG | |
| SEQIDNO.43 | SEQIDNO.:135 |
| CCCACGCGTCCGCACCACCTTCTCTCTTTACGAATAACTCAGGTCACGCTGACTGGAAATCAGTTGACTGACATCAGT GAAGCAGTGCTTCCTGAGTTTGAAGAAAAGAGAGTCTCCTGCCTGGACAGAGGAGTGTGTGCCTTTCTCCAAGCCGTCTCT GGACATATCTTCCCAGCATCCTCTAACAAAGATGCGTCAACTCGTAACAGATGCGTCAACTCGTTGTGCCTTTCTCCAAGCCGTCTCT AGGAGCCGAAGCAGGCCATGCAGGAGGCCCCAGAGGCGCCACACGAGGAGTGGCCACACCGTGGCTGCGAGCTGAGCGGAGCTCTGCCCACCCTGGCTGTGGTGCTC CTCATTGTCGTGTTTGTGTATGTGGAAGCTCTGAGCAGGAGGGATAGGGAACATTTTATCAGTGAATGTCCATTTACTTGATCAATATTTCTCACTTTTT ATGTCCGAAATGCCAAGCTCTGAAGCAGGATGGCCAGCAGGGGATAGGGAACATTTTATCAGTGAATGTCCATTTACTTGATCAATATTTCTCACTTTTT GGGGGGTGGGGTGGGGATAGGGGAACATTTTATCAGTGAATGTCCATTTACTTGATGGTCCGAAATCGATGCATGCTG TCAGACTTCAAAGCTGTGTGTGTGTGGGTGTGTGATGCTGTTGGGATCAGAGATCAGATGGGCGCCCCTCCCCATCCAGCAGCATGCTTCCCGGCTCCAC CCCCTGAGGAGAGCCTCTCTGGGGACAGCCTTTCTCTCTGTGCTTGATGGGATTTGAAATATGTTGACTCAAAGTGAAATATT | MRQLKGKPKKETSKDKKERKQA MQEARQQITTVLPTLAVVVLL IVVFVYVAIRPAVTE |

FIG. 67

| NucleotideSequence (5'-3') | ORFs |
|---|---|
| ATTTTTGAATAAAGGAGATAATAGTCTTAAAAAAAAAAAAA | |
| SEQIDNO.44 | SEQIDNO.:136 |
| ACATCCTCTCTTTGGCTTCCAGGGGTGACTGCAGGTTTTCTCTCTTTCACAGTGAGGGCCTGGGGTGGGCTCTGTC | MTMQPAIQVWFGEDLPLSPRCP |
| TGAAAGACTTCTGCTTTGGACGGGTCCCTGCTTGGTTGGTTGTTTCTGAAACCTCAGTGCCTCCGATGATGT | LTPRHGPLADVCQYDEWIAVR |
| AAGCAGATTTAGGGTTGGAAGGAGCTCAAAGTCCTGGAAGAGCAACATTCCAGGGCGCTCAGCAGCCTTGAGAGG | HEATLLPMQEDLSIWLSGLLGV |
| CGGGCTTCACACACTCTCTGAACGACGGACAAATAGGAGGGGTTGTCACTGCCACTGCGACCACGCCTCTGATAGAGACTGACTGGAAAG | DIKAERLLEELDNGVLLCQLIN |
| GTCGCTACGAATTCTTCGTGCGGTAGAAAGTCTCCGAGGCGTGCCGCGGCCGGTTGTTGTGCAGGCTTGCTGGCACGCACAGATTG | VLQNMVKGCHSDEPGNFPMRKV |
| TCGAAACAGGCGGCCGCGTGGGCGACGAAGTGATCTCGCTCCCCGGCGTTGCCTCCGAGAAGTTAGCACCGTTGTGCCCGTATAGATGGTT | PCKKDAASGSFFARDNTANFLH |
| AGCCCGAGTCGCCCGACCAGGAGTTGAACCGAGGAATCCCGTGCTTTGACGGATTATCACGGGAGGTACATAGAAGTTTCATCTCAGTG | WCRHIGVDETYLFESBGLVLHK |
| TACGCTGGAGCAGGAGGAGTTGAACCGAGCCGTTGCGCCGCCTTTGGGTTGTGTTGGGAAGATCTGCCTCTAAGTCGTGAGACATGAAGCACCTCAGTGTCCCCTGCTGCTATGC | DPRQVLCLLEIGRIVSRYGVE |
| AGCTTTGGAGCCAACGCTGCCGCCTCTTTGGGTTGTGGTTTGGGAAGATCTGCCTCTAAGTCGTGAGACATGAAGCACCTCAGTGTCCCCTGCTGCTATGC | PPVLVKLEKEIELEETLLNASG |
| TAGATGACCATGCAGCCTGCAATCCAAGTGCTTTGCCAGTATGACGTTTGCCAGTAATCAAGTTGGTTATCTCGGTTGTATCGGCTTATCAATGTTCTTCAGAATGTTGAAGATGTGAAGATGTGAACATGTGAAAACATGTGAAAACATGTGAAAAC | LEESISIPKSCCQQEELHEAVK |
| ACATGGCCCGGACTGGCTGCTGATTTGGTTATCGGCTTATCAATGTTCTTCAGAATGTGAAGATGTGAACATGTGAAAACATGTGAAAACATG | HIAEDPPCSCSHRFSIEYLSEG |
| AGGAAGATCTCTGTTGTCAGCTAATCAATGTTCTTCAGAATGTCAAGATGTGAACATGTGAAAACATGTGAAAACATG | RYRLGEKILFIRMLHGKHVMVR |
| GGAGTGCTGTTTGAGATGGTCGATTGTGTCAAGATACGGAGTTGAGCCACCAGTAGTAGTAAAATCCTGCTGTCAGCAAG | VGGGWDTLQGFLLKYDPCRILQ |
| AATTGAGTTGGAAGAGACCTTGCTTAATGCCTCGGGGGCTTGAAAGAGTCCATCAGCATCCCAAATCCTGCTGTCAGCAAG | FATLEQKILAFQKGVSNESVPD |
| AAGAACTACATGAAGCTGTTAAACACACATTGCGGAGGAGATTCTCTTTATAAGGATGCTTCATGGAAAACACGTTTGCTACACTAGAACAA | SPARTPQPPEMNPLSAVNMFQK |
| TCCGAAGGGCGGTACCGGCTAGGGGATACTCTACAGGAGATTTTTGCTGAAGATGAACCCTGCTGAATATCGAGTTGCTACACTAGAACAA | QNLRPGTPVSVPKNKEKQVRLP |
| TGAGGCTGGGATACTCTACAGGAGATTTTTGCTGAAGATGAACCCTGCTGAATATCGAGTTGCTACACTAGAACAA | GARLPASSVKGNLASPSTRAKR |
| AAATTTAGCATTCAAAAGGAGTTTCTAATGAAACAAATTAAGACCTGCCACACAGTAATTGGCTTCCCGTTCCGAAGAACAAGGA | PDSPASFPHPKVTSLKDAAKKT |
| AACCCTTTGTCAGTAATATGTTCAGAAAACAAAAATTAAGACCTGCCACACAGTAATTGGCTTCCCGTTCCGAAGAACAAGGA | TAPSNSVSQSLASPNPGSKPST |
| GAAACAGTACGTCTACCAGTGCACGTTCGCATCGTCAGTAAAGTCTTGAAGGACGCAGCAAAAAGACGACTGCTCCT | AQCASESSRKCVTFPKTAQTKA |
| AACGGCCAGATTCTCCAGCATCATTTCCACATCCCAAATCCAGGTCTAAACCAAGCACTGCCAGGTGCCTCAGAGTCATC | IPAQNSRDLSKSRLLPSKSPGK |
| TCCAACAGTGTATCGCAGTCCCTGGCTTCTCCCAAGACTGCACAGAGAATCTGCAGAAACAATCATCTTTCTTCCTTTCCAGCC | MEPKHLKHNHLSSRDESRINLS |
| GCGAAAATGTCACCTTGCACCTAAATCTCCTGGAAAAATGGAACAGACTACCTTAAAACCGGAAGCTCTAAAAACCGGAACTACCTTAAAACCGGAAGCTCTAAAAACCGGAAGCTCTAAAAGGACGCTGCTAAAAACCGGAAGCTCTAAAA | SKSPKLPKGAMHGRPNPSPFQP |
| GACTTTTACCAAGTAAATCTCCTGGAAAAATGGAACAGACTACCTTAAAACCGGAAGCTCTAAAAACCGGAAGCTCTAAAA | PAKVTKPSSKTGAIGLGTQSOP |
| CGTATAAACTTATCATCCAAGTGCCCCAAGTTCTAAAACCGGAGCCATAGTGTCTAGGGACACAGTCCAGCTTCTCCAGCTCCAGCTCCAGC | PTRTPRSGAVSAQRLQSTLNLN |
| ACCTGCCAAAGTGACCAAGCCAGTTGTACCACAGAAGACTTCAGTCTACATTGAATTTAAACAGTTGAATTTAAAACGACTTCAGTCTACATTGAATTTAAACAGTTCCAGCTTCTGTGCTCAGGTCC | SPASVCSGSSAKATQGSKGKNT |
| CGAGGTCAGGAGCAGTCTCAGCACAGAAGACTTCAGTCTACATTGAATTTAAACAGTTGAATTTAAAACAGTTCCAGCTTCTGTGCTCAGGTCC | VSVAKKQPQSKGVCRNPGPGSS |
| | KSPGRTPLSIVTVPQSATKTET |
| | VSKSAKTAMKGQYSAKGPPKSS |
| | KPPTSFRDPPSSGKGADSGDKM |

FIG. 68

| NucleotideSequence (5'-3') | ORFs |
|---|---|
| TCTGCAAAGCTACTCAGGATCGAAAGGTAAGAATACAGTTTCAGTTGCCAAAAGCAACCTCAGAGTAAGGGTGTCTG<br>CCGGAATCCGGGACCTGCTCTCGAAGTCTCCTGCCCGTGTCTATTGTGACTGTTCCCAATCTGCTACCA<br>AGACAGAAACTGTCTCGAAGTCAGCCAAGACTGCCATTGAAGGGCCAGTACTCAGCTAAAGGCCTCCAAAAGCAGCAAG<br>CCACCAACTTCCTTCAGGGACCCACCCTCGTATGACCGAAGATCACCAAGAAGCTTAGGAAATAAATACACTGTTTCAGCAAAT<br>GGAAGAAGATGACCATTATTTGTTATGACCGGAGAGCTTAGGAAATAAGAAGCTTAGGAAATAAATACACTGTATCGTTTCAGCAAAT<br>CAGGGTGATCATGATGAAGCTGGGTCAGGGAAGCTGGGTCAGGGAAAGGACCCATGCATTTGTGTATCAATGACACTAGAATTTAACTATTGG<br>AAGTCAAGATGGGATGAAGCTGGGTCAGGGAAGCTGGGTCAGGGAAAGGACCCATGCATTTGTGTATCAATGACACTAGAATTTAACTATTGG<br>CTGTATCATCTTGCTAATGATGTCTGCTGTTTGAAGGAGGTTATCTGCTAATAGCAACTCCGATACTCTTAAACACTAGTTACTGT<br>TGGTATATTTTTGAACACAGGTAACACAGGTAACTGTTGGTGTCACCGTCTGCGCTAGTGTGCCCTGTAATCCCAGCTGAGGCTGAGGCAGGGTACAC<br>GCTCAGCCACAAAGCCAGCAAGGTTTGAAATGTGCTACTTTGATATTATTCTGATTAAATGGAATTCTTACTATTCTTATAATCTCTATAATATT<br>AGTACCAATGGCTCCTGCTGTTTACTTTGGTTTTTTAATTAAATGGCTTTTTAATCATAAGCTAACTAATTTATAACTGTATCATTTATAAGAATTAAGTTTTATA<br>TCCGTATCAGAGGGACTATTGGTTTTAATTAAATGGCTTTTTAATCATAAGCTAACTAATTTATAACTGTATCATTTATAAGAATTAAGTTTTATA<br>ATAAAAGAAGAAAAAAAATCAACCAAGTAAGTTAACTAATCTAAGACACTTTGTATCTTATATTTTAAGATGAAGCTCGTGCAGTGTGACAGGG<br>AAAAAAAAATATAATAGCTTTTAGCATATAAGAATGTTTAAGAGAATATTTAAATGTTTAAGATTTAAAGGGATGGGCTCAATGGATAAGTCAT<br>TAATGTGTTTTGATACCAGAATTAGGTTTAATGATCTTAAAATTAAAAGGGATGGGGTGGCTCAATGGATAAGTCAT<br>GTCTAGTACAGGCATGGGATTGGAGTTTGTGTCCCATACATAACAAATCTGGCTGGCGAGAGGAGCCGATGGATGAGAGGCAGCT<br>GTCCCAGCACTCAGAGGAAGACAGAGATTTGTAAAAAAGGAAGATTCCAAAGTCAATGTCTGTTCTCTATGAATGCATATACA<br>CTTTTGAGAGACACTCAGAGGAAGACAGAGATTTCTTGTTTGCAGTGCCCAGCAGACCTTCCACCCACAGACGCGTACAAAAGATTAAGATGTATTAAGAACCTTGTG<br>ACATATATCCTGTTCACATATGCATGCATCTCATCCAGGTGACTTGTCTCAGTCAGCCAGCCATGTTAAGGGTGTTAAGTAACTATGGTATTAAGAACCTTGTG<br>CACAGACTCACATACACACCATCTCATCCAGGTGACTGTCTCCGTCAGGCCAGCCATGTTAAGGGTGTTAAGTAACTATGGTATTAAGAACCTTGTG<br>TGATGCTATGACACACCATATTAGTAAGGCATGTTAAGGTTAATTAAGTTATACTTTGGAACTTTGTAACTAGGAAGTGGAGGCAGGAG<br>TACAGGCTTGTCAGGAATATCCAATGATTTCATGACAGCAGTCTAAGACTAGAACAACAGGCTATGTATGATAAAACCAGCCTTGACTCTCTTTTAT<br>GATCAGAAATTCAAGTCATGTTGTAGAGATAAGCAGGTCTAAGACTATGCACAAAAATTCAGCACGCGGTTCTAGACCTACACAGCA<br>GGTGTCTTACATTGATAGATAAGCATTGCGACTGAGCTTCTCCATCCTCGGCCCTTCTCGGCCCCTTCTCGGCTGGCTGGCATCGTGGCTGCTGAAATACGTTTCTAAACACAAACAAA<br>ATAGTTGACCCAGACCTGCCATCATTGAATGACTGACTGAGCATGAGCATGCATAAATCAAAGATCTACTACAGCA<br>AGAGAACCTTGGGTAAAGACCACTCGATCTTTACCCAAGCAGTATGCATAAATGCAATAATGCACTACTCAGGATCCCTTACA<br>ACAAAAACCACCAAAAACTTGCCAAAACGTTCCGGTTCTGAGCATCTGAGCTCTGAGCAATACTACTCAGGATCCCTTACA<br>CTTAGCACTCAAAAGAGAGATGCCAGGGCATTTCTGTAATCAGGAATATCTAACACACCCTTTCAAGAGAGAAGGATTGTAG | PTARKKEEDDHYFVMTGNKKLR<br>K |

FIG. 69

| Nucleotide Sequence (5'-3') | ORFs |
|---|---|
| CTTTAGAGAGGCTATTCCCTCATAGAGAGGGCCGCCGAAACTATTTCTAGATCAGTAACTTCTGAGAATTAAAAGAAAAA<br>TATAAATTACACTATAGGCAGACTAAACCTATGACTGACTACATTGTACAGTTTTATAAACATTATCTTTTGTGCTGGGT<br>AATCAAGAATAAAGATATTCTCAGACGCACACCTGGCACAAATTCCCAACTGTAGTACATTTAGGATTATTTATTTAAGATAAAGATT<br>GGGTTTTTGTTTTGTCTGCTGTTCAGTAGCATTTCTCAGTGTAGTACATAGGGTGAATTTCTTTGTGTGTGTACC<br>TTGTCTTTCCTAAGCATAGGTTGTATGTAGAACCTGAGTTCTATTTGAATAAGTAATTCCATGGGAACTGAGAACACTCAGCAACTCAGAA<br>CACTTGGTATTCTTGCAGAGAACCTGAGTCTCGCTTCTGCCCTCTGCAATCCTATTTCCAGACACAGGCACCAGGCATTCATATTGCACACATACAGCAAAACATTC<br>CAGGGTATCTGATGCTCGCTTCTGCCCTCTGCCAATCCTATTTCCAGACACAGGCACCAGGCATTCATATTGCACACATACAGCAAAACATTC<br>ATACATGCAATCAATCAATTAGTAAGTAGATATCTTTCCCTCCCAGAATTAAAAAACAAGTATAAATCAGTTGTACTCACTCTTTTTACTACTA<br>TTTCTAAAGAGCTGATAAGTCTTTGCCACATTTAATATATTAATAAACAAATATTAACCAATATTAAGCATAAATGCTGATGTACCTGAA<br>GTGAAATTACATAAGGTCTTTTTGTGTTTAATATATTAATAAACAAATATTAACCAATATTAAGCATAAATGCTGATGTACCTGAA<br>GACACATGTGTGGTTTCTAAAAATAGAATGTTTTGTTTGTTTGGAAATGCTTGCTAATGTGTAATTATATAAAGCTGAACA<br>GGGACGGAAGGGATTTTTTTTTTTTTTTTTTAAGATTTATTTATTTTATGTAAGTACACTGTAGCTGTCTTC<br>AGACACACCAGAAGAGAGGAGTCAGAATCTGTTACGATGGTTGTGAGCCACCATGTGGTTGCTGGGATTGAACTCTGGA<br>CCTTCCGAAGAGCACTCGGGTGCTCTTACCACTGACCTTCCACCAGCCCATGAAGGATTCTTTTACACTCTCGCTT<br>CTGGGGAGGTGTTTGAAGAGAGCACCTTCCCAATGTATGGACTTTAGTGCCCTGAGCTCATGCAATCCTCCTGCCTCAGTC<br>TCACGCAGATGCAGCTTGCCTGGCAGTTTCGGGTACCACATCAGCTTGATTTCATAATCGTTACTTCCTTAAAAGGAGCTAATAAAGTTTTGA<br>AATTTCTTCTGCAGTCTTTTTTATTTCTGTCTAATTAAAATCGTTACTTCCTTAAAAGGAGCTAATAAAGTTTTGA<br>TGTATTCTTACATCCAAGTTTCATGCCATCTCGTGTCAGTTTGGATTTGTATATATTCTGTTGTTTTAATTGTGTT<br>GTTGTTTCAGTGTCAGCAGTATTTGTATCCAACTTAACTTATATTTGACCATGTTGGAAATTGCATATATGTTTCAGAAAGACCAGACTCG<br>GTTTGCTCTTTTTAAATATATTATGTATTTAAACATTTTTTATTGTTTAAAGTCAAATTTATAGGACACCAACACTGTCTACA<br>AAGAGTTTTAAATATCTTTGAGATAATGGAAATGATCAGTAGTCAGTAGTCAAATTTATAGGACACCAACACTGTCTACA<br>TGGCTAATTACTCACTGATAATAGAATTCAAACTTCTTCTTTATGCTCGTTTTCAGGGTCACACTTTGATCACCGTAAATG<br>GAAAGTCACTCACTGATAATAGAATTCAAACTTCTTCTTTATGACCAGAGCAATTATATGTTTGCCTAACTTATAAATGAGTTAACCTACTACTATGTATTTCCTGG<br>TATTTGAAATCCTTTCTAAGAATAAATCCCAAATGAAGTTTATGTTTGCCTAACTTTATAAATGAGTTAACCTACTACTATGTATTTCCTGG<br>GCTGTTTCTAAGAATTCGAAAAGATGAGGCACACTTAAGTCCACTTTTTTGGTAAATATGAAGAATAATGCAAAGATAATGTTTTCTTTTCT<br>ATTTTATGACATTCTGAAAAGATGAGGCACACTTAAGTCCACTAATCTTGAAGAATAATGCAAAGATAATGTTTTCTTTTCT<br>GGTTTTTACAATATCTATACTGTTAAGTAGAAAAACCCAATCTTGAAGAATAATGCAAAGATAATGTTTTCTTTTCT<br>ACATTAGTGGGAACAATTAAGCACTGGTTGGAGATATAGCCTCAGTACAGTACACCAATTAAAATTAACCTCT | |
| SEQIDNO.45 | SEQIDNO.:137 |
| AAGAGGACTCGCGGGCGGCCGCTTCGGCTTCTTCTCGGGCTTCCTGCTCCCTGCCGGCCTTCCCGCGCCTTCAGCCGGCCACC<br>ATGGGGAAACGGGATAATCGCGTGGCCTACATGAATCCAATAGCAATGGCTCGATCAAGGGGTCCAATCCAGTCTTCAGG<br>ACCAACAATCCAGGATTATCTGAATCGACCAAGGCCTACCTGGGAGGAAGTCAAGGAACAGCTGGAAAAGACAGCTGGAAAAAGAAGG | MGKRDNRVAYMNPIAMARSRGP<br>IQSSGPTIQDYLNRPRPTWEEV |

FIG. 70

| NucleotideSequence (5'-3') | ORFs |
|---|---|
| GCTCCAAGGCTTTGGCTGAGTTTGAAGAAAAAATGAATGAAGAAAGAACTAGAAAAACATAGAGAAAAATTA<br>TTAAGTGGAAATGAGAGCTCATCCAAAAAAGACAGAAAAAGAAGAAAATCTGGTAGGGTGAGCAAAAG<br>TTTTCTATTTTCTAAAATGTTACAGCCCTGTAAAGCAAAGTAAGAATGATTGGGTTTCCTTGTATGCGAACGCT<br>AACTTAGACTGTGGGTTCACCACGCAGTCCACAGTTCTCTCTCTGACATGAAGACGTGACAATGTCCTCATAG<br>CCTGGTAACGTCTCTGCTGCTACTTCTAAATCTAATGAGGACGAGTTGTCATTGCTGCATGTGTTCTTAGACAC<br>GGAGGAGACTTTATATTTAGCTTCTAAATCTATGAATATGGCATCTGTTTCTTAGACACTGTTGAGTTCACTAAG<br>TGCTTGAGAGACTTAGTAAAGAAAACCAATTCCTGCATCTCCAGCAGTTCTTCAGATTCCGAAGATGAGGATAA<br>TCTTCTCATCGAGCTCTGATTCTTCCAGCAGTTCTTCAGATTCCGAAGATGAGGATAAAACAAACAAAAGAAGA<br>AGAAAAAGAAGAAGTCCAAGGATGTAACTGACAAGCCCGTTGCCATAAGTCTCCTGAGAAGAGACACTAAAGGT<br>AAGAAAAGAAGTCCAAGGATGTAACTCGAGTCGTGTCAGATCGACTGTCAGAGGTGCAAGCAACACAGCAAAAG<br>TAAACCGTTGTCATCTGAGTCGTGTCAGATCGACTGTCAGAGGTGCAAGCAACACAGCAAAAGAAGACCCCTT<br>GTGAGAGAACAACAGACAAAGCCAAAAGAGGAAGCATAAGAGAAGCAAGACAGCAAGATGTCAAAGGAGCTCAA<br>TCCAGCTCAGATCCGCCGTAGCCCATGAATTCCCTTGTTCTTCAAACACTTTTCCTGCTTCAACACCTTTCTGC<br>TTGCGACACACTTAGTAACGTGCATGAATTCCCTTGTTCTTCAAACACTTTTCCTGCTTCAACACCTTTCTGC<br>CTTTGCAGTCATACTAGTAACGTGCATGAATTCCCTTGTTCTTCAAACACTTTTCCTGCTTCAACACCTTGC<br>GAAACTGAATCTGGATTCATCTTTAAGATGTAACCAGAAAATGAGATGACTCTAGTAAAAATTTCAAGTAGGAT<br>TACATTAATATTTCAGAATCCTTACTCTGTAGATCTCTTTAGCTACCAGAACAGTGTCCATGTCACACATCCTACTTTTA<br>AGGAGCTTTTAAAGGGGGGTGGTTTGCTATCTCTTTAGCTACCAGAACAGTGTCCATGTCACACATCCTACTTTTA<br>TGGACACAGTAGCCATGCTTCCTGGAATGAACCAGAGAACCCGGCCCTTTGCAGCATGAGAAAGCCCCAAAGCTCTGGAATT<br>ACTTGTTGTATGCTGCTTCGAATGAATGTTTCAGGGTTAAAAAAAAAAAAAAAAAAAAAAAAAAAAAAAAAAAA<br>TACCTCCACATCAATAATAAGTGAATGTTTCAGGGTTAAAAAAAAAAAAAAAAAAAAAAAAAAAAAAAAAAAA<br>AAAAAAAAAAAAAAAAAAAAAA | KEQLEKKKGSKALAEFEEKMN<br>ENWKKELEKHREKLLSGNESSS<br>KKRQKKKKEKKKSGRVSKSFLF<br>SKCYS |
| SEQIDNO.:46 | |
| GCAGCCCGAGCCCGCGAACTGCATCATGGAGGTTTCCTGTGCCAAGCAGAAGTAGTGAGAAGCCCAACGCTGAGGACAT<br>GACATCCAAAGACTACTACTTTGACTTCTATGCCCACTTTGGCATCCACGAGGAGATGCTGAAGGATGAGGTGCGCACCC<br>TCACATACCGCAACTCCAATGTTCACATGTTCAACAGGTTATTGCTCAAAGACAAGTGGTGCTGGACGTGGCTCAGGCACTGGC<br>ATCCTCTGCATGTTTGCTGCCAAGGCGGGAGCCATGGTGGTGACCATCATCAAGGTTATTGGGATGACCAAGAGGGGCACCTG<br>GAAGATTGTCAAAGCCATCATCATCAAGGTTATTGGGATGACCAAGAGGCAAGGTTAGACCATCAAGGTTGAGAGCTGCCCGTGG<br>AGAAGGTGGACATCATCATCAAGGGCAAGGTTGAGGTTACTGCCTTCTCACGAGTCCATGCTCAACACCGTCTGCATGCT<br>CGGGACAAGTGGCTGGACCCTGATCTTCCCAGACCGGCCCACCTTGTATGTGACAGCCATTGAGGACCGACA<br>ATATAAAGACTACAAGATCCACTGGTGGGAGAACGTATGCTCTGCAATTAAAGACTGCCATCAAGG | MEVSCGQAESSEKPNAEDMTSK<br>DYYFDSYAHFGIHEEMLKDEVR<br>TLTYRNSMFHNRHLFKDKVVLD<br>VGSGTGILCMFAAKAGARKVIG<br>IECSSISDYAVKIVKANKLDHV<br>VTIIKGKVEEVELPVEKVDIII<br>SEWMGYCLFYESMLNTVLHARD |
| | SEQIDNO.:138 |

FIG. 71

| Nucleotide Sequence (5'-3') | ORFs |
|---|---|
| AGCCCCTGGTGTGGACGTGGTGACCCAAAGCAGCTGGTCACCAATGCCTGCCTCATAAAGGAGGTGGACATTCACACAGTC AAGGTGGAGGACCTGACCTTCACCTCCCCCTTCTGCCTGCAGGAACGACTACGTGCATGCGTTGGTGCTTA CTTCAACATCGAGTTCACCGATGCCACAAGAGGACCGGCTTCTCCACCAGTCCTGAGTCCCGTACACACACTGAAGC AGACTGTGTTCTACATGGAGGACTACTTGACTTTACGTCGACTTGGACTTCAAGGTCAGCTGTGTGAGCTCTCTTGTTCCACCGA GCCAAAACAATCGTGACTTGGACTTGACTTTACGTCGACTTGGACTTCAAGGTCAGCTGTGTGAGCTCTCTTGTTCCACCGA CTACCGGATGCGCTGAGGAGGTGCCAGGCTGGCCTCCTGCAGAAGGGGCTTGGGGATGGGCTTGGGGGATGGGGG GTACATCGTGACTGTGTGTTTTCATAACTTATGTTTTTATAGGTGCGTTATGCCAATAAATCCTCAGCTGACCATGAA AAAAAAAAAAAA SEQ ID NO. 47 | KWLAPDGLIFPDRATLYVTAIE DRQYKDYKIHWENVYGFDMSC IKDVALKEPLVDVDPKQLVTN ACLIKEVDIYTVKVEDLTFTSP FCLQVKRNDYVHALVAYFNIEF TRCHKRTGFSTSPESPYTHWKQ TVFYMEDYLTVKTGEBIFGTIG MRPNAKNNRDLDFTIDLDFKGQ LCELSCSTDYRMR  SEQ ID NO.: 139 |
| GGGTCCGAGCTGAAGCTTCCCCGGCTTCCCCAATTGCCCAAGGTAATAATCTTCAGTAGCCAAGATGTCTTCAGCACCTG ATCCTCCAACAGTTAAAAAGAACCATTAAAGAGAAAAACTTGAAAACCAGGCCTCCGAGGGCGCACACAACCACC TTATTCGAGCTGTGAATCCCGAGCTCTTCATTAAACCCAACAACCTGTGATGGCTTTGATTGGTAACCTTTCACT TGTGTGGCTTACATTGGTTATCGCATGAAAACATCTAAGTGGGACTAACTGCTCTCCTCAGGTGAGTGTTATTAGGCTCCGACA ATCGGTACATGAGGAGAAAGACTGTTAGTGCACAGAATTGTTTCTTGTTCCATAATATGTTAACAAGGAGAATATAAAATTGAAA CCTTTGAAAGAAAGACTGTTAGTGCACAGAATTGTTTCTTGTTCCATAATATGTTAACAAGGAGAATATAAAATTGAAA GCAGTTCCACTGTGGTGAGTTTAGTCTCATTACAGCTGAAGGCATTAAATTCTGTATAATAAAGTACCCAGTACTCTTCC ATTTGCATGGAGTTTCTAACGTTTTAGAGTGGATTGTGCCTTTGCAGCAATGCTTTACTGTTTAGGAGAGAGACAACCC CTTCAGTTACTAAAAATCATAATTAAAATGAAAGAATAAAAAAAAAAAAAAAAAAAA SEQ ID NO. 48 | MSSAPDPPTVKKEPLKEKNFEN PGLRGAHTTLFRAVNPELFIK PNKPVMAFGLVTLSLCVAYIGY LHATQENRKDLYEAIDSEGHRY MRRKTSKWD  SEQ ID NO.: 140 |
| GCTCCCACCCCCCTCCCGGCCTCCGGCCCGTGGCACTCTGGGGCTCTCGCCGTCGACATGGGCGCCGCCGTGGGCACCGC CACACCTGCTGCTGGGGCGTCTTTCCTGCTTCCTGCTGCTGTGCGCCGCCGGTCAGCGGCGGCTCCCCTGGAC CTGGCCGGTTACCTGCTGCTACTGTCCCTGCATGGGCCCTTGGGAACCAGGCTGATCACTTCTTGGGGCTCCTGGCATT TGCGAAGCTGCTGAACCGCACCTGCTGAACCTTGCGTATCCATGGATTGAATACAATCAAGCGAAGCCTCCTTTCACCAACCTCC ATGTGTCCTACCAAAGTACTTCAAACTGGAGCCCTCAAAACTGGGTTGTCAGCCTGAGGACTTCATGGAA AATCTGGCACCCTCCAATGAAGGAGAATCCTTTGGGCCATTCTGGGACCAGTTCATGTGAGTTTCAATAAGTCAGAAC GAAGACATGTCCCATGAAGGAGAAATCCTTTGGGCCATTCTGGGACCAGTTCATGTGAGTTTCAATAAGTCAGAAC TGTTCACAGGACATTCCTTCAGCGCCTCCAGACAGTTCCCTGTCCTGAGGAACACAGGAGAGCTCCAGAAGTACATGGTGTGTCAGATGA GCACTGCCTGGGGCCCCAGCACAGTTCCCTGTCCTGAGGAACACAGGAGAGCTCCAGAAGTACATGGTGTGTCAGATGA | MGAAAWAPPHLLRASFLLLLL LLPLRGRSAGSWDLAGYLLYCP CMGRFGNQADHFLGSLAFAKLL NRTLAVPPWIEYQHHKPPFTNL HVSYQKYFKLEPLQAYHRVVSL EDFMENLAPSHWPPEKRVAYCF EVAAQRSPDKKTCPMKEGNPFG PFWDQFHVSFNKSELFTGISFS |

FIG. 72

| Nucleotide Sequence (5'-3') | ORFs |
|---|---|
| GATGGTTGAGGACGGGAGAGCCCCTGATCAGTGCCCACCTGTCCGSCCCTATGTGGGCATTCATCTGCGCATTGGCTCCG ACTGGAAGAATGCCTGTGCCATGCTGAAGGATGGAACTGCAGGGTCACACTTCATGGCTTCCCCTGCAGTGTGTGGCTAT AGCCGCAGCACAGCGACCCCTCTCACCATGACCAATCGCCTCCCCTGACCTGAAGGAAATCCAGCGGGCTGTGACGCTTTG GGTGAGAGCACTGAATGCCAGATCGGTCTACATCGCCACAGACTCTGAGAGCTACGTGTCAGAGATCCAGAGCTCTTCA AAGACAAGGTGAGGGTGGTGAGCCTTGAAACCCGAGGTGGCCAGTGTACCTGTCAGCCAGGCTGTCTTCCTTCTTTGG ATTGGAAACTGTGTCTCCTCGAGCTTCGGGATGAATTTGATCCATTCGAAGCCCACCCTCGAAGGCAGTCGTCCTTCTTTGG CATGGACAGACCCTCCTGGGATTACACATCCCTTTTTCTGCCAGAGGTGGAGAACAGTACCAAGGACGTCCTGGAAG TGCTAAGGATGCTCCCCAGGCATTCCATCCCAGCACTGGCTCCCAGGCCCTGCTCTGGGCTGCATGATCATGCACATACAA AGAAGGCATTCCATCCCAGCACTGGCTCCCAGGCCCTGCTCTGGGCTGCATGATCATGCACATACAA AGCAGCCCACCTCCAGCCTGGGCACACCCTGATATATACACATAATATATCATATATATATAAAAAAAAA AAAAAAAAA | MAQFPTAMNGGPNMWAITSEE RTKHDKQFDNLKPSGGYITGDQ ARTFPLQSGLPAPVLAETWALS DLNKDGKMDQQEFSIAMKLIKL KLQGQQLPVVLPPIMKQPPMFS PLISARFGMGSMPNLSIHQPLP PVAPIATPLSSATSGTSIPPLM MPAPLVPSVSTSSLPNGTASLI QPLSIPYSSSTLPHASSYSLMM GGFGGASIQKAQSLIDLGSSSS TSSTASLSGNSPKTGTSEWAVP QPSRLKYRQKFNSLDKGMSGYL SGFQARNALLQSNLSQTQLATI WTLADIDGDQLKAEFFILAMH LTDMAKAGQPLPLTLPPELVPP SFRGGKQVDSVNGTLPSYQKTQ EEEPQKKLPVTFEDKRKANYER GNMELEKRRQVLMEQQQREAER KAQKEKEEWERKQRELQEQEWK KQLELEKRLEKQRELERQREEE |
| SEQ ID NO.:49 | SEQ ID NO.:141 |
| TTCCTGCGGAGGCCGCGCGGCCGCCATGTTGTTGTGGGCTGAGGCGGCTGAGAGCCCGGCTGAGACAGGCTG CGCAACAGGTTCGCTGCGCCGCGGCCTGACTGACCCCGGCCGGCCCGGGCACCGCAGGGTCTTCCCGGAGCTTG GCCGCGCCCACGCCGGTGTCGACGGCGCGGGTCGCGCAGCGCCCAGATGCGGAGGCTGAGAGCTGC AAGAAGAAGTCAGGATCATGATGATAAACAGTTTGATAACCTTCAAACCTTCAGGAGGTTACATAACAGTTTGATCAGTGAACATAACAGCCCGTACTTT TTTCCTACAGTCAGGTCTGCCGGCCCGGTTTTAGCTGAAACTCATCAAGTTAAAGTTGCAGGCAACAAGCCCGTGACTGCTCCTCCCCT ACCAGCCAAGAGTTCTTCATAGCTATGAAACTCATCAAGTTAAAGTTGCAGGCAACAAGCCCGTGACTGCTCCTCCCCT ATCATGAAAACAACCCCTCAGTGCACCTAGCAACACCCTGTCTTCCATTACCAACATCATCAGCCTTACAACTTCCTCCAATGGAACTGAACTGCCAGTGTCTTCCATTACCAACATCATCAGCCTTACAACTTCCTCCAATGGAACTGAACTGCCAGTGTCTTCCATTACCAACATCATCAGCCTTCAAACTTCCTCCAATGGAAGTCCAGTTGTCAGATTTGGTGTCAGTATCATCAGCCTTCAACGCTTCAACGCTTCAACGCTTCAACGCTTCAACGCTTCAACGCTTCAACGCTTCAACGCTTCAACGCTTCAACTTCAACGCTTCAACTTCAACGCTTCAACTTCAAC | |

| NucleotideSequence (5'-3') | ORFs |
|---|---|
| AGGGAGTCCGGGAGAAGGAAAAATTCAGACCGGCTGAGTGGATGCCAGGCACACGTGCAGTGCGAAGGCTTGGCAGAGCAA CTTATTTCAACTCCCTCACCAACTGCCTGGCCCCGGAAGCTTCTGCACAGCGGGAAGCTGTACAAGACCAAGAGCAA TAAGGAGCTGCACGCCTTCCTTCAACGACTTCCTGCTCAGTCCGGTCAGCCAGTTGCCGCCGCCTCTGCC ACGAGAAGCTCTTCAACTCCAAGTCCAGTGCTCAGTTCCGGATGCACAAAACGCCATTTTCCTGAATGAAGTGTTGGTG AAACTTCCCACAGACGACCCTTCCAGCGATGAGCCCGGTCCAGAAGACTTCCTCAAAAGACTTCAGTGTGTCATGTGTCTCATTGAAGCTACAGAA CAACATCAACGAGGAGACGGCCTGGGTCCAGAAGATCAAGGGTGCCTCAGAGACATCAAGGGTCTCGATGTGTCTCATTGAAGCTACAGAA GGGAAAAGCTTACCAAGCCCGTTCTCAAAAGACTTCAGTTGGGCTGTCTGATGTGTCTCATTGAAGCTACAGAA TTAAAGCCTGCAAACCAAACGGGAAAGTAATCTGTGAAGTCAGCATGGGCTCCAAAGTATACCACCAGGAC CCTGCAGGACACACTAAACCCAAGTGGAACTTCATCAACTGCCAGTTCTTCATCAAGGATCTTTACCAGGACGTTCTGTGTC TCACTATGTTGACAGAGACCCAGTTTCTCCAGATGACTTCTGGGTCGTACTGCAGTGGCAAAAATCCGAACA GAACAGGAAAGCAAAGCCCACCACCGCCACTCTCCTTTGAAGCAAAACTCTCCTTTGAGGGCCTGGGAAGCCAGGGAAGCTGCCACACAGGCTGGGT CCTGCAACTTTTGAACAAAAACTCTCCTTTGAGGGCCTGGGAAGCCAGGAAGCTCTCATCAAACAGCCACACTCGCTGGGCCTG CTAAAGACAGATTTTGCTCTCCCAGAGGAGCAATCTATGCAAACATGATCTTTTAAACAAACGCCACAGCACAGTGGAAATGAGGCA TATTTATTGCACACTAAATGCTAGCAATCTATGCAAACATGATCTTTTCCATTTTCAGGGCTATAAAAGTATTATGTGGAAATGAGGCA TAGTGTTAACCTGTTCAGCTGTTAGATGCCAAATCTGTCCACTGTGGAGTTGGTGATGTTGAACCATTCCACATCTGAC TCAGACCACCGGACGTTACCACTTGCCAAATCTGTCCACTGTGGAGTTGGTGATGTTGAACCATTCCACATCTGAC CTCTGCTGGGTCACACACTCAGGAGGTGAAGGCTGAATAAATAGAAACTTGATCGTTTATTCTGACTAGATATTATATACTGTGAACTCTAAGATG AATAGCATCCACTTGTGCACTAAATATTATAGTTTGAATAAATAGTTTCTTAAGTATAATAAATTCTTTGTTTTGCATATTTCATAGAACAT TGGGGATATTTTCAACTTAATTTCTTAAGTATAATAAATTCTTTGTTTTGCATATTTCATAGAACAT GCATCTTAAGCTTATCATTGCCAACAATGTACCAGAAGAGAGAATAAAAGTATAAGTTATGAATGTAAAAAAAAAA A SEQIDNO.50 | LQLIVIEVFQKRMAESGFLTEAD MALIFVNWKELIMSNTKLLRAL RVRKKTGGEKMPVQMIGDILAA ELSHMQAYIRFCSQLNGATLL QQKTDEDTDFKEFLKKLASDPR CKGMPLSSFLLKPMQRITRYPL LIRSILENTPQSHVDHSSLKLA LERAEBLCSQVNEGVREKENSD RLEWIQAHVQCEGLABQLIFNS LITNCLGPRKLLHSGKLYKTKSN KELHAFLFNDFLLLTYLVRQFA AASGHEKLFNSKSSAQFRMYKT PIFLNEVLVKLPTDPSSDEPVF HISHIDRVYTLRTDNINERTAW VQKIKGASEQYIDTEKKREKA YQARSQKTSGIGRLMVHVIEAT ELKACKPNGKSNPYCEVSMGSQ SYTTRTLQDTLNPKWNFNCQFF IKDLYQDVLCLIMFDRDQFSPD DFLGRTEVPVAKIRTEQESKGP TIRRLLHEVPTGEVWVRFDLQ LFEQKTLL |
| CAAGTGGGGTGTAGAGGCTGAGCGTGAGCCTCCCTCGCTCTCTCTGGGCAGTGCCTGCAGCGAGAGACCTTTCGCTGA CCTCAGCCGTCCCGCTGCTGCGCAAGGAAGGGCGGAGGGCCGCTCCTAAGCCAGTCCTCTCGGAGCC GCCGTAGTCCGGGGGAGTTCGGTGGTCACATGACCATGAGCTTCCACCAAACCGCTGTCTCGTTTCTGGG AGTGGGGCAAGAATATCGTCTGCCGTGGGGAGAACTATCACGTCAGCAGATCACGTCAGATGCGCAGCAGCCGTGCTGAGTGAG CCTGTGCTTTTCCTGAAGCCGTCCACCGGTGAGTGCTTCTGGGCTCGTAATGCTCCCGGTGTTAATGCCGAGGCT CCACCACGAGGTGGAGTTGGAGTGCTTCTGGACATGACTGCCAGAGATGCCAAGCGTGGTGAAGCGATGCGGAGCTGGACTACGTGG CCGGCTATGCCCTGTGCCTGGACATGACTGCCAGAGATGCCAAGCGTGGTGAAGCGATGCGGAGCTGGACTACGTGG GCTAAGAGCTTTACGTCCTCGCCGGTCAGTGCTTCAGGGCAAAAGGGTGCCCCTGACCCTGACCCCTAAGACT GTGGCTCAAGGTCAACGAGAGCTCAGGCAGGAGGGCAAACATGCATCTATGATCTTTCCATCCCCTACACTCATCAGCT SEQIDNO.:142 | MTQSCTMASTKPLSRFWEWGKN IVCVGRNYADHVKEMRSTVLSE PVLFLKPSTAYAPEGSPVLMPA YCRNLHHEVELGVLLGKRGEAI PEAAAMDYVAGYALCLDMTARD VQEECKKKGLPWTLAKSFTSSC PVSAFVPKEKIPDPHALRLWLK VNGELRQBGKTSSMIFSIPYII SYVSKIITLEEGDLILTGTPKG |

| NucleotideSequence (5'-3') | ORFs |
|---|---|
| ATGTTTCTAAGATAATAACCTTGGAAGAAGGAGATCTTATCTTGACCGGGACTCCAAAGGGAGTTGGGCTAAAGAA AACGATGAGATCGAGGCCGGCATAGAGATGGGGTTGGTTAGTATGAGTTCAAGGTGAAAGATCAGAATACTGAGAGTAGAG TGCCAAAGGGAAGGGAGACAGAAGCAAGGAGAATGAAATATAATGACACTAATAATGAAAAATTATGCTAGACATGTC AAAAAGATGAATGCTTCCAAGAGGGCAATGTTAAACTAAACTAAAAAAAAAAAAAAAAAAAAAAAAAAAAAAAAAAAAAAAAAAAAAAAAAAAAAAAAAAAAAA ATATAGAATGCTTCCAAGAGGGCAATGTTAAACTAAACTAAAAAAAAAAAAAAAAAAAAAAAAAAAAA AGACTTTTCAATAAATCATTCTGAAGTCTAAAGAGTCTAAAAAAAAAAAAAAAAAAAAAAAA | VGPVKENDEIEAGIDGVVSMRF KVKRSEY |
| SEQIDNO.51 | SEQIDNO.:143 |
| GCTGGAGAGACCCGGCCCCTAGTCGCCGGCCCCACCGCGCCCCAATCGAGACGACGCGGCCCCGCGGCGCGAGGA GGAGCCATGGGCAAGTGCAGCGGCGCGTCGACGTCAGTGTCGCCTTCTGCACGCTGGTGGCTGCACTCCAGCGGCA GATCTTCGATTTCCTGGGCTACCAGTGGGCTCCTATCCTGGCCNACTTCCTGCATATCATGGCTGTCATCTGGGCATCT TTGGTACCGTGCAGTATCGGTCCCGGATCTCATCCGTATGCAGCCTGGCTTGTACTCTGGGTTGGCTGGAACGCCTTC ATCATCTGCTTCTACCTGGAAGTTGGACAGCTATCCAGGACTTCATGACCTTCAACACATCCTGCATCG CTCCTGGTGGATGGAGAATGTCCAGGTCCTGCTTGATTATCCTCGAACCCTCCGTAGTGCTCGACTTCATCGGTGGCTCTG TCATCTCGGTCTTCGTGTTGCCTTGTTATGTGAGCAAAGTATTCCTGGAAGAGGAGACAGCTTTGACTTCCGGTGGCTTTGA CTCCTATGCGATACCAGGCGCCGACAAGACGTCGCATTTACAGCTGCAGCCTCTGTACGTCCGGATAGCTTCTGTCCC ACCCGGTACAGTTTCCCTAGGCCTAACTGCAGTCTCAGCCTCTGCAGCTCTAGGACGACTCTAGAGGGCTTGTGAGCTGATGCGAGTGCGACTCTCCAAGA CTGAACTTGACCTGACCCTAGCTCGACGAGACTCAGGGTCGGTTGGGGCAGGACGGGACAGCGGGAATCACTG GGTTTGTATTTTTTTAATCTCAGCTCTGCGCCGGGGTCTTCCTCTTCAGTCTCATTCACCTGCCCTGGGAAGATACTG TGCCTCAGTCAAACAGCAAGACAAGACAGACCGAACTCACCCATCTCGCTCCCGCCAGTCGGCATCGGGCAGTCGGCAGCTATTTGCT TGAACTAGAAGCAGCAGTTCCTGCGCTCCAGCTACGCACCCCTATCACCATCCGGTGTGACATCGGCTCGGGCAGCGGGCAGTCGTTGCT TCCTCCGGGCCTCAGTTTCCCACATCAATAAATTAAAATTATCCCTTAGTTG | MGKCSGRCTLVAFCCLQLVAAL QRQIFDFLGYQWAPILAXFLHI MAVILGIFGTVQYRSYLILYA AWLVLWVGWNAFIICFYLFVGQ LSQDRDFIMTFNTSLHRSWWME NGPGCLVTPVLNSRLALEDHHV ISVTGCLLDYPYIEALSSALQI FLALFGFVFACYVSKVFLEEED SFDFIGGFDSYGYQAPQKTSHL QLQPLYTSG |
| SEQIDNO.52 | SEQIDNO.:144 |
| ACGATCGAACGGCTCAACTTTGCGAGTGAGGTGCAAAAAGGAAAGTGAATGTGGCTTTCGCTCCACGGGTGTGCT GTCGTCTGGGGCCGTCAGGGAGCTCAGGCTCAGCCTTGTGTGTTGCCAGGGTCGCAGGTCTGGCCACTGAGGAGGTAGCC TGCTGGCTGAAGTGGCAGAGCAGTGGCCTTGATTGTCTTGTGGAAGATTAAAAACAAAAGCATAAATATTCGTTC CTTCAGCAATGCTTTCTCTGAAGAATATTTAACGGAAGGACTTCTCCAGTTCACCATCCTGCTGAGTCTGATTGGGGTT CGGGTGGACGTGGATACTTACCTGACCTCACAGCTCACCTGGGCCCAGCTCTGCCTATAC ALDRFQVPTTEVNAWLVHRDPE CCAGAGACCCAGTTCCAACCCTGAGGAATACCTTTGGATGGCTATGGGATCCACCCCAAGAGCATAGACCTGACAATTACT GSVSGSQPNSGLALESSSGLQD | MLSLKKYLTEGLLQFTILLSLI GVRVDVTYLTSQLPPLREILL GPSSAYTQTQFHNLRNTLDGYG IHPKSIDLDNYFTARRLLSQVR ALDRFQVPTTEVNAWLVHRDPE GSVSGSQPNSGLALESSSGLQD |

FIG. 76

| NucleotideSequence (5'-3') | ORFs |
|---|---|
| TCACTGCCCGGCGCGGGCTCCTCTTAGTCAGGTGAGGGCCCTGATAGGTTCCAGGTGCCTACCACTGAGGTCAATGCTTGCTG | VTTGPDNGVRESETEQGFGEDLE |
| GTCCACCGAGACCCGGAGGGGTCTGTCCTCTGGCCAGCCGCCAACTCAGCCTGAGAGTTCCAGTGGCCTCCA | DLGAVAPPVSGDLTKEDIDLID |
| AGATGTGACAGGCCCAGACAACGGGTCGCAGGCAGGATTCGGTGAAGATTTGGAGGACCTGGGGG | ILWRQDIDLGAGREVFDYSHRQ |
| CTGTAGCCCCTCCTGTCAGTGGAGACTTAACCAAAGAGGATATAGATCTGATTGACATCCTTTGGCGACAGGATATTGAT | KEQDVDKELQDGREREDTWSGE |
| CTGGGGCTGGGCGTGAGGTTTTGACTACAGTCATCGCCAAGGAGCAGGATGTGGATAAGGAACTGCAAGATGACG | GABALARDLLVDGETGESFPAQ |
| AGAACGAGAGGACACCTGGTCAGGCGAGGGTGCGGAAGCTCTGGCCCGAGACCTGCTAGTAGATGGAGAGTGAGGAGA | FPADVSSIPEAVPSESESPALQ |
| GCTTCCCTGCACAGTTCCCAGCTGACGTTTCCAGCATCCAGAAGCAGTGCCTAGTGAGAGTGAGTCCCCGCCTTCAG | NSLLSPLLTGTESPFDLEQQWQ |
| AACAGCCTTCTATCCTCTTCTGACGGGACAGAATCACCATTTGATTTGAACACGAGTGCAAGATCTCATGTCCAT | DLMSIMEMQAMHVNTSASEILY |
| CATGGAAATGCAGGCTATGGAACTAAATACATCAGCAAGTGAGATTCTGTACAGCCCCTCCTGGAGACCCTCTTAGCA | NAPPGDPLSTNYSLAPNTPINQ |
| CCAACTACAGCCTTGCACCCAACTCCCATCAATCAGAATGTCAGCCTGTGGCTAGCAGCCTGCCACACTGGCTCAGTCAG | NVSLHQASLGGCSQDFSLFSPE |
| GACTTCTCCCTCTTCAGCCCCGAGGTGAGAGCCTTGGCTCTACCAACTCAGCAGGGCTTTTCTTTCCATCCCAGCAACCA | VESLPVASSSTLLPLVPSNSTS |
| CTCCACCAGTTCTCAACTCCCACCTTTGGCTCTACCAACTAGCAGGGCTCTTTCTTTCCATCCCAGCTCAATGGCACAGCCA | LNSTFGSTNLAGLFFPSQLNGT |
| ATGACACATCAGGCCCTGAGCTACCTGACCCCCTTGGGGGCCTGTTAGACCGAAGCTATGCTGGATGAGATCAGCCTGATG | ANDISGPELPDPLGGLLDEAML |
| GACCTGGCCATTGAGGAGGGCTTCAACCCGGTGCAGGCTTCCCAGCTCGAAGGAGAGTTTGACTCTCCTCCTCTCTCT | DEISLMDLAIEEGFNPVQASQL |
| CTTGGACTCCTGCACCTGAGCCCTTCCTCCTTCTCTGAGCAGCTGAGAAGGAGCCTCCCTGCTCTGACTTCAGGGAGAG | EEEFDSDSGLSLDSSHSPSSLS |
| CTGCTTCCTCCCTGCCTCTCCTCCTTCCTTTCCTCTGAGGAGGTGCTGTGTTACAGCTCTGACTCTGAGACCCTTAGACCTA | SSEGSSSSSSSSSSSASSSAS |
| GAAGAGGCTGAGGGTGCAGTGGGCTACCAGCCGGAATACTCCAAGTTCTGCCGCATGAGCTATCAGGATCCTTCTCAGCT | SSFSEEGAVGYSSDSRTLDLEE |
| CTCTTGCCTTCCCACTTAGAGCATGTGGGCCACAATCATACATAAAAGCTGACTTCCTGGACAAGCAGTCCAGTGCCTTGATC | AEGAVGYQPEYSKFCRMSYQDP |
| TACCACCAGTACCTGAGCTGACTGGAGCACCTCAAGAAAGGTAGCAGGTAGCTTCCTGGACAAGCAGTCCAGATGAGCCGAGATGAG | SQLSCLPYLEHVGHNHTYNMAP |
| CACAGAGCCCGAGCAGCCAGCTGAGGCCAAGTGACACAGATAAGATCCATTCACCAGATGAGCCTCAGCCTCAGCTTGCCCTGTAGAAGAATTCAATGAGCTGCT | SALDSADLPPPSTLKKGSKEKQ |
| GTCCAAATACCAGCTGAGCAGCGCCAAGTGACACAGATAAGATCCATCCGGATATCCGGGCAAAAACAAGATGCTGCAC | ADFLDKQMSRDEHRARAMKIPF |
| AGAACTGCCGAAGCAGCCAAGTTGGACAACAGTGAGAGCCAACTTCGTCAGCGAGCTGATGTGAGGAGACTTGCAGCGAGATAAGGCCCGA | INDKIINLPVEEFNELLSKYQL |
| TTGCTTCGAGAAAAGTAGAGTTCCTTCGGTCTCTGCGACAGATGAAGCAGAAGTTCAAAGCTTATACCAGGAGGTGTT | SEAQLSLIRDIRRGKNKMAAQ |
| TGGGGGCTGCCGGGATGAGCATGGAGGCCCTACTCACCCAGTCAGTATGCCCTTCAGTATGCTGGGGATGGCAGTGTCC | NCRKRKLDTIILNLERDVEDLQR |
| TCCTCATTCCTGCACGATGGCTGACCAGGCCTCGGCGACAGGAAAGCCAAAGGACCGGAGGAAGTGAGCCTGG | DKARLLREKVEFLRSLRQMKQK |
| GGAGGCAGGAGCCGGTGACGCTCACTAAGACCGAAACTGGACAACCGAAACATTGGGGACTTAAATGCC | VQSLYQEVFGRLRDEHGRPYSP |
| TTCTTATCCAATATATCTTCTGAGATGGAATGACTGCGGGTCAGTGCAGTGAAGAGGCGGCCAGCCTATTCCCTTTCTCTTGAGG | SQYALQYAGDGSVLLIPRTMAD |
| AGCTGCCCCCTTGGGGTGTCGGCATGCTGGAAGCAGGAGTAGAGGAGCTTGGCGTGAGTGATTGGGGTCCCAGCACTGT | QQARRQERKPKDRRK |
| GGATGGGTAGTGTCCGAGCATGCTGGAAGCAGGAGTAGAGGAGCTTGGCGTGAGTGATTGGGGTGTCCAGCACTGTT | |
| AGGAGAAAGGAAGGAAGAATCCCCGAAAATCAAAGCAGTCAGAGAATTACTGGTAGTTCAGAGTCCTGTCTGTAATAATCGCGCCTGATCTCAATATCTTAGTTACTGA | |
| TAGGCAGCGAGTGCAGTGACAAGGTGTCTAGGGAGTCGCATCCTGGAGAGGAATCTCTTGATGCAGCGAGAGTCGCCTGTGTCCGCAGCCCAGCATCAA | |
| CCTTTGTAACTGTTTCTTCTTGGGGCCGGAGCGGAGCGCGAGGAGCGGAGCCCCTATAGGCGATGCTCTTGGATGGAAGTGAAGAACGAGGAGCCTGTGTCGCAGCAGCCCAGCATCAA | |
| ATGGGAAGCTGTAGGGCCGAGGAGCGGAGCCCCTATAGGCGATGCTCTTGGATGGAAGTGAAGAACGAGGAGCCTGTGTCGCGGCAGCCCAGCATCAA | |
| GCATGTCACACTGCCCTGCCACAGCCCACCTGCCACTCCCAGAGCCCATCCCGAGCTTCCCACTGTCCTCAGAGAGC | |

FIG. 77

| NucleotideSequence (5'-3') | ORFs |
|---|---|
| CTGCAATGGAAATGCTGTCCTCTTCCACTCTCCTCCTCTTTTGATACCAAGCCCTCACTAGCTGCCTCCAGCTCTCGGAGTG GGGTGCTATTCTGGCAGTATCTGGAACTTGGCCTACAGCTTCCTCCTGCAGTTCCTCTGCAGGGTCTAAACAGGGAAGGCACGTGTGGAGGA GTGGTCCCAGTGACATCCAGGCACCATTCAGCACACAACACTGGGAAGTGATTCTTCCCTCAGCCCCCTCTGCCTACCAACA CCTGGGCTCCTCCTACACTGGGCCTGTGCCGCCTTGGAAACAAAAGCCTATAAGGCCACTTATAGGCCTGTTGTGTTACACTAGCCCCAATAT GATTTTTTAGGGCGTGTCTAAATGTTCTCTTTGCCATAAGCCTGGTTCTTTTTCTAGAGAAAATGAGAAGTGCATGCAAGGGGCAGGAGATGACCCTCC TCAAAGCTGCTAAATGTTCTCTTTGCCATAAGCCTGGTTCTTTTTCTAGAGAAAATGAGAAGTGCATGCAAGGGGCAGGAGATGACCCTCC GAGGTCTGGTCTTGATTCTTTTTTTGGTTCTTCTTCACAGCCTTCTTCACAGCTGTCTTTTTTGTTGTTTTGTTTTGTTGTT CCTAGGCTTCAGCTTCAGCTTCAGGCAGCTTCCAGGACCACAGTGTCTTTTTTTTGGTTGTTTGTGTTTTGTTTTGTTGTT AGGGGCAGCGCCAAGATAGCCAGGTGGTTGGTTCCGGCACTTGGAGGACTCGGAGGCAGTG GTTGTTGTTGTTGTTTTAACTGCCACTGCCACCTGCCCGCCCCGAACCCCGATCCTCCCTGGGCAGGAGGGCTTTCCTAACCAGCAGTAGGATA GACGAGCAGGGGGTTGGGGGGAGCACTGATCCTCTTTATAAATTATTTTCCTTGTAGATTTATTTTAATTTATCTCTGTGACCTGCCA GAAAGCCTGAGCCTGCGGAGTGCTTTTATAAATTATTTTCCTTGTAGATTTATTTTAATTTATCTCTGTGACCTGCCA GGGAGAGAGCAGAAGAAATGCTGTGAGCACATGACACATGACAAATAAATCAAAAAAAAAAAAAAAAAAAAAAAAAA AAAAAAAAAAAAAAAAAAA SEQIDNO.53 | |
| CCCACGCGTCCGCGGTTTACCCGGAGCATGGCGGATACCGGCTTGCCGCCGTGGTTCCCAGCGACCTTTATCCCTTT GTGCTCAGATTTCTGCGGGATAGCCAACTCTCGGAGGTGGCCAGTAAATTTGCAAAAGCGACCGGCCTACACAGCAGGA CGCCAATGCCTTCCTCGTCCTCTTGGACATCTATAGCTTCTGGCTCAAGTCCACCAAGGTGAAGTTACAGTCAA ATGGACCAGTGACCAAGAAGAGGCTAAGAAGACTTCATCCAGTGACAGCAGTCAAGCAGCTCGGAGGACAGAGGCAGC AAAGCCCAAGGACTTCCCACACAGAAGGCTGCCGCCAGTGGCCCGCCAGTGTGCCTCAGCATGCTGGAAAGGCCAGC AGCCAAAGCTTCAGAGGAGCAGCAGTGAAGAATCCAGTGAGGAAGAAGAGGACAAAAAAAAAGCCTGTCCAGA AGGCAGCTAAGCCCAAGCCAGTGAAGGCAAGAAAAACACCAGACCTCCTGCGAAGAAGCCAAAGGCAGTGTGGCAGCA TCCGACTCCAGATCCAGGTACACCAGGAAGACTCAGGAGAAGAACACAAAGCCGAAATGGCAAATGCACCTCCCAGCAGCAGGATCAGACTAAAGC CGAAGCCAAACCAGGTACACCAGGAAGACTCAGAGAGAAGACACAAAGCCGAGAGAAGCCAGCAGCCGCAGCAGCA GCAGCAGCAGCCAAGCCGATGACTCAGTGAAGTAGCTCCCGCCAAGAGCTGCCACTCCCCAGCAGAGCTGAAGAAAAAGCAA GTCGTGGCCAAGGCCACAGACAACCCCAGTGCAACCCCAGGGCCGCCAAAGCGCCGGCAGTTCTTCCACCACCCTCGTTCTTCAGTGAAGA GGAGGAGGACAGAGAAGCCCATGAAGAAGAAAAGCAGTGCTGCGCAGACACGCTGCCAGAGCACAGACAGCAGCTCC AGAAGTCCCCGGGAAGCCCAGTGCCAGACAGCTGCGCAGACACGCTGCCAGAGCACAGCAGCAGCTCC AGAAGTCTCAAGTTCTGAGGAAGCAGAAGCTCTTCAGACAGCTCCAGACAGCTCCAGACAGCTCCAAAGCAGCAGCTCC GATTCTGATTCAAGTTCTGAGGAAGCAGAAAGCTCTTCAGACAGCTCGGGTAACGCTGGATTTGGGGAGCTTGATTTGGGGAGCTTGATTCTGACA AGTGAAGAAAAGCAGAAAGCTCTTACAGGGCTCCCCTGAGGTTGATTTGGGGAGCTTGTTCATTCTGCTTCCTCCTCCCCTAGATTCTGACA CTTGGGCTGCTGTCTTACAGGGCTCCCCTGAGGTTGATTTGGGGAGCTTGTTCATTCTGCTTCCTCCTCCCCTAGATTCTGACA GTTCTGAGGATGAAAGCTCCTGCCAAGCTCAGTCAGTCAACCAAGAGTCCCAAGCCAGCTGTCACTCCGAAGCCATCTGCA | SEQIDNO.:145<br/>MADTGLRRVVPSDLYPLVLRFL<br/>RDSQLSEVASKFAKATGATQQD<br/>ANASSLLDIYSFWLKSTKAPKV<br/>KLQSNGPVTKKAKKETSSSDSS<br/>EDSSEDEDKKAQGLPTQKAAAQ<br/>VKRASVPQHAGKAAAKASESSS<br/>SEESSEEEEDKKKKPVQKAAK<br/>PQAKAVRPAKKAESSESDSDS<br/>DSDSSSEEETPQTQKPKAAVAA<br/>KAQTKAEAKPGTPAKAQPKVAN<br/>GKAAASSSSSSSSSDDSEEE<br/>KKAAAPPKKTVPKKQVVAKAPV<br/>KVAAAPTQKSSSSEDSSSEEE<br/>GQRPMKKAGPYSSVPPSVP<br/>LPKKSPGTQAPKAAAQTQPAD<br/>SSDDSSDDSDSSSEEKKPPAK<br/>TVVSKTPAKAAPVKKKAESSSD |

FIG. 76

| NucleotideSequence (5'-3') | ORFs |
|---|---|
| GCAAAGGCAGTGACAACTCCTAAGCAACCAGAGCAGCAGGAAGGCTGACAGCAGCTCCAG CGAGGAGGAAAAGCAGCTCCAGCGAGGAGGAGGCCTCTGGGGACAGCAAGGCCAAGGTGACTGCTA AAGCAGCACCCGCCAAACAGGCCCCCTCAGCCTGCTGGGGACAGCTCTGACTCCAGATAGTTCCAGCAGTGAAGAGCAGA GAGAAGACTCCTAAGCCCCCAGCTAAGAAGAAGCAGCAGGTGGAGCCGTTTCTACACCAGCCCCTGGAAGAAGCAGA GGCCGAGAGCAGCAGCAGCAGCTCTGAAGATTCCAGTGAAGAGGAGAAAAAAAAGAGCCAAAGCTACTA CCCTAAAATACAGGCAAGCCAATGGCACTCCAGCTTCTCTGAATGAAAAGCAGCCAAGAAAGTGAGGAGGAA GAGGAGGAGAAGAAACAAAAAAAAAAAAAA<br><br>SEQIDNO.54 | SSGNAAQSSGLLGYSLPWAALT GLP |
| AAGCAGAGCCTGAAGTGCCGAGTGTGCGAGTGTGTGCGGAGCCGGGGGCCCGGGAGGAGAAGTCGCGCACGATGAACACCGTCCTGTCGCGCG CGAACTCCCTGTTCGCCTTCTCGCTGTCAGTGATGGCGGCGCTCACCTTCGGCTGTTTCATCACCGCCCTTCAAAGAC AGGAGCGTCCAGTGCGCTGCACGTCTCGCGGATCATGCTAAAAAATGTAGAAGACTTCACGGGCCCTAGAGAAGAAG TGACCTGGGATTCATCACATTTGATATAACAGCTGATCTAGAGAATAATTGATTGGAATGTTAAGCAGTTATTCTTT ATTATCTGCAGAGTATTCAACAAAAATAATGCTCTGAACCAAGTTGTCCTTTGGACAAATGTTTTGAGAGTGAT AATCCGAAGCTACTTTTGAAAGATATGAAAGACAAAGTATTTCTTCCTGGAATTCTACCTCTTGTGACAGGAAACAGAA TGTCACTCTGACGCTCTCCTGGAACGTTGTACCAAGAGTTACTAAACGCTGAATTATTCTGAATTGAAGCATATTTATACATGTGTCTG TGCCATTTCCAGATACATACGAATACAAGAGTTACTAAACGCTGAATAACAGAATCATTCAAGGTGTCATAAAGAATGTGATCCTAAGT AACTCACGTCAGAAGACGTAGTTATGAAGAACGAGGCAACTGCATAGGGCTGTTAGACATTCTATATCTTCTATATGTATACACTTAGAGATCTAAGT CCCAGAGGAGTAGTTATGAAGAACGAGGCAACTGCATAGGGCTGTTAGACATTCTATATCTTCTATATGTATACACTTAGAGATCTAAGT TGTGTTCATGTCAAGGCAGTTGACTTACTACTGGTTCTTTCTTTGAAGTCGGTGAGTAGCAGCTTCCAAATGTAGCTTCAGATGTTTCT ATGCGAAAAAATCTAGCAGCCCAATCATGCTCATTTTAAAGTTTCAACCAGCAAATGTTGCATGGATTTCCTCCTGAACCTGTTGT TTGGTGTATTTCTTTAAATTTCTTGTGTTAAGCCTCGTGTTCATGCAAAGTTGCATTGGGCAAATGTGGCATCCATATTTACGAGTTGGAACAGTAGGAGACAGCTGCC CCCACTGAGCTTGCCTCTGTGTTAAGCTACAGTTTGCATAGCTCCATATTTACAGTTGGAACAGTAGGAGACAGCTGC AGTGCTTTTCCACCCACAGGTTCTCTCCGTGTTGAGTGTTGTCTTGAGTGATCCTAAATTAAAAAGCAAGCAGTGGTCTTGT AGCTCTTTGCAGGTGAAGAAACTGAAACCCAGAAACTTCATTAATTTATTGTAGTTGCACCCAAATTTTATTATCTTCATTTTCCTTGGAATGA TTTATCCTCAGTTTACATTGGTCACATTCTAGCAGCCAACACTACAAGTGATACCAGTATCTCATTTTATTGTATATGGTATCAATTAAAAA TAAGTTTGAAACTAATTTGTAAATGTTGAATGATTAGATTTGTAAAATTTAGAGATTAAATAATTAGACAGTTGTATTGAACATGAAA TTTATTTCCTTCATTGATAAATACTCTCAGATTAGCATCTGCATCTCTTAAATGCAAGAGTAGACACTACG | SEQIDNO.:146<br><br>MNTVLSRANSLFAFSLSVMAAL TFGCFITTAPKDRSVPVRLHVS RIMLKNVEDFTGPRERSDIGFI TFDITADLENIFDWNVKQLFLY LSAEYSTKNNALNQVVLMDKIV LRGDNPKLLLKDMKTKYFFDD GNGLKGNRNVTLTLSWNVVPNA GILPLVTGSGHVSVPPPDTYEI TKSY |

FIG. 79

| NucleotideSequence (5'-3') | ORFs |
|---|---|
| CACATTCTAAAGTAACCTAAAAGGGCTGTTTACTAGCAATAGACATAAATTAGCATTTGTTCTGTTTACCTCATGTCTTA GTGACATTCATCAAACAGCTCTTGTATGTGGTGGCACCAGCAGTTCTTACAAATGCATGTGTTTCTTCCAGCAGA AAGGTCAGAGGCGCACCTTGAGATTGGCACCAGCAGTTCCTTAAACATTTCGGGGTCTCTGTTCTTGTCTATAAAAG GATCCTTTACTAGGATAGAAAAGTTGTGATATGTTTCTGTTCAGCAGATTTGAACAGAGAAACCACTTAGTGATCTGAA GTCAGAAAAGTGATGAGAATAGTAGATGTGTAAAGTCGTCAAGCTGTCAGAGTTAGAGGGTCTGGGTGTCCTAGCTAAGGAA TTATACATCGATGAGAATAGTAGATGTGTAAAGTCTGAAGCTCATTAAGCACCACACTGACATTTATGTATCTGAAAAGCCCAGTTCAGGTGTTTGGTAAGAAAGCCCAAT GCCCTCCCAAGCCTAGGGCATTAAGCCACACACTGACATTTATGTATCTGAAAAGCCCAGTTCAGGTGTTTGGTAAGAAAGCCCAAT TGGTTGAGCACACAGACTATCTAACACTGACATTTATGTATCTGAAAAGCCCAGTTCAGGTGTTTGGTAAGAAAGCCCAAT ATGGCAAATGCCCTTTGTTTTAGCAGCTGAGGGAGCAGCTGCTCCGGCATGCCATCAGCCCTGTCTCTCAGGAACTCCA TTGCGTGCGTGCACGGCTTTATCAGTCTGTGATGATGCTGTAACTTGCAAAGTTCGTATGTGTGATAAGCATCTCTGGTC TCAGTGTTTTAGAGAAGACTCAGTGCTTCAGTGGGCTGAGCCCAGAGTGATTCTATGAAAAGAAGATGATTGCAAGAGTG TTAGTAAAGAGGTTGCAGTTAGAAATGAACTTGAACATGTAGCACCCAGCTATCCCTCAGTCTTAACTAGACAACTG TGTGCTTTTGTGTCTGGCCCCTATTGCATTTGAATTCCTTGGTTGAATTGCATTACGTGCTCAAAGGAAGTAACAGCTTTTACAGCTTCTCCAGTAT AAAATAGGAAAACAGGCTGGGTTGAGGAGCTAAAGCTTGATGTAGCAAACATCGATTTCAAAGCTTCAAAAAGTTCTTTCAGTGCA TCCTGTGAAGAAATTGGACTTCCGAGCTGTGACTGCGAGACAAATGCACAAGATGTAGCAAACATCGATTTCAAAAAGTTCTTTCAGTGCA TCAGATACTTTAACCTCGAGCTGTGACTGCGAGACAAATGCACAAGATGTAGCAAACATCGATTTCAAAAAGTTCTTTCAGTGCA AGCCTGCGTACCTTACTGCGAGACAAATGCACAAGATGTAGCAAACATCGATTTCAAAAAGTTCTTTCAGTGCA TTGGGAAGTTGTTTACTTAAACAATGCACAAGAAATAATTCATAAAAAT

| Nucleotide Sequence (5'-3') | ORFs |
|---|---|
| GGCTGCAGCATAAAGGCAGCGGCCCAGCTGGTGTAGTGGAAGACAGGGCAGGCCAAGCGCAAGGGCGCTACA CTGGAGCCTGAGGAGCTACTCAGGGCTGGAACGCCTCTCACCTTACCCACTCACTCTAAAGGATGAGGGACCTA CATCTGCCAGATCTCCACTCTCTGTATCAAGCTCAACAGATCATGCCACTTAACATCCTGGCTCCCCAAGTACAAC TGCACTTGGCAAACAAGGAGCTCCTGCTTCCCTGTCCAGCATTGCCGGCTACTATCCTCCAGCCTCCAGTGACG TGGATTCGAGAGGAGCTGGGTGTGGAATTCCAGGCTGACACCCAAGTGTCCCACTTACCTCCAAGTCGCCCAGTCT AACCTACAGCATTCTTCCACGGTGATGGCTACCAGTCCACCCACAGTGCCACTTATACCTGGAAATCTCGCACGTCT CCCTGGAGGAGCCCCCTTACAACCAGCATGAGGGGTTTTGCCAAATCCAGGACTTCACAGAGCAGACAAGCTTCTTCGTCAAGTCCACCAGCC AGCATCATCTTCCTTCTGCGCTGTTGTGTTTCTGGGACTGCCTGAATACAAAGTACTCCACATCCTGGCTCTTCGACTGTACAAGTT TATGAGGCATTCTGGGTGTGGGGCTGAGCTGTGGGCCTGAAGGTGCCAGCACATTGGGAGCTGAGAGAACCCTGGAGGACCC CGTGTGAGGTGTGGGGCTGAGCTGTGGGCCTGAAGGTGCCAGCACATTGGGAGCTGAGAGAACCCTGGAGGACCC TCTGCTTTCTGCTATTGAGAAGGACAGAGAGCCCTGGGCTGATGAAAAGGGACAGGACACATTGGGGGTGGGGCTGTGAGATGGCTCAGTGGGTAAGAGCACCC GGAAGCTAACACCATCTATGTGAGGTATCTGAGTTCAAATCCCAGCAACCACATGGTGGCTCACAACCATCGTAAACGAGATCTGACTC GACTGCTCTTCCGAAGATCTGGAGTTCAAATCCCAGCAACCACATGGTGGCTCACAACCATCGTAACGAGATCTGACTC CCTCTTCTCGAGTGTCTGAAGACAGCTACAGTGTACTTACATGTACATATAATAAATCTAATAAAAAGAAAAAAAAAAA AAAAAA | LLRAGNASLTLPNLTLKDEGTY ICQISTSLYQAQQIMPLNILAP PKVQLHLANKDPLPSLVCSIAG YYPLDVGVTWIRELGIPAQV SGASFSSLRQSTMGTYSISSTV MADPGPTGATYTCQVAHVSLEE PLTTSMRVLPNPEQRGTLGVIF ASIIFLSALLIFLGLHRQQASS SRSTRPMRHSG |
| SEQIDNO.56 | |
| GTGCTTTGTGCTTGTGGAGGAACTTAGACACAGGAGAATGAGGCTCTGACCTTGGGCACCAGTATTT TCCTGAGCCTTTGGGGGACTTATGTGTTTCCACGAAGCCCTAGCTGGACTTCCAGCAGTCTGGGAGTCTGTGC TTTGTGCCTTCCTTCGGTGAGCCTCTCTGCAGCCCTTTTACTGGATCCTGCACCCGTTGCCCTGCTCTCTTCTGT CTGGATGATCACCTGTGTTTTCTATGCGTGTTCCAAGCGCACGATGCTTCATTCTTCTGGCCATGTGGAAATATTTTTATAAC TCGGTGAAGTGAGGTCTCCTAGACAGCATGACTTGCAACCTAAGGCAAAGGGCAAAGAGCTTTTCAGTACATTTCCCACTTTTAAACGGTA TTCAGAGGTCTCCTAGACAGCATGACTTGCAACCTAAGGCAAAGGGCAAAGAGCTTTTCAGTACATTTCCCACTTTTAAACGGTA TACTGAAGCCATCCAGTGATTACGGCTGATTCCCAGCAGCTGTTGACTTCAGCCTCATATGAATGACACTAGAGGAAGTCTGGAGTCCTG TGGTGGTCTCTCTCTTTAGTCCCAGCAGCTGTTGACTTCAGCCTCATATGAATGACACTAGAGGAAGTCTGGAGTCCTG CACCATATGGTGGTCACGACAGAGCTGTTGCTTCGGGTTCCGTGGCCAGAAGTTGCTTGCCCTTGCCGGGCTTCTGCTCATCCT AGTCAGCACTGGCCTTCTTCGGTGAGCGATTCCTGGAGCGCACGATTCTCGGGCCGCAACAGCGGCACTCCTAAGGAGGAGAAACCCTTGGGCTGCATCTCGTCTATCGGCTCATGTCCTGTGACTATCGCGTGTGTCTCTCCTCATGAACAAACACAGTTCCAAAGCT TGTTCCGGTTTGATGAAAAGGAGAACGCTTTGCAGCTGACTCGTGTCCATTGGCTCATCTGCTGTGACTATCGCGTGTGTCTCCTCATGAACAAACACAGTTCCAAAGCT GTCATGTGGGCTGAAGTTCACTGAAGTCTGAAACTGAAACACTGTTTAAATTCCTGTCTCAGTCTTCCAGTCTCAGTCTTCCAGTCTCAGAGAAGCAGAGACGAGACAATCCCTGCGAAATG GAGCCTGTACTTACTTTAAAAGATTCATTTCATTCTGGTTCCAGTCGTGGAAGAACCAGAATCAAAGCTGTGACCAGATCAGAACAATCCCTGCAAATG | MRLWTLGTSIFLRLWGTYVFPR SPSWLDFIQHLGVCCFVAFLSV SLFSAAFYWILPPVALLSSVWM ITCVFLCCSKRARCFILLAVLS CGLREGRNALIAAGTGVVIFGH VENIFYNFRGLLDSMTCNLRAK SFSVHFPLLKRVTEAIQWIYGL ATPLNLFDDLVSWNQTLVVSLF SPSHALEAHMNDTRGEVLGVLH HMVTTIELIITSVGQKLLALAGL LLILVSTGLFLKRFLGPCGWKY ENVYITKQFVRFDEKERHQQRP CVLPLNKKERKYVIVPSLQLT PKEKKTLGLFFLPVLTYLYMWV LFAAVDYLLYRLISSMNKQFQS LPGLEVHLKLRGELKILVSVSF |

*Fig. 81*

| NucleotideSequence (5'-3') | ORFs |
|---|---|
| AAGATGATCTATGAGCAACACAGTCCCTCTTCTGGGCCAACTGCTGCTTCTGTCTACTCAACAAGAGGGGGCTATCTGA GAAGGTCTACAGATGTTTGAGTTTGCAAGGCTGCCTTCTCTCTTTGGTGATCCTTCAAGATACATGTCGATCATAATGCCA AATAGCCCCTAGTAGTAAATAGTTTCAGAGTCTGTCTTCTTCCAAACAAACACAGTATCTAAACTGTGTCATAGTTAAAGCTAT GGTGATGGCTGGCATGGAAATGTCCTGAAAGGCTTAGATAGCTTCCCAGTAGTCATCTGGGGAG GCTTATAAGGTGTCATGTTGCTGGACAAAGTGTGACTGAGGAGTGTTTTGCAGTGTTTAAAAGTCATGTGCTACTCCT GTTCACTCTACTCAGCCTGTGGCTGGAGATGGGCTCTCAGCTGTCCCTGCTCTGTCTGTCTGTAATAGAGTTCCC AACTGTGATATTGATGGAGTCTTACCTCTCTGAAACCTTAAGCCCAAATAAATCCTTCCTTCTAT | YPKVERERIEYLHAKLLEKRSK QPLREADGKPSLYFKKIHFWFP VLKMIRKKQTIPANEDDL |

FIG. 82

| SEQ ID NO. | Nucleotide Sequence (5'-3') | SEQ ID NO. | ORFs |
|---|---|---|---|
| SEQ ID NO. 83 | TGGAGGAACCTAGCGGAGCGCGCAATGGAGCCCTGGTGCGGGGCAGAGGTTCGTGGGCAGGGCCCTCAGGGTCCCCGTGTGCCT<br>GGGGCTTCCCGCTCCCCGACGCCCTCCCCCGAGCGCCCCCGCCCTCCTGCCCTCCTGCCTGAGCGCCAGG<br>TGAGCGCATCCGCCAGGAGCATCCCGGGACGCTGTCCACCACCGCCACCTCGCTGGAGACCTTCCACAGCT<br>ACTTGGCCCGCAGGAGCATCCCGGGACGCTTCGCCTTCGCGGGACTCTCGGCAAGCGCTCACCGAACTCACAGAC<br>ACCTGTCCCTCAGGCAGGCTTCGCCTTCGCGGGGACTCTCGGCAAGCGCTCACCGAACTCACAGAC<br>CATGGCTCCACTGAAACGGTGGGACTCTCTCCCACGAGCCAGACCCTACTTCAGGGACCAGAAGCCATGATGACACCCCTTT<br>ACCTCCCCCTTCTGTGCCTGCAGCTAACGCTCACACGTCTGTGCTGCATCCTTATCGCTCCCAGTGGGTGCTGACCGTGGCCCA<br>ATGGTCAGCGTGCAGGCTAACGCTCACACGTCTGTGCTGCATCCTTATCGCTCCCAGTGGGTGCTGACCGTGGCCCA<br>TGCTTGAGCCAGAACCATGTAACTACATAGTGAGGGCGGGAGCCTACCAACCCAGACGTACTGGTTGGCCGGGCCATGAC<br>ATGTGCCGGTCCATCGAAGCTCATCATCAAGTCAAGTGGGGCTCAAGTACAGTAAATACGTGTGGCCCATCTGCCTGGATTACAT<br>ATCGGCCTTCTCAAGCTCTCTGCACTGTGACAGGCTGGGAATGATGAGCTGGAAGATCTCCAGGCTAACTGGGAGCTAACTGGGCCCTGT<br>GGTGGAGGACAGTTCTCTGCACTGTGACAGGCTGGGAATGATGAGCTGGAAGATGAGCGACCCTTCCCACCCAT<br>TGCTCTTCAGATGGCACATGTACCTGGTGGGAATGATGAGCTGGACCCGATCGGGGAATGATGAGCTGGACCCGATCGGGGACCTTCCCACCCAT<br>CTTTCTGCAGCTTGCCCTGGCCTTTCCTTCTGCTCATCCTCTGGGCACACTGTGACACTGCATGTCCTCTCCTCCCT<br>GGACCCTTGCTCCTAAGTGCTGCTGTGGGGCGTGGGCCTCAGCCTGCGGGAGGGGGAGCCTAGCAGAGATTAAACACTTCTTTT<br>TCCTTCTAAGTGCTGCTGTGGGGCGTGGGCCTCAGCCTGCGGGAGGGGGAGCCTAGCAGAGATTAAACACTTCTTTT<br>CCCAAAAAAAAAA | SEQ ID NO. 149 | MEPWCGAEVRGQGPQGPRVPGA<br>SRSRSRALLLLLLLLLPRR<br>PAGERIRPRRPPRHAHPRPPLT<br>RWRPSTGYLAAGASPGTLSTTV<br>PTGPGVSCGSRGTCPSGRLRLP<br>RQAQTNQTTAPENSQTMAPLK<br>TVGTLGMDTTGSVLKTVHSSN<br>LPFCGSSHEPDPTLRDPEAMTR<br>RWPNMVSVQANGSHVCAGILIA<br>SQWVLTVAHCLSQNHVNYIVRA<br>GSPWINQTAGTSSDVPVHRVII<br>NHGYQPRRYWSWVGRAHDIGLL<br>KLKWGLKYSKYVWPICLPGLDY<br>MVEDSSLCTVTGWGYPRANGDN<br>WRAPGLLFRWHMVPGGNDELGP<br>RLQEERGPTHLSAGLLLQALDL<br>GPAQWGAPGPSSPIQDLAPGFP<br>SAPHPSGHTVTLPCLSFLPFLL<br>SAAVGVALSLPEAGRS |
| SEQ ID NO. 84 | GAGCTGTTTCACCCTACCTTGGCTTCAATCTCTTCCCCATGCTCGAAGGTGCGGAGCTGTACTTCAACGTGGACCATGG<br>CTACCTGGAGGGCCTGGTTCGAGGATGCAAGGCCAGCCTCTGACCCAGCAGACTATATCAACCTGGTCCAGTGTGAGA<br>CCCTAGAAGACCTGAAAATTCATCTCCAGACTACTGATTATGGTAACTTTTTGGCTAATCACAACAATCCTCTTACTGTT<br>TCCAAAATTGACACTGAGATGCGAAAAGACTATGTGAGAATTTGAGTATTCCGGAATCATTCCCTGAGCCCTCAG<br>CACATTTCTCACCTATATGACGTGCAGTTATATGATAGACAATGTGATTCTGCTGATGAATGTGCATTGCAGAGAAAAT<br>CTGTGAAGAGAAAATCTGGGAAGTGCCACCCTTGGGCGTTTCACAGAAATGAAGCTGTCAACATTGCAGAGAATGCTCTAGA<br>TCAGATCTCTTTAATGCCATTCTGATCGAACGCCAATAACATACAAGTCTTACCTTGAGGCATTCTATAAATTCGTAAGAATCATG<br>TGAACTGAATATTGAATTGCTACGCAATAACATACAAGTCTTACCTTGAGGCATTCTATAAATTCGTAAGAATCATG<br>GTGATGTCACAGCAAGTTATGTGCCCATTCTTGAGTTTGAGGCCGACAGACCCTCTACAACCTTCGGCAAACTCTATCCTGAGGGGTTGCGCT<br>TTTGGCACTGAATTGACAGAAGACTTTGACCAGATGAAGAACGTAGCGGATCATTACGAGTATACAAACCTTTATTTGAAGCTG | SEQ ID NO. 150 | MLEGABLYFNVDHGYLEGLVRG<br>CKASLLTQQDYINLVQCETLED<br>LKIHLQTTDYGNFLANHTNPLT<br>VSKIDTEMRKRLCGEFEYFRNH<br>SLEPLSTFLIYMTCSYMIDNVI<br>LLMNGALQKKSVKEILGKCHPL<br>GRFTEMEAVNIAETPSDLFNAI<br>LIETPLAPFFQDCMSENALDEL<br>NIELLRNKLYKSYLEAFYKFCK<br>NHGDVTAEVMCPILEFEADRRA<br>FIITLNSFGTELSKEDRETLYP |

FIG. 83

| Nucleotide Sequence (5'-3') | ORFs |
|---|---|
| TAGGTGGCAGTGGGGAAAGACATTGGAGGACGTGTTTTACGAGCGTGAGGTACAAATGAATGTGCTGGCATTCAACAGA CAGTTCCACTACGGTGTGTTTTATGCATATCAAACTAAAGCTGAAGGAACAGGAAATATTAGAAACATTTGTGTGACAGAATG TATTTCACAGAGGCATCGAACTAAAATCAACTACATTCAATTTTATAACCAAGCTAGAGTGCAATGGCGTGATCT CGGCTCACTGCAACCTCCAGTTCTCCAGATTCAAGCAACTCTCTGCTTCAGCCTCCGAGTAGCTTGGCCAGGTGAACATCC ACCACTACACTCAGTGATTTTTTGTAATTTTAGTAGAGCCGGGTTTCACCTTGGCCAGGCTGATCTTGAACTCCT GAGCTCATGATCTCACCCGCCTCAGCCTCTTGTCTAATATACTTTGATGATGATGTAATCAGCTTGAGAAAGCAACACATTTCAAATCCTATCTTCTAGATG CAAGCAG | TFGKLYPEGLRLLAQAEDFDQM KNVADHYGVYKPLFEAVGGSSG KTLEDVFYEREVQMNVLAFNRQ FHYGVFYAYVKLKEQEIRNIVW IAECISQRHRTKINSYIPIL |
| SEQ ID NO. 85 | SEQ ID NO.: 155 |
| GAGCTGTTTCACCCTGAGCTCTTCCCCATGCTCGAAGGTGCGGAGCTGTACTTCAACGTGGACCATGG CTACCTGGAGGCCTTGTTCGAGGATGCAAGGCCAGCCTCCTGACCCAGATCAACCTGGTCCAGTGTGAGA CCCTAGAAGACCTGAATTCATCTCCAGATCATTCCCAGTTTTTGGCTAACTTTTGCTAATCACACAAATCTCTTACTGTT TCCAAAATTGACACTGAGATGAGGAAAAGACTATGTGGAGAATTGAGTATTCTGCTGATGAATGTGCATTGCAGAAAAAT CACATTTCTCACCTATATGACGTGCAGTTATATGATAGGCAATGTGATTCTGACAGAAATGGAAGCTGTCAACATTGCAGAGACACCT CTGTGAAAGAATTCTGGGGAAGTGCCACCCTTGGCCACCATTAGCTCCATTCTTCCAAGACTGCATGTCTGATAAATTCTGTAAGAATCATG TCAGATCTCTTAATGCCATTCGAATTGCTACGCAATAACTATACAAGTCTTACTTGAGCGCCAAGTCCATTCTCCAATTTCTGACTCTTAAGTTGCACTCGAAATCTGAGGGGTTCGGCT GTGATGTCACAGCAGAAGTTATGTGTCCCATTCTGAGTTTGAGCGCCAAGTCCATTCTCCAATTCTGCTTTATCATCCATTCCTGAGGGGTTCGGCT TTTGGCACTGCAATTGAGCAAAGACACTTTGACCCTGGAAGATCATTACGGAGTACAAATGAATGTGCTGGCATTCAAGCAACTCTCTG GTTGGCTCAAGCAGGCTAGAGTGCAATGCCGTGATCTCGGGCCTCAACTCCAGATTCAAGCAACTCTCTG CAGTTCCACTAGGCTCCGAGTAGCTTGGCCAGGTGATTACAGGCACCACCACTGAGCTGATCTTGAACTCTGAACCTG CCTCAGCCTCATGATCACCCGAGTAGCTGGGATTACAGGCACCACCACTGAGCTGATCTTGAACTCTGAACCTG GTTTCACCATCTTGGCCAGGCTGCTCAGCACTGGCCTGGCCCTCTGTCTTCAGCCTCCCAAAGTGCTGGGATT ACAGGCCCCTGTTGTTCAGCACTGGCCTGGCCCTCTGTCTTCAGCCTCCCAAAGTGCTGGGATT GAAGCAACAACAATTTCAAATCCTATCTCTCTGAGATGCAAGCAG | MLEGAELYFNVDHGYLEGLVRG CKASLLTQQDYINLVQCETLED LKIHLQTTDYGNFLANHTNPLT VSKIDTEMRKRLCGEFEYFRNH SLEPLSTFLTYMTCSYMIGNVI LLMNGALQKKSVKEILGKCHPL GRFTEMEAVNIAETPSDLFNAI LIETPLAPFFQDCMSENALDEL NIELLRNKLYKSYLRAFYKFCK NHGDVTAEVMCPILEFEADRRA PIITLNSFGTELSKEDRETLYP TFGKLYPEGLRLLAQAEDFDQM KNVADHYGVYKPLFEAVGGSSG KTLEDVFYEREVQMNVLAFNRQ FHYG |
| SEQ ID NO. 86 | SEQ ID NO. 151 |
| ATTAAGACAGTTGTTTATAGAAGCTGCAGGCGTGCAGGGATCTTCTAATCCCTAGCACTACTCAGGGGTA CCCAGCCCTTGGCCACAAGGAGGAGCAGGGAGCCATGGCTGCCGAAGGCCATGCTGCCTCGGCGCTCCACCTATCCTGAAG CATCCAGATGACGAAGATGATGAAGACATGGAGTATGAAGAGCTTGCCTGGAGCCGAGGACCACATTAAAGACTTCCG CGAAACCAAGTCGTACAAGTCGCGCCGGTTCCGACTTCCATCTCAAGGCCTTCTGCAGCCTGCCCTGCGAGTGCCCTGGAGATCAAG ACATGGAGCTCGCGTTCCGACTTCCTCAAGGCCTTCTGCAGCCTGCCCTGCGAGTGCCCTGGAGATCAAG GACTTCAAGGACTTCTACCTGTCCATAGCACAGATCACTATGTGAAGTTCTGGAGTTGTAAGATTCGTTGTGAGAGACCCT | MLEGAELYFNVDHGYLEGLVRG CKASLLTQQDYINLVQCETLED LKIHLQTTDYGNFLANHTNPLT VSKIDTEMRKRLCGEFEYFRNH SLEPLSTFLTYMTCSYMIGNVI LLMNGALQKKSVKEILGKCHPL |

FIG. 84

| Nucleotide Sequence (5'-3') | ORFs |
|---|---|
| CACCCCAGTCATAGGAGGCTATCCCGTGGAGAAATTTGTGGCGACCATGTACCACTATTTACAGTTTGCGTATTACAAGT TGAATGATCTGAAGAATGCAGCCCCGTGTGCCTCAGCTGCCGTCAGCTGCTCTTTGACCAGAGTGACAGGTCATGCAACAGAAC CTGGGTGTACTATCAGTACCACCGGGACAAGTGGGCCTCTCGGATGAGCACTTCCAGCCAGACCCAGAAGCAGTTCAGTT CTTAATGTGACGACGCTCCAGAAGGAACTTGTTGGAGACGACTTGTACGACTTCGCTCCAGTCCACAGGGCTAAGAAGT TGGAGTATGTGGACCACTTGGGTGTTGATACCTCACAGCTCTGTCTTCTTAAAGTAAGAAGGAAGCCACCATCTCCCTAC CTTCTTCAAGTGCAAGCCTGACTTCCCGTCCCGTTGTTCCCGTCATCTAGTTGTCCCCTCCAAGTGCTGTCTTCATGCCTGTCTT CAAGGTCAAGCCTGACTTCCCGTGTTCCCGTCATCTAGTTGTCCCCTCCAAGTCACGTTCGTCTCCCCTCTGATCCATGTGTCTC TCCCTTCACACATGTCTTCCCGTCATCTAGTTGTCCCCTCCAAGTCACGTTCGTCTCCCCTCTGATCCCATGTGTCTC CCCCATGTTC | GRFTEMEAVNIAETPSDLFNAI LIETPLAPFFQDCMSENALDEL NIELLRNKLYKSYLEAFYKFCK NHGDVTAEVMCPILEFEADRRA FIITLNSFGTELSKEDRETLYP TFGKLYPEGLRLLAQAEDFDQM KNVADHYGVYKPLFEAVGSSGG KTLEDVFYEREVQMNVLAFNRQ FHYG |
| SEQ ID NO. 87 | SEQ ID NO. 152 |
| ATTTGGAGTTGAACTGAAGAGGACATGTGGTCATTTGGGCTGGGGGGTGTAGCTCAGTGGTAGAGGGTTTGCATATCCCGC ACAGCAGCCCTGGGTTCATTCCCGTGCCAGCACTGTATAAAACTGGCATGATGGTCATACCCGAGAGTGCCAGCACAGCAGT TCAAGAGCCCTGTTTGTCCGTGCGGTGCGGCCTACAACGGAGAACTGGAGAACGTCCATTCCGACATGGAGCTCGCG CTTCCCGACTTCCTCAAGGCCTTCGTACAGCCTCTCTACAGATGTGAAGTTCTGAAGTTCGTCTGTGAGATCTCAAGGACTT CTACCTGTCCATAGCAGATCACTATGTGAAGTCTGAAGTTCGTCTGTGAGGAGAATTGTTACAGTTGGTAAGATGACCACCCCAGTCATAG GAGGCTATCCGGTGGAGAAATTGTGGCGAACTACCACTATTTACAGTTTGCGTATTACAAGTGAAG AATGCAGCCCCGTGTGCCTCAGCTGTTGCGGCGTCATGCAACAGAACCTGGGTGTACTATCA GTACCACCGGGACAAGTGGGCCTCTCGGATGAGCACTTCAGCCAGACCCAGAAGCAGTTCAGTTCTTAATGTGACGA CGCTCCAGAAGGAACTGTACGACTTCGCTCCAGTCCACAGGGCTAAGAAGAAGGAAGCCACCATCTCCCTACCTTCTCTTCAAGTGC CAAGGTCAAGCCTGACTTCCCGTGTTGTCTCCCGTGTTGATACCTCACACTCAGTGTCTTCATGGTTACACGTCTTCCCGAGTTGAGTCGAC CTGGGTTGTGTTGATACCTCACACTCAGTGTCTTCCCTCCAAGTAAGAAGAAGGAAGCCACCATCTCCCTACCAAGGTCAAGCCTG ACTTCCCCCTTGTCATCTAGTGGTCGTCTCCCCTCCAAAGTGTTACACGTCTTCATGCCTGCCTTCCCCTTCCCCTTCACACATG TGTTCCCGTCATCTAGTCGTGTCCCTCCAAAGTCACGTTCGTCTCCCCTCTGATCCCATGTGTCTCCCCATGTTCA | MMVHTRESSTQQFKSLFVRAVR AYNGENWRTSISDMELALPDFL KAFYECLAACEGSREIKDFKDF YLSIADHYVEVLECKIRCEETL TPVIGGYPVEKFVATMYHYLQF AYYKLNDLKNAAPCAVSYLLFD QSDRVMQQNLVYYQYHRDKWGL SDEHFQRPEAVQFFNVTTLQK ELYDFAQEHLMDDDEGEVVEYV DDLLETEESA |

FIG. 85

| Nucleotide Sequence (5'-3') | ORFs |
|---|---|
| SEQ ID NO. 88 | SEQ ID NO.:153 |
| AGCGGACTGGGAGCGCCTTCCGGAGAGACGCAGTCGGCTGCCACCCCGGGATGGGTCGCTGGTGCCAGACCGTCGCGCGC GGGCAGCGCCCCCGGACGTCTGCCCCTCCCCGCGGGGGCGCTGCTGCTGCTGCTGCTGCGCAGCCTGCAGGTTG CTGGGGCGCAGGGGAAGCCCCGGGGCGCTGTCCACTGCTGCTCTGCCGACCAGAGCGTCAGTGTGTCCCAAGGCCA CCTGTCCTTCCAGCCGCCGGCCCTTCTCTGGCAGACCCCGACACCAGACTGCCCTCCAGCCTGTGTCCAGGAGACCCAA TTCCCAGTTTCTGAAGGCAAAGTCGACCCATACCGCTCCTGTGCCTTTTCCTACGAGCAGGACCCCACCCTCAGGACCC AGAAGCCGTGCTCGGCGTGGCCTGGAGTGCCAATGCACGTGCAGCGTCAGCCTGATGTTATCTACTGAGGTGCACCATCATTG CCTCCAGTGGGTGCTGACTGTGCCCACTGCTGGGCCACTGTCCGGTGCTCCAGTGCTCATCATGCAGAACTCAAGTACAGCAGTCCGTGG ATTGACCAGATGACGCAGACCGCCAGGCCAACGACATCGGCCTCCTCAAGCTCAAGGAACTCAAGTACAGCAGTACGTGCGGC CTGGTCCTGGGTGGGCCTGGCCACGACTATGTTCCGGACCATTCCCGCCACTGTGACGGCGTGGGACTTTCGAAGGCT CCATCGCCTGCCTGCCTCAGTTGCCCACTGTTCCGGACCATTCGGTCCAGATCATGTCCAGATCATGAACACAAGAGTGTGACAATTCTA GACGGCATGTGGCCTCACAAATCCCACTTCGGTTCAGATGAGGACTGTCCAGATGATGTGCGGAGACACCACAGGAGA CACAACTTCACCAAGATCCCACTTCTGCTATGAGAGCTAACTGGAGAGCCCTTGCTGTCTGTCCCATCATACCAGTGATCGAGTGCCT AGTTCTGCCGATGGCTGGCTCCAGAAGAGCGAGGCCCCTGCCAGCCCCATCCAGAGACCCCTGCTCCTCGGCACTGCCT CAACGGGCAGGCCCTGACTCTGTGTGCCCTCTGTGGGCCCCACTTGTGGGCCCCTGCCCCAGGTTGCCTAGGTGCCAGCTGTCAC AGCCCTGAGAGTCAGGGTGAGAGGTGAGATGAGGTGCTCAATTAAACATTACTGTTTCATGCAAAAAAAAAAAAAAAA | MGRWCQTVARGQRPRTSAPSRA GALLLLLLRSAGCWGAGEAP GALSTADPADQSVQCVPKATCP SSRPRLLWQTPTTQTLPSTTME TQFPVSEGKVDPYRSCGFSYEQ DPTLRDPEAVARRWPMVSVRA NGTHICAGTIIASQWVLTVARC LIWRDVIYSVRVGSPWIDQMTQ TASDVPVLQVIMHSRYRAQRFW SWVGQANDIGLLKLKQELKYSN YVRPICLPGTDYVLKDHSRCTV TGWGLSKADGMWPQFRTIQEKE VIILNNKECDNFYHNFTKIPTL VQIIKSQMCAEDTHREKPCYE LTGEPIVCSMEGTWYLVGLVSW GAGCQKSEAPPIYLQVSSYQHW IWDCLNGQALALPAPSRTLLIA LPLPLSLLAAL |
| SEQ ID NO. 89 | SEQ ID NO.:154 |
| GCAAATCTTCAGGGGCCGTCCAGGACTACAGAGCTGTTTCACCCTACCTTGGCTTCAATCTCTTCCCCATGCTCGAAGG TGCGGAGCTGTACTTCAACGTGGACCATGGCTACCTGGAGGGCCTGGTTCGAGGATGCAAGGCCAGCCTCCTGACCCAGC AAGACTATATCAACCTGGTCCAGTGTGCAGACCCTAGAGAGACCTGAAATTCATCTCCAGACTACTGATTATGGTAACTTT TTGGCTAATCACACAACATTCCCTGACGTGTTCCAAAATTGACACTGAGATGAGGAAAAGACTATGTGGAGAATTTGAGTA TTTCCGGAATCATTCCCTGGAGCCCTCAGCACATTCTCACCTAGCGTGCAGTTATATGATGATAGACAATGTGATTC TGCTGATGAATGGTGCATTGCAGAAGAAATCTGTGAAAGAAATTCTGGGAAGTGCCACCCCGTTTCACAGAA ATGGAAGCTGTCAACATTGCAGAGACACCTTCAGATCTCTTTAATGCCATTCTGATCGAAACGCCATTAGCTCCATTCTT CCAAGACTGCATGTCTGAAAATGCTCTAGAATGACTGAATATTGAATTGCTACGCAGAGTAGTTGTCCCATTCTTGAGTTTGAGGCCGAC AGGCATTCTATAAATTCTGTAAGAATCATGGTGATGTCACTGCACTGAATTGAGCAGAAGTTATGTGTCCATTCTTGAGTTTGAGGCCGAC AGACGTGCTTTTATCATCACTCTTAACTCCTTTGCGACTGAATTGAGCAGAAGACCTCTATCCAACCTT CGGCAAACTCTATCCTGAGGGTTGCGGCTGTTGCTCAAGCTGCTCAAGCTGCTCTCTTCCTGATCATT | MLEGAELYFNVDHGYLEGLVRG CKASLLTQQDYINLVQCETLED LKIHLQTTDYGNFLANHTNPLT VSKIDTEMRKRLCGEFEYFRNH SLEPLSTFLTIMTCSYMIDNVI LLMNGALQKKSVKEILGKCHPL GRFTEMEAVNIAETPSDLFNAI LIETPLAPFFQDCMSENALDEL NIELLRNKLYKSYLEAFYKFCK NHGDVTAFVMCPILEFEADRRA FIITLNSFGTELSKEDRETLYP |

FIG. 86

| Nucleotide Sequence (5'-3') | ORFs |
|---|---|
| ACGGAGTATACAAACCTTTATTTGAAGCTGTAGTGGCAGTGGGGGAAAGACATTGGAGGACGTGTTTTACGAGCGTGAG GTACAAATGAATGTGCTGGCATTCAACAGACAGTTCCACTACGGTGTGTTTTATGCATATGTAAAGCTGAAGGAACAGGA AATTAGAAATATTGTGTGGATAGCAGAAATGTATTTCAGAGAGGCATCGAACTAAAATCAACAGTTACATTCCAATTTAT AACCCAAGTAAGGTTCTCAAATGTTCAAAATATTATAAAATTGTTAAAAGGAAGTTATTGAAGAAAAGAAATTATGTTA TATTATCTAGACTACTACACAAAGTAAGCCACACTACTATATCTTCATGGAGTTGCAAATCCATGAAGTCTAAACCAGCCCT GAAACAAAGCATTCCTTGTTTTCAGTGGTATTAGATCTTGTTCCACATGTCTGTTCATTCTTCACTGGGCCTTACAG GTAGTTTTAATTAACTCTATGGTATTTTCTTATTCTTGTGTTGATCATGTTAAAATTGGACCTAATAAAGTATTTTA TTCTTGCTTTTCCATGCTCTCTACAGGTCCAAATACTGAATGTCTCCTTACTTTTCTCTTTAAATTTTTTCTAGA CAGGGTCTCACTCTGTCACTAGGTCACAAGTAGCTACGTGGTGTGATCACAGTCGAGTGGCACTACAAGTGTACACCCCCACAGCCTGACTTCCCAGGCTCAAG TGATCCTCCCAGCTCTCAGCCTCCAAAGTAGCTCTCCAGGTCGAATTCCTGGGCTCCAGGGATCCACAGTCCCCTTGGCCT TGTAGAGACAGGGTTTCAACATATTACATGAGCCACTGATTTACATTTACATTCTGTGTCCTAGATT CCCAAAGTGTTGGGATTACAGCTGTATGTAGTCAACATGGTTCACAAGTGTTGGAAAATGTGTTTTTGTTTGTTGTT CACAGAAATCCAAAGCTCGGTAGCAGAGTTCCCTCTGCCTGGCCTCCGCCCAGGCTAGAGTAGCTGGATTACAAGCACCCTACCACTGAGTCCAGCTAA TCGTTTTGTTTGAGACAGGGTGTCAACAGCTTGGCTAGCAACCTCCAGCTCCTCACTCAGCTCC ACCTCCAGATTCAAGCAACTCTGCCTCGGGATTACAGGCGTGAGCCACTGCCGGCTAA TTTTGTATTTAGTAGAGCGGGTTTCACCATGTTGGCAGGCTGATCTTGAACTTGAACTTGAGTCATGATCCACCCG CCTCAGCCTCCCAAAGTGCTGGGATTACAGGCGTGAGCCACCTGCCCTTATTTTGTTTTCT AATATACTTTGATGTAATCAGCTTGAGAAAGCAACACAATTTCAAATCCATCTTCTAGATGCAAGCAGTGTTAAATTG TTAATAAATTTGCTTTTCACACCTTTCTTTAAATAAAGGTATATCTCTC | TFGKLYPEGLRLLAQAEDFDQM KNVADHYGVYKPLFEAVGGSGG KTLEDVFYEREVQMNVLAPNRQ FHYGVFYAYVKLKEQEIRNIVW IAECISQRHRTKINSYIPIL |

*Fig. 87*

POLYNUCLEOTIDES AND POLYPEPTIDE SEQUENCES INVOLVED IN THE PROCESS OF BONE REMODELING

The present application is a U.S. National Phase Application of International Application No. PCT/CA2005/001917, filed Dec. 13, 2005, which claims the benefit of U.S. Provisional Application No. 60/634,981, filed Dec. 13, 2004, all of which are hereby incorporated by reference in their entirety.

FIELD OF THE INVENTION

This invention relates, in part, to unique and newly identified genetic polynucleotides involved in the process of bone remodeling; variants and derivatives of the polynucleotides and corresponding polypeptides; uses of the polynucleotides, polypeptides, variants and derivatives; methods and compositions for the amelioration of symptoms caused by bone remodeling disorders, including but not limited to osteoporosis, osteopenia, osteomalacia, hyperparathyroidism, hypothyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Tumer syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes.

In particular, this invention relates to polynucleotide expression profiles of active osteoclasts, the isolation and identification of polynucleotides, polypeptides, variants and derivatives involved in osteoclast activity, validation of the identified polynucleotides for their potential as therapeutic targets and use of the polynucleotides, polypeptides, variants and derivatives for the amelioration of disease states and research purposes, as well as in diagnosis of disease states or in the predisposition to develop same.

BACKGROUND OF THE INVENTION

Bone is a dynamic connective tissue comprised of functionally distinct cell populations required to support the structural, mechanical and biochemical integrity of bone and the human body's mineral homeostasis. The principal cell types involved include, osteoblasts responsible for bone formation and maintaining bone mass, and osteoclasts responsible for bone resorption. Osteoblasts and osteoclasts function in a dynamic process termed bone remodeling. The development and proliferation of these cells from their progenitors is governed by networks of growth factors and cytokines produced in the bone microenvironment as well as by systemic hormones. Bone remodeling is ongoing throughout the lifetime of the individual and is necessary for the maintenance of healthy bone tissue and mineral homeostasis. The process remains largely in equilibrium and is governed by a complex interplay of systemic hormones, peptides and downstream signalling pathway proteins, local transcription factors, cytokines, growth factors and matrix remodeling genes.

Any interference or imbalance arising in the bone remodeling process can produce skeletal disease, with the most common skeletal disorders characterized by a net decrease in bone mass. A primary cause of this reduction in bone mass is an increase in osteoclast number and/or activity. The most common such disease, and perhaps the most well known, is osteoporosis occurring particularly in women after the onset of menopause. In fact osteoporosis is the most significant underlying cause of skeletal fractures in late middle-aged and elderly women. While estrogen deficiency has been strongly implicated as a factor in postmenopausal osteoporosis, there is longstanding evidence that remodeling is a locally controlled process being that it takes place in discrete packets throughout the skeleton as first described by Frost over forty years ago (Frost H. M. 1964).

Since bone remodeling takes place in discrete packets, locally produced hormones and enzymes may be more important than systemic hormones for the initiation of bone resorption and the normal remodeling process. Such local control is mediated by osteoblasts and osteoclasts in the microenvironment in which they operate. For example, osteoclasts attach to the bone matrix and form a separate compartment between themselves and the bone surface delimited by a sealing zone formed by a ring of actin surrounding the ruffled border. Multiple small vesicles transport enzymes toward the bone matrix and internalize partially digested bone matrix. The microenvironment within the sealing zone is rich with the presence of lysosomal enzymes and is highly acidic compared to the normal physiological pH of the body. The ruffled border membrane also expresses RANK, the receptor for RANKL, and macrophage-colony stimulating factor (M-CSF) receptor, both of which are responsible for osteoclast differentiation, as well as the calcitonin receptor capable of rapidly inactivating the osteoclast (Baron, R. 2003).

In a complex pattern of inhibition and stimulation not yet fully understood, growth hormone, insulin-like growth factor-1, the sex steroids, thyroid hormone, calciotrophic hormones such as PTH and prostaglandin E2, various cytokines, such as interleukin-1 beta, interleukin-6, and tumour necrosis factor-alpha, and 1,25-dihydroxyvitamin D (calcitriol) act coordinately in the bone remodeling process (Jilka et al. 1992; Poli et al. 1994; Srivastava et al. 1998; de Vernejoul 1996).

Thus, it stands to reason that the unique local environments created by these specialized cells is due to the expression of either unique genetic sequences not expressed in other tissues and/or splice variants of polynucleotides and polypeptides expressed in other tissues. The isolation and identification of polynucleotides, polypeptides and their variants and derivatives specific to osteoclast activity will permit a clearer understanding of the remodeling process and offer tissue specific therapeutic targets for the treatment of disease states related to bone remodeling.

Many diseases linked to bone remodeling are poorly understood, generally untreatable or treatable only to a limited extent. For example, osteoarthritis is difficult to treat as there is no cure and treatment focuses on relieving pain and preventing the affected joint from becoming deformed. Non-steroidal anti-inflammatory drugs (NSAIDs) are generally used to relieve pain.

Another example is osteoporosis where the only current medications approved by the FDA for use in the United States are the anti-resorptive agents that prevent bone breakdown. Estrogen replacement therapy is one example of an anti-resorptive agent. Others include alendronate (Fosamax—a biphosphonate anti-resorptive), risedronate (Actonel—a bisphosphonate anti-resorptive), raloxifene (Evista—selective estrogen receptor modulator (SERM)), calcitonin (Calcimar—a hormone), and parathyroid hormone/teriparatide (Forteo—a synthetic version of the human hormone, parathyroid hormone, which helps to regulate calcium metabolism).

Bisphosphonates such as alendronate and risedronate bind permanently to the surface of bone and interfere with osteoclast activity. This allows the osteoblasts to outpace the rate of resorption. The most common side effects are nausea, abdominal pain and loose bowel movements. However, alendronate is reported to also cause irritation and inflammation of the esophagus, and in some cases, ulcers of the esophagus. Risedronate is chemically different from alendronate and has less likelihood of causing esophagus irritation. However, certain foods, calcium, iron supplements, vitamins and minerals, or antacids containing calcium, magnesium, or aluminium can reduce the absorption of risedronate, thereby resulting in loss of effectiveness.

The most common side effect of Raloxifen and other SERMS (such as Tamoxifen) are hot flashes. However, Raloxifene and other hormone replacement therapies have been shown to increase the risk of blood clots, including deep vein thrombosis and pulmonary embolism, cardiovascular disease and cancer.

Calcitonin is not as effective in increasing bone density and strengthening bone as estrogen and the other anti-resorptive agents. Common side effects of either injected or nasal spray calcitonin are nausea and flushing. Patients can develop nasal irritations, a runny nose, or nosebleeds. Injectable calcitonin can cause local skin redness at the site of injection, skin rash, and flushing.

A situation demonstrative of the link between several disorders or disease states involving bone remodeling is that of the use of etidronate (Didronel) first approved by the FDA to treat Paget's disease. Paget's disease is a bone disease characterized by a disorderly and accelerated remodeling of the bone, leading to bone weakness and pain. Didronel has been used 'off-label' and in some studies shown to increase bone density in postmenopausal women with established osteoporosis. It has also been found effective in preventing bone loss in patients requiring long-term steroid medications (such as Prednisone or Cortisone). However, high dose or continuous use of Didronel can cause another bone disease called osteomalacia. Like osteoporosis, osteomalacia can lead to weak bones with increased risk of fractures. Because of osteomalacia concerns and lack of enough studies yet regarding reduction in the rate of bone fractures, the United States FDA has not approved Didronel for the treatment of osteoporosis.

Osteoporosis therapy has been largely focused on antiresorptive drugs that reduce the rate of bone loss but emerging therapies show promise in increasing bone mineral density instead of merely maintaining it or slowing its deterioration. The osteoporosis early stage pipeline consists largely of drug candidates in new therapeutic classes, in particular cathepsin K inhibitors, osteoprotegerin and calcilytics as well as novel bisphosphonates. Some of these are examples where novel drugs exploiting genomics programs are being developed based on a deeper understanding of bone biology and have the potential to change the face of treatment of bone disorders in the long term.

The present invention satisfies a need in the art. There thus remains a need to better understand the bone remodeling process and to provide new compositions that are useful for the diagnosis, prognosis, treatment, prevention and evaluation of therapies for bone remodeling and associated disorders. A method for analysing polynucleotide expression patterns has been developed and applied to identify polynucleotides, polypeptides, variants and derivatives specifically involved in bone remodeling.

The present invention seeks to meet these and other needs.

The present description refers to a number of documents, the content of which is herein incorporated by reference in their entirety.

SUMMARY OF THE INVENTION

The present invention relates to polynucleotides comprising sequences involved in the process of bone remodeling including their open reading frame, substantially identical sequences, substantially complementary sequences and fragments thereof.

The present invention relates to polypeptide comprising sequences involved in the process of bone remodeling including biologically active analogs and biologically active fragments thereof.

The present invention also relates to compositions that are useful for the diagnosis, prognosis, treatment, prevention and/or evaluation of therapies for bone remodeling and associated disorders.

In addition, the present invention relates to a method for analyzing polynucleotide expression patterns, and applied to identify polynucleotides, polypeptides, variants and derivatives specifically involved in bone remodeling.

Furthermore, the present invention relates to polynucleotide and polypeptide sequences, variants and derivatives thereof which have been validated as potential therapeutic targets.

The identification of gene products involved in regulating osteoclast differentiation and function has led to the discovery of novel targets for the development of new and specific therapies of disease states characterized by abnormal bone remodeling.

The present invention relates to polynucleotide expression profiles of osteoclasts, the isolation and identification of polynucleotides, their corresponding polypeptides, variants and derivatives involved in osteoclast activity, validation of these identified elements for their potential as therapeutic targets and use of said polynucleotides, polypeptides, variants and derivatives for the amelioration of disease states.

It is an object of the present invention to provide polynucleotides and related polypeptides that have been isolated and identified. More specifically, the invention provides polynucleotides comprising any one of SEQ. ID. NOs:1 to 57 or 83 to 89, their coding sequence (open reading frame) and related polypeptides comprising any one of SEQ ID NO.: 93 to 155 which have been shown to be upregulated in a highly specific fashion in osteoclasts.

The present invention more particularly relates to polynucleotides, their coding sequence (open reading frame), and related polypeptides, which have been demonstrably shown to be necessary or crucial for osteoclast differentiation (e.g. SEQ. ID. NOs:1 to 7, 88 and 89).

Of the polynucleotides (e.g. SEQ. ID. NOs:8 to 56) whose gene expression is upregulated, 37 were tested in the model using siRNA for biological validation leaving 12 still to be tested, 28 does not appear to phenotypically perturb osteoclast differentiation in the model used whereas 9 did (SEQ ID NO.:16, SEQ ID NO.:19, SEQ ID NO.:21, SEQ ID NO.:24, SEQ ID NO.:29, SEQ ID NO.:31, SEQ ID NO.:37 and SEQ ID NO.:42). However, a more discrete effect not phenotypically measurable cannot be ruled out for those 28. Without being limited to a particular model, this may be due in part to non-functional siRNA and/or to their roles in the downstream bone remodeling activities of osteoclasts. For example, polynucleotides for cathepsin K (CTSK) and matrix metalloproteinase 9 (MMP-9) are well known markers which are essential for osteoclast activities in bone remodelling but are not required for osteoclast differentiation. NSEQ refers generally to polynucleotide sequences of the present invention and includes for example, SEQ. ID. NOs:1 to 56 and 83 to 89, whereas PSEQ refers generally to polypeptide sequences of the present invention and includes, for example, SEQ ID NO.:93 to 99 and 101 to 155. Of course it will be understood that NSEQ also encompasses polynucleotide sequences which are designed or derived from SEQ. ID. NOs:1 to 57 and 83 to 89 and more particularly from their coding sequence. Non-limiting examples of such sequences are disclosed herein (e.g. SEQ ID Nos 64-82 and 90).

The present invention also provides a method of using a polynucleotide selected from SEQ ID NO's 1 to 57 and 83 to 89 and more particularly their coding sequence and encoded polypeptides thereof to screen a library of molecules or compounds (e.g. DNA molecules, RNA molecules, PNAs, mimetics and proteins) to identify or purify a ligand which specifically binds the polynucleotide by combining a polynucleotide with a library of molecules or compounds under conditions to allow specific binding, and detecting specific binding, thereby identifying or purifying a ligand which specifically binds the polynucleotide.

The present invention relates in one aspect thereof to an isolated polynucleotide sequence having at least from about 80% to about 100% (e.g., 80%, 90%, 95%, etc.) nucleic acid sequence identity to a polynucleotide sequence selected from the group consisting of polynucleotides comprising (a) any one of a SEQ. ID. NOs:1 to 57 and 83 to 89; (b) an open reading frame of (a); (c) a full complement of (a) or (b), and; (d) a fragment of any one of (a) to (c).

Complements of the isolated polynucleotide sequence encompassed by the present invention may be those, for example, which hybridize under high stringency conditions to any of the nucleotide sequences in (a), or (b). The high stringency conditions may comprise, for example, a hybridization reaction at 65° C. in 5×SSC, 5×Denhardt's solution, 1% SDS, and 100 µg/ml denatured salmon sperm DNA.

In accordance with the present invention, the polynucleotide sequence may be used, for example, in the treatment of diseases or disorders involving bone remodelling.

Fragments of polynucleotides may be used, for example, as probes for determining the presence of the isolated polynucleotide (or its complement or fragments thereof in a sample, cell, tissue, etc. for experimental purposes or for the purpose of diagnostic of a diseases or disorders involving bone remodelling.

The present invention also relates to a combination comprising a plurality of polynucleotides (substantially purified and/or isolated) that may be co-expressed with one or more genes known to be involved in bone remodelling, the plurality of polynucleotides may be selected, for example, from the group consisting of a polynucleotide comprising (a) any one of SEQ. ID. NOs:1 to 57, 83 to 89; (b) an open reading frame (a); (c) a full complement of (a) or (b); (d) a sequence that hybridizes under high stringency conditions to any one of the nucleotide sequences in (a), or (b) and; (e) fragments of (a), (b), (c) or (d).

The present invention further relates to a polynucleotide encoding any one of the polypeptides described herein. In accordance with the present invention, the polynucleotide (RNA, DNA, etc.) may encode a polypeptide which may be selected from the group consisting of any one of SEQ ID NO.:93 to 155, analogs or fragments thereof (e.g., biologically active fragments, immunologically active fragments, etc.).

The present invention also relates to an isolated nucleic acid molecule comprising the polynucleotides of the present invention, operatively linked to a nucleotide sequence encoding a heterologous polypeptide thereby encoding a fusion polypeptide.

The invention further relates to a polypeptide encoded by a polynucleotide of SEQ. ID. NOs: 1 to 56 or 83 to 89 and more particularly from the open reading frame of any one of SEQ. ID. NOs:1 to 56 or 83 to 89, or a portion thereof, comprising the product of a gene that is co-expressed with one or more genes known to be involved in bone remodeling.

The invention additionally relates to the use of the polypeptide or a portion thereof to screen a library of molecules or compounds (DNA molecules, RNA molecules, PNAs, mimetics, proteins, agonists, antagonists, and antibodies) to identify or purify at least one ligand which specifically binds the polypeptide by combining the polypeptide or a portion thereof with the library of molecules or compounds under conditions to allow specific binding, and detecting specific binding between the polypeptide and ligand, thereby identifying or purifying a ligand which specifically binds the polypeptide.

Isolated naturally occurring allelic variant are also encompassed by the present invention as well as synthetic variants (e.g., made by recombinant DNA technology or by chemical synthesis, etc.) such as biologically active variant which may comprise one or more conservative amino acid substitutions (compared to a naturally occurring polypeptide).

The present invention, further provides a vector (mammalian, bacterial, viral, etc.) comprising the polynucleotides described herein or fragments thereof, such as an expression vector. The vector may further comprise a nucleic acid sequence which may help in the regulation of expression of the polynucleotide and/or a nucleotide sequence encoding a tag (e.g., affinity tag; HA, GST, His etc.).

In accordance with the present invention, an expression vector may comprise, for example, the following operatively linked elements:
 a) a transcription promoter;
 b) a polynucleotide segment (which may comprise an open reading frame); and
 c) a transcription terminator.

The invention also relates to an expression vector comprising a polynucleotide described herein, a host cell transformed with the expression vector and a method for producing a polypeptide of the present invention.

More particularly, the present invention therefore provides a cell which may be genetically engineered to contain and/or to express the polynucleotide (including complements and fragments) and/or polypeptides of the present invention. The cell may be, for example, a mammalian cell, an insect cell, a bacteria cell, etc.

The present invention, therefore provides a host cell which may comprise a vector as described herein. The cell may be, for example, mammalian cell, an insect cell, a bacteria, etc. The cell may be able to express or expresses a polypeptide encoded by the polynucleotide described herein.

Methods of producing the polypeptides of the present invention encompassed herewith includes for example, culturing the cell in conditions allowing the expression of the polypeptide. The polypeptide may be recovered, for example, from cell lysate or from the cell supernatant.

The present invention also relates to a method of using a polynucleotide sequence described herein to screen a library of molecules or compounds including but not limited to, DNA molecules, RNA molecules, PNAs (peptide nucleic acids), peptides, ribozymes, antibodies, agonists, antagonists, immunoglobulins, inhibitors, proteins including transcription factors, enhancers, repressors, and drugs and the like which regulate the activity of the selected polynucleotide sequence in a biological system, to identify or purify a ligand which may specifically bind the polynucleotide by combining a polynucleotide with a library of molecules or compounds under conditions which may allow specific binding, and detecting specific binding, thereby identifying or purifying a ligand which may specifically bind the polynucleotide.

The antagonist, agonist, ligand thus identified may be used in the treatment of bone remodelling diseases or disorders.

The invention relates to the use of at least one polynucleotide comprising any one of SEQ. ID. NOs:1 to 57 and/or 83 to 89, their coding sequence, substantially identical sequences, substantially complementary sequences and fragments thereof on an array and for the use of that array in a method for diagnosing a bone remodeling disease or disorder by hybridizing the array with a patient sample under conditions to allow complex formation, detecting complex formation, and comparing the amount of complex formation in the patient sample to that of standards for normal and diseased tissues wherein the complex formation in the patient sample indicates the presence of a bone remodeling disease or disorder. Of course, the use of a polynucleotide of the present invention in a diagnosis method is not dependent exclusively by way of an assay. The sequence or sequences may be used in conventionally used diagnosis methods known in the art.

The present invention also relates to a method of ameliorating bone remodelling disease or disorder symptoms, or for inhibiting or delaying bone disease or disorder, the method may comprise: contacting a compound capable of specifically inhibiting activity or expression of a polynucleotide sequence described herein or a polypeptide described herein, in osteoclasts so that symptoms of the bone remodelling disease or disorder may be ameliorated, or the disease or disorder may be prevented, delayed or lowered.

The present invention further relates to a method for ameliorating bone remodelling disease or disorder symptoms, or for inhibiting or delaying bone disease or disorder, the method may comprise: contacting a compound capable of specifically promoting activity or expression of a polynucleotide sequence described herein or a polypeptide described herein, in osteoclasts so that symptoms of the bone remodelling disease or disorder may be ameliorated, or the disease or disorder may be prevented, delayed or lowered.

The present invention also relates to a method of treating a condition in a mammal characterized by a deficiency in, or need for, bone growth or replacement and/or an undesirable level of bone resorption, which method may comprise administering to a mammalian subject in need of such treatment an effective amount of a suitable compound described herein.

The present invention further relates to a method of using a polynucleotide sequence described herein, a polypeptide described herein on an array and for the use of the array in a method for diagnosing a bone remodelling disease or disorder by hybridizing the array with a patient sample under conditions to allow complex formation, detecting complex formation, and comparing the amount of complex formation in the patient sample to that of standards for normal and diseased tissues wherein the complex formation in the patient sample may indicate the presence of a bone remodelling disease or disorder.

In accordance with the present invention the isolated polynucleotide sequence described herein, the antagonist described herein, the ligand described herein, or the method described herein, may be used for diseases or disorders which may be selected from the group consisting of, but not limited to, osteoporosis, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Tumer syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes.

In accordance with the present invention, the method of administration may be selected from, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In accordance with the present invention, the polynucleotide sequence described herein may be used for somatic cell gene therapy or for stem cell gene therapy.

The invention also relates to a pharmaceutical composition comprising a polynucleotide described herein, a polypeptide encoded by the selected polynucleotide, a portion thereof, a ligand (agonist or antagonist) identified or purified using a selected polynucleotide or a polypeptide encoded by the selected polynucleotide, or a portion thereof, which modulates the activity (activation, enhancement or inhibition) of the selected polynucleotide or a polypeptide encoded thereby, a portion thereof, and a suitable pharmaceutical carrier.

Additionally, the invention relates to products, compositions, processes and methods that comprises a polynucleotide described herein, a polypeptide encoded by the polynucleotides, a portion thereof, their variants or derivatives, for research, biological, clinical and therapeutic purposes.

The NSEQs and PSEQs may be used in diagnosis, prognosis, treatment, prevention, and selection and evaluation of therapies for diseases and disorders involving bone remodeling including, but not limited to, osteoporosis, osteopenia, osteomalacia, hyperparathyroidism, hyperthyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Tumer syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes.

Use of NSEQ as a Screening Tool

The polynucleotides obtained by the present invention may be used to detect and isolate expression products, for example, mRNA, complementary DNAs (cDNAs) and proteins derived from or homologous to the NSEQs. In one embodiment, the expression of mRNAs homologous to the NSEQs of the present invention may be detected, for example, by hybridization analysis, reverse transcription and in vitro nucleic acid amplification methods. Such procedures permit detection of mRNAs In a variety of tissue types or at different stages of development. The subject nucleic acids which are expressed in a tissue-specific or a developmental-stage-specific manner are useful as tissue-specific markers or for defining the developmental stage of a sample of cells or tissues that may define a particular disease state. One of skill in the art may readily adapt the NSEQs for these purposes.

Those skilled in the art will also recognize that the NSEQs, and its expression products such as cDNA nucleic acids and genomic DNA may be used to prepare short oligonucleotides sequences. For example, oligonucleotides having ten to twelve nucleotides or more may be prepared which hybridize specifically to the present NSEQs and cDNAs and allow detection, identification and isolation of unique nucleic sequences by hybridization. Sequences of for example, at least 15-20 nucleotides may be used and selected from regions that lack homology to other known sequences. Sequences of 20 or more nucleotides that lack such homology show an increased specificity toward the target sequence. Useful hybridization conditions for probes and primers are readily determinable by those of skill in the art. Stringent hybridization conditions encompassed herewith are those that may allow hybridization of nucleic acids that are greater than 90% homologous but which may prevent hybridization of nucleic acids that are less than 70% homologous. The specificity of a probe may be determined by whether it is made from a unique region, a regulatory region, or from a conserved motif. Both probe specificity and the stringency of diagnostic hybridization or amplification (maximal, high, intermediate, or low) reactions may be determined whether the probe identifies exactly complementary sequences, allelic variants, or related sequences. Probes designed to detect related sequences may have at least 50% sequence Identity to any of the selected polynucleotides.

It is to be understood herein that the NSEQs (substantially identical sequences and fragments thereof) may hybridize to a substantially complementary sequence found in a test sample. Additionally, a sequence substantially complementary to NSEQ may bind a NSEQ found in a test sample.

Skilled practitioners will also recognize that the NSEQs and PSEQs may be used to screen a library of molecules for specific binding affinity. Typical assays may be used to screen a library of DNA molecules, RNA molecules, PNAs (peptide nucleic acids), peptides, ribozymes, antibodies, agonists, antagonists, immunoglobulins, inhibitors, proteins including transcription factors, enhancers, repressors, and drugs and the like which regulate the activity of the selected polynucleotide sequence in a biological system. Typical assays may involve providing a library of molecules, combining the polynucleotide sequence or a fragment thereof with the library of molecules under conditions suitable to allow specific binding, and detecting specific binding to identify or purify, at least one molecule (ligand) which may specifically bind the polynucleotide sequence. One of skill in the art may readily adapt the NSEQs for these purposes.

Those of skill in the art may readily label the NSEQs and PSEQs by standard methods to add them to a sample from a subject under conditions for the formation and detection of hybridization complexes. After incubation the sample may be washed, and the signal associated with hybrid complex formation may be quantified and compared with a standard or normal value. Standard or normal values may be derived from any control sample, typically one that may be free of a suspect disease. If the amount of signal in the subject sample is altered in comparison to the standard value, then the presence of altered levels of expression in the sample may indicate the presence of the disease. Qualitative and quantitative methods for comparing the hybridization complexes formed in subject samples with previously established standards are well known in the art.

Furthermore, a probe may be labelled by any procedure known in the art, for example by incorporation of nucleotides linked to a "reporter molecule". A "reporter molecule", as used herein, may be a molecule that provides an analytically identifiable signal allowing detection of a hybridized probe. Detection may be either qualitative or quantitative. Commonly used reporter molecules include fluorophores, enzymes, biotin, chemiluminescent molecules, bioluminescent molecules, digoxigenin, avidin, streptavidin or radioisotopes. Commonly used enzymes include horseradish peroxidase, alkaline phosphatase, glucose oxidase and β-galactosidase, among others. Enzymes may be conjugated to avidin or streptavidin for use with a biotinylated probe. Similarly, probes may be conjugated to avidin or streptavidin for use with a biotinylated enzyme. Incorporation of a reporter molecule into a DNA probe may be by any method known to the skilled artisan, for example by nick translation, primer extension, random oligo priming, by 3' or 5' end labeling or by other means. In addition, hybridization probes include the cloning of nucleic acid sequences into vectors for the production of mRNA probes. Such vectors are known in the art, are commercially available, and may be used to synthesize RNA probes in vitro. The labelled polynucleotide sequences may be used in Southern or northern analysis, dot blot, or other membrane-based technologies; in PCR technologies; and in micro arrays utilizing samples from subjects to detect altered expression. Oligonucleotides useful as probes for screening of samples by hybridization assays or as primers for amplification may be packaged into kits. Such kits may contain the probes or primers in a pre-measured or predetermined amount, as well as other suitably packaged reagents and materials needed for the particular hybridization or amplification protocol.

In another embodiment, the invention entails a substantially purified polypeptide encoded by the polynucleotides of NSEQs, polypeptide analogs or polypeptide fragments thereof. The polypeptides whether in a premature, mature or fused form, may be isolated from lysed cells, or from the culture medium, and purified to the extent needed for the intended use. One of skill in the art may readily purify these proteins, polypeptides and peptides by any available procedure. For example, purification may be accomplished by salt fractionation, size exclusion chromatography, ion exchange chromatography, reverse phase chromatography, affinity chromatography and the like.

The invention further provides for a polypeptide encoded by the polynucleotides of NSEQs, or a portion thereof, comprising the product of a gene that is co-expressed with one or more genes known to be involved in bone remodeling. The invention additionally provides for the use of the polypeptide or a portion thereof to screen a library of molecules or compounds (DNA molecules, RNA molecules, PNAs, mimetics, proteins, agonists, antagonists, and antibodies) to identify or purify at least one ligand which specifically binds the polypeptide by combining the polypeptide or a portion thereof with the library of molecules or compounds under conditions to allow specific binding, and detecting specific binding between the polypeptide and ligand, thereby identifying or purifying a ligand which specifically binds the polypeptide. One of skill in the art may readily adapt the NSEQs for these purposes.

The portion of a polypeptide employed in such screening may be free in solution, affixed to an abiotic or biotic substrate or located intra-cellularly. Specific binding between the polypeptide and the molecule may be measured. The assay may be used to screen a library of DNA molecules, RNA molecules, PNAs, peptides, mimetics, ribozymes, antibodies, agonists, antagonists, immunoglobulins, inhibitors, peptides, polypeptides, drugs and the like, which may specifically bind the polypeptide. Many such assay methodologies are well known in the art and may be readily adapted by a skilled practitioner.

Use of NSEQ for Development of an Expression System

In order to express a biologically active polypeptide, NSEQ, or derivatives thereof, may be inserted into an expression vector, i.e., a vector that contains the elements for transcriptional and translational control of the inserted coding sequence in a particular host. These elements include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

A variety of expression vector/host cell systems known to those of skill in the art may be utilized to express NSEQ. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long-term production of recombinant proteins in mammalian systems, stable expression in cell lines may be effected. For example, NSEQ may be transformed into cell lines using expression vectors that may contain viral origins of replication and/or endogenous expression elements and a selectable or visible marker gene on the same or on a separate vector. The invention is not to be limited by the vector or host cell employed.

In general, host cells that contain NSEQ and that express a polypeptide encoded by the NSEQ, or a portion thereof, may be identified by a variety of procedures known to those of skill in the art. These procedures include, but are not limited to, DNA-DNA or DNA-RNA hybridizations, PCR amplification, and protein bioassay or immunoassay techniques that include membrane, solution, or chip based technologies for the detection and/or quantification of nucleic acid or amino acid sequences. Immunological methods for detecting and measuring the expression of polypeptides using either specific polyclonal or monoclonal antibodies are known in the art. Examples of such techniques include enzyme-linked immunosorbent assays (ELISAs), radioimmunoassays (RIAs), and fluorescence activated cell sorting (FACS). Those of skill in the art may readily adapt these methodologies to the present invention.

The present invention additionally relates to a bioassay for evaluating compounds as potential antagonists of the polypeptide described herein, the bioassay may comprise:
a) culturing test cells in culture medium containing increasing concentrations of at least one compound whose ability to inhibit the action of a polypeptide described herein is sought to be determined, wherein the test cells may contain a polynucleotide sequence described herein in a form having improved trans-activation transcription activity, relative to wild-type polynucleotide, and comprising a response element operatively linked to a reporter gene; and thereafter
b) monitoring in the cells the level of expression of the product of the reporter gene as a function of the concentration of the potential antagonist compound in the culture medium, thereby indicating the ability of the potential antagonist compound to inhibit activation of the polypeptide encoded by, the polynucleotide sequence described herein.

The present invention further relates to a bioassay for evaluating compounds as potential agonists for a polypeptide encoded by the polynucleotide sequence described herein, the bioassay may comprise:
a) culturing test cells in culture medium containing increasing concentrations of at least one compound whose ability to promote the action of the polypeptide encoded by the polynucleotide sequence described herein is sought to be determined, wherein the test cells may contain a polynucleotide sequence described herein in a form having improved trans-activation transcription activity, relative to wild-type polynucleotide, and comprising a response element operatively linked to a reporter gene; and thereafter
b) monitoring in the cells the level of expression of the product of the reporter gene as a function of the concentration of the potential agonist compound in the culture medium, thereby indicating the ability of the potential agonist compound to promote activation of a polypeptide encoded by the polynucleotide sequence described herein.

Host cells transformed with NSEQ may be cultured under conditions for the expression and recovery of the polypeptide from cell culture. The polypeptide produced by a transgenic cell may be secreted or retained intracellularly depending on the sequence and/or the vector used. As will be understood by those of skill in the art, expression vectors containing NSEQ may be designed to contain signal sequences that direct secretion of the polypeptide through a prokaryotic or eukaryotic cell membrane. Due to the inherent degeneracy of the genetic code, other DNA sequences that encode substantially the same or a functionally equivalent amino acid sequence may be produced and used to express the polypeptide encoded by NSEQ. The nucleotide sequences of the present invention may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In addition, a host cell strain may be chosen for its ability to modulate expression of the inserted sequences or to process the expressed polypeptide in the desired fashion. Such modifications of the polypeptide include, but are not limited to, acetylation, carboxylation, glycosylation, phosphorylation, lipidation, and acylation. Post-translational processing, which cleaves a "prepro" form of the polypeptide, may also be used to specify protein targeting, folding, and/or activity. Different host cells that have specific cellular machinery and characteristic mechanisms for post-translational activities (e.g., CHO, HeLa, MDCK, HEK293, and W138) are available commercially and from the American Type Culture Collection (ATCC) and may be chosen to ensure the correct modification and processing of the expressed polypeptide.

Those of skill in the art will readily appreciate that natural, modified, or recombinant nucleic acid sequences may be ligated to a heterologous sequence resulting in translation of a fusion polypeptide containing heterologous polypeptide moieties in any of the aforementioned host systems. Such heterologous polypeptide moieties may facilitate purification of fusion polypeptides using commercially available affinity matrices. Such moieties include, but are not limited to, glutathione S-transferase (GST), maltose binding protein, thioredoxin, calmodulin binding peptide, 6-His (His), FLAG, c-myc, hemaglutinin (HA), and monoclonal antibody epitopes.

In yet a further aspect, the present invention relates to an isolated polynucleotide which may comprise a nucleotide sequence encoding a fusion protein, the fusion protein may comprise a fusion partner fused to a peptide fragment of a protein encoded by, or a naturally occurring allelic variant polypeptide encoded by, the polynucleotide sequence described herein, which peptide fragment, when administered to a member of a mammalian species, may be capable of inducing the production of antibodies that bind specifically to the protein encoded by, or a naturally occurring allelic variant polypeptide encoded by, the polynucleotide sequence described herein.

Those of skill in the art will also readily recognize that the nucleic acid and polypeptide sequences may be synthesized, in whole or in part, using chemical or enzymatic methods well known in the art. For example, peptide synthesis may be performed using various solid-phase techniques and machines such as the ABI 431A Peptide synthesizer (PE Biosystems) may be used to automate synthesis. If desired, the amino acid sequence may be altered during synthesis and/or combined with sequences from other proteins to produce a variant protein.

Use of NSEQ as a Diagnostic Screening Tool

The skilled artisan will readily recognize that NSEQ may be used for diagnostic purposes to determine the absence, presence, or altered expression (i.e. increased or decreased compared to normal) of the gene. The polynucleotides may be at least 10 nucleotides long or at least 12 nucleotides long, or at least 15 nucleotides long up to any desired length and may comprise complementary RNA and DNA molecules, branched nucleic acids, and/or peptide nucleic acids (PNAs). In one alternative, the polynucleotides may be used to detect and quantify gene expression in samples in which expression of NSEQ is correlated with disease. In another alternative, NSEQ may be used to detect genetic polymorphisms associated with a disease. These polymorphisms may be detected in the transcript cDNA.

The invention provides for the use of at least one polynucleotide comprising NSEQ (e.g., an open reading frame of NSEQ, a substantially complementary sequence, a substantially identical sequence, and fragments thereof) on an array and for the use of that array in a method for diagnosing a bone remodeling disease or disorder by hybridizing the array with a patient sample under conditions to allow complex formation, detecting complex formation, and comparing the amount of complex formation in the patient sample to that of standards for normal and diseased tissues wherein the complex formation in the patient sample indicates the presence of a bone remodeling disease or disorder.

In another embodiment, the present invention provides one or more compartmentalized kits for detection of bone resorption disease states. A first kit has a receptacle containing at least one isolated probe. Such a probe may be a nucleic acid fragment which is present/absent in the genomic DNA of normal cells but which is absent/present in the genomic DNA of affected cells. Such a probe may be specific for a DNA site that is normally active/inactive but which may be inactive/active in certain cell types. Similarly, such a probe may be specific for a DNA site that may be abnormally expressed in certain cell types. Finally, such a probe may identify a specific DNA mutation. By specific for a DNA site is meant that the probe may be capable of hybridizing to the DNA sequence which is mutated, or may be capable of hybridizing to DNA sequences adjacent to the mutated DNA sequences. The probes provided in the present kits may have a covalently attached reporter molecule. Probes and reporter molecules may be readily prepared as described above by those of skill in the art.

Use of NSEQ as a Therapeutic

One of skill in the art will readily appreciate that the expression systems and assays discussed above may also be used to evaluate the efficacy of a particular therapeutic treatment regimen, in animal studies, in clinical trials, or to monitor the treatment of an individual subject. Once the presence of disease is established and a treatment protocol is initiated, hybridization or amplification assays may be repeated on a regular basis to determine if the level of expression in the patient begins to approximate the level observed in a healthy subject. The results obtained from successive assays may be used to show the efficacy of treatment over a period ranging from several days to many years.

Therefore, in a further aspect, the present invention relates to an antibody (e.g., isolated antibody), or antigen-binding fragment thereof, that may specifically bind to a protein or polypeptide described herein. The antibody may be, for example, a monoclonal antibody or a polyclonal antibody. The antibody may originate for example, from a mouse, rat or any other mammal.

The antibody may also be a human antibody which may be obtained, for example, from a transgenic non-human mammal capable of expressing human Ig genes. The antibody may also be a humanised antibody which may comprise, for example, one or more complementarity determining regions of non-human origin. It may also comprise a surface residue of a human antibody and/or framework regions of a human antibody. The antibody may also be a chimeric antibody which may comprise, for example, variable domains of a non-human antibody and constant domains of a human antibody.

Suitable antibodies may also include, for example, an antigen-binding fragment, an Fab fragment; an F(ab')$_2$ fragment, and Fv fragment; or a single-chain antibody comprising an antigen-binding fragment (e.g., a single chain Fv).

The antibody of the present invention may be mutated and selected based on an increased affinity and/or specificity for one of a polypeptide described herein and/or based on a reduced immunogenicity in a desired host.

The antibody may further comprise a detectable label attached thereto.

The present invention further relates to a method of producing antibodies able to bind to one of a polypeptide, polypeptide fragments, or polypeptide analogs described herein, the method may comprise:
  a) immunizing a mammal (e.g., mouse, a transgenic mammal capable of producing human Ig, etc.) with a suitable amount of a desired polypeptide or a polypeptide fragment thereof;
  b) collecting the serum from the mammal; and
  c) isolating the polypeptide-specific antibodies from the serum of the mammal.

The present invention also relates to a method of producing a hybridoma which secretes an antibody that binds to a polypeptide described herein, the method may comprise:
  a) immunizing a mammal (e.g., mouse, a transgenic mammal capable of producing human Ig, etc.) with a suitable amount of a desired polypeptide, a polypeptide fragment or analog thereof;
  b) obtaining lymphoid cells from the immunized animal obtained from (a);

c) fusing the lymphoid cells with an immortalizing cell to produce hybrid cells; and
d) selecting hybrid cells which produce antibody that specifically binds to the polypeptide, a polypeptide fragment or analog thereof.

The present invention further relates to a method of producing an antibody that binds to one of the polypeptide described herein, the method may comprise:
a) synthesizing a library of antibodies on phage or ribosomes;
b) panning the library against a sample by bringing the phage or ribosomes into contact with a composition comprising a polypeptide or polypeptide fragment described herein;
c) isolating phage which binds to the polypeptide or polypeptide fragment, and;
d) obtaining an antibody from the phage or ribosomes.

The antibody of the present invention may thus be obtained, for example, from a library (e.g., bacteriophage library) which may be prepared, for example, by
a) extracting cells which are responsible for production of antibodies from a host mammal;
b) isolating RNA from the cells of (a);
c) reverse transcribing mRNA to produce cDNA;
d) amplifying the cDNA using a (antibody-specific) primer; and
e) inserting the cDNA of (d) into a phage display vector or ribosome display cassette such that antibodies are expressed on the phage or ribosomes.

The host animal may be immunized with polypeptide and/or a polypeptide fragment and/or analog described herein to induce an immune response prior to extracting the cells which are responsible for production of antibodies.

The present invention also relates to a kit for specifically assaying a polypeptide described herein, the kit may comprise, for example, an antibody or antibody fragment capable of binding specifically to the polypeptide described herein.

Further, an antagonist, agonist, or an antibody that may bind specifically to a polypeptide encoded by the polynucleotides of NSEQ, or a portion thereof, may be administered to a subject to treat or prevent diseases or disorders associated with bone remodeling. The antagonist, antibody, or fragment may be used directly to inhibit the activity of the polypeptide or indirectly to deliver a therapeutic agent to cells or tissues that express the NSEQ. An immunoconjugate comprising a polypeptide-binding site of the antibody or the antagonist and a therapeutic agent may be administered to a subject in need to treat or prevent disease. The therapeutic agent may be a cytotoxic agent selected from a group including, but not limited to, abrin, ricin, doxorubicin, daunorubicin, taxol, ethidium bromide, mitomycin, etoposide, tenoposide, vincristine, vinblastine, colchicine, dihydroxy anthracin dione, actinomycin D, diphteria toxin, *Pseudomonas* exotoxin A and 40, radioisotopes, and glucocorticoid. Yet further, an agonist of the polypeptide may be administered to a subject to treat or prevent a disease associated with decreased expression, longevity or activity of NSEQ.

The present invention further contemplates antibodies that may bind to the polypeptide encoded by the polynucleotides of NSEQ, polypeptide analogs or portions thereof. Suitable antibodies may bind to unique antigenic regions or epitopes in the polypeptides, or a portion thereof. Epitopes and antigenic regions useful for generating antibodies may be found within the proteins, polypeptides or peptides by procedures available to one of skill in the art. For example, short, unique peptide sequences may be identified in the proteins and polypeptides that have little or no homology to known amino acid sequences. Preferably the region of a protein selected to act as a peptide epitope or antigen is not entirely hydrophobic; hydrophilic regions are preferred because those regions likely constitute surface epitopes rather than internal regions of the proteins and polypeptides. These surface epitopes are more readily detected in samples tested for the presence of the proteins and polypeptides. Such antibodies may include, but are not limited to, polyclonal, monoclonal, chimeric, and single chain antibodies, Fab fragments, and fragments produced by a Fab expression library. The production of antibodies is well known to one of skill in the art.

Peptides may be made by any procedure known to one of skill in the art, for example, by using in vitro translation or chemical synthesis procedures. Short peptides which provide an antigenic epitope but which by themselves are too small to induce an immune response may be conjugated to a suitable carrier. Suitable carriers and methods of linkage are well known in the art. Suitable carriers are typically large macromolecules such as proteins, polysaccharides and polymeric amino acids. Examples include serum albumins, keyhole limpet hemocyanin, ovalbumin, polylysine and the like. One of skill in the art may use available procedures and coupling reagents to link the desired peptide epitope to such a carrier. For example, coupling reagents may be used to form disulfide linkages or thioether linkages from the carrier to the peptide of interest. If the peptide lacks a disulfide group, one may be provided by the addition of a cysteine residue. Alternatively, coupling may be accomplished by activation of carboxyl groups.

The minimum size of peptides useful for obtaining antigen specific antibodies may vary widely. The minimum size must be sufficient to provide an antigenic epitope that is specific to the protein or polypeptide. The maximum size is not critical unless it is desired to obtain antibodies to one particular epitope. For example, a large polypeptide may comprise multiple epitopes, one epitope being particularly useful and a second epitope being immunodominant. Typically, antigenic peptides selected from the present proteins and polypeptides will range from 5 to about 100 amino acids in length. More typically, however, such an antigenic peptide will be a maximum of about 50 amino acids in length, and preferably a maximum of about 30 amino acids. It is usually desirable to select a sequence of about 10, 12 or 15 amino acids, up to about 20 or 25 amino acids.

Amino acid sequences comprising useful epitopes may be identified in a number of ways. For example, preparing a series of short peptides that taken together span the entire protein sequence may be used to screen the entire protein sequence. One of skill in the art may routinely test a few large polypeptides for the presence of an epitope showing a desired reactivity and also test progressively smaller and overlapping fragments to identify a preferred epitope with the desired specificity and reactivity.

Antigenic polypeptides and peptides are useful for the production of monoclonal and polyclonal antibodies. Antibodies to a polypeptide encoded by the polynucleotides of NSEQ, polypeptide analogs or portions thereof, may be generated using methods that are well known in the art. Such antibodies may include, but are not limited to, polyclonal, monoclonal, chimeric, and single chain antibodies, Fab fragments, and fragments produced by a Fab expression library. Neutralizing antibodies, such as those that inhibit dimer formation, are especially preferred for therapeutic use. Monoclonal antibodies may be prepared using any technique that provides for the production of antibody molecules by continuous cell lines in culture. These include, but are not limited to, the hybridoma, the human B-cell hybridoma, and the EBV-hybridoma techniques. In addition, techniques developed for the production of chimeric antibodies may be used. Alternatively, techniques described for the production of single chain antibodies may be employed. Fabs that may contain specific binding sites for a polypeptide encoded by the polynucleotides of NSEQ, or a portion thereof, may also be generated. Various immunoassays may be used to identify antibodies having the desired specificity. Numerous protocols for competitive binding or immunoradiometric assays using either polyclonal or monoclonal antibodies with established specificities are well known in the art.

To obtain polyclonal antibodies, a selected animal may be immunized with a protein or polypeptide. Serum from the animal may be collected and treated according to known procedures. Polyclonal antibodies to the protein or polypeptide of interest may then be purified by affinity chromatography. Techniques for producing polyclonal antisera are well known in the art.

Monoclonal antibodies (Mabs) may be made by one of several procedures available to one of skill in the art, for example, by fusing antibody producing cells with immortalized cells and thereby making a hybridoma. The general methodology for fusion of antibody producing B cells to an immortal cell line is well within the province of one skilled in the art. Another example is the generation of Mabs from mRNA extracted from bone marrow and spleen cells of immunized animals using combinatorial antibody library technology.

The major drawback of Mabs derived from animals or from derived cell lines is that although they may be administered to a patient for diagnostic or therapeutic purposes, they are often recognized as foreign antigens by the immune system and are unsuitable for continued use. Antibodies that are not recognized as foreign antigens by the human immune system have greater potential for both diagnosis and treatment. Methods for generating human and humanized antibodies are now well known in the art.

Chimeric antibodies may be constructed in which regions of a non-human Mab are replaced by their human counterparts. A preferred chimeric antibody is one that has amino acid sequences that comprise one or more complementarity determining regions (CDRs) of a non-human Mab that binds to a polypeptide encoded by the polynucleotides of NSEQ, or a portion thereof, grafted to human framework (FW) regions. Methods for producing such antibodies are well known in the art. Amino acid residues corresponding to CDRs and FWs are known to one of average skill in the art.

A variety of methods have been developed to preserve or to enhance affinity for antigen of antibodies comprising grafted CDRs. One way is to include in the chimeric antibody the foreign framework residues that influence the conformation of the CDR regions. A second way is to graft the foreign CDRs onto human variable domains with the closest homology to the foreign variable region. Thus, grafting of one or more non-human CDRs onto a human antibody may also involve the substitution of amino acid residues which are adjacent to a particular CDR sequence or which are not contiguous with the CDR sequence but which are packed against the CDR in the overall antibody variable domain structure and which affect the conformation of the CDR. Humanized antibodies of the invention therefore include human antibodies which comprise one or more non-human CDRs as well as such antibodies in which additional substitutions or replacements have been made to preserve or enhance binding characteristics.

Chimeric antibodies of the invention also include antibodies that have been humanized by replacing surface-exposed residues to make the Mab appear human. Because the internal packing of amino acid residues in the vicinity of the antigen-binding site remains unchanged, affinity is preserved. Substitution of surface-exposed residues of a polypeptide encoded by the polynucleotides of NSEQ (or a portion thereof)-antibody according to the invention for the purpose of humanization does not mean substitution of CDR residues or adjacent residues that influence affinity for a polypeptide encoded by the polynucleotides of NSEQ, or a portion thereof.

Chimeric antibodies may also include antibodies where some or all non-human constant domains have been replaced with human counterparts. This approach has the advantage that the antigen-binding site remains unaffected. However, significant amounts of non-human sequences may be present where variable domains are derived entirely from non-human antibodies.

Antibodies of the invention include human antibodies that are antibodies consisting essentially of human sequences. Human antibodies may be obtained from phage display libraries wherein combinations of human heavy and light chain variable domains are displayed on the surface of filamentous phage. Combinations of variable domains are typically displayed on filamentous phage in the form of Fab's or scFvs. The library may be screened for phage bearing combinations of variable domains having desired antigen-binding characteristics. Preferred variable domain combinations are characterized by high affinity for a polypeptide encoded by the polynucleotides of NSEQ, or a portion thereof. Preferred variable domain combinations may also be characterized by high specificity for a polypeptide encoded by the polynucleotides of NSEQ, or a portion thereof, and little cross-reactivity to other related antigens. By screening from very large repertoires of antibody fragments, ($2$-$10 \times 10^{10}$) a good diversity of high affinity Mabs may be isolated, with many expected to have sub-nanomolar affinities for a polypeptide encoded by the polynucleotides of NSEQ, or a portion thereof.

Alternatively, human antibodies may be obtained from transgenic animals into which un-rearranged human Ig gene segments have been introduced and in which the endogenous mouse Ig genes have been inactivated. Preferred transgenic animals contain very large contiguous Ig gene fragments that are over 1 Mb in size but human polypeptide-specific Mabs of moderate affinity may be raised from transgenic animals containing smaller gene loci. Transgenic animals capable of expressing only human Ig genes may also be used to raise polyclonal antiserum comprising antibodies solely of human origin.

Antibodies of the invention may include those for which binding characteristics have been improved by direct mutation or by methods of affinity maturation. Affinity and specificity may be modified or improved by mutating CDRs and screening for antigen binding sites having the desired characteristics. CDRs may be mutated in a variety of ways. One way is to randomize individual residues or combinations of residues so that in a population of otherwise identical antigen binding sites, all twenty amino acids may be found at particular positions. Alternatively, mutations may be induced over a range of CDR residues by error prone PCR methods. Phage display vectors containing heavy and light chain variable region gene may be propagated in mutator strains of *E. coli*. These methods of mutagenesis are illustrative of the many methods known to one of skill in the art.

Antibodies of the invention may include complete anti-polypeptide antibodies as well as antibody fragments and derivatives that comprise a binding site for a polypeptide encoded by the polynucleotides of NSEQ, or a portion thereof. Derivatives are macromolecules that comprise a binding site linked to a functional domain. Functional domains may include, but are not limited to signalling domains, toxins, enzymes and cytokines.

The antibodies obtained by the means described herein may be useful for detecting proteins, variant and derivative polypeptides in specific tissues or in body fluids. Moreover, detection of aberrantly expressed proteins or protein fragments is probative of a disease state. For example, expression of the present polypeptides encoded by the polynucleotides of NSEQ, or a portion thereof, may indicate that the protein is being expressed at an inappropriate rate or at an inappropriate developmental stage. Hence, the present antibodies may be useful for detecting diseases associated with protein expression from NSEQs disclosed herein.

A variety of protocols for measuring polypeptides, including ELISAS, RIAs, and FACS, are well known in the art and provide a basis for diagnosing altered or abnormal levels of expression. Standard values for polypeptide expression are established by combining samples taken from healthy subjects, preferably human, with antibody to the polypeptide under conditions for complex formation. The amount of complex formation may be quantified by various methods, such as photometric means. Quantities of polypeptide expressed in disease samples may be compared with standard values. Deviation between standard and subject values may establish the parameters for diagnosing or monitoring disease.

Design of immunoassays is subject to a great deal of variation and a variety of these are known in the art. Immunoassays may use a monoclonal or polyclonal antibody reagent that is directed against one epitope of the antigen being assayed. Alternatively, a combination of monoclonal or polyclonal antibodies may be used which are directed against more than one epitope. Protocols may be based, for example, upon competition where one may use competitive drug screening assays in which neutralizing antibodies capable of binding a polypeptide encoded by the polynucleotides of NSEQ, or a portion thereof, specifically compete with a test compound for binding the polypeptide. Alternatively one may use, direct antigen-antibody reactions or sandwich type assays and protocols may, for example, make use of solid supports or immunoprecipitation. Furthermore, antibodies may be labelled with a reporter molecule for easy detection. Assays that amplify the signal from a bound reagent are also known. Examples include immunoassays that utilize avidin and biotin, or which utilize enzyme-labelled antibody or antigen conjugates, such as ELISA assays.

Kits suitable for immunodiagnosis and containing the appropriate labelled reagents include antibodies directed against the polypeptide protein epitopes or antigenic regions, packaged appropriately with the remaining reagents and materials required for the conduct of the assay, as well as a suitable set of assay instructions.

The present invention therefore provides a kit for specifically assaying a polypeptide described herein, the kit may comprise, for example, an antibody or antibody fragment capable of binding specifically to the polypeptide described herein.

In accordance with the present invention, the kit may be a diagnostic kit, which may comprise:
a) one or more antibodies described herein; and
b) a detection reagent which may comprise a reporter group.

In accordance with the present invention, the antibodies may be immobilized on a solid support. The detection reagent may comprise, for example, an anti-immunoglobulin, protein G, protein A or lectin etc. The reporter group may be selected, without limitation, from the group consisting of radioisotopes, fluorescent groups, luminescent groups, enzymes, biotin and dye particles.

In yet another aspect of the invention, an NSEQ, a portion thereof, or its complement, may be used therapeutically for the purpose of expressing mRNA and polypeptide, or conversely to block transcription or translation of the mRNA. Expression vectors may be constructed using elements from retroviruses, adenoviruses, herpes or vaccinia viruses, or bacterial plasmids, and the like. These vectors may be used for delivery of nucleotide sequences to a particular target organ, tissue, or cell population. Methods well known to those skilled in the art may be used to construct vectors to express nucleic acid sequences or their complements.

Alternatively, NSEQ, a portion thereof, or its complement, may be used for somatic cell or stem cell gene therapy. Vectors may be introduced in vivo, in vitro, and ex vivo. For ex vivo therapy, vectors are introduced into stem cells taken from the subject, and the resulting transgenic cells are clonally propagated for autologous transplant back into that same subject. Delivery of NSEQ by transfection, liposome injections, or polycationic amino polymers may be achieved using methods that are well known in the art. Additionally, endogenous NSEQ expression may be inactivated using homologous recombination methods that insert an inactive gene sequence into the coding region or other targeted region of NSEQ.

Vectors containing NSEQ may be transformed into a cell or tissue to express a missing polypeptide or to replace a non-functional polypeptide. Similarly a vector constructed to express the complement of NSEQ may be transformed into a cell to down-regulate the over-expression of a polypeptide encoded by the polynucleotides of NSEQ, or a portion thereof. Complementary or anti-sense sequences may consist of an oligonucleotide derived from the transcription initiation site; nucleotides between about positions −10 and +10 from the ATG are preferred. Similarly, inhibition may be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee et al. 1994)

Ribozymes, enzymatic RNA molecules, may also be used to catalyze the cleavage of mRNA and decrease the levels of particular mRNAs, such as those comprising the polynucleotide sequences of the invention. Ribozymes may cleave mRNA at specific cleavage sites. Alternatively, ribozymes may cleave mRNAs at locations dictated by flanking regions that form complementary base pairs with the target mRNA. The construction and production of ribozymes is well known in the art.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiester linkages within the backbone of the molecule. Alternatively, nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases, may be included.

One of skill in the art will readily appreciate that antibodies and antibody conjugates of the invention, where used in the human body for the purpose of the therapeutic applications discussed above, may be administered in the form of a composition. Such pharmaceutical compositions may consist of a polypeptide encoded by the polynucleotides of NSEQ, a portion thereof, or antibodies, mimetics, agonists, antagonists, or inhibitors of the polypeptide. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a subject alone or in combination with other agents, drugs, or hormones.

In addition to the active ingredients, these pharmaceutical compositions may contain pharmaceutically acceptable carriers comprising excipients and auxiliaries that facilitate processing of the active compounds into preparations that may be used pharmaceutically. Further details on techniques for formulation and administration may be found in the latest edition of Remington's Pharmaceutical Sciences (Maack Publishing Co., Easton Pa.).

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, and most preferably, humans.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

The term "Treatment" for purposes of this disclosure refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

Use of NSEQ in General Research

The Invention finally provides products, compositions, processes and methods that utilize an NSEQ, their open reading frame, or a polypeptide encoded by the polynucleotides of NSEQ or their open reading frame, or a portion thereof, their variants, analogs and derivatives for research, biological, clinical and therapeutic purposes. For example, to identify splice variants, mutations, and polymorphisms NSEQ may be extended utilizing a partial nucleotide sequence and employing various PCR-based methods known in the art to detect upstream sequences such as promoters and other regulatory elements. Additionally, one may use an XL-PCR kit (PE Biosystems, Foster City Calif.), nested primers, and commercially available cDNA libraries (Life Technologies, Rockville Md.) or genomic libraries (Clontech, Palo Alto Calif.) to extend the sequence.

The polynucleotides may also be used as targets in a micro-array. The micro-array may be used to monitor the expression patterns of large numbers of genes simultaneously and to identify splice variants, mutations, and polymorphisms. Information derived from analyses of the expression patterns may be used to determine gene function, to understand the genetic basis of a disease, to diagnose a disease, and to develop and monitor the activities of therapeutic agents used to treat a disease. Microarrays may also be used to detect genetic diversity, single nucleotide polymorphisms which may characterize a particular population, at the genomic level.

In yet another embodiment, polynucleotides may be used to generate hybridization probes useful in mapping the naturally occurring genomic sequence. Fluorescent in situ hybridization (FISH) may be correlated with other physical chromosome mapping techniques and genetic map data.

The present invention more particularly relates in one aspect thereof to a method of representatively identifying an endogeneously differentially expressed sequence involved in osteoclast differentiation. The sequence may be, for example, differentially expressed in a differentiated osteoclast cell compared to an undifferentiated osteoclast precursor cell.

The method of the present invention may comprise;
a) separately providing total messenger RNA from differentiated osteoclast cell and undifferentiated osteoclast precursor cell, the total messenger RNA may comprise, for example, at least one endogeneously differentially expressed sequence,
b) generating (e.g., single copy of a) single-stranded cDNA from each messenger RNA of differentiated osteoclast cell and (e.g., randomly) tagging the 3'-end of the single-stranded cDNA with a RNA polymerase promoter sequence and a first sequence tag;
c) generating (e.g., single copy of a) single-stranded cDNA from each messenger RNA of undifferentiated osteoclast precursor cell and (e.g., randomly) tagging the 3'-end of the single-stranded cDNA with a RNA polymerase promoter sequence and a second sequence tag;
d) separately generating partially or completely double-stranded 5'-tagged-DNA from each of b) and c), the double-stranded 5'-tagged-DNA may thus comprise in a 5' to 3' direction, a double-stranded RNA polymerase promoter, a first or second sequence tag and an endogenously expressed sequence,
e) separately linearly amplifying a first and second tagged sense RNA from each of d) with a RNA polymerase enzyme (which may be selected based on the promoter used for tagging),
f) generating single-stranded complementary first or second tagged DNA from one of e),
g) hybridizing the single-stranded complementary first or second tagged DNA of f) with the other linearly amplified sense RNA of e),
h) recovering unhybridized RNA with the help of the first or second sequence tag (for example by PCR or hybridization), and;
i) identifying (determining) the nucleotide sequence of unhybridized RNA.

The method may further comprise the step of comparatively determining the presence of the identified endogeneously and differentially expressed sequence in a differentiated osteoclast cell relative to an undifferentiated osteoclast precursor cell.

A sequence which is substantially absent (e.g., totally absent or present in very low quantity) from one of differentiated osteoclast cell or an undifferentiated osteoclast precursor cell and present in the other of differentiated osteoclast cell or an undifferentiated osteoclast precursor cell may thus be selected.

In accordance with the present invention, the sequence may be further selected based on a reduced or substantially absent expression in other normal tissue, therefore representing a candidate sequence specifically involved in osteoclast differentiation and bone remodeling.

The method may also further comprise a step of determining the complete sequence of the nucleotide sequence and may also comprise determining the coding sequence of the nucleotide sequence.

The present invention also relates in a further aspect, to the isolated endogeneously and differentially expressed sequence (polynucleotide and polypeptide) identified by the method of the present invention.

More particularly, the present invention encompasses a polynucleotide which may comprise the identified polynucleotide sequence, a polynucleotide which may comprise the open reading frame of the identified polynucleotide sequence, a polynucleotide which may comprise a nucleotide sequence substantially identical to the polynucleotide identified by the method of the present invention, a polynucleotide which may comprise a nucleotide sequence substantially complementary to the polynucleotide identified by the method of the present invention, fragments and splice variant thereof, provided that the sequence does not consist in or comprise SEQ ID NO.:57.

In accordance with the present invention, the isolated endogeneously and differentially expressed sequence of the present invention may be a complete or partial RNA molecule.

Isolated DNA molecule able to be transcribed into the RNA molecule of the present invention are also encompassed herewith as well as vectors (including expression vectors) comprising the such DNA or RNA molecule.

The present invention also relates to libraries comprising at least one isolated endogeneously and differentially expressed sequence identified herein (e.g., partial or complete RNA or DNA, substantially identical sequences or substantially complementary sequences (e.g., probes) and fragments thereof (e.g., oligonucleotides)).

In accordance with the present invention, the isolated endogeneously and differentially expressed sequence may be selected, for example, from the group consisting of a polynucleotide which may consist in or comprise;
   a) any one of SEQ ID NO.:1 to SEQ ID NO.56, SEQ ID NO.: 83, SEQ ID NO.:84 or SEQ ID NO.:87,
   b) the open reading frame of any one of SEQ ID NO.:1 to SEQ ID NO.56, SEQ ID NO.: 83, SEQ ID NO.:84 or SEQ ID NO.:87,
   c) a polynucleotide which may comprise a nucleotide sequence substantially identical to a) or b), and;
   d) fragments of any one of a) to c).

Exemplary substantially identical sequence of a) or b) may comprise, for example, a sequence which may be selected from the group consisting of SEQ ID NO.:84, SEQ ID NO.: 85, SEQ ID NO.:88, SEQ ID NO.:89 and the open reading frame of the SEQ ID NO.:84, SEQ ID NO.:85, SEQ ID NO.:88, SEQ ID NO.:89.

In a further aspect the present invention relates to a polypeptide which may be encoded by the isolated endogeneously and differentially expressed sequence of the present invention.

Exemplary polypeptides may comprise a sequence selected from the group consisting of any one of SEQ ID NO.: 93 to 99, 101 to 155.

In accordance with the present invention, when the sequence is from a non-human mammal, the method further comprises identifying a corresponding human ortholog polynucleotide sequence using a method described herein or other methods known in the art.

The present invention therefore also relates to an isolated human ortholog polynucleotide sequence (involved in bone remodeling), the open reading frame of the human ortholog, substantially identical sequences, substantially complementary sequences, fragments and splice variants thereof.

The present invention as well relates to an isolated polypeptide encoded by the human ortholog polynucleotide as well as biologically active analogs and biologically active fragments thereof.

Exemplary embodiments of human ortholog polynucleotides encompassed herewith include, for example, a sequence selected form the group consisting of SEQ ID NO.: 84, SEQ ID NO.:85, SEQ ID NO.:88, SEQ ID NO.:89 and the open reading frame of the SEQ ID NO.:84, SEQ ID NO.:85, SEQ ID NO.:88, SEQ ID NO.:89.

Exemplary embodiments of isolated polypeptide encoded by some human orthologs identified herein include for example, a polypeptide selected from the group consisting of SEQ ID NO.:150, SEQ ID NO.:153, SEQ ID NO.:154 and SEQ ID NO.:155.

The present invention also more particularly relates, in an additional aspect thereof, to an isolated polynucleotide which may be differentially expressed in differentiated osteoclast cell compared to undifferentiated osteoclast precursor cell.

The isolated polynucleotide may comprise a member selected from the group consisting of;
   a) a polynucleotide which may comprise any one of SEQ ID NO.:1 to SEQ ID NO.56, SEQ ID NO.: 83, SEQ ID NO.:86 or SEQ ID NO.:87,
   b) a polynucleotide which may comprise the open reading frame of any one of SEQ ID NO.:1 to SEQ ID NO.56, SEQ ID NO.: 83, SEQ ID NO.:86 or SEQ ID NO.:87,
   c) a polynucleotide which may comprise a sequence substantially identical (e.g., from about 50 to 100%, or about 60 to 100% or about 70 to 100% or about 80 to 100% or about 85, 90, 95 to 100% identical over the entire sequence or portion of sequences) to a) or b),
   d) a polynucleotide which may comprise a sequence substantially complementary (e.g., from about 50 to 100%, or about 60 to 100% or about 70 to 100% or about 80 to 100% or about 85, 90, 95 to 100% complementarity over the entire sequence or portion of sequences) to a) or b), and;
   e) a fragment of any one of a) to d)
   f) including polynucleotides which consist in the above.

Exemplary polynucleotides which are substantially identical to those listed above, includes for example, polynucleotides selected from the group consisting of SEQ ID NO.:84, SEQ ID NO.:85, SEQ ID NO.:88, SEQ ID NO.:89 and the open reading frame of any one of SEQ ID NO.:84, SEQ ID NO.:85, SEQ ID NO.:88 or SEQ ID NO.:89.

Exemplary polynucleotides fragments of those listed above comprises polynucleotides of at least 10 nucleic acids which may be substantially complementary to the nucleic acid sequence of any one of SEQ ID NO.: 1 to 56 or SEQ ID NO.: 83 to SEQ ID NO.:89, such as, for example, fragments selected from the group consisting of any one of SEQ ID NO.: 64 to 80 or 90.

The present invention also relates to an isolated polynucleotide involved in osteoclast differentiation, the isolated polynucleotide may be selected, for example, from the group consisting of;

a) a polynucleotide comprising any one of SEQ ID NO.: 1 to 56 or 83 to 89,
b) a polynucleotide comprising the open reading frame of any one of SEQ ID NO.: 1 to 56 or 83 to 89, and;
c) a polynucleotide substantially Identical to a) or b).

The present invention also further relates to an isolated polynucleotide which may be able to promote osteoclast differentiation (e.g., in a mammal or mammalian cell thereof). The polynucleotide may be selected, for example, from the group consisting of polynucleotides which may comprise;
a) any one of SEQ ID NO.:1 to 5, 8 to 56 or 83 to 89;
b) the open reading frame of any one of SEQ ID NO.:1 to 5, 8 to 56 or 83 to 89, and;
c) a sequence of at least 10 nucleic acids which may be complementary to the nucleic acid sequence of any one of SEQ ID NO.:6 or SEQ ID NO.:7.

In yet a further aspect, the present invention relates to an isolated polynucleotide which may be able to inhibit osteoclast differentiation (e.g., in a mammal or mammalian cell thereof). The polynucleotide may be selected, for example, from the group consisting of polynucleotides which may comprise;
a) any one of SEQ ID NO.:6 or SEQ ID NO.:7,
b) the open reading frame of any one of SEQ ID NO.:6 or SEQ ID NO.:7, and;
c) a sequence of at least 10 nucleic acids which is complementary to the nucleic acid sequence of any one of SEQ ID NO.:1 to 5 or 8 to 57 or 83 to 89.

Suitable polynucleotides include, for example, a polynucleotide having or comprising those which are selected from the group consisting of SEQ ID NO. 64 to 82 and 90.

Suitable polynucleotides may be those which may be able to inhibit osteoclast differentiation which has been induced by an inducer of osteoclast differentiation such as those listed herein.

In accordance with the present invention, the polynucleotide may be, for example, a RNA molecule, a DNA molecule, including those which are partial or complete, single-stranded or double-stranded, hybrids, etc.

The present invention also relates to a vector (e.g., an expression vector) comprising the polynucleotide of the present invention.

The present invention additionally relates in an aspect thereof to a library of polynucleotide sequences which may be differentially expressed in a differentiated osteoclast cell compared to an undifferentiated osteoclast precursor cell. The library may comprise, for example, at least one member selected from the group consisting of
a) a polynucleotide which may comprise any one of SEQ ID NO.:1 to SEQ ID NO:57 and 83 to 89,
b) a polynucleotide which may comprise the open reading frame of any one of SEQ ID NO.:1 to SEQ ID NO.57 and 83 to 89,
c) a polynucleotide which may comprise a sequence substantially identical (e.g., from about 50 to 100%, or about 60 to 100% or about 70 to 100% or about 80 to 100% or about 85, 90, 95 to 100% identical over the entire sequence or portion of sequences) to a) or b),
d) a polynucleotide which may comprise a sequence substantially complementary (e.g., from about 50 to 100%, or about 60 to 100% or about 70 to 100% or about 80 to 100% or about 85, 90, 95 to 100% complementarity over the entire sequence or portion of sequences) to a) or b), and;
e) a fragment of any one of a) to d).

The present invention also relates to an expression library which may comprise a library of polynucleotides described herein. In accordance with the present invention, each of the polynucleotide may be contained within an expression vector.

Arrays and kits comprising a library of polynucleotide sequences (comprising at least one polynucleotide including complementary sequences) of the present invention are also encompassed herewith.

The present invention also provides in an additional aspect, a pharmaceutical composition for inhibiting osteoclast differentiation (bone resorption and bone resorption related diseases or disorders), the pharmaceutical composition may comprise, for example;
a) an isolated polynucleotide as defined herein (e.g., able to inhibit osteoclast differentiation) and;
b) a pharmaceutically acceptable carrier.

The present invention also provides in yet an additional aspect, a method for inhibiting osteoclast differentiation (e.g., for inhibiting bone resorption or for ameliorating bone resorption) in a mammal (individual) in need thereof (or in a mammalian cell), the method may comprise administering an isolated polynucleotide (e.g., able to inhibit osteoclast differentiation) or a suitable pharmaceutical composition.

In accordance with the present invention, the mammal in need may suffer, for example and without limitation, from a condition selected from the group consisting of osteoporosis, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Tumer syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes, etc.

In a further aspect, the present invention relates to the use of an isolated polynucleotide (e.g., able to inhibit osteoclast differentiation) for the preparation of a medicament for the treatment of a bone resorption disease.

The present invention in another aspect thereof, provides a pharmaceutical composition for promoting osteoclast differentiation in a mammal in need thereof. The pharmaceutical composition may comprise, for example;
a. an isolated polynucleotide (e.g., able to promote osteoclast differentiation) and;
b. a pharmaceutically acceptable carrier.

The present invention also further provides a method for promoting osteoclast differentiation in a mammal in need thereof (or in a mammalian cell), the method may comprise, for example, administering an isolated polynucleotide (e.g., able to promote osteoclast differentiation) or a suitable pharmaceutical composition as described above.

The present invention additionally relates to the use of an isolated polynucleotide (e.g., able to promote osteoclast differentiation) for the preparation of a medicament for the treatment of a disease associated with insufficient bone resorption (e.g., hyperostosis).

The present invention also relates to the use of at least one polynucleotide which may be selected from the group consisting of;
a) a polynucleotide comprising the any one of SEQ ID NO.:1 to SEQ ID NO.57 and 83 to 89,
b) a polynucleotide comprising the open reading frame of any one of SEQ ID NO.:1 to SEQ ID NO.57 and 83 to 89,
c) a polynucleotide comprising a sequence substantially identical (e.g., from about 50 to 100%, or about 60 to 100% or about 70 to 100% or about 80 to 100% or about 85, 90, 95 to 100% identical over the entire sequence or portion of sequences) to a) or b), d) a polynucleotide comprising a sequence substantially complementary (e.g., from about 50 to 100%, or about 60 to 100% or about 70 to 100% or about 80 to 100% or about 85, 90, 95 to 100% complementarity over the entire sequence or portion of sequences) to a) or b), e) a fragment of any one of a) to d) and;

f) a library comprising any one of a) to d)

in the diagnosis of a condition related to bone remodeling.

Also encompassed by the present invention are kits for the diagnosis of a condition related to bone remodeling. The kit may comprise, for example, at least one sequence substantially complementary to any one of SEQ ID NO.:1 to SEQ ID NO.57 or 83 to 89, the open reading frame of any one of SEQ ID NO.:1 to SEQ ID NO.57 or 83 to 89 and fragments thereof.

The present invention also provides in an additional aspect, an isolated polypeptide (polypeptide sequence) which may be able to promote osteoclast differentiation (in a mammal or a mammalian cell thereof). The polypeptide may comprise (or consist in) a sequence selected from the group consisting of;

a) any one of SEQ ID NO.: 93 to 97 or 101 to 155, b) a biologically active fragment of any one of a), c) a biologically active analog of any one of a).

In accordance with the present invention, the biologically active analog may comprise, for example, at least one conservative amino acid substitution compared to the original sequence.

In yet a further aspect, the present invention provides a pharmaceutical composition for promoting osteoclast differentiation (e.g., for promoting bone resorption). The pharmaceutical composition may comprise, for example a polypeptide (e.g., able to promote osteoclast differentiation) and a pharmaceutically acceptable carrier.

Methods for promoting osteoclast differentiation in a mammal in need thereof (or in a mammalian cell) are also provided by the present invention, which methods may comprise administering an isolated polypeptide (e.g., able to promote osteoclast differentiation) or suitable pharmaceutical composition described herein.

In additional aspects, the present invention relates to the use of an isolated polypeptide (e.g., able to promote osteoclast differentiation) for the preparation of a medicament for the treatment of a disease associated with insufficient bone resorption.

In a further aspect, the present invention relates to an isolated polypeptide able to inhibit osteoclast differentiation (in a mammal or mammalian cell thereof), the polypeptide may comprise, for example, a sequence selected from the group consisting of a) a sequence which may comprise or consist in any one of SEQ ID NO.:98 and SEQ ID NO.:99, b) a biologically active fragment of any one of a), c) a biologically active analog of any one of a).

In accordance with the present invention, the biologically active analog may comprise, for example, at least one conservative amino acid substitution in the amino acid sequence in comparison to another polypeptide The present invention further encompasses pharmaceutical compositions which may comprise the isolated polypeptide described herein.

Methods for ameliorating bone resorption in an individual in need thereof are also encompassed herewith, which method may comprise, for example, administering an isolated polypeptide (e.g., able to inhibit osteoclast differentiation) or suitable pharmaceutical compositions which may comprise such polypeptide.

In a further aspect the present invention provides a method for ameliorating bone resorption in an individual in need thereof which may comprise administering a compound capable of inhibiting (e.g., in an osteoclast precursor cell) the activity or expression of a polypeptide involved in (or able to promote) osteoclast differentiation such as for example, a polypeptide selected from the group consisting of SEQ ID NO.: 93 to 97 and 101 to 155.

In accordance with the present invention, the mammal may suffer, for example, from a condition selected from the group consisting of osteoporosis, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Tumer syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes, etc.

In yet a further aspect, the present invention relates to the use of a polypeptide able to inhibit osteoclast differentiation in the preparation of a medicament for the treatment of a bone resorption disease in an individual in need thereof.

The present invention also relates to the use of a compound able to inhibit (e.g., in an osteoclast precursor cell) the activity or expression of a polypeptide which may be selected, for example, from the group consisting of SEQ ID NO.: 93 to 97 and 101 to 155 in the preparation of a medicament for the treatment of a bone resorption disease in an individual in need thereof.

Antibodies and antigen-binding fragment thereof which are able to bind to any of the polypeptide described herein, including those which may be selected from the group consisting of SEQ ID NO.: 93 to 97 and 101 to 155 are also encompassed by the present invention.

In accordance with the present invention, the antibody may be able, for example, to inhibit osteoclast differentiation.

The present invention also relates to a composition (e.g., pharmaceutical composition) which may comprise;

a) an antibody and;

b) a pharmaceutically acceptable carrier.

The present invention relates in a further aspect to a method of inhibiting osteoclast differentiation which may comprise administering to a mammal in need thereof the antibody described herein or a pharmaceutical composition comprising such antibody.

The present invention relates in yet a further aspect to the use of an antibody as defined herein for the preparation of a medicament for the treatment of a bone resorption disease in an individual in need thereof.

In an additional aspect, the present invention relates to an immunizing composition which may comprise a polypeptide, such as a polypeptide selected from the group consisting of SEQ ID NO.: 93 to 155, analogs or fragments thereof or a nucleic acid (polynucleotide) selected, for example, from the group consisting of those comprising or consisting in (a) SEQ ID NO.: 1 to 56 and 83 to 89, (b) a polynucleotide which may comprise the open reading frame of SEQ ID NO.: 1 to 56 and 83 to 89, (c) substantially identical sequences of any one of (a)

or (b) or fragments of any one of (a), (b) or (c) able to encode immunologically active polypeptides thereof.

In yet an additional aspect, the present invention relates to a method of diagnosing a condition related to a bone resorption disorder or disease in an individual in need thereof. The method may comprise, for example, quantifying a polynucleotide described herein, such as, for example, those selected from the group consisting of those comprising or consisting of (a) SEQ ID NO.:1 to 56 and 83 to 89 (b) a polynucleotide which may comprise the open reading frame of SEQ ID NO.: 1 to 56 and 83 to 89, (c) substantially identical sequences of any one of (a) or (b), or a polypeptide sequence which may be selected, for example, from the group consisting of 93 to 155 and analogs thereof in a sample from the individual compared to a standard or normal value.

In an additional aspect, the present invention provides a method for identifying an inhibitory compound (inhibitor, antagonist) which may be able to impair the function (activity) or expression of a polypeptide described herein, such as, for example, those which may be selected from the group consisting of SEQ ID NO.: 93 to 97 and 100 to 155 and analogs thereof. The method may comprise contacting the polypeptide or a cell expressing the polypeptide with a candidate compound and measuring the function (activity) or expression of the polypeptide. A reduction in the function or activity of the polypeptide (compared to the absence of the candidate compound) may positively identify a suitable inhibitory compound.

In accordance with the present invention, the impaired function or activity may be associated with a reduced ability of the polypeptide to promote osteoclast differentiation, such as osteoclast differentiation induced by an inducer described herein or known in the art.

In accordance with the present invention the cell may not naturally (endogenously) express (polypeptide may substantially be unexpressed in a cell) the polypeptide or analog or alternatively, the expression of a naturally expressed polypeptide analog may be repressed.

For example, suitable method of screening for an inhibitor of SEQ ID NO.:153, may comprise repressing the expression of SEQ ID NO.:93 in a mouse osteoclast cell and evaluating differentiation of the osteoclast cell in the presence or absence of a candidate inhibitor.

The impaired function or activity may also be associated with a reduced ability of the polypeptide to interact with a known partner.

For example, suitable method of screening for an inhibitor of SEQ ID NO.: 154 may comprise measuring (evaluating) the interaction of the polypeptide with the v-ATPase-a3 subunit in the presence or absence of a candidate inhibitor.

The present invention also provides a method for identifying an inhibitory compound (inhibitor, antagonist) able to impair the function (activity) or expression of a polypeptide such as, for example SEQ ID NO.: 98 or SEQ ID NO.:99. The method may comprise, for example, contacting the polypeptide or a cell expressing the polypeptide with a candidate compound and measuring the function (activity) or expression of the polypeptide. A reduction in the function or activity of the polypeptide (compared to the absence of the candidate compound) may thus positively identify a suitable inhibitory compound.

In accordance with the present invention, the impaired function or activity may be associated, for example, with a reduced ability of the polypeptide to inhibit osteoclast differentiation.

The cell used to carry the screening test may not naturally (endogenously) express the polypeptide or analogs, or alternatively the expression of a naturally expressed polypeptide analog may be repressed.

As used herein the term "sequence identity" relates to (consecutive) nucleotides of a nucleotide sequence which with reference to an original nucleotide sequence. The identity may be compared over a region or over the total sequence of a nucleic acid sequence.

Thus, "identity" may be compared, for example, over a region of 3, 4, 5, 10, 19, 20 nucleotides or more (and any number there between). It is to be understood herein that gaps of non-identical nucleotides may be found between identical nucleic acids. For example, a polynucleotide may have 100% identity with another polynucleotide over a portion thereof. However, when the entire sequence of both polynucleotide is compared, the two polynucleotides may have 50% of their overall (total) sequence identical to one another.

Polynucleotides of the present invention or portion thereof having from about 50 to about 100%, or about 60 to about 100% or about 70 to about 100% or about 80 to about 100% or about 85%, about 90%, about 95% to about 100% sequence identity with an original polynucleotide are encompassed herewith. It is known by those of skill in the art, that a polynucleotide having from about 50% to 100% identity may function (e.g., anneal to a substantially complementary sequence) in a manner similar to an original polynucleotide and therefore may be used in replacement of an original polynucleotide. For example a polynucleotide (a nucleic acid sequence) may comprise or have from about 50% to 100% identity with an original polynucleotide over a defined region and may still work as efficiently or sufficiently to achieve the present invention.

Percent identity may be determined, for example, with n algorithm GAP, BESTFIT, or FASTA in the Wisconsin Genetics Software Package Release 7.0, using default gap weights.

As used herein the terms "sequence complementarty" refers to (consecutive) nucleotides of a nucleotide sequence which are complementary to a reference (original) nucleotide sequence. The complementarity may be compared over a region or over the total sequence of a nucleic acid sequence.

Polynucleotides of the present invention or portion thereof having from about 50 to about 100%, or about 60 to about 100% or about 70 to about 100% or about 80 to about 100% or about 85%, about 90%, about 95% to about 100% sequence complementarity with an original polynucleotide are thus encompassed herewith. It is known by those of skill in the art, that an polynucleotide having from about 50% to 100% complementarity with an original sequence may anneal to that sequence in a manner sufficient to carry out the present invention (e.g., inhibit expression of the original polynucleotide).

An "analogue" is to be understood herein as a molecule having a biological activity and chemical structure similar to that of a polypeptide described herein. An "analogue" may have sequence similarity with that of an original sequence or a portion of an original sequence and may also have a modification of its structure as discussed herein. For example, an "analogue" may have at least 90% sequence similarity with an original sequence or a portion of an original sequence. An "analogue" may also have, for example; at least 70% or even 50% sequence similarity (or less, i.e., at least 40%) with an original sequence or a portion of an original sequence.

Also, an "analogue" may have, for example, at least 50% sequence similarity to an original sequence with a combination of one or more modification in a backbone or side-chain of an amino acid, or an addition of a group or another molecule, etc.

"Polynucleotide" generally refers to any polyribonucleotide or polydeoxyribonucleotide, which may be unmodified RNA or DNA, or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus "polynucleotide" embraces chemically, enzymatically or metabolically modified forms of polynucleotides as typically found in nature, as well as the chemical forms of DNA and RNA characteristic of viruses and cells. "Polynucleotide" includes but is not limited to linear and end-closed molecules. "Polynucleotide" also embraces relatively short polynucleotides, often referred to as oligonucleotides.

"Polypeptides" refers to any peptide or protein comprising two or more amino acids joined to each other by peptide bonds or modified peptide bonds (i.e., peptide isosteres). "Polypeptide" refers to both short chains, commonly referred as peptides, oligopeptides or oligomers, and to longer chains generally referred to as proteins. As described above, polypeptides may contain amino acids other than the 20 gene-encoded amino acids.

As used herein the term "polypeptide analog" relates to mutants, variants, chimeras, fusions, deletions, additions and any other type of modifications made relative to a given polypeptide.

As used herein the term "biologically active" refers to a variant or fragment which retains some or all of the biological activity of the natural polypeptide, i.e., to be able to promote or inhibit osteoclast differentiation.

Thus, biologically active polypeptides in the form of the original polypeptides, fragments (modified or not), analogues (modified or not), derivatives (modified or not), homologues, (modified or not) of the polypeptides described herein are encompassed by the present invention.

Therefore, any polypeptide having a modification compared to an original polypeptide which does not destroy significantly a desired biological activity is encompassed herein. It is well known in the art, that a number of modifications may be made to the polypeptides of the present invention without deleteriously affecting their biological activity. These modifications may, on the other hand, keep or increase the biological activity of the original polypeptide or may optimize one or more of the particularity (e.g. stability, bioavailability, etc.) of the polypeptides of the present invention which, in some instance might be desirable. Polypeptides of the present invention may comprise for example, those containing amino acid sequences modified either by natural processes, such as posttranslational processing, or by chemical modification techniques which are known in the art. Modifications may occur anywhere in a polypeptide including the polypeptide backbone, the amino acid side-chains and the amino- or carboxy-terminus. It will be appreciated that the same type of modification may be present in the same or varying degrees at several sites in a given polypeptide. Also; a given polypeptide may contain many types of modifications. It is to be understood herein that more than one modification to the polypeptides described herein are encompassed by the present invention to the extent that the biological activity is similar to the original (parent) polypeptide.

As discussed above, polypeptide modification may comprise, for example, amino acid insertion (i.e., addition), deletion and substitution (i.e., replacement), either conservative or non-conservative (e.g., D-amino acids, desamino acids) in the polypeptide sequence where such changes do not substantially alter the overall biological activity of the polypeptide.

Example of substitutions may be those, which are conservative (i.e., wherein a residue is replaced by another of the same general type or group) or when wanted, non-conservative (i.e., wherein a residue is replaced by an amino acid of another type). In addition, a non-naturally occurring amino acid may substitute for a naturally occurring amino acid (i.e., non-naturally occurring conservative amino acid substitution or a non-naturally occurring non-conservative amino acid substitution).

As is understood, naturally occurring amino acids may be sub-classified as acidic, basic, neutral and polar, or neutral and non-polar. Furthermore, three of the encoded amino acids are aromatic. It may be of use that encoded polypeptides differing from the determined polypeptide of the present invention contain substituted codons for amino acids, which are from the same type or group as that of the amino acid to be replaced. Thus, in some cases, the basic amino acids Lys, Arg and His may be interchangeable; the acidic amino acids Asp and Glu may be interchangeable; the neutral polar amino acids Ser, Thr, Cys, Gin, and Asn may be interchangeable; the non-polar aliphatic amino acids Gly, Ala, Val, Ile, and Leu are interchangeable but because of size Gly and Ala are more closely related and Val, Ile and Leu are more closely related to each other, and the aromatic amino acids Phe, Trp and Tyr may be interchangeable.

It should be further noted that if the polypeptides are made synthetically, substitutions by amino acids, which are not naturally encoded by DNA (non-naturally occurring or unnatural amino acid) may also be made.

A non-naturally occurring amino acid is to be understood herein as an amino acid which is not naturally produced or found in a mammal. A non-naturally occurring amino acid comprises a D-amino acid, an amino acid having an acetylaminomethyl group attached to a sulfur atom of a cysteine, a pegylated amino add, etc. The inclusion of a non-naturally occurring amino acid in a defined polypeptide sequence will therefore generate a derivative of the original polypeptide. Non-naturally occurring amino acids (residues) include also the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, norleucine, etc. Phenylglycine may substitute for Trp, Tyr or Phe; citrulline and methionine sulfoxide are neutral nonpolar, cysteic acid is acidic, and ornithine is basic. Proline may be substituted with hydroxyproline and retain the conformation conferring properties.

It is known in the art that analogues may be generated by substitutional mutagenesis and retain the biological activity of the polypeptides of the present invention. These analogues have at least one amino acid residue in the protein molecule removed and a different residue inserted in its place. For example, one site of interest for substitutional mutagenesis may include but are not restricted to sites identified as the active site(s), or immunological site(s). Other sites of interest may be those, for example, in which particular residues obtained from various species are identical. These positions may be important for biological activity. Examples of substitutions identified as "conservative substitutions" are shown in Table A. If such substitutions result in a change not desired, then other type of substitutions, denominated "exemplary substitutions" in Table A, or as further described herein in reference to amino acid classes, are introduced and the products screened.

In some cases it may be of interest to modify the biological activity of a polypeptide by amino acid substitution, insertion, or deletion. For example, modification of a polypeptide may result in an increase in the polypeptide's biological activity, may modulate its toxicity, may result in changes in bioavailability or in stability, or may modulate its immunological activity or immunological identity. Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile)
(2) neutral hydrophilic: Cysteine (Cys), Serine (Ser), Threonine (Thr)
(3) acidic: Aspartic acid (Asp), Glutamic acid (Glu)
(4) basic: Asparagine (Asn), Glutamine (Gin), Histidine (His), Lysine (Lys), Arginine (Arg)
(5) residues that influence chain orientation: Glycine (Gly), Proline (Pro); and aromatic: Tryptophan (Trp), Tyrosine (Tyr), Phenylalanine (Phe)

Non-conservative substitutions will entail exchanging a member of one of these classes for another.

TABLE A

Examplary amino acid substitution

| Original residue | Exemplary substitution | Conservative substitution |
|---|---|---|
| Ala (A) | Val, Leu, Ile | Val |
| Arg (R) | Lys, Gin, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

It is to be understood herein, that if a "range" or "group" of substances (e.g. amino acids), substituents" or the like is mentioned or if other types of a particular characteristic (e.g. temperature, pressure, chemical structure, time, etc.) is mentioned, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to a percentage (%) of identity of from about 80 to 100%, it is to be understood as specifically incorporating herein each and every individual %, as well as sub-range, such as for example 80%, 81%, 84.78%, 93%, 99% etc.; and similarly with respect to other parameters such as, concentrations, elements, etc. . . .

It is in particular to be understood herein that the methods of the present invention each include each and every individual steps described thereby as well as those defined as positively including particular steps or excluding particular steps or a combination thereof; for example an exclusionary definition for a method of the present invention, may read as follows: "provided that said polynucleotide does not comprise or consist in SEQ ID NO.:57 or the open reading frame of SEQ ID NO.:57" or "provided that said polypeptide does not comprise or consist in SEQ ID NO.:100" or "provided that said polynucleotide fragment or said polypeptide fragment is less than X unit (e.g., nucleotides or amino acids) long or more than X unit (e.g., nucleotides or amino acids) long".

Other objects, features, advantages, and aspects of the present invention will become apparent to those skilled in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

In the appended drawings:

FIG. 3 is a picture illustrating the representative macroarray results of osteoclast specificity of the differentially expressed sequences selected for biological validation;

FIG. 10 are pictures illustrating the phenotypic effect on osteoclast differentiation in the presence of siRNAs specific for SEQ. ID. NO:5 panel a; control RAW-hU6 cells, panel b; RAW-hU6 treated with RANK ligand, and panel c; RAW-hU6 treated with RANK ligand and siRNA specific for SEQ ID NO.:5 (RAW-01035.1);

FIG. 11A are pictures illustrating the phenotypic effect on osteoclast differentiation in the presence of siRNAs specific for SEQ. ID. NO:6 panel a; control RAW-hU6 cells, panel b; RAW-hU6 treated with RANK ligand, panel c; RAW-hU6 treated with siRNA specific for SEQ ID NO.:6 (RAW-1200.mix) and panel d; RAW-hU6 treated with RANK ligand and siRNA specific for SEQ ID NO.:6 (RAW-1200.mix);

FIG. 12 are pictures illustrating the stimulation of the osteoclast-specific marker genes, TRAP and Cathepsin K, in RAW cells expressing specific siRNAs for SEQ. ID. NO:6 in the presence or absence of RANK ligand.

FIG. 14B is an histogram illustrating the results of FIG. 14A in a quantitative manner;

FIG. 15B is an histogram illustrating the results of FIG. 15A in a quantitative manner;

FIG. 16A is a picture representing an exemplary embodiment of a macroarray hybridization results of differential expression of some human orthologues in the different human tissues and human osteoclasts samples;

FIGS. 22 to 87 represents some polynucleotides and polypeptides identified using an exemplary method of the present invention.

Figure 1:
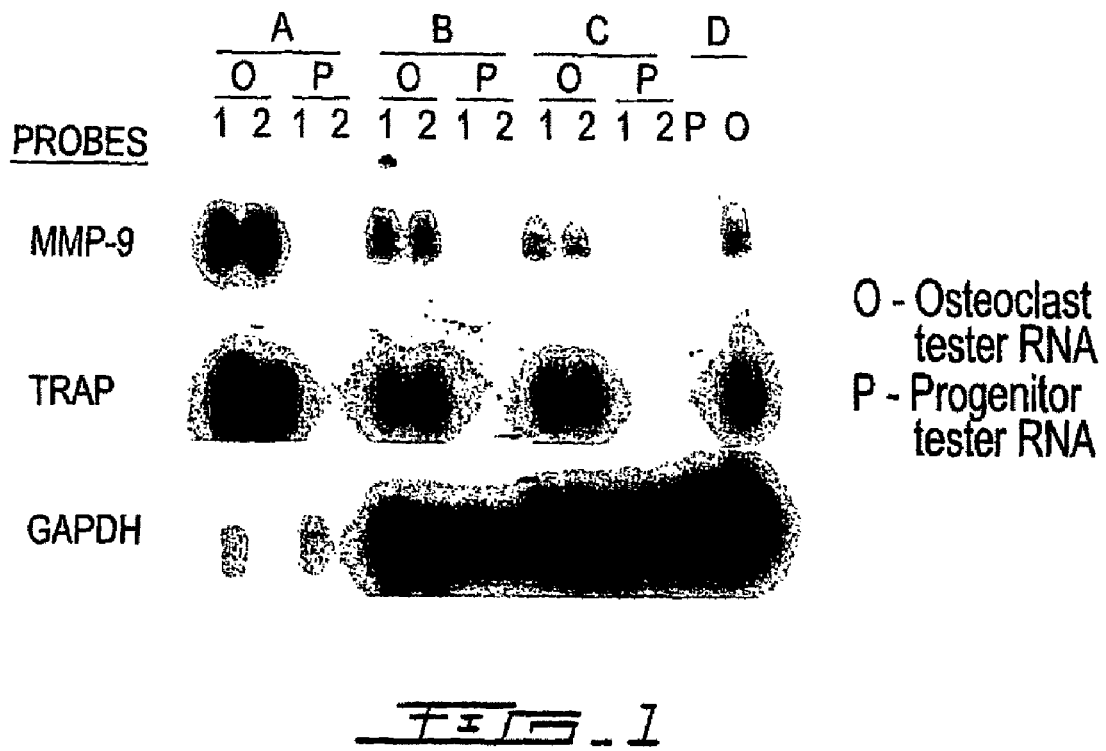
FIG. 1 is a picture of a Southern blot hybridization analysis of the "STAR" subtracted libraries with probes specific for MMP-9, TRAP and GAPDH demonstrating RNA subtraction using STAR.

SEQ ID NOs: 1-7, and 57 show differentially expressed sequences found in osteoclasts and demonstrated to have an effect on osteoclastogenesis following inhibition with specific siRNAs. SEQ ID NOs: 8-56 show differentially expressed sequences found in osteoclasts with putative roles in bone remodelling. SEQ ID NOs: 58-82 show the nucleotide sequences of plasmids, oligonucleotide primers and siRNAs used for experiments performed herein.

SEQ ID NOs: 83-87 show the mRNA sequence of spliced variants isolated from RNA prepared from osteoclasts for some of the osteoclast-specific sequences identified. SEQ ID NOs 83-87 thus show by way of examples that unique spliced variants exist and strongly suggest that others also exist for the model system under study and others. More specifically, SEQ ID NO: 83 is a variant of SEQ ID NO: 1; SEQ ID NO: 84 is a human sequence of the corresponding mouse variant #1 for SEQ ID NO: 2; SEQ ID NO: 85 is a human sequence of the corresponding mouse variant #2 for SEQ ID NO: 2; SEQ ID NO: 86 is a variant of SEQ ID NO: 3; and SEQ ID NO: 87 is a variant of SEQ ID NO: 3.

SEQ ID NO.: 88 and 89 shows the mRNA sequence of human orthologs of SEQ ID NO.:1 and 2 respectively.

SEQ ID NO.: 64 to 82 and 90 shows fragments which are complementary to a portion of a sequence of selected polynucleotides described herein.

SEQ ID NO.: 93 to 155 shows polypeptides encoded by the polynucleotides of the present invention.

DESCRIPTION OF ILLUSTRATIVE EMBODIMENTS

The applicant employed a carefully planned strategy to identify and isolate genetic sequences involved in osteoclastogenesis and bone remodeling. The process involved the following steps: 1) preparation of highly representative cDNA libraries using mRNA isolated from precursors and osteoclasts; 2) isolation of sequences upregulated during osteoclastogenesis; 3) identification and characterization of upregulated sequences; 4) selection of upregulated sequences for tissue specificity; 5) determination of knock-down effects on osteoclastogenesis and 6) determination of knock-down effects on bone resorption.

The results discussed in this disclosure demonstrate the advantage of targeting osteoclast genes that are specific to this differentiated cell type and provide a more efficient screening method when studying the genetic basis of diseases and disorders. Genes that are known to have a role in other areas of biology have been shown to play a critical role in osteoclastogenesis and osteoclast function. Genes that are known but have not had a role assigned to them until the present disclosure have also been isolated and shown to have a critical role in osteoclastogenesis and osteoclast function. Finally, novel genes have been identified and play a role, however, applicant reserves their disclosure until further study has been completed.

The present invention is illustrated in further details below in a non-limiting fashion.

A—Material and Methods

Commercially available reagents referred to in the present disclosure were used according to supplier's instructions unless otherwise indicated. Throughout the present disclosure certain starting materials were prepared as follows:

B—Preparation of Osteoclast Differentiated Cells

The RAW 264.7 (RAW) osteoclast precursor cell line and human CD34+ progenitors are well known in the art as murine and human models of osteoclastogenesis. These murine and human osteoclasts are therefore excellent sources of materials for isolating and characterizing genes specialized for osteoclast function.

RAW cells were purchased from American Type Culture Collection and maintained in high glucose DMEM containing 10% fetal bovine serum and antibiotics. The cells were sub-cultured bi-weekly to a maximum of 10-12 passages. For osteoclast differentiation experiments, RAW cells were seeded in 96-well plates at a density of 4×103 cells/well and allowed to plate for 24 h. Differentiation was induced in high glucose DMEM, 10% charcoal-treated foetal bovine serum (Hyclone, Logan, Utah), 0.05% BSA, antibiotics, 10 ng/ml macrophage colony stimulating factor (M-CSF), and 100 ng/ml receptor activator of NF-kB (RANK) ligand. The plates were re-fed on day 3 and osteoclasts were clearly visible by day 4. Typically, the cells were stained for tartrate-resistant acid phosphatase (TRAP) on day 4 or 5 unless otherwise indicated. For TRAP staining, the cells were washed with PBS and fixed in 10% formaldehyde for 1 h. After two PBS washes, the cells were rendered lightly permeable in 0.2% Triton X-100 in PBS for 5 min before washing in PBS. Staining was conducted at 37° C. for 20-25 min in 0.01% Naphtol AS-MX phosphate, 0.06% Fast Red Violet, 50 mM sodium tartrate, 100 mM sodium acetate, pH 5.2. Cells were visualized microscopically.

Human osteoclasts were differentiated from G-CSF-mobilized peripheral blood mononuclear cells (Cambrex, East Rutherford, N.J.) as described by the supplier in the presence of 35 ng/ml M-CSF and 100 ng/ml RANK ligand. Multinucleated TRAP-staining osteoclasts were visible by 11-14 days. Osteoclasts from human cells were also derived from human osteoclasts precursor cells (Cambrex, East Rutherford, N.J.) and cultured as described by the supplier. In the latter case, osteoclasts are obtained after 7 days.

C—Method of Isolating Differentially Expressed mRNA

Key to the discovery of differentially expressed sequences unique to osteoclasts is the use of the applicant's patented STAR technology (Subtractive Transcription-based Amplification of mRNA; U.S. Pat. No. 5,712,127 Malek et al., Jan. 27, 1998). In this procedure, mRNA isolated from fully differentiated osteoclasts is used to prepare "tester RNA", which is hybridized to complementary single-stranded "driver DNA" prepared from osteoclast precursor mRNA and only the un-hybridized "tester RNA" is recovered, and used to create cloned cDNA libraries, termed "subtracted libraries". Thus, the "subtracted libraries" are enriched for differentially expressed sequences inclusive of rare and novel mRNAs often missed by micro array hybridization analysis, which are anticipated to be among the important gene targets for the development of better diagnostic and therapeutic strategies.

The clones contained in the enriched "subtracted libraries" are identified by DNA sequence analysis and their potential function assessed by database analysis. The non-redundant clones are then used to prepare DNA micro-arrays, which are used to quantify their relative differential expression patterns by hybridization to fluorescent cDNA probes. Two classes of cDNA probes are used, which are generated from either RNA transcripts prepared from the same subtracted libraries (subtracted probes) or mRNA isolated from different osteoclast samples (standard probes). The use of subtracted probes provides increased sensitivity for detecting the low abundance mRNA sequences that are preserved and enriched by STAR. Furthermore, the specificity of the differentially expressed sequences to osteoclast is measured by hybridizing radiolabeled probes prepared from each selected sequence to macroarrays containing RNA from different osteoclast samples and different murine and/or human tissues. Additionally, Northern blot analysis is performed so as to confirm the presence of one or more specific mRNA species in the osteoclast samples. Following this, the full-length cDNAs representative of the mRNA species and/or spliced variants are cloned in *E. coli* DH10B.

A major challenge in gene expression profiling is the limited quantities of RNA available for molecular analysis. The amount of RNA isolated from many osteoclast samples or human specimens (needle aspiration, laser capture microdissection (LCM) samples and transfected cultured cells) is often insufficient for preparing: 1) conventional tester and driver materials for STAR; 2) standard cDNA probes for DNA micro-array analysis; 3) RNA macroarrays for testing the specificity of expression; 4) Northern blots and; 5) full-length cDNA clones for further biological validation and characterization. Thus, the applicant has developed a proprietary technology called RAMP (RNA Amplification Procedure) (U.S. patent application Ser. No. 11/000,958 published under No. US 2005/0153333A1 on Jul. 14, 2005 and entitled "Selective Terminal Tagging of Nucleic Acids"), which linearly amplifies the mRNA contained in total RNA samples yielding microgram quantities of amplified RNA sufficient for the various analytical applications. The RAMP RNA produced is largely full-length mRNA-like sequences as a result of the proprietary method for adding a terminal sequence tag to the 3'-ends of single-stranded cDNA molecules, for use in linear transcription amplification. Greater than 99.5% of the sequences amplified in RAMP reactions show <2-fold variability and thus, RAMP provides unbiased RNA samples in quantities sufficient to enable the discovery of the unique mRNA sequences involved in osteoclastogenesis.

D—Preparation of Murine Osteoclasts Subtracted Library

RAW precursor cells and the corresponding fully differentiated (day 5) osteoclasts were prepared as described above. Isolation of cellular RNA followed by mRNA purification from each was performed using standard methods (Qiagen, Mississauga, ON). Following the teachings of Malek et al. (U.S. Pat. No. 5,712,127), 2 μg of poly A+ mRNA from each sample were used to prepare highly representative (>$2\times10^6$ CFU) cDNA libraries in specialized plasmid vectors necessary for preparing tester and driver materials. In each case, first-strand cDNA was synthesized using an oligo $dT_{11}$ primer with 3' locking nucleotides (e.g., A, G or C) and containing a Not I recognition site. Next, second-strand cDNA synthesis was performed according to the manufacturer's procedure for double-stranded cDNA synthesis (Invitrogen, Burlington, ON) and the resulting double-stranded cDNA ligated to linkers containing an Asc I recognition site (New England Biolabs, Pickering, ON). The double-stranded cDNAs were then digested with Asc I and Not I restriction enzymes (New England Biolabs, Pickering, ON), purified from the excess linkers using the cDNA fractionation column from Invitrogen (Burlington, ON) as specified by the manufacturer and each ligated into specialized plasmid vectors—p14 (SEQ. ID. NO:58) and p17+ (SEQ. ID. NO:59) used for preparing tester and driver materials respectively. Thereafter, the ligated cDNAs were transformed into E. coli DH10B resulting in the desired cDNA libraries (RAW 264.7-precursor-p14, RAW 264.7-precursor-p17+, RAW 264.7-osteoclasts-p14 and RAW 264.7-osteoclasts-p17+). The plasmid DNA pool for each cDNA library was purified and a 2-μg aliquot of each linearized with Not I restriction enzyme. In vitro transcription of the Not I digested p14 and p17+ plasmid libraries was then performed with T7 RNA polymerase and sp6 RNA polymerase respectively (Ambion, Austin, Tex.).

Next, in order to prepare 3'-represented tester and driver libraries, a 10-μg aliquot of each of the in vitro synthesized RNA was converted to double-stranded cDNA by performing first-strand cDNA synthesis as described above followed by primer-directed (primer OGS 77 for p14 (SEQ. ID. NO:62) and primer OGS 302 for p17+ (SEQ. ID. NO:63)) second-strand DNA synthesis using Advantage-2 Taq polymerase (BD Biosciences Clontech, Mississauga, ON). The sequences corresponding to OGS 77 and OGS 302 were introduced into the in vitro synthesized RNA by way of the specialized vectors used for preparing the cDNA libraries. Thereafter, 6×1-μg aliquots of each double-stranded cDNA was digested individually with one of the following 4-base recognition restriction enzymes Rsa I, Sau3A1, Mse I, Msp I, MinPI I and Bsh 12361 (MBI Fermentas, Burlington, ON), yielding up to six possible 3'-fragments for each RNA species contained in the cDNA library. Following digestion, the restriction enzymes were inactivated with phenol and the set of six reactions pooled. The restriction enzymes sites were then blunted with T4 DNA polymerase and ligated to linkers containing an Asc I recognition site. Each linker-adapted pooled DNA sample was digested with Asc I and Not I restriction enzymes, desalted and ligated to specialized plasmid vectors, p14 and p17 (p17 plasmid vector is similar to the p17+ plasmid vector except for the sequence corresponding to SEQ. ID. NO:63), and transformed into E. coli DH10B. The plasmid DNA pool for each p14 and p17 3'-represented library was purified (Qiagen, Mississauga, ON) and a 2-mg aliquot of each digested with Not I restriction enzyme, and transcribed in vitro with either T7 RNA polymerase or sp6 RNA polymerase (Ambion, Austin, Tex.). The resulting p14 3'-represented RNA was used directly as "tester RNA" whereas, the p17 3'-represented RNA was used to synthesize first-strand cDNA as described above, which then served as "driver DNA". Each "driver DNA" reaction was treated with RNase A and RNase H to remove the RNA, phenol extracted and desalted before use.

The following 3'-represented libraries were prepared:
Tester 1—RAW 264.7-osteoclast-3' in p14
Tester 2—RAW 264.7-precursor-3' in p14
Driver 1—RAW 264.7-precursor-3' in p17
Driver 2—RAW 264.7-osteoclast-3' in p17

The tester RNA samples were subtracted following the teachings of U.S. Pat. No. 5,712,127 with the corresponding driver DNA in a ratio of 1:100 for either 1- or 2-rounds following the teachings of Malek et al. (U.S. Pat. No. 5,712,127). Additionally, control reactions containing tester RNA and no driver DNA, and tester RNA plus driver DNA but no RNase H were prepared. The tester RNA remaining in each reaction after subtraction was converted to double-stranded DNA, and 5% removed and amplified in a standard PCR reaction for 30-cycles for analytical purposes. The remaining 95% of only the driver plus RNase H subtracted samples were amplified for 4-cycles in PCR, digested with Asc I and Not I restriction enzymes, and one half ligated into the pCATRMAN (SEQ. ID. NO:60) plasmid vector and the other half, into the p20 (SEQ. ID. NO:61) plasmid vector. The ligated materials were transformed into E. coli DH10B and individual clones contained in the pCATRMAN libraries were picked for further analysis (DNA sequencing and hybridization) whereas, clones contained in each p20 library were pooled for use as subtracted probes. Each 4-cycles amplified cloned subtracted library contained between 25,000 and 40,000 colonies.

The following cloned subtracted libraries were prepared:
T04-22—tester 1 (osteoclast) minus driver 1 (precursor) (1-round) in pCATRMAN
SL22—tester 1 (osteoclast) minus driver 1 (precursor) (2-rounds) in pCATRMAN
SL22—tester 1 (osteoclast) minus driver 1 (precursor) (2-rounds) in p20
SL27—tester 2 (precursor) minus driver 2 (osteoclast) (2-rounds) in pCATRMAN
SL27—tester 2 (precursor) minus driver 2 (osteoclast) (2-rounds) in p20

A 5-μL aliquot of the 30-cycles PCR amplified subtracted materials described above were visualized on a 1.5% agarose gel containing ethidium bromide and then transferred to Hybond N+ (Amersham Biosciences, Piscataway, N.J.) nylon membrane for Southern blot analysis. Three identical Southern transfers were prepared and were hybridized separately to radiolabeled probes specific to the MMP-9 (matrix metalloproteinase 9; NM_013599.2) and TRAP (tartrate resistant acid phosphatase; NM_007388.1) genes, which are known to be upregulated in osteoclasts, and GAPDH (glyceraldehyde-3-phosphate dehydrogenase; M32599.1), which is a non-differentially expressed house-keeping gene. The results of the hybridization analysis are shown in FIG. 1 where the following lanes contain the following materials:
AO 1—tester 1 RNA plus driver 1 DNA plus RNase H (1-round)
AO 2—tester 1 RNA plus driver 1 DNA plus RNase H (2-rounds)

AP 1—tester 2 RNA plus driver 2 DNA plus RNase H (1-round)
AP 2—tester 2 RNA plus driver 2 DNA plus RNase H (2-rounds)
BO 1—tester 1 RNA plus driver 1 DNA minus RNase H (1-round)
BO 2—tester 1 RNA plus driver 1 DNA minus RNase H (2-rounds)
BP 1—tester 2 RNA plus driver 2 DNA minus RNase H (1-round)
BP 2—tester 2 RNA plus driver 2 DNA minus RNase H (2-rounds)
CO 1—tester 1 RNA minus driver 1 DNA plus RNase H (1-round)
CO 2—tester 1 RNA minus driver 1 DNA plus RNase H (2-rounds)
CP 1—tester 2 RNA minus driver 2 DNA plus RNase H (1-round)
CP 2—tester 2 RNA minus driver 2 DNA plus RNase H (2-rounds)
DP—tester 2 RNA
DO—tester 1 RNA These results clearly show reduction of the GAPDH mRNA levels, representative of a non-differentially expressed gene, when both driver DNA and RNase H were present in the reactions (complete) (GAPDH panel: Lanes AO 1, AO 2, AP 1 and AP 2) in comparison to the incomplete reactions (GAPDH panel: BO 1, BO 2, BP 1, BP 2, CO 1, CO 2, CP 1 and CP 2). Additionally, there was better subtraction of GAPDH after 2-rounds (GAPDH panel: AO 2 and AP 2) compared to 1-round (GAPDH panel: AO 1 and AP 1). On the other hand, the differentially expressed upregulated genes (MMP-9 and TRAP) were enriched in the complete reactions (MMP-9 and TRAP panels: Lanes AO 1 and AO 2) in comparison to the incomplete reactions (MMP-9 and TRAP panels: BO 1, BO 2, CO 1 and CO 2), which showed amounts similar to the intact tester RNA (MMP-9 and TRAP panels: Lane DO).

Based on these results, it was anticipated that the subtracted libraries would be enriched for differentially expressed sequences. Thus, for T04-22 and SL22 libraries, genes up regulated in osteoclasts would be represented whereas, for SL27, the down-regulated genes would be represented.

E—Sequence Identification and Annotation of Clones Contained in the T04-22 and SL22 Subtracted Libraries:

Since GAPDH (see above) was most efficiently subtracted after 2-rounds (SL-22), it was anticipated that this library would be most enriched for differentially expressed osteoclast-related sequences. Thus, more exhaustive DNA sequence analysis was performed on clones contained in SL22 (1536 clones) compared to T04-22 (576 clones).

The individual colonies contained in the T04-22- and SL22-pCATRMAN libraries prepared as described previously were randomly picked using a Qbot (Genetix Inc.; Boston, Mass.) into 60 µL of autoclaved water. Then, 42 µL of each was used in a 100-µL standard PCR reaction containing oligonucleotide primers, OGS 1 and OGS 142 and amplified for 40-cycles (94° C. for 10 minutes, 40× (94° C. for 40 seconds, 55° C. for 30 seconds and 72° C. for 2 minutes) followed by 72° C. for 7 minutes) in 96-wells microtitre plates using HotStart™ Taq polymerase (Qiagen, Mississauga, ON). The completed PCR reactions were desalted using the 96-well filter plates (Corning) and the amplicons recovered in 100 µL 10 mM Tris (pH 8.0). A 5-µL aliquot of each PCR reaction was visualized on a 1.5% agarose gel containing ethidium bromide and only those reactions containing a single amplified product were selected for DNA sequence analysis using standard DNA sequencing performed on an ABI 3100 instrument (Applied Biosystems, Foster City, Calif.). Each DNA sequence obtained was given a Sequence Identification Number and entered into a database for subsequent tracking and annotation.

Figure 2:
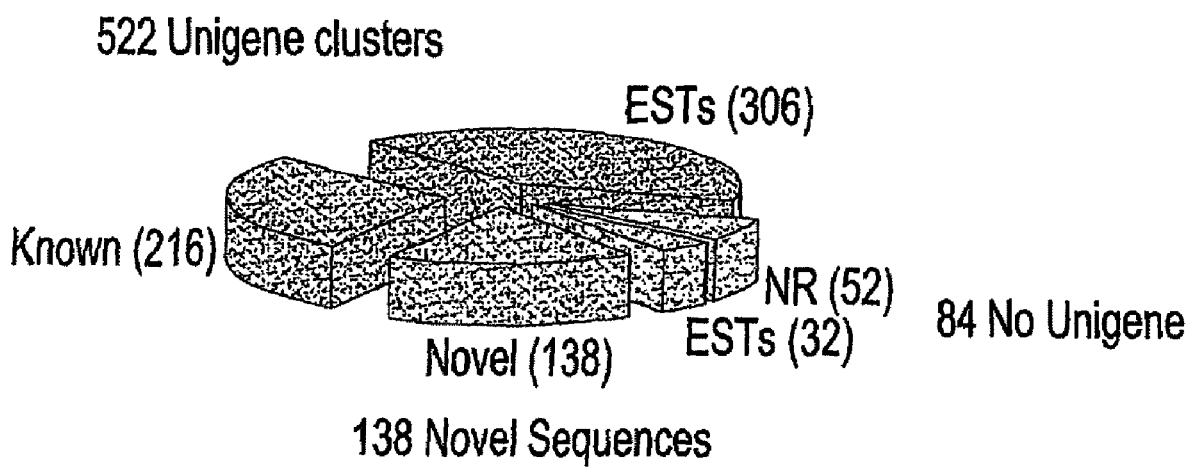
FIG. 2 shows a pie chart annotation of the clones isolated and sequenced from the SL22 subtracted library.

For the purpose of illustrating the ensuing strategies for identification of the clones, only the DNA sequences obtained for clones contained in SL22 will be discussed further. Of those sequences, 1408 were selected for BLAST analysis of public databases (e.g. NCBI), which yielded 744 unique sequences representing a redundancy of approximately 53% and thus, a sufficiently representative sampling of the subtracted library. Absent from these sequences were the standard housekeeping genes (GAPDH, actin, most ribosomal proteins etc.), which was a good indication that the subtracted library was depleted of at least the relatively abundant non-differentially expressed sequences. A limited survey of 96 clones from a corresponding un-subtracted library resulted in largely known and abundant housekeeping sequences such as GAPDH and beta-actin (data not shown). The 744 unique sequences were broadly classified into three categories shown in FIG. 2: 522 genes with Unigene clusters (70.2%), 84 genes with no Unigene cluster (11.3%) and 138 novel sequences (18.5%). Of the Unigene-clustered genes, only 114 were associated with GO (Gene Ontology) functional categories. Thus, it was evident from these results that the subtracted library (SL22) was enriched for known and novel sequences.

Once sequencing and annotation of the selected clones were completed, the next step involved identifying those sequences that were actually upregulated in osteoclasts compared to precursors.

F—Hybridization Analysis for Identifying Upregulated Sequences

The PCR amplicons representing the annotated sequences from the T04-22 and SL22 libraries were used to prepare DNA microarrays. The purified PCR amplicons from contained in 70 µL prepared in the previous section was lyophilized and each reconstituted in 20 µL of spotting solution comprising 3×SSC and 0.1% sarkosyl. DNA micro-arrays of each amplicon in triplicate were then prepared using CMT-GAP2 slides (Corning, Corning, N.Y.) and the GMS 417 spotter (Affymetrix, Santa Clara, Calif.).

The DNA micro-arrays were then hybridized with either standard or subtracted cy3 and cy5 labelled cDNA probes as recommended by the supplier (Amersham Biosciences, Piscataway, N.J.). The standard cDNA probes were synthesized using. RAMP amplified RNA prepared from five different murine osteoclast samples and the corresponding precursors. It is well known to the skilled artisan that standard cDNA probes only provide limited sensitivity of detection and consequently, low abundance sequences contained in the cDNA probes are usually missed. Thus, the hybridization analysis was also performed using subtracted cDNA probes. These subtracted cDNA probes were synthesized from in vitro transcribed RNA prepared from the SL22-p20 and SL25-p20 subtracted libraries described above in D. These subtracted libraries may be enriched for low abundance sequences as a result of following the teachings of Malek et al., and therefore, may provide increased detection sensitivity.

All hybridization reactions were performed using the dye-swap procedure as recommended by the supplier (Amersham Biosciences, Piscataway, N.J.). Following analysis of the hybridization results obtained using the standard cDNA probes, 161 of the 744 unique sequences contained in SL22 appeared to be upregulated in the osteoclasts, showing >2-fold difference compared to the precursors. On the other hand, when the subtracted cDNA probes were used, 289 additional SL22-sequences appeared to be upregulated in the osteoclast samples as well.

Thus, it was evident from these results that the SL22 subtracted library was highly enriched for upregulated sequences (>60%), which were probably involved in osteoclastogenesis. A similar analysis was performed for the T04-22 clones, which showed a lower percentage of differentially expressed sequences likely due to insufficient subtraction after only 1-round of the STAR procedure.

G—Determining Osteoclast Specificity of the Differentially Expressed Sequences Identified:

The differentially expressed sequences identified in Section F for both SL22 and T04-22 libraries were tested for osteoclast specificity by hybridization to nylon membrane-based macroarrays. The macroarrays were prepared using RAMP amplified RNA from murine precursors and osteoclasts of five independent experiments, and various normal murine tissues (liver, brain, thymus, heart, lung, testicle, ovary, kidney and embryo) purchased commercially (Ambion, Austin, Tex.). Because of the limited quantities of mRNA available for many of these samples, it was necessary to first amplify the mRNA using the RAMP methodology. Each amplified RNA sample was reconstituted to a final concentration of 250 ng/µL in 3×SSC and 0.1% sarkosyl in a 96-well microtitre plate and 1 µL spotted onto Hybond N+ nylon membranes using the specialized MULTI-PRINT™ apparatus (VP Scientific, San Diego, Calif.), air dried and UV-cross linked. A total of 556 different sequences selected from SL22 and T04-22 were individually radiolabeled with $\alpha$-$^{32}$P-dCTP using the random priming procedure recommended by the supplier (Amersham, Piscataway, N.J.) and used as probes on the macroarrays. Hybridization and washing steps were performed following standard procedures well known to those skilled in the art.

Of the 556 sequences tested, approximately 80% were found to be upregulated in at least the primary osteoclast RNA sample that was used to prepare the subtracted libraries. However, many of these sequences were also readily detected in the different murine tissues. Based on these results, those sequences that appeared to be associated with experimental variability and those that were detected in many of the other murine tissues were eliminated. Consequently, only 73 sequences, which appeared to be highly osteoclast-specific, were selected for biological validation studies. This subset of 73 sequences included sequences present in two or less murine tissues relative to the precursor levels since it is entirely possible that the hybridization signals obtained for these tissues maybe due to family members or spliced variants.

FIG. 3 shows examples of the macroarray patterns representative of the sequences selected for validation. Subsequently, RNA from 8 additional normal murine tissues (lymph node, eye, prostate, smooth muscle, spinal cord, stomach, uterus and bone marrow) were incorporated into secondary macroarrays and used to further test the specificity of many of the 73 selected sequences (data not shown). Amongst the 73 selected sequences were 41 genes with functional annotation of which, only two were previously linked to osteoclastogenesis (Unigene Clusters Mm.103560 and Mm.271689), 20 genes with no functional annotation and 12 novel sequences (data not disclosed). Representative sequences are characterized as follows:

SEQ. ID. NO:1:

The candidate protein encoded by SEQ. ID. NO:1 is a previously identified gene with the designation, testis-specific protease or Tsp50. The mouse polynucleotide contains an open reading frame of 1317 bp and encodes a polypeptide of 439 amino acids. The human polynucleotide contains an open reading frame of 1155 bp and encodes a polypeptide of 385 amino acids. It was originally described and cloned because of its expression in a hypomethylated region of genomic DNA in human breast cancer cells (Yuan et al., 1999). Analysis of the primary amino acid sequence suggests the presence of an amino-terminal signal peptide that will presumably target the protein to the plasma membrane, a carboxy-terminal transmembrane domain to anchor the protein in the plasma membrane, and a predicted catalytic domain homologous to serine proteases (Shan et al., 2002; Netzel-Arnett et al., 2003). The nature of the predicted catalytic activity and the exact cellular localization of Tsp50 have yet to be conclusively established. Applicant directs the reader's attention to U.S. Pat. No. 6,617,434 (Duffy, Sep. 9, 2003) and U.S. Pat. No. 6,451,555 (Duffy, Sep. 17, 2002) where Tsp50 is the subject matter. Despite all of the above information, no functional association with osteoclasts or bone remodeling disorders has been described prior to the present disclosure.

SEQ. ID. NO:2:

The candidate protein encoded by SEQ. ID. NO:2 is a previously identified gene that encodes the d2 subunit of the vacuolar (V-) ATPase multi-subunit complex. Although the d2 subunit does not span the membrane, it is part of the membrane-spanning complex and interacts directly with the larger a subunit that contains the transmembrane properties (Nishi and Forgac, 2002). The cDNA encoding the mouse V-ATPase d2 protein has recently been described but its function in bone physiology has yet to be established (Nishi et al., 2003). No functional association with osteoclasts or bone remodeling disorders has been described prior to the present disclosure.

SEQ. ID. NO:3:

The candidate protein encoded by SEQ. ID. NO:3 is a previously identified gene that encodes the cartilage-associated protein, Crtap (Morello et al., 1999; Tonachini et al., 1999). The gene was originally cloned from chick embryo and localized to cartilaginous tissues (Morello et al., 1999). No functional association with osteoclasts or bone remodeling disorders has been described prior to the present disclosure.

SEQ. ID. NO:4:

The candidate protein encoded by SEQ. ID. NO:4 is found in current databases and was cloned as part of the RIKEN Genome Exploration Research Group (Kawai et al., 2001). Although the mRNA contains a predicted open reading frame, no function has been assigned to this sequence prior to the present disclosure.

SEQ. ID. NO:5:

The candidate protein encoded by SEQ. ID. NO:5 is found in current databases and was cloned as part of the RIKEN Genome Exploration Research Group (Strausberg et al., 2002). Although the mRNA contains a predicted open reading frame, no function has been assigned to this sequence prior to the present disclosure.

SEQ. ID. NO:6:

The candidate protein encoded by SEQ. ID. NO:6 is found in current databases and was cloned as part of the RIKEN Genome Exploration Research Group (Strausberg et al., 2002). Although the mRNA contains a predicted open reading frame, no function has been assigned to this sequence prior to the present disclosure.

SEQ. ID. NO:7:

The candidate protein encoded by SEQ. ID. NO:7 is a previously identified gene that encodes the linker for activation of B cells. The gene has been reported as playing a role in thymocytes (Janssen et al., 2003). No functional association with osteoclasts or bone resorption disorders has been described prior to the present disclosure.
SEQ. ID. NO:57

The candidate protein encoded by SEQ; ID. NO:57 is a previously identified gene that encodes the jun dimerization protein 2. This gene has been shown to be involved in osteoclastogenesis using antisense technology (Kawaida et al., 2003). This example serves as further proof of concept of applicant's approach in identifying osteoclast-specific genes.
H—Cloning of Full-Length cDNAs of Selected Sequences from Osteoclast mRNA:

It was necessary to obtain full-length cDNA sequences in order to perform functional studies of the expressed proteins. Spliced variants are increasingly being implicated in tissue specific functions and as such, it is critically necessary to work with cDNA clones from the system under study. Applicant also recognizes that spliced variants may not always be involved. Thus, the applicant's approach has been to isolate the relevant full-length cDNA sequences directly from osteoclasts in order to identify variants and their potential role with respect to specificity.

Coding cDNA clones were isolated using both a 5'-RACE strategy (Invitrogen, Burlington, ON) and a standard two-primer gene specific approach in PCR. The 5'-RACE strategy used cDNA prepared from cap-selected osteoclast RNA and/or RAMP amplified osteoclast RNA. For amplification using gene specific primers, either cDNA prepared from RAMP RNA or total RNA was used. All cDNAs were synthesized following standard reverse transcription procedures (Invitrogen, Burlington, ON). The cDNA sequences obtained were cloned in E. coli DH10B and the nucleotide sequences for multiple clones determined. Thereafter, the cDNA sequences for each set were aligned and the open reading frame(s) (ORF) identified using standard software (e.g. ORF Finder-NCBI). Table 3 shows examples of cDNA clones of spliced variants, which were obtained for some of the sequences under investigation.
I—RNA Interference Studies RNA interference is a recently discovered gene regulation mechanism that involves the sequence-specific decrease in a gene's expression by targeting the mRNA for degradation and although originally described in plants, it has been discovered across many animal kingdoms from protozoans and invertebrates to higher eukaryotes (reviewed in Agrawal et al., 2003). In physiological settings, the mechanism of RNA interference is triggered by the presence of double-stranded RNA molecules that are cleaved by an RNAse III-like protein active in cells, called Dicer, which releases the 21-23 bp siRNAs. The siRNA, in a homology-driven manner, complexes into a RNA-protein amalgamation termed RISC (RNA-induced silencing complex) in the presence of mRNA to cause degradation resulting in attenuation of that mRNA's expression (Agrawal et al., 2003).

Current approaches to studying the function of genes, such as gene knockout mice and dominant negatives, are often inefficient, and generally expensive, and time-consuming. RNA interference is proving to be a method of choice for the analysis of a large number of genes in a quick and relatively inexpensive manner. Although transfection of synthetic siRNAs is an efficient method, the effects are often transient at best (Hannon G. J., 2002). Delivery of plasmids expressing short hairpin RNAs by stable transfection has been successful in allowing for the analysis of RNA interference in longer-term studies (Brummelkamp et al., 2002; Elbashir et al., 2001). In addition, more recent advances have permitted the expression of siRNA molecules, in the form of short hairpin RNAs, in primary human cells using viral delivery methods such as lentivirus (Lee et al., 2004; Rubinson et al., 2003).
J—Determination of Knockdown Effects on Osteoclastogenesis The design and subcloning of individual siRNA expression cassettes and the procedure utilized for the characterization of each nucleotide sequence is described below. Selection of polynucleotides were chosen based on their RANK ligand-dependent upregulation in osteoclasts and the selective nature of their expression in osteoclasts compared to other tissues (see sections F and G above). The design of siRNA sequences was performed using web-based software that is freely available to those skilled in the art (Qiagen for example). These chosen sequences, usually 19-mers, were included in two complimentary oligonucleotides that form the template for the short hairpin RNAs, i.e. the 19-nt sense sequence, a 9-nt linker region (loop), the 19-nt antisense sequence followed by a 5-6 poly-T tract for termination of the RNA polymerase III. Appropriate restriction sites were inserted at the ends of these oligonucleotides to facilitate proper positioning of the inserts so that the transcriptional start point is at a precise location downstream of the hU6 promoter. For each sequence selected, at least two different siRNA expression vectors were constructed to increase the chance of observing RNA interference.

The transfection plasmids expressing the siRNAs under the control of the human U6 promoter were constructed as follows. Two primers containing an AseI site (forward) and a KpnI site (reverse) were used to PCR amplify a 330-bp fragment containing the human U6 promoter from 5 ng of human genomic DNA. This fragment was ligated in similarly digested pd2EGFP-N1 (BD Biosciences Clontech, Mississauga, ON) resulting in the replacement of the CMV E1 promoter of pd2EGFP-N1 by the human (h)U6 promoter sequence. Digesting with AgeI and NotI and relegating the blunted ends to generate pd2-hU6 accomplished removal of the d2EGFP fragment. The template for the siRNA hairpin was designed by annealing two oligonucleotides yielding a 57-bp fragment blunt at the 5'-end and having a BamHI overhang at the 3'-end. The annealed oligonucleotides were ligated into pd2-hU6 that had been previously digested with KpnI (blunted) and BamHI resulting in pd2-hU6/siRNA. All plasmids were verified by sequencing to confirm presence of the siRNA hairpin sequence and proper positioning of the transcriptional start site following the hU6 promoter.

Figure 4A:
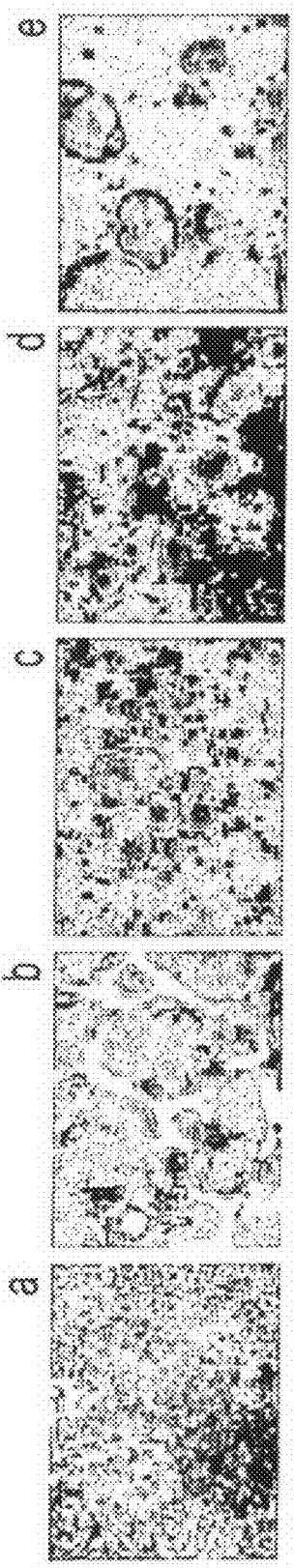
FIG. 4A is a picture showing the phenotypic effect on osteoclast differentiation in the presence of siRNAs specific for SEQ. ID. NO:1.
Figure 4B:
FIG. 4B is a picture showing the phenotypic effect on osteoclast differentiation in the presence of a mixture of siRNAs specific for SEQ. ID. NO:1.

RAW cells were seeded in 6-well plates in high glucose DMEM containing 10% fetal bovine serum at a density of $6 \times 10^5$ cells/well, allowed to plate overnight and transfected with 1 μg of pd2-hU6/siRNA plasmid using the Fugene 6 reagent (Roche, Laval, QC). After 16 h of incubation, fresh medium was added containing 400 μg/ml G418 to select for stable transfectants. Control cells were transfected with pd2-hU6. After approximately 10 days, pools and/or individual clones of cells were isolated and analyzed for their ability to form osteoclasts in 96-well plates. The resulting phenotypes were observed microscopically by viewing cells assayed for TRAP staining. The efficacy of RNA interference was also assessed by conducting Northern blots on total RNA isolated from cells subjected to in vitro osteoclastogenesis.
K—Results of RNA Interference Studies
SEQ. ID. NO:1:

The sequences used for RNA interference were derived from the polynucleotide SEQ. ID. NO:1 and have the SEQ. ID. NOs: 64, 65 and 66 (of course other sequences may be used). The cell lines derived from RAW cells transfected with plasmids encoding the three siRNAs pd2-hU6/0440.1, pd2- hU6/0440.2 and, pd2-hU6/0440.3 are designated hereafter as RAW-0440.1 (SEQ. ID. NO.:64), RAW-0440.2 (SEQ. ID. NO.:65), and RAW-0440.3 (SEQ. ID. NO.:66), respectively and collectively as RAW-0440. In addition, as a positive control for normal osteoclastogenesis, RAW cells were transfected with the empty vector (pd2-hU6) that does not contain a siRNA. Phenotypic analysis of all cell lines is shown in FIG. 4A. Panel a of FIG. 4A shows the control cell line, RAW-hU6, in the absence of RANK ligand where the presence of multinucleated osteoclasts is not observed and the undifferentiated RAW cells are completely devoid of TRAP staining. Upon treatment with RANK ligand, large, multinucleated; TRAP positive osteoclasts are seen demonstrating normal differentiation (panel b). The presence of the siRNA specific for SEQ. ID. NO:1 in RAW cells resulted in a greatly reduced ability of these cells to form large and mature osteoclasts in the presence of RANK ligand (panels c-e). In addition to a decreased number of osteoclasts per well, the RAW-0440 cells were smaller and most of exhibited a slight decrease in TRAP staining. Closer inspection revealed that these smaller osteoclasts were multinucleated suggesting normal cellular fusion of the RAW-0440 precursors. Analysis of another RAW cell line, RAW-0440.mix, transfected with an equivalent amount of all three siRNA expression vectors confirmed the previous phenotypic observations. As before, the control cell line transfected with the empty vector formed large multinucleated osteoclasts that stained for TRAP (FIG. 4B, panel b). As shown in panel c, the RAW-0440.mix osteoclasts were multinucleated but small and fewer in number.

Figure 5:
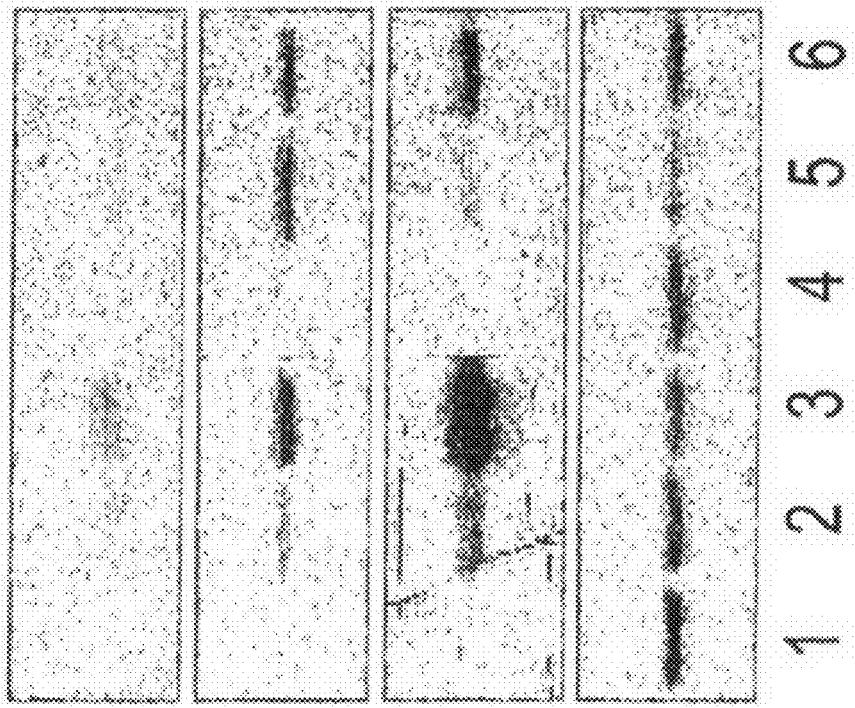
FIG. 5 is a picture of a Northern blot showing the attenuation of SEQ. ID. NO:1 gene expression in RAW cells in the presence of specific siRNAs compared to osteoclast-specific marker genes, TRAP and CTSK.
Figure 5B:
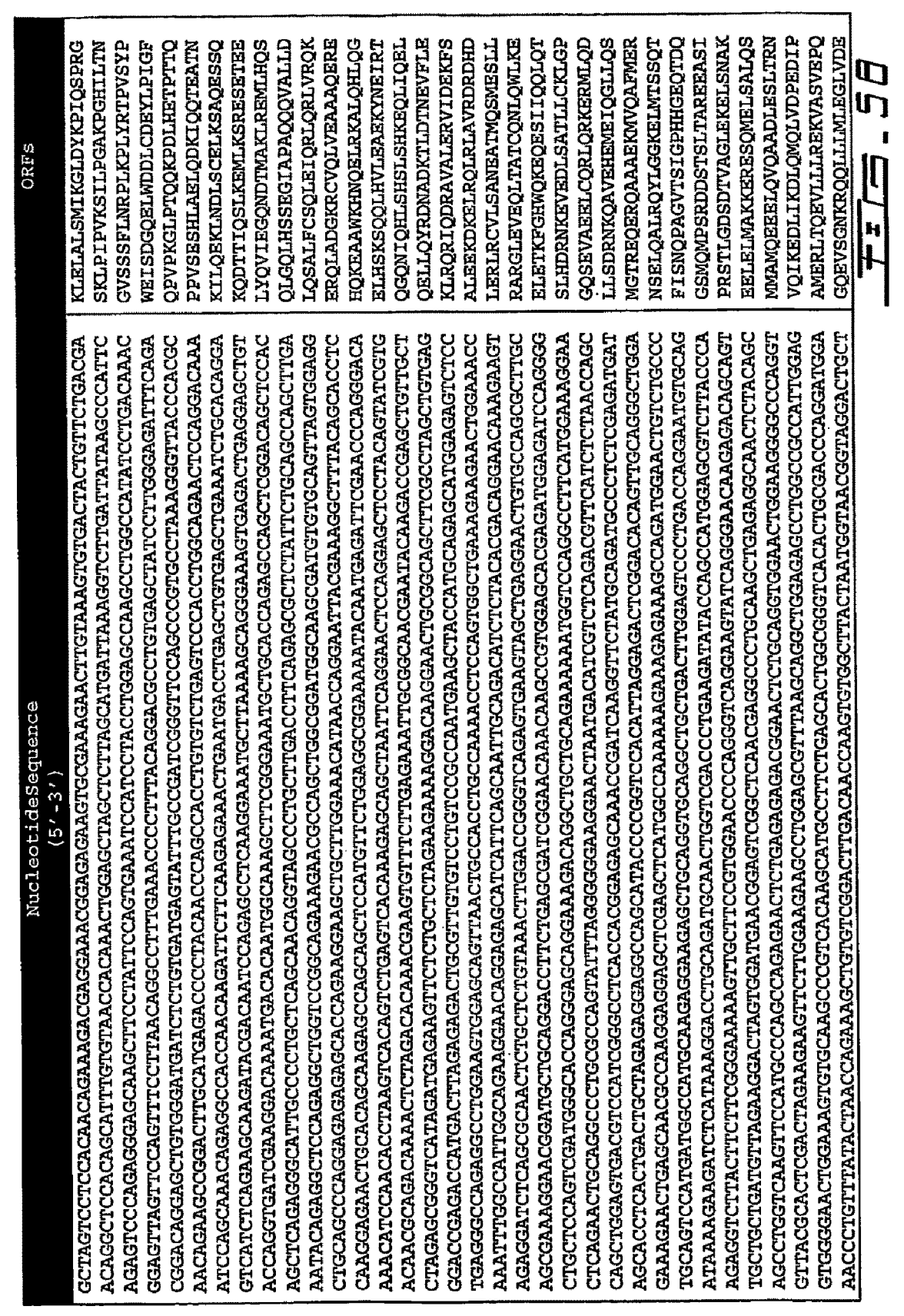

The effect of each siRNA was assessed by isolating total RNA from the mature osteoclasts after 3 and 4 days of RANK ligand treatment and probing with a fragment of the SEQ. ID. NO:1 cDNA to determine if knockdown of endogenous gene expression occurred. A representative experiment is shown in FIG. 5. When 10 μg of total RNA was probed with a fragment of the SEQ. ID. NO:1 cDNA, a single mRNA of 1.7 Kb was observed. A decrease, especially at day 4, in the amount of the SEQ. ID. NO1 mRNA was seen in the RNA isolated from the RAW-0440.1 cell line indicating RNA interference occurred in these cells (FIG. 5, top panel, compare lanes 3 and 6). Similarly, the expression of two known osteoclast marker genes, TRAP and Cathepsin K (Boyle et al., 2003), was significantly reduced in RAW-0440.1 cells (FIG. 5). The osteoclast-specific character of SEQ. ID. NO:1 was evident by the lack of expression in the precursor cells (see lanes 1 and 4). The difference in the expression of the SEQ. ID. NO:1 gene was not due to the difference in the amount of total RNA loaded on the gel as evidenced by the probing of the same membrane with a fragment of the housekeeping gene glyceraldehyde-3-phosphate dehydrogenase (GAPDH, FIG. 5).

These results demonstrate that the absence of physiological levels of SEQ. ID. NO:1 in RAW cells impairs their ability to differentiate into osteoclasts properly and implies an important role for this gene in these cells.

Figure 6:
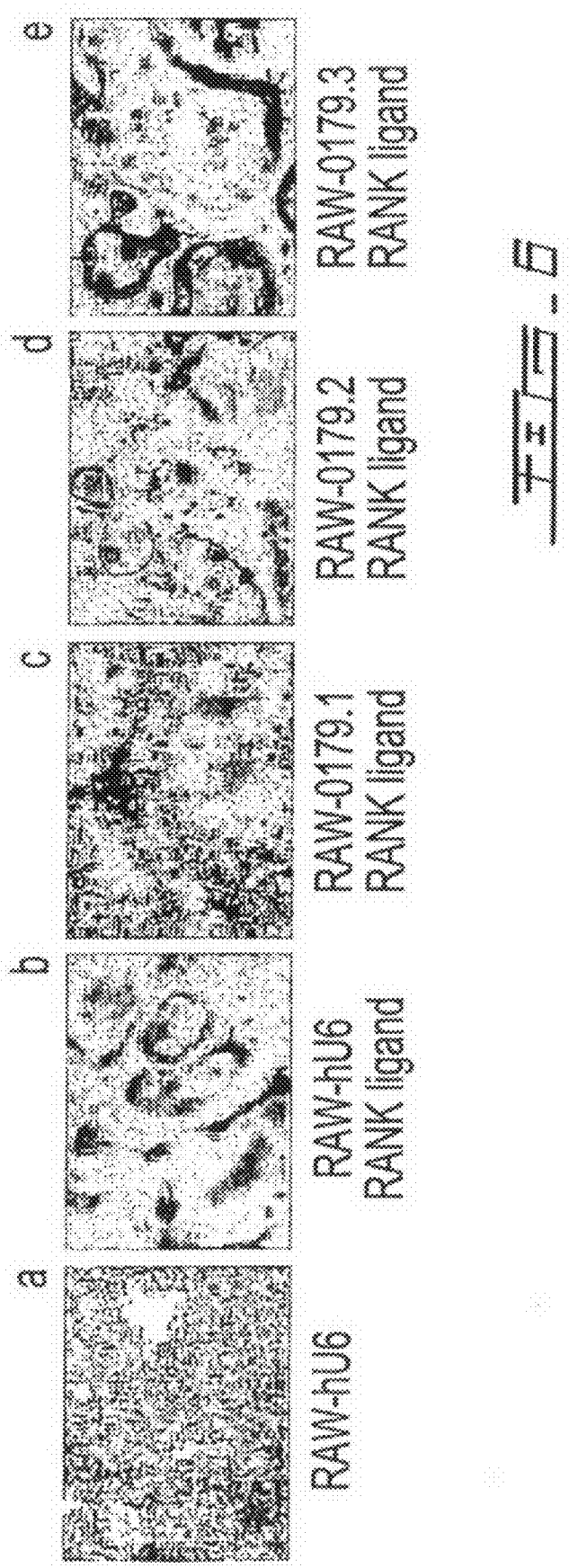
FIG. 6 are pictures illustrating the phenotypic effect on osteoclast differentiation in the presence of siRNAs specific for SEQ. ID. NO:2, panel a; control RAW-hU6 cells, panel b; RAW-hU6 treated with RANK ligand, panel c; RAW-hU6 treated with RANK ligand and siRNA specific for SEQ ID NO.:2 (RAW-0179.1), panel d; RAW-hU6 treated with RANK ligand and siRNA specific for SEQ ID NO.:2 (RAW- 0179.2) and panel e; RAW-hU6 treated with RANK ligand and siRNA specific for SEQ ID NO.:2 (RAW-0179.3)

SEQ. ID. NO:2:

The sequences used for RNA interference were derived from the polynucleotide SEQ. ID. NO:2 and have the SEQ. ID. NOs:67, 68 and 69. The cell lines derived from RAW cells transfected with plasmids encoding the three siRNAs pd2-hU6/0179.1, pd2-hU6/0179.2 and, pd2-hU6/0179.3 are hereby-designated RAW-0179.1 (SEQ. ID. NO.:67), RAW-0179.2 (SEQ. ID. NO.:68), and RAW-0179.3 (SEQ. ID. NO.:69), respectively. In addition, as a positive control for normal osteoclastogenesis, RAW cells were transfected with the empty vector (pd2-hU6) that does not contain any siRNA. Phenotypic analysis of all cell lines is shown in FIG. 6. Panel a of FIG. 6 shows the control-cell line, RAW-hU6, in the absence of RANK ligand where the presence of multinucleated osteoclasts is not observed and the undifferentiated RAW cells are completely devoid of TRAP staining. Upon treatment with RANK ligand, large and multinucleated, TRAP positive osteoclasts are seen demonstrating normal differentiation (panel b). Two of the siRNAs, namely those encoded by RAW-0179.1 and RAW-0179.2, resulted in a noticeable reduction in the ability of these cells to form large, mature osteoclasts in the presence of RANK ligand (panels c, d). A third siRNA sequence, RAW-0179.3, was not effective (see FIG. 6, panel e). In addition to a decreased number of osteoclasts per well, the RAW-0179.1 and RAW-0179.2 cells were generally smaller and contained less nuclei.

Figure 7:
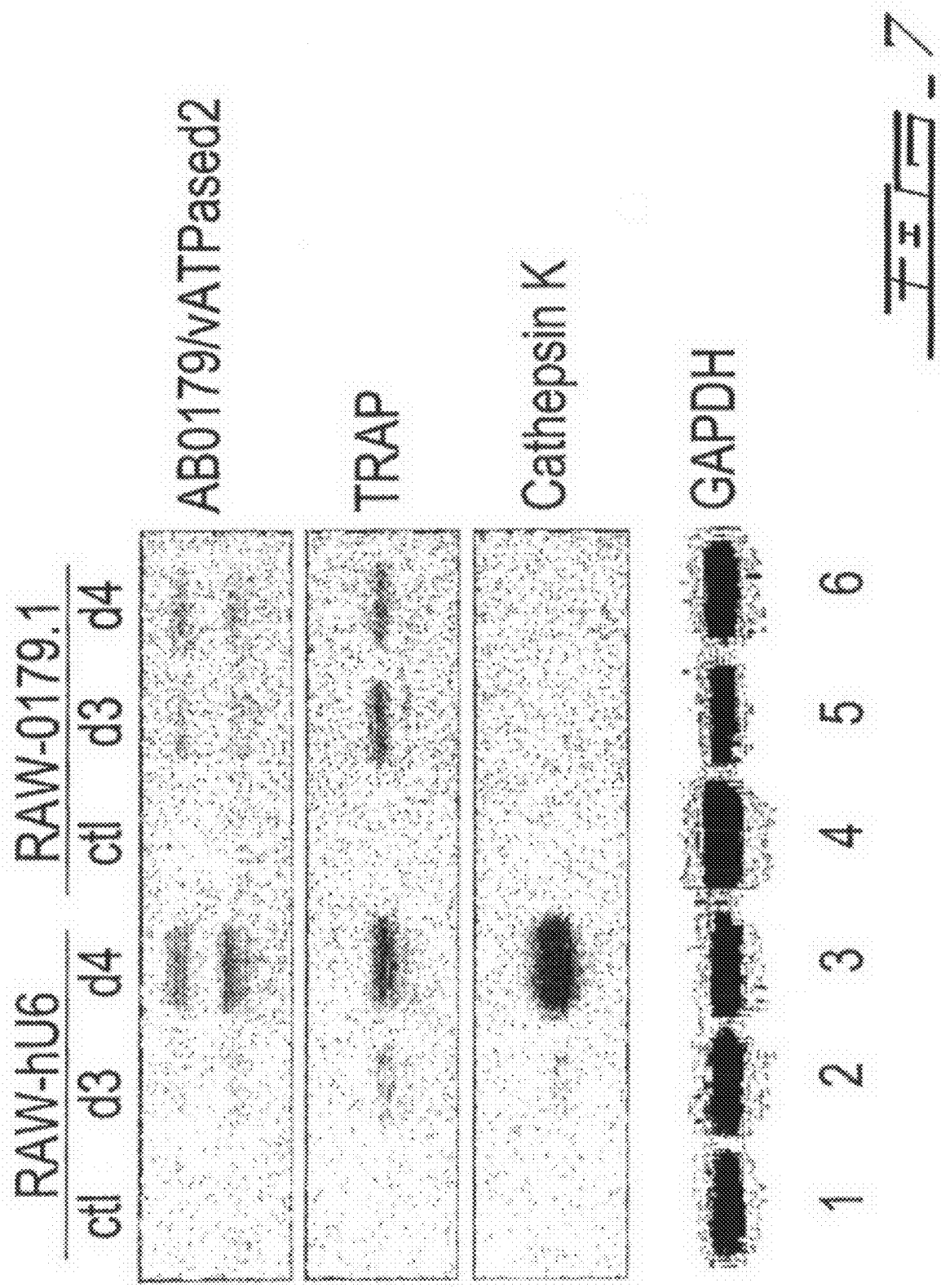
FIG. 7 is a picture of a Northern blot showing the attenuation of SEQ. ID. NO:2 gene expression in RAW cells in the presence of specific siRNAs. Also shown is the effect on the osteoclast-specific marker genes, TRAP and Cathepsin K.

Isolating total RNA from the mature osteoclasts after 3 and 4 days of RANK ligand treatment and probing with a fragment of the SEQ. ID. NO2 cDNA to determine if knockdown of endogenous gene expression occurred assessed the effect of each siRNA. A representative experiment is shown in FIG. 7. When 10 μg of total RNA was probed with a fragment of the SEQ. ID. NO2 cDNA, two mRNAs of 2.3 Kb and 1.6 Kb were observed. A decrease, especially at day 4, in the amount of the SEQ. ID. NO2 mRNA was seen in the RNA isolated from the RAW-0179.1 cell line indicating RNA interference occurred in these cells (FIG. 7, top panel, compare lanes 3 and 6). Furthermore, although the RAW-hU6 precursor cells expressed detectable levels of SEQ. ID. NO2 in the absence of RANK ligand, expression was not seen in RNA from the RAW-0179.1 cells under similar conditions (compare lanes 1 and 4 in FIG. 7, top). Taken together, these results show that effective RNA interference occurred. Two known osteoclast marker genes were also significantly reduced, especially Cathepsin K which was virtually undetectable in RAW-0179.1 cells compared to the control cell line. The difference, in the expression of the SEQ. ID. NO2 gene was not due to the difference in the amount of total RNA loaded on the gel as evidenced by the probing of the same membrane with a fragment of the housekeeping gene glyceraldehyde-3-phosphate dehydrogenase (GAPDH, FIG. 7).

These results demonstrate that SEQ. ID. NO2 is required for proper osteoclast differentiation in RAW cells suggesting an important role for this gene in these cells.

Figure 8:
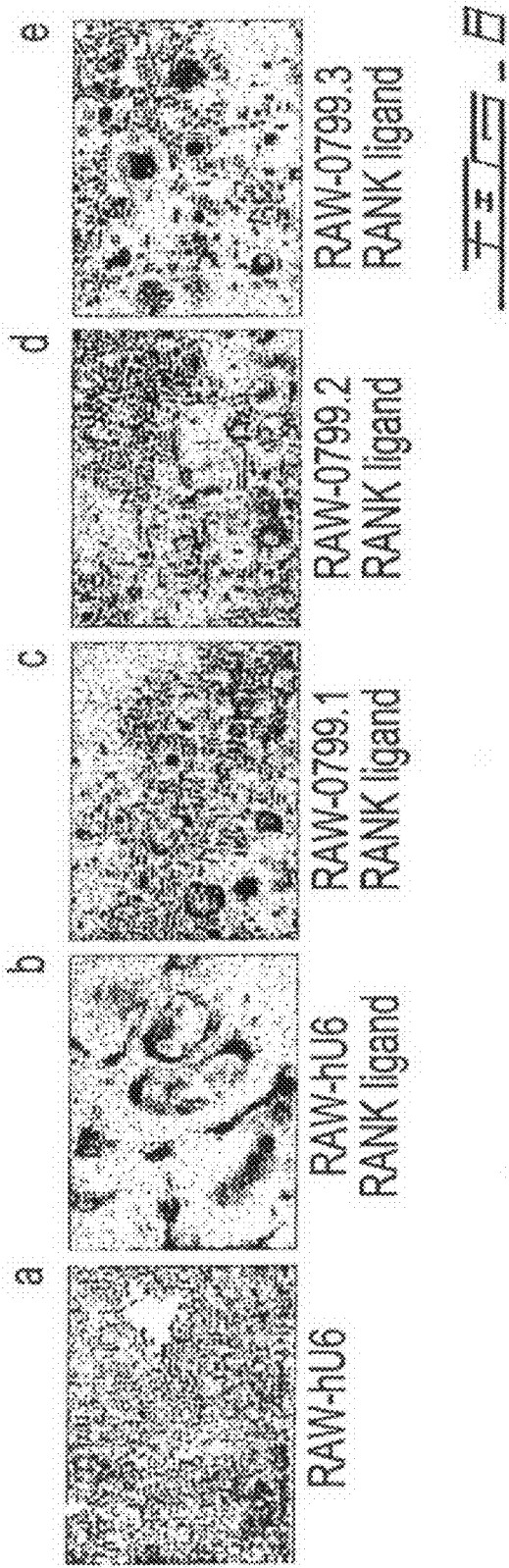
FIG. 8 are pictures illustrating the phenotypic effect on osteoclast differentiation in the presence of siRNAs specific for SEQ. ID. NO:3 panel a; control RAW-hU6 cells, panel b; RAW-hU6 treated with RANK ligand, panel c; RAW-hU6 treated with RANK ligand and siRNA specific for SEQ ID NO.:3 (RAW-0799.1), panel d; RAW-hU6 treated with RANK ligand and siRNA specific for SEQ ID NO.:3 (RAW-0799.2) and panel e; RAW-hU6 treated with RANK ligand and siRNA specific for SEQ ID NO.:3 (RAW-0799.3)

SEQ. ID. NO:3:

The sequences used for RNA interference were derived from the polynucleotide SEQ. ID. NO:3 and have the SEQ. ID. NOs:70, 71 and 72. The use of RNA interference as described in the invention for SEQ. ID. NOs1 and 2 was applied to SEQ. ID. NO:3. The results obtained were similar showing that this gene is also required for proper differentiation of RAW osteoclasts. An illustration of this result is depicted in FIG. 8.

Figure 9:
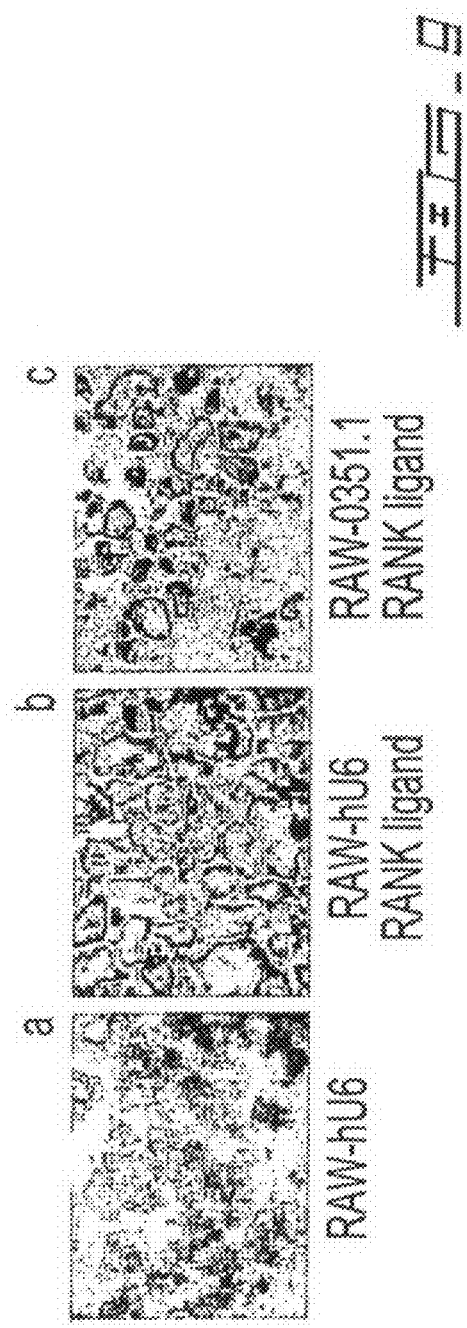
FIG. 9 are pictures illustrating the phenotypic effect on osteoclast differentiation in the presence of siRNAs specific for SEQ. ID. NO:4 panel a; control RAW-hU6 cells, panel b; RAW-hU6 treated with RANK ligand, and panel c; RAW-hU6 treated with RANK ligand and siRNA specific for SEQ ID NO.:4 (RAW-0351.1)

SEQ. ID. NO:4:

The sequences used for RNA interference were derived from the polynucleotide SEQ. ID. NO:4 and have the SEQ. ID. NOs:73 and 74. The use of RNA interference as described in the invention for SEQ. ID. NOs1 and 2 was applied to SEQ. ID. NO:4. The results obtained were similar showing that this gene is required for proper differentiation of RAW osteoclasts. An illustration of this result is depicted in FIG. 9.

SEQ. ID. NO:5:

The sequences used for RNA interference were derived from the polynucleotide SEQ. ID. NO:5 and have the SEQ. ID. NOs:75 and 76. The use of RNA interference as described in the invention for SEQ. ID. NOs 1 and 2 was applied to SEQ. ID. NO:5. The results obtained were similar showing that this gene is required for proper differentiation of RAW osteoclasts. An illustration of this result is depicted in FIG. 10.

SEQ. ID. NO:6:

The sequences used for RNA interference were derived from the polynucleotide SEQ. ID. NO:6 and have the SEQ. ID. NOs:77 and 78. The same approach for RNA interference was applied for this sequence with the following modification. The siRNA expression plasmids pd2-hU6/1200.1 and pd2-hU6/1200.2 were transfected as a mixture where equivalent amounts were used. As was observed for SEQ. ID. NO:1, pooling the siRNA expression plasmids produces similar results to those obtained from individual plasmid transfections. Thus, the cell line that was obtained from this transfection was termed RAW-1200.mix (see FIG. 11).

Figure 11B:
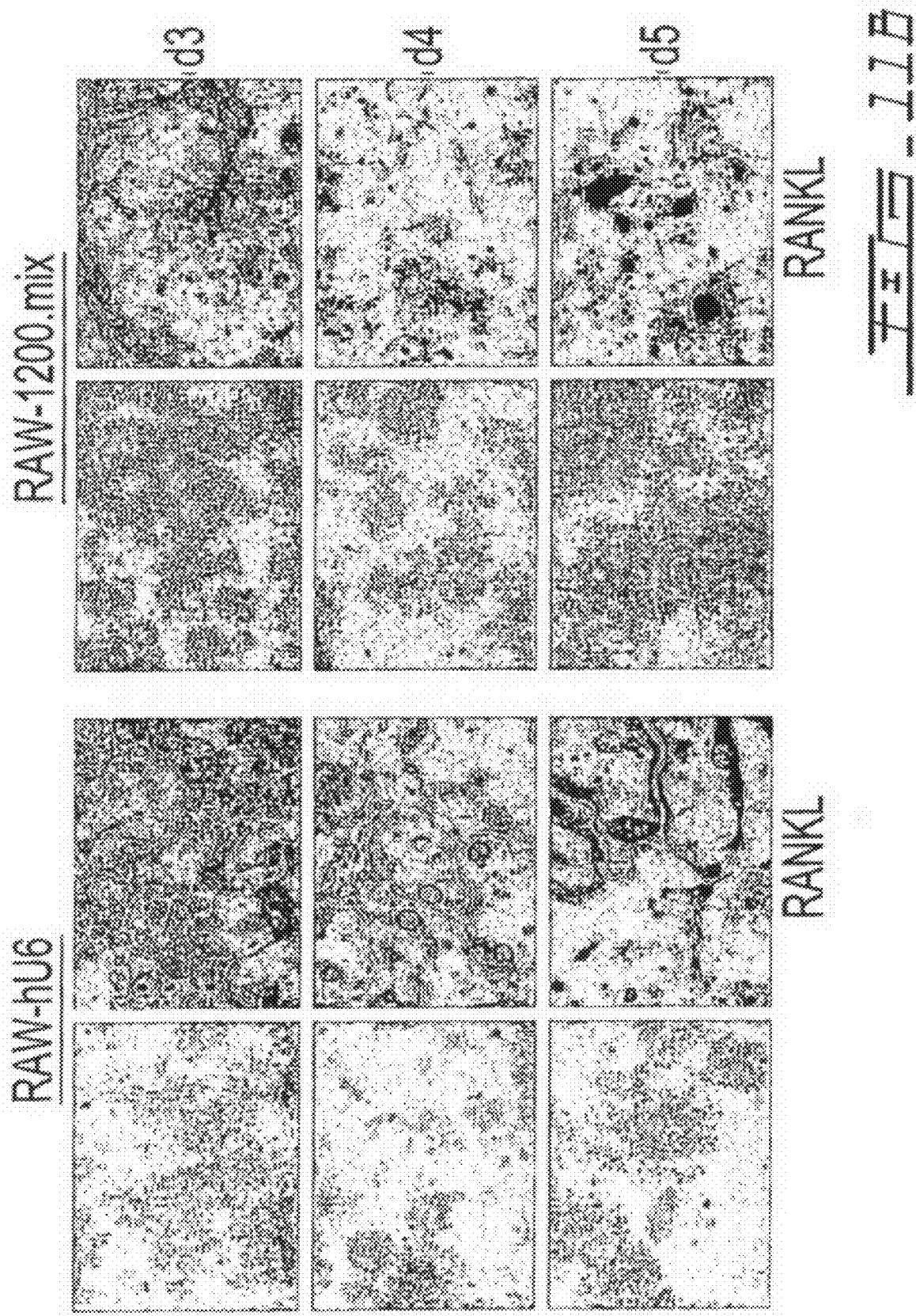
FIG. 11B are pictures illustrating a time-course of the phenotypic effect on osteoclast differentiation of RAW-hU6 observed in the presence or absence of RANK ligand and in the presence or absence siRNAs specific for SEQ. ID. NO:6 (RAW-1200.mix)

Treatment of this cell line with RANK ligand resulted in RAW cells that differentiated sooner than the control cell line, RAW-hU6. In addition, the osteoclasts were larger and contained more nuclei per cell (compare panels b and d in FIG. 11A). The experiment was repeated with TRAP staining conducted at days 3, 4 and 5 five to directly compare the RAW-1200.mix line with the control. As shown in FIG. 11B, the osteoclasts from the RAW-1200.mix cells appeared much sooner and were mature by day 3, a point at which the control RAW cells are just starting to form small multinucleated cells. Furthermore, osteoclasts derived from the RAW-1200.mix cell line seem to have a reduced survival as a decrease in the number of remaining osteoclasts is observed starting at day 4. The control cells are mature by day 4 and many osteoclasts are still present even on day 5.

This result demonstrates that RNA interference of osteoclast-specific genes using the approach of this invention not only identifies those genes that play a role in stimulating osteoclastogenesis, but also serves to validate those candidates that are negative regulators of this process.

To further substantiate the observations described above, Northern blot analysis was conducted on the total RNA isolated from the RAW-1220.mix cell line and compared to the control RAW-hU6. The blot was initially probed with a fragment of the SEQ. ID. NO:6 cDNA but the message was almost undetectable by this method. The same blot was probed for the osteoclast marker genes, TRAP and Cathepsin K, as before. As shown in FIG. 12, the expression of TRAP was significantly increased in the RAW-1200.mix cells in agreement with the phenotypic observation. Cathepsin K was also upregulated albeit to a lesser extent. Again, GAPDH demonstrated that equal amounts of RNA were loaded in each lane. These results, like those from the osteoclastogenesis experiments, suggest that SEQ. ID. NO:6 is a negative regulator of osteoclast differentiation in RAW cells.

SEQ. ID. NO:7:

The sequences used for RNA interference were derived from the polynucleotide SEQ. ID. NO:7 and have the SEQ. ID. NOs:79 and 80. The use of RNA interference as described in the invention for SEQ. ID. NOs 1 and 2 was applied to SEQ. ID. NO:7. The results obtained (data not shown) were similar to those of SEQ. ID. NO:6 showing that knock-down of this gene resulted in an increase in osteoclast differentiation suggesting that SEQ. ID. NO:7 is a negative regulator of this process in RAW cells.

Figure 13:
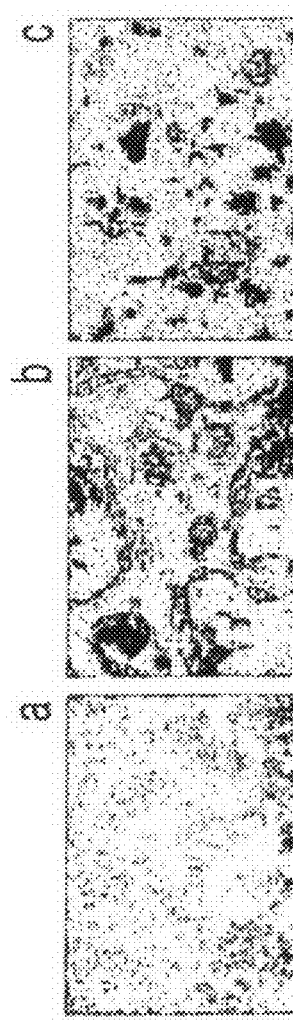
FIG. 13 are pictures illustrating the phenotypic effect on osteoclast differentiation in the presence of siRNAs specific for SEQ. ID. NO:8, panel a; control RAW-hU6 cells, panel b; RAW-hU6 treated with RANK ligand, and panel c; RAW-hU6 treated with RANK ligand and siRNA specific for SEQ ID NO.:8 (RAW-0682.1)

SEQ. ID. NO:57:

The sequences used for RNA interference were derived from the polynucleotide SEQ. ID. NO:57 and have the SEQ. ID. NOs:81 and 82. The use of RNA interference as described in the Invention for SEQ. ID. NOs 1 and 2 was applied to SEQ. ID. NO:57. The results obtained were similar showing that this gene is required for proper differentiation of RAW osteoclasts. An illustration of this result is depicted in FIG. 13.

L—Determination of Knockdown Effects on Bone Resorption

The functionality of the identified osteoclast-specific sequences was explored by seeding the cells on Osteologic™ (BD Biosciences, Mississauga, ON) discs to measure their bone resorptive activity. Osteologic™ discs are commercially available and contain a synthetic calcium phosphate substrate and are well known to the skilled artisan as a model for bone degradation.

RAW cells were seeded in 24-well plates containing a calcium phosphate-coated disc (Osteologic™) at a density of 35 000 cells/well. Treatment with differentiation medium containing 100 ng/ml RANK ligand was carried out for 5 days where after the osteoclasts were stained for TRAP expression as described above to determine the position and number of multinucleated cells. Osteoclasts were removed with bleach and stained with 5% silver nitrate according to manufacturer's modified von Kossa method. Resorbed pits were observed microscopically. The percentage of resorbed surface area is determined by scanning the negative image of the disc and using Photoshop™ (Adobe) to calculate the percentage of black pixels at maximum contrast. The control, RAW-hU6, was set to the value of 1 and the maximal amount of resorption that was observed with the RAW-hU6 cell line in the presence of RANK ligand was set to 100%.

Figure 14A:
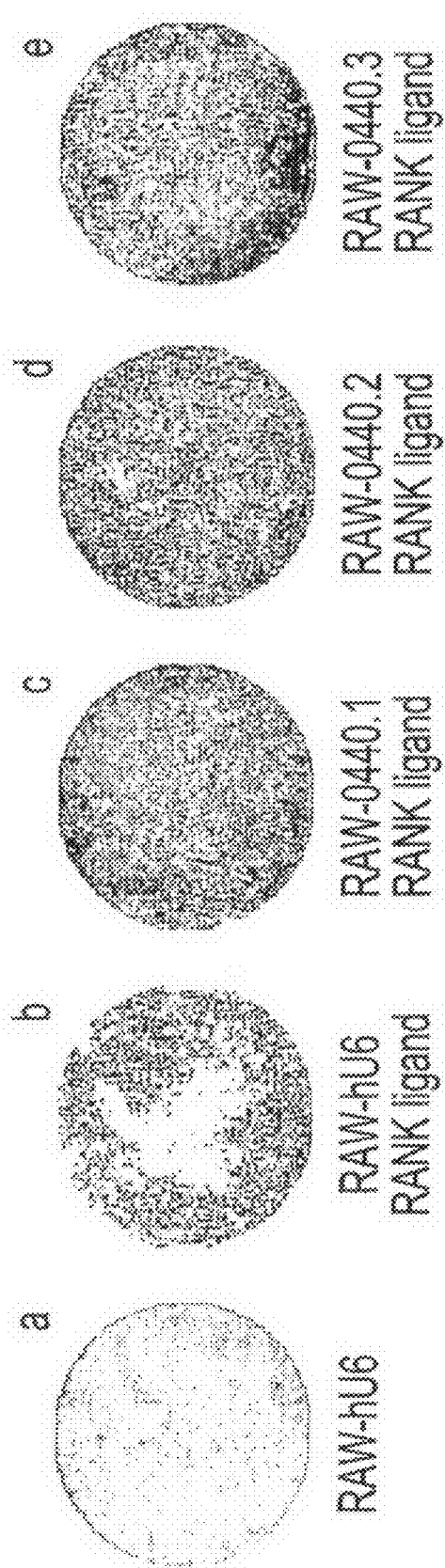
FIG. 14A are pictures illustrating the reduced resorptive activity of osteoclasts expressing specific siRNAs for SEQ. ID. NO:1 panel a; control RAW-hU6 cells, panel b; RAW-hU6 treated with RANK ligand, panel c; RAW-hU6 treated with RANK ligand and siRNA specific for SEQ ID NO.:1 (RAW-0440.1), panel d; RAW-hU6 treated with RANK ligand and siRNA specific for SEQ ID NO.:1 (RAW-0440.2) and panel e; RAW-hU6 treated with RANK ligand and siRNA specific for SEQ ID NO.:1 (RAW-0440.3)

SEQ. ID. NO:1:

In order to determine if the function of the RAW-0440 cell lines were affected by knockdown of SEQ. ID. NO:1, the cells were cultured and differentiated on Osteologic™ discs. An equal number of RAW cells was seeded on each disc and treated with RANK ligand for a period of 4 days before being fixed and stained by the manufacturer's modified von Kossa method that stains the calcium phosphate substrate. White areas on the disc indicate osteoclast resorption. As shown in FIG. 14A, the control cell line, RAW-hU6, did not cause a large increase in the resorbed area on the disc (panel a) but treatment of RANK ligand to induce osteoclastogenesis resulted in a significant amount of substrate being degraded by the osteoclasts (panel b). All three RAW-0440 cell lines had a reduced ability to degrade the substrate and the discs had a larger area of unresorbed calcium phosphate substrate (panel c-e). The results are shown in FIG. 14B. The values (% black pixels) for the total resorbed area for osteoclasts from the RAW-0440.1, RAW-0440.2, and RAW-0440.3 cell lines were 8.7%, 45.9%, and 22.2%, respectively. These results indicate that targeting the SEQ. ID. NO:1 gene in osteoclasts has the effect of reducing their ability to resorb bone substrate.

Figure 15A:
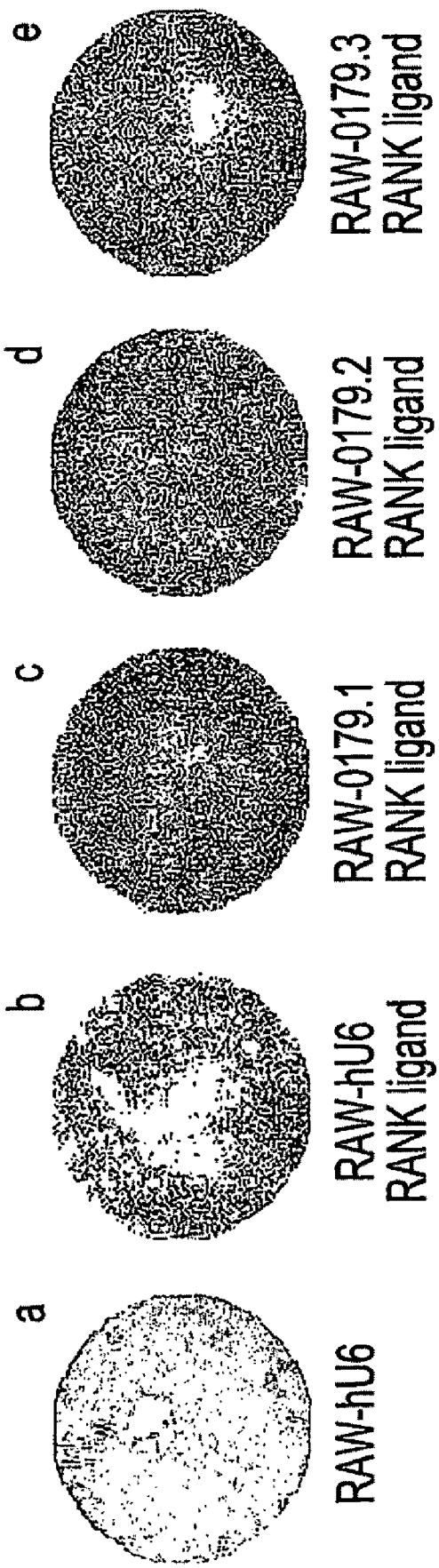
FIG. 15A shows the reduced resorptive activity of osteoclasts expressing specific siRNAs for SEQ. ID. NO:2 panel a; control RAW-hU6 cells, panel b; RAW-hU6 treated with RANK ligand, panel c; RAW-hU6 treated with RANK ligand and siRNA specific for SEQ ID NO.:2 (RAW-0179.1), panel d; RAW-hU6 treated with RANK ligand and siRNA specific for SEQ ID NO.:2 (RAW-0179.2) and panel e; RAW-hU6 treated with RANK ligand and siRNA specific for SEQ ID NO.:2 (RAW-0179.3)

SEQ. ID. NO:2:

The approach used for SEQ. ID. NO:1 was used to analyze the RAW-0179 cell lines. As illustrated in FIG. 15, the osteoclasts exhibited a reduced ability to resorb the substrate (FIG. 15A). Quantitative analysis of the remaining material on the discs showed that total resorbed area was 36.1%, 29.4, and 51.2% for the RAW-0179.1, RAW-0179.2, and RAW-0179.3 cell lines, respectively (FIG. 15B). These results indicate that targeting the SEQ. ID. NO:2 gene in osteoclasts has the effect of reducing their ability to resorb bone substrate.

Figure 16B:
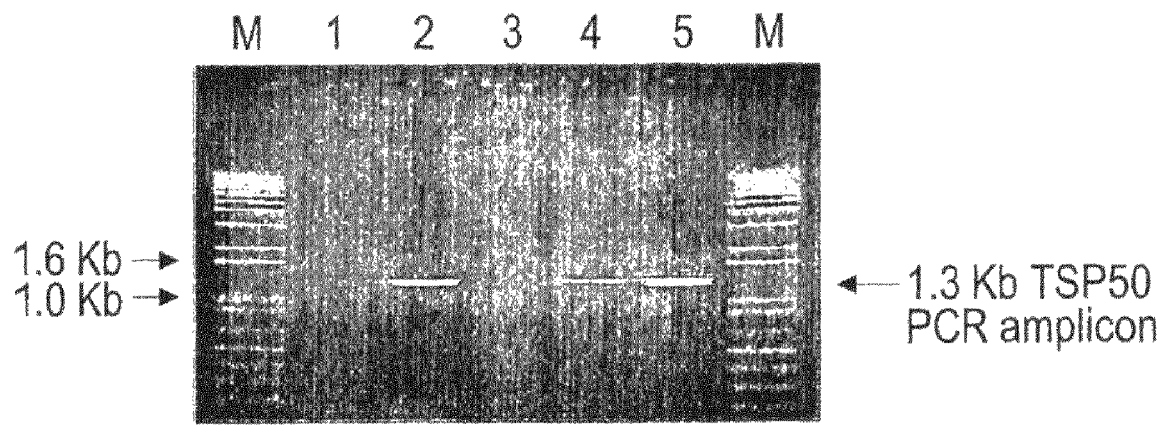
FIG. 16B is a picture of an agarose gel of RT-PCR-amplified SEQ ID NO.:1 in human precursor and osteoclast samples.
Figure 17:
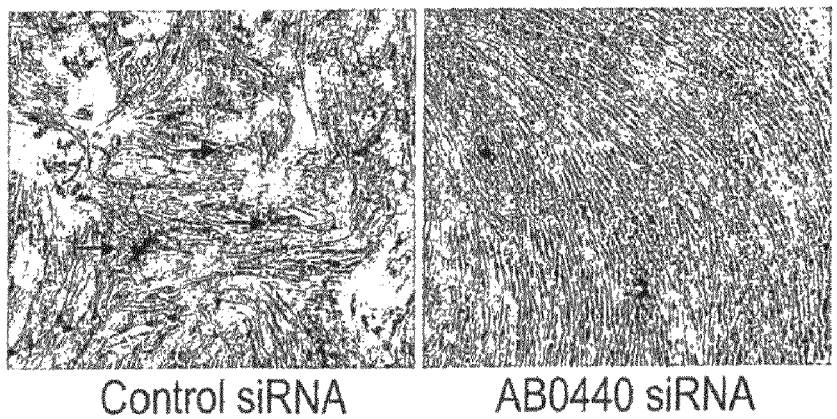

M—Differential Expression of Human Orthologues of Some of the Murine Osteoclast-Specific Sequences:

The human orthologues for some of the murine osteoclast-specific genes have been isolated using gene specific primers for RT-PCR amplification and cloning of the corresponding double-stranded cDNA from mRNA of human osteoclasts and their differential expression pattern measured using RNA from human CD34+ precursor and osteoclasts. Also, their tissue specificity was determined using RNA from 30 different human tissues (adrenal, breast, jejunum, trachea, liver, placenta, aorta, brain, lung, adrenal cortex, esophagus, colon, ovary, kidney, prostate, thymus, skeletal muscle, vena cava, stomach, small intestine, heart, fallopian tube, spleen, bladder, cervix, pancreas, ileum, duodenum, thyroid and testicle) purchased from Ambion (Austin, Tex.). All RNA samples were amplified using RAMP and macroarrays were prepared as described in Section G. Each human orthologue cDNA was radiolabeled with $\alpha$-$^{32}$P-dCTP using a random priming procedure as specified by the supplier (Amersham, Piscataway, N.J.) and used as, probe against the RNA present on the macroarrays. Hybridization and washing steps were performed following standard procedures well known in the art. FIG. 16A shows examples of the differential expression of human orthologues for SEQ. ID. NO:2 and SEQ. ID. NO:4 in the various tissues and osteoclasts samples represented on the macroarrays. However, in the case of SEQ. ID. NO:1, the hybridization signal on the macroarray was undetectable due to the relatively low abundance of this sequence. As such, standard RT-PCR with gene specific primers for human TSP50 was performed on human precursor and osteoclast samples in order to measure its expression (FIG. 16B). The 1.3 Kb TSP50 PCR amplicon was detected in the human osteoclast samples for both donor 1 and donor 4 (FIG. 16B, Lanes 2 and 4 respectively) but not the corresponding precursor samples (FIG. 16B, Lanes 1 and 3 respectively). The 1.3 Kb PCR amplicon was confirmed by sequence analysis as TSP50. It is evident from these results that the human orthologues of some of the murine selected osteoclast-specific gene sequences are similarly upregulated in the human CD34+ derived osteoclasts and are also highly specific. Thus, these results suggest that the use of the murine RAW264.7 model to identify osteoclast-specific genes involved in human osteoclastogenesis is a valid strategy.

N—Biological Validation of the Human Orthologue for SEQ. ID. No. 1 (SEQ. ID. No. 88) in osteoclastogenesis.

In order to validate the biological significance of the human orthologue for SEQ. ID. No. 1 (SEQ. ID. NO.88), it was important to demonstrate that the function observed in the mouse osteoclast model for SEQ. ID. NO. 1 was conserved in human osteoclasts. Unlike the mouse model where a cell line could be used for osteoclast differentiation, no equivalent model exists in humans. Thus, validation studies were conducted in human primary bone marrow cells using a commercial lentiviral short hairpin (sh) RNA delivery system as described by the manufacturer (Invitrogen, Burlington, ON) unless otherwise stated. The siRNA sequence, 5'-CTGCCT-GATCTGGCGTGAT-3' (SEQ ID. NO. 90) was used to specifically target SEQ. ID. NO. 88, the coding sequence of which was cloned form a human osteoclast cDNA library in-house.

A template for the expression of the shRNA was cloned into the lentiviral expression vector and co-transfected in 293FT cells with expression vectors for the viral structural proteins. After two days, supernatants containing the lentivirus were collected and stored at −80° C. After titering, 20 MOIs (multiplicity of infection) were used to infect human osteoclast precursors purchased from Cambrex (East Rutherford, N.J.). The following day, the medium was replaced with fresh medium containing RANK ligand to initiate osteoclast differentiation. Approximately 7 days later, the cells were fixed and TRAP staining performed as described in section B—Preparation of osteoclast differentiated cells. In parallel, lentiviral particles containing a control shRNA against β-galactosidase were also used to infect the human osteoclast precursor cells.

Figure 17:
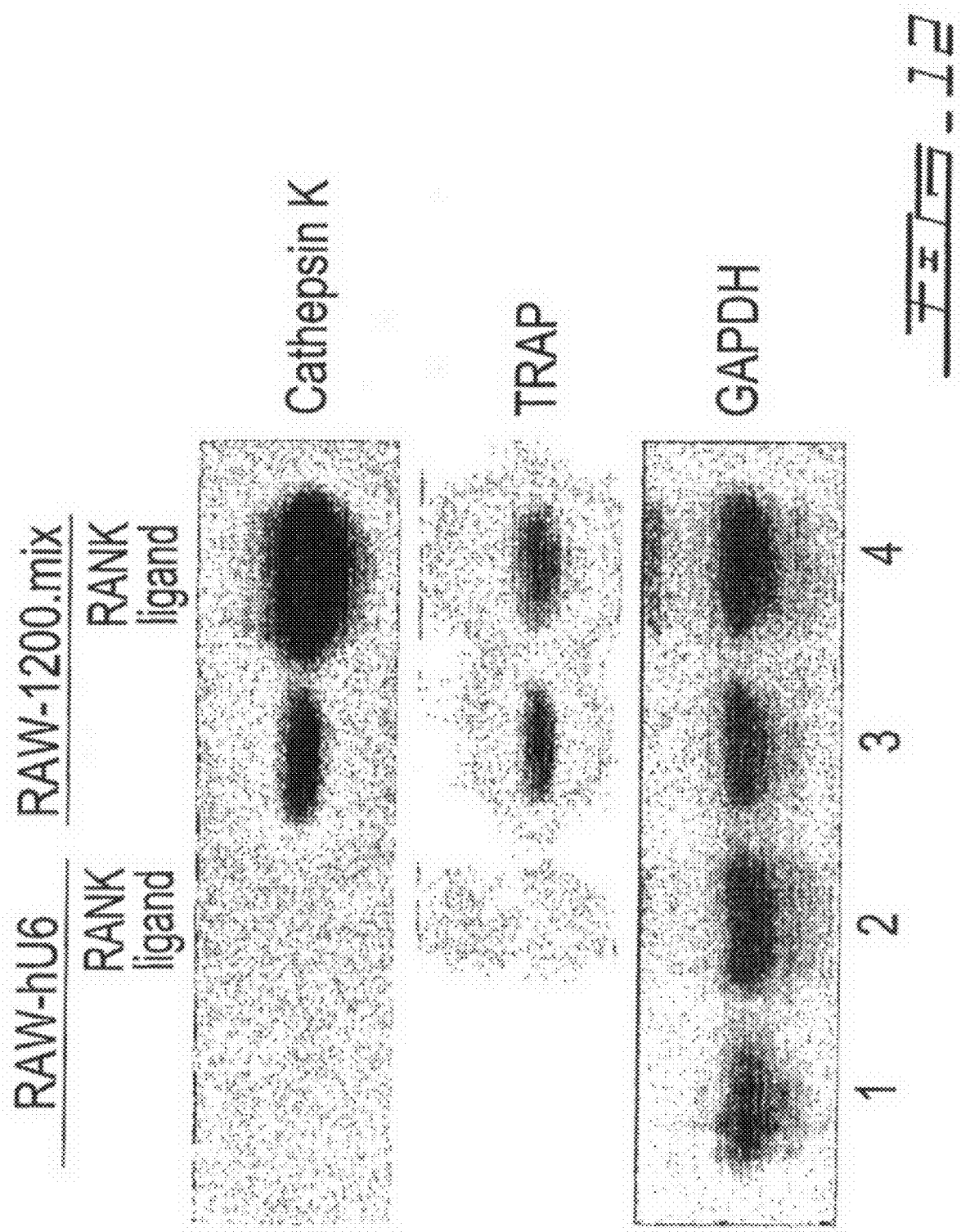
FIG. 17 is a picture illustrating the phenotypic effect on osteoclast differentiation in the presence of siRNAs specific for the human orthologue for SEQ ID NO.:1 (SEQ. ID. NO:88) right panel; control siRNA, left panel AB0440 siRNA.

FIG. 17 shows that infection of human bone marrow cells with lentiviruses expressing the specific shRNA for SEQ. ID. NO. 88 (AB0440 siRNA) resulted in a marked decrease of TRAP-positive multinucleated osteoclasts compared to human bone marrow cells infected with lentiviruses expressing the control shRNA (control siRNA) (see arrows in left panel of FIG. 17) in the presence of RANK ligand. These results were in agreement with the validation results obtained in the mouse model (section K—Results of RNA Interference studies) and thus, evidence that the human orthologue for SEQ. ID. NO. 1 (SEQ. ID. NO. 88) plays a similarly important role in differentiation of human osteoclasts.

O—A Functional Complementation Assay for SEQ. ID. NO. 88 to Screen for Inhibitors of Osteoclastogenesis.

A complementation assay was developed to test the function of SEQ. ID. NO. 88 in the differentiation of mouse osteoclasts from RAW264.7 cells devoid of the corresponding endogenous mouse protein. The RAW264.7 cell line containing the mouse-specific shRNA (RAW-AB0440si) for SEQ. ID. NO. 1, which showed greatly reduced ability to differentiate into mature osteoclasts, was transfected with an eukaryotic expression vector containing the entire coding sequence for SEQ. ID. NO. 88, termed Ip200-hAB0440. This Ip200 expression vector (SEQ. ID. NO. 91) was modified from a commercial vector, pd2-EGFP-N1 (Clontech, Mountain View, Calif.) where the NEO-KAN antibiotic cassette was replaced by a hygromycin resistance gene for selection in mammalian cells and an ampicillin resistance gene for propagation in prokaryotes. Expression of the inserted human gene sequence is under control of a strong CMV promoter in Ip200. Approximately $2.5 \times 10^5$ RAW-0440si cells/well were seeded in 6-well plates and transfected with either 1 µg Ip200 or Ip200-hAB0440 using Fugene 6 (Roche, Laval, QC), and stable transfectants selected for 5 days in the presence of 50 µg/ml hygromycin. Two RAW 264.7-0440si stable cell lines were selected—one that expressed SEQ. ID. NO. 88 (Ip200-hAB0440) and the other containing only the vector (Ip200). After expansion of these two cell lines, 4 000 cells/well for each were seeded in 96-well plates and left either untreated or treated for 4 days with 100 ng/ml RANK ligand. The cells were fixed and stained for TRAP expression in order to visualize mature osteoclasts.

Figure 18:
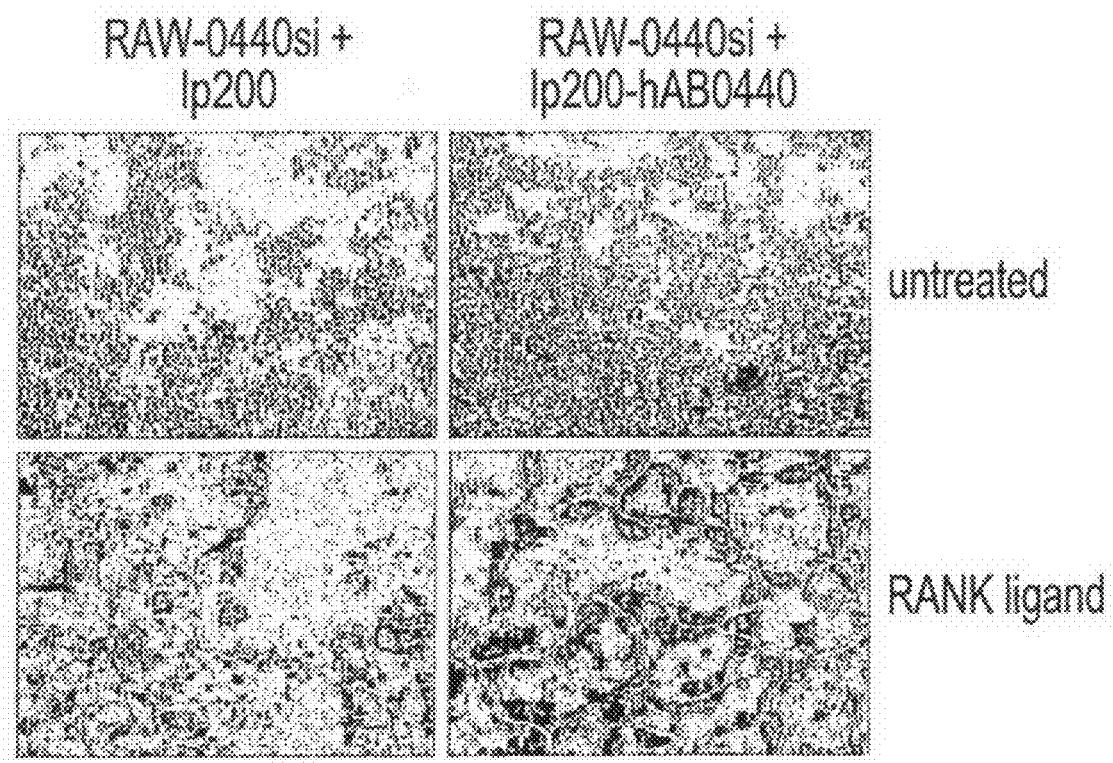
FIG. 18 are pictures illustrating the efficiency of the functional complementation assay for SEQ. ID. NO. 88 to screen for inhibitors of osteoclastogenesis.

FIG. 18 shows that the RAW-0440si cells transfected with only the empty Ip200 vector were unable to efficiently form osteoclasts (left panels). Conversely, the cells transfected with Ip200-hAB0440 (SEQ. ID. NO. 88) were rescued (complemented) and thus, differentiated in response to RANK ligand treatment into osteoclasts (right panels). These results confirm that the function for the mouse and human sequences corresponding to SEQ. ID. NO. 1 is conserved and essential for osteoclast differentiation.

Thus, it is anticipated that this type of complementation cell-based assay may serve as the basis for screening compounds capable of binding to and inhibiting the function of SEQ. ID. NO. 88. A compound library may be applied to this 'rescued' cell line in order to identify molecules (small molecule drugs, peptides, or antibodies) capable of inhibiting the complementation effect of SEQ. ID. NO. 88. Consequently, any measurable reduction in osteoclast differentiation would be indicative of compounds that attenuate the complementation activity of SEQ. ID. NO. 88 in the assay. It is further anticipated that this assay format may be applicable to any gene required for differentiation of RAW264.7 cells into osteoclast, which may be used for drug screening.

P—The Human Orthologue Protein of SEQ. ID. NO. 1 (SEQ. ID. NO. 88) is Membrane-Bound and Glycosylated.

It is contemplated in the literature that SEQ. ID. NO. 88 may encode a membrane-bound or secreted protease, termed Tsp50. In order to determine if the polypeptide for SEQ. ID. NO. 88 is truly membrane-bound or secreted, a plasmid (pCMX-HA-hAB0440) containing the entire coding sequence for SEQ. ID. NO. 88 was constructed. The expression vector, pCMX-HA (SEQ. ID. NO. 92) contains a strong CMV promoter for expression of the HA epitope and cDNA insert. Approximately, $2.5 \times 10^5$ Cos-7 cells/well were seeded in 6-well plates and transiently transfected with 1 µg of the pCMX-HA-hAB0440 expression plasmid using Fugene 6 (Roche, Laval, QC). Cells in some wells were not treated (−) while others were treated with either 2 µg/ml tunicamycin (T) for 24 hours or 0.5 units/ml phosphoinositol phospholipase C (P) for 1 hour. Tunicamycin blocks the reaction of UDP-GlcNAc and Dol-P in the first step of glycoprotein synthesis, thus inhibiting the synthesis of all N-linked glycoproteins. Phosphoinositol phospholipase C specifically cleaves glycosyl-phosphoinositol (GPI) linkages, which releases GPI anchored proteins into the surrounding medium. The expressed HA fused polypeptide for SEQ. ID. NO. 88 was detected by Western blot analysis with an anti-HA antibody (Sigma, St. Louis, Mo.). Following lysis of the pCMX-HA-hAB0440-Cos-7 cells, soluble fractions were prepared, separated on a SDS-polyacrylamide gel and transferred to a PVDF membrane. The protein blot was then incubated with anti-HA antibody for 1 hour and the bands visualized using the ECL kit from Roche (Laval, QC). The same Western blot was stripped and reacted with an anti-actin antibody to control for equal loading of protein samples.

Figure 19:
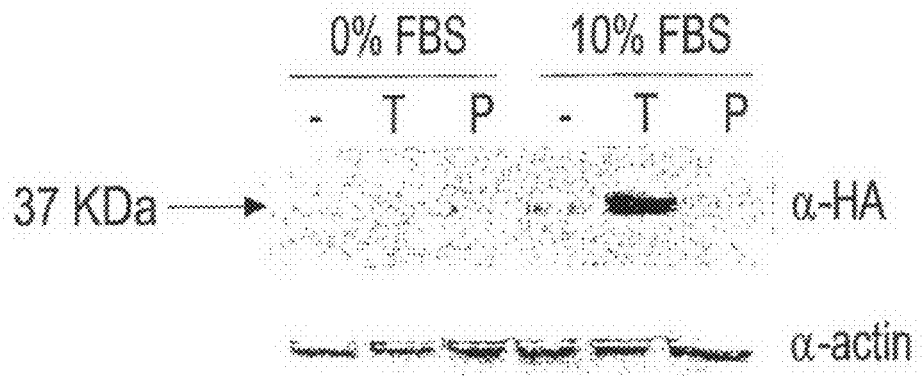
FIG. 19 is a picture of a Western blot from cell lysate obtained from cells expressing a SEQ ID NO.:88 fusion protein and treated or not with tunicamycin or phosphoinositol phospholipase C.

FIG. 19 shows a polypeptide with a predicted size of 37 KDa corresponding to the full-length polypeptide for SEQ. ID. NO. 88. Interestingly, expression of this polypeptide was only observed when the transiently transfected cells were treated with tunicamycin in the presence of 10% FBS in the culture media compared to serum-starved cells (0% FBS) (FIG. 19, Lanes T). This finding suggested that inhibition of N-linked glycosylation resulted in trapping of the SEQ. ID. NO. 88 polypeptide within the cells, which is evidence that the protein is glycosylated. Following treatment with phosphoinositol phospholipase C, the SEQ. ID. NO. 88 polypeptide was no longer detected in the soluble fraction (FIG. 19, Lanes P), which suggested that it was released into the media likely due to cleavage of the proposed GPI linkage. As a control for equal loading, the membrane was stripped and reacted with an antibody against the housekeeping protein, α-actin, which showed that the observed differences in expression of the SEQ. ID. NO. 88 polypeptide was not a result of unequal loading of the gel (FIG. 19, α-actin panel).

Q—Inhibition of RAW264.7 Differentiation into Osteoclast Using a Monoclonal Anti-Tsp50 (SEQ. ID. NO. 1) Antibody.

In light of the results demonstrating that of the polypeptide for SEQ. ID. NO. 88 (depicted in SEQ ID NO.:153) is essential for osteoclast differentiation (see Example N) and it is localized at the cell surface (see Example P), then this protein represents an excellent candidate for the development of an antibody therapeutic strategy for treating the symptoms of osteoporosis. A monoclonal antibody against mouse Tsp50 (R&D Systems, Minneapolis, Minn.) was purchased and used to test whether or not a specific antibody against the polypeptide for SEQ. ID. NO. 1 (depicted in SEQ ID NO.:93) would inhibit osteoclast differentiation in the RAW 264.7 model. Approximately, 4 000 RAW264.7 cells/well were seeded in 96-well plates and treated with 100 ng/ml RANK ligand in the presence of increasing concentrations of either the mouse monoclonal antibody against Tsp50 or a control anti-HA antibody (Sigma, St. Louis, Mo.). Three days later, the cells were fixed and stained for TRAP expression and the multinucleated cells were scored.

Figure 20A:
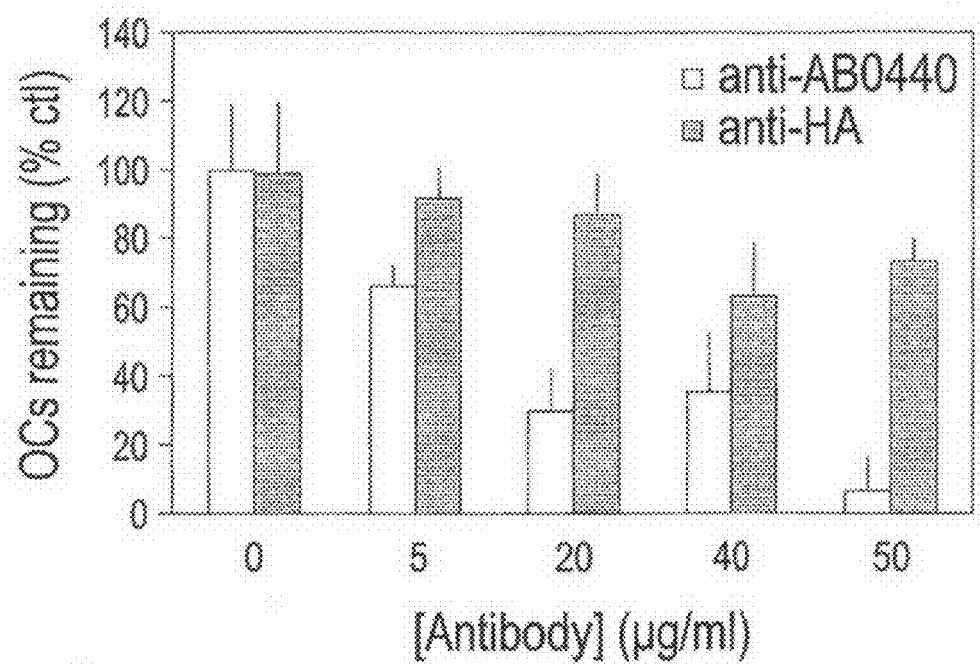
FIG. 20A is an histogram quantifying the inhibition of RAW264.7 differentiation into osteoclast using a monoclonal anti-Tsp50 (SEQ. ID. NO. 1) antibody.
Figure 20B:
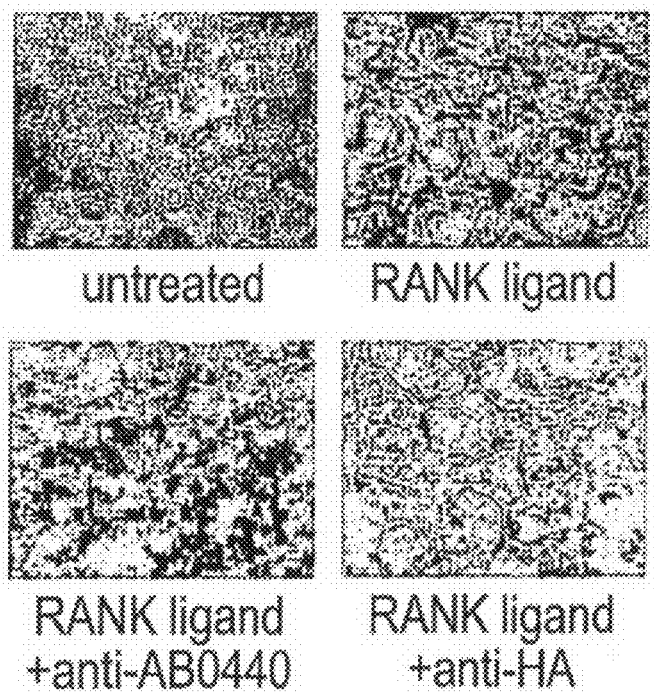
FIG. 20B are pictures representing the phenotypic inhibition of RAW264.7 differentiation into osteoclast using a monoclonal anti-Tsp50 (SEQ. ID. NO. 1) antibody

FIG. 20A is a histogram showing that increasing concentrations of anti-Tsp50 antibody (anti-AB0440) resulted in a dose-dependent decrease in the number of multinucleated osteoclasts with maximal inhibition seen at 50 µg/ml. Whereas, treatment of the RAW264.7 cells with equivalent concentrations of the anti-HA antibody resulted in no statistically significant effect. FIG. 20A represents an average of two experiments conducted in triplicate. Treatment with the anti-AB0440 did not result in death of the RAW264.7 cells but rather, inhibition of differentiation as measured by the loss in mature osteoclasts seen after TRAP staining and no significant reduction in precursor cell numbers (FIG. 20B). These results indicate that antibodies which specifically target osteoclast-specific cell surface or secreted proteins required for differentiation, as exemplified by anti-AB0440, have the potential to serve as therapeutic drugs for treating osteoporosis by reducing osteoclast numbers and consequently, bone resorption activity. It is contemplated that recombinant and/or monoclonal antibodies developed to the polypeptide for SEQ. ID. NO. 88 may function similarly to anti-AB 0440 seen for the mouse model in this example.

R—Development of a Functional Interaction Assay to Screen for Inhibitors of Osteoclast Activity Using SEQ. ID. NO. 2 as a Model.

SEQ. ID. NO. 2 (AB0179) belongs to an osteoclast-specific vacuolar (v)-ATPase, a large protein complex containing several subunits. The v-ATPase a subunit comprises four isoforms (a1-a4), which constitutes the $V_O$ domain. This domain is important for the hydrolysis of ATP in order to provide the energy required for the secretion of protons across the plasma membrane into the pocket that is created between the ruffled membrane of the mature osteoclast and the bone surface. In osteoclasts, the a3 subunit interacts with the d subunit, which is important for the structural integrity of the ATPase complex (Nishi and Forgac, 2002). There are two d subunits in humans, d1 and d2, the latter found almost exclusively in osteoclasts and is coded for by the human orthologue of SEQ. ID. NO. 2 which corresponds to polynucleotide SEQ. ID. NO. 89 (encoding SEQ ID NO.:154). Validation studies using the RAW264.7 model have clearly demonstrated the importance of d2 in osteoclast function (section K—Results of RNA Interference studies) where in the presence of siRNAs against SEQ. ID. NO. 2, the bone resorbing activity of mature osteoclasts was markedly reduced. Additionally, it has been well documented that the a3 isoform is the major form of the v-ATPase a subunit in osteoclasts and bone in general (Smith et al., 2005). Thus, in order to identify molecules that are capable of inhibiting the function of the v-ATPase in osteoclasts, the specific interaction between the d2 and a3 subunits will be exploited.

The expression of the d isoforms in human osteoclast and precursor cells (HOPs) was measured by Northern blot analysis. Approximately, $1.5 \times 10^4$ precursor cells/well were seeded in 96-well plates and a portion was treated with 33 µg/ml M-CSF and 100 ng/ml RANK ligand for 7 days to form osteoclasts. Total RNA was prepared from the precursors and osteoclasts using Trizol™ (Invitrogen, Burlington, ON) and 10 µg/lane was electrophoresed in a 1% agarose/TAE gel. The RNA was electrotransfered to a nylon membrane and hybridized sequentially to [$^{32}$P]dCTP labeled probes specific for the d2 (SEQ. ID. NO. 89) and d1 subunits, for the osteoclast-specific gene, Cathepsin K and for the housekeeping gene, β-actin. The washed membrane was exposed to film for the required amount of time to detect the corresponding mRNA bands.

Figure 21A:
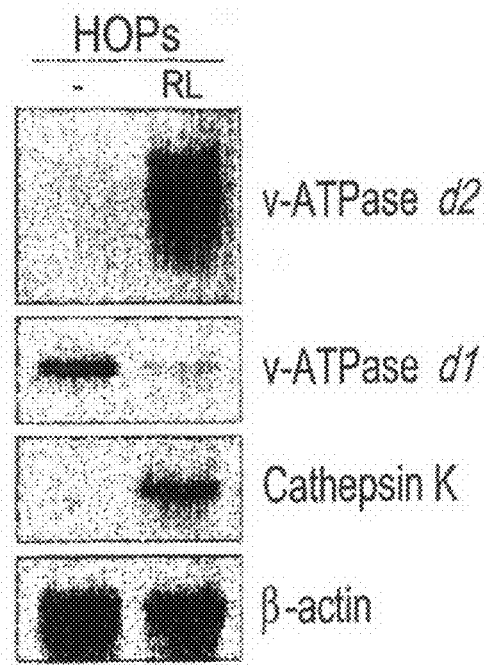
FIG. 21A is a picture of a Northern blot illustrating that SEQ. ID. NO. 89 (d2) expression is upregulated in osteoclasts compared to the d1 isoform, FIG. 21B are pictures of Western blots of a pull-down assay illustrating interaction of d2 with the v-ATPase a3 subunit but not the a4 subunit.

FIG. 21A shows that SEQ. ID. NO. 89 (d2) was upregulated in response to RANK ligand (Panel 1; Lane RL) compared to precursors (Panel 1; Lane-). With the probe specific for v-ATPase d1, the opposite expression pattern was observed indicating that this d isoform was downregulated in osteoclasts (Panel 2; Lane RL) compared to precursors (Panel 2; Lane-). As expected, the osteoclast-specific gene, Cathepsin K was highly upregulated in response to RANK ligand and not present in the precursors (Panel 3). Equal loading of the RNA samples was evident by the non-differential expression pattern of the housekeeping gene, β-actin (Panel 4). Since a3 is predominantly found in the v-ATPase a subunit of osteoclasts, these results then suggests that the d2 subunit would most likely be complexed with the a3 subunit in human osteoclasts v-ATPase. Thus, isolation of a specific inhibitor of this interaction would preferentially reduce the osteoclast-specific v-ATPase activity and thus, bone resorption.

Figure 21B:
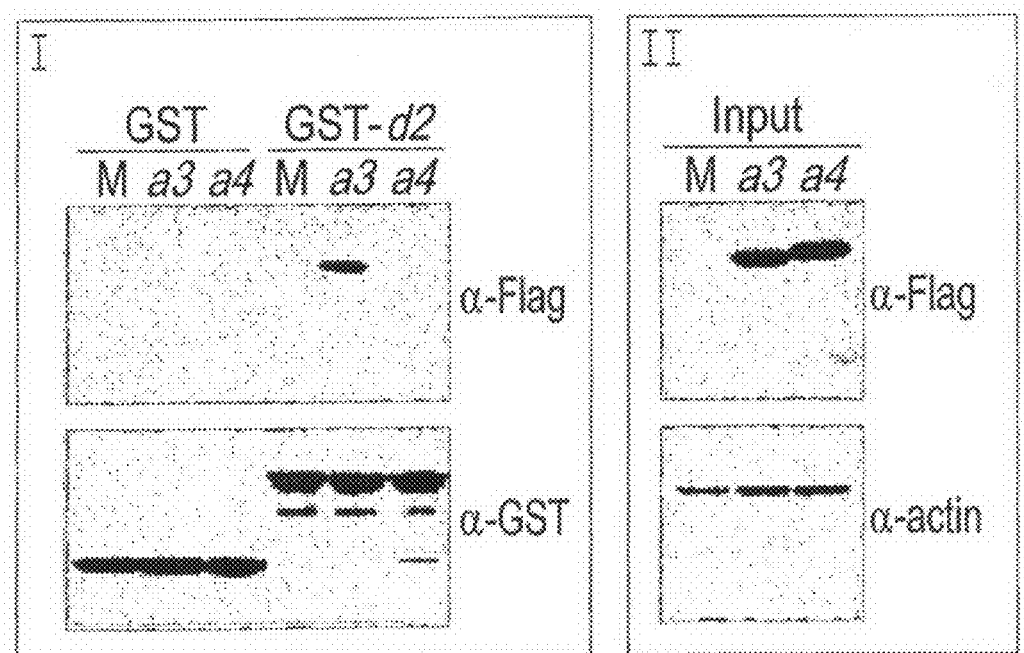

In order to experimentally demonstrate the interaction between d2 and a3, the coding sequence corresponding to SEQ. ID. NO. 89 (d2) (SEQ ID NO.:154) was cloned into the prokaryotic expression vector, pGEX-2T (Pharmacia, GE Healthcare), expressed as a GST fusion protein in $E. coli$ and purified with glutathione beads. In parallel, cDNA fragments of mouse v-ATPase-a3 (amino acids 1-385) and v-ATPase a4 (amino acids 1-388) were cloned into the eukaryotic expression vector, pCMX-Flag in order to express a Flag-tagged a3 subunit or a4 subunit in mammalian cells. The pCMX-Flag/v-ATPase-a3 and pCMX-Flag/v-ATPase-a4 recombinant plasmids were transfected in 293FT cells and cell lysates were generated in which, the v-ATPase-a3 and v-ATPase-a4 FLAG-tagged polypeptides were readily detected with an anti-Flag antibody (FIG. 21B, II, upper panel).

In order to measure the interaction between d2 (SEQ. ID. NO. 89) and a3 or a4, equal amounts of 293FT lysates containing either Flag-tagged a3 or a4 were incubated with purified GST or GST-d2 at 4° C. for 90 minutes under mild agitation. After washing, the protein mixes were separated on a SDS-PAGE and transferred to PVDF membrane. The membrane was then incubated with anti-Flag antibody (Sigma, St. Louis, Mo.) and the bands visualized using the ECL kit from Roche (Laval, QC). Clearly, only the a3 fragment could be detected in the GST-d2 reactions compared to the GST reactions indicating a specific interaction between d2 and a3 (FIG. 21B, I-a3, upper panel) but not between d2 and a4 (FIG. 21B, I-a4, upper panel). The membrane was then re-probed with anti-GST antibody, which showed that equal amounts of GST fusion protein were used in each reaction (FIG. 21B, I, lower panel). Additionally, the use of an anti-Flag antibody showed that equal quantities of a3 and a4 were present in the binding reactions (FIG. 21B, II, upper panel) and the same membrane re-probed with an anti-actin antibody, demonstrated that equal amounts of the corresponding cell lysate was used (FIG. 21B, II, lower panel). Thus, this observed specific interaction between d2 and a3 forms the basis for developing a screening assay to interrogate compound libraries (small molecule drugs, peptides, or antibodies) in order to identify those compounds capable of inhibiting this interaction. Such a screening assay may be developed as a FRET (fluorescence resonance energy transfer) method or any similar methods, which are highly sensitive and easily upscalable for high throughput screening in multiwell plates. These compounds may be useful as therapeutics for modulating the bone resorption activity of osteoclasts by inhibiting the function of the osteoclast-specific v-ATPases.

v-ATPases present in other tissues, most notably the kidney (Nishi and Forgac, 2002) where the d2 gene is expressed at low levels as shown by us and others (Nishi et al., 2003; Smith et al., 2005) do not appear to contain the a3 subunit but rather, the a4 subunit (Stehberger et al., 2003; Smith et al., 2000). Therefore, an inhibitor of the interaction between d2 and a3 would preferentially be effective in human osteoclasts and would not interfere with v-ATPases in other tissues.

One of skill in the art will readily recognize that orthologues for all mammals maybe identified and verified using well-established techniques in the art, and that this disclosure is in no way limited to one mammal. The term "mammal(s)" for purposes of this disclosure refers to any animal classified as a mammal, including humans, domestic and farm animals, and zoo, sports, or pet animals, such as dogs, cats, cattle, horses, sheep, pigs, goats, rabbits, etc. Preferably, the mammal is human.

The sequences in the experiments discussed above are representative of the NSEQ being claimed and in no way limit the scope of the invention. The disclosure of the roles of the NSEQs in osteoclastogenesis and osteoclast function satisfies a need in the art to better understand the bone remodeling process, providing new compositions that are useful for the diagnosis, prognosis, treatment, prevention and evaluation of therapies for bone remodeling and associated disorders.

The art of genetic manipulation, molecular biology and pharmaceutical target development have advanced considerably in the last two decades. It will be readily apparent to those skilled in the art that newly identified functions for genetic sequences and corresponding protein sequences allows those sequences, variants and derivatives to be used directly or indirectly in real world applications for the development of research tools, diagnostic tools, therapies and treatments for disorders or disease states in which the genetic sequences have been implicated.

Although the present invention has been described hereinabove by way of preferred embodiments thereof, it maybe modified, without departing from the spirit and nature of the subject invention as defined in the appended claims.

TABLE 1

Differentially expressed sequences found in osteoclasts and demonstrated to have an effect on osteoclastogenesis following inhibition with specific siRNAs.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 1 | Mm.102265/ Tsp50/ 235631 | NM_146227 | 26-1345 encoding SEQ ID NO.: 93 | peptidase activity |
| SEQ ID NO. 2 | Mm.19298/ Atp6v0d2/ 242341 | NM_175406 | 70-1122 encoding SEQ ID NO.: 94 | hydrogen-transporting ATPase activity, rotational mechanism |

TABLE 1-continued

Differentially expressed sequences found in osteoclasts and demonstrated to have an effect on osteoclastogenesis following inhibition with specific siRNAs.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 3 | Mm.20904/ Crtap/ 56693 | NM_019922 | 72-1274 encoding SEQ ID NO.: 95 | extracellular space protein; function unknown |
| SEQ ID NO. 4 | Mm.12654/ A230106M15Rik/ 231717 | NM_175474 | 314-1114 encoding SEQ ID NO.: 96 | hypothetical protein LOC231717; function unknown |
| SEQ ID NO. 5 | Mm.181860/ Tubb6/ 67951 | NM_026473 | 28-1371 encoding SEQ ID NO.: 97 | GTPase activity; structural molecule activity |
| SEQ ID NO. 6 | Mm.323393/ Josd1/ 74158 | NM_028792 | 905-1513 encoding SEQ ID NO.: 98 | hypothetical protein LOC74158; function unknown |
| SEQ ID NO. 7 | Mm.332739/ Lat2/ 56743 | NM_022964 | 162-737 encoding SEQ ID NO.: 99 | extracellular space; function unknown |
| SEQ ID NO. 57 | Mm.103560/ Jundm2/ 81703 | NM_030887 | 232-723 encoding SEQ ID NO.: 100 | transcriptional repressor activity; shown to play a role in RANK-mediated signal transduction, especially in osteoclast differentiation |

TABLE 2

Differentially expressed sequences found in osteoclasts with putative roles in bone remodeling.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 8 | Mm.10154/ Tesk1/ 21754 | NM_011571 | 1497-3380 encoding SEQ ID NO.: 101 | Protein kinase activity |
| SEQ ID NO. 9 | Mm.142827/ Otud5/ 54644 | NM_138604 | 287-1987 encoding SEQ ID NO.: 102 | hypothetical protein LOC54644 |
| SEQ ID NO. 10 | Mm.146001/ Rassf8/ 71323 | BC004678 | 1-311 encoding SEQ ID NO.: 103 | Ras association possibly involved in signal transduction |
| SEQ ID NO. 11 | Mm.153014/ Gcn1l1/ 231659 | BC068244 | 251-1246 encoding SEQ ID NO.: 104 | possibly involved in amino acid biosynthesis with exact function unknown |
| SEQ ID NO. 12 | Mm.153159/ Cct6a/ 12466 | NM_009838 | 55-1650 encoding SEQ ID NO.: 105 | chaperonin containing TCP-1 possibly involved in protein folding and binding |
| SEQ ID NO. 13 | Mm.157103/ Hsd3b7/ 101502 | NM_133943 | 53-487 encoding SEQ ID NO.: 106 | involved in steroid biosynthesis |
| SEQ ID NO. 14 | Mm.169234/ 2310005O14Rik/ 67914 | NM_026452 | 6-947 encoding SEQ ID NO.: 107 | hypothetical protein LOC67914 |
| SEQ ID NO. 15 | Mm.266341/ Nrp2/ 18187 | NM_010939 | 537-3281 encoding SEQ ID NO.: 108 | receptor activity and cell adhesion |
| SEQ ID NO. 16 | Mm.17917/ Efhd2/ 27984 | NM_025994 | 55-777 encoding SEQ ID NO.: 109 | calcium ion binding |
| SEQ ID NO. 17 | Mm.200499/ Eif2ak1/ 15467 | NM_146165 | 116-958 encoding SEQ ID NO.: 110 | protein kinase or transferase activity |
| SEQ ID NO. 18 | Mm.20845/ Abcc5/ | NM_013790 | 200-4510 encoding SEQ | ATPase activity, coupled to |

TABLE 2-continued

Differentially expressed sequences found in osteoclasts with putative roles in bone remodeling.

| Nucleotide Sequence No. | NCBI Unigene #/Gene Symbol/Gene ID | Accession Number | ORF Nucleotide Positions/ Polypeptide sequence No. | Function |
|---|---|---|---|---|
| | 27416 | | ID NO.: 111 | transmembrane movement of substances |
| SEQ ID NO. 19 | Mm.21880/ Htra2/ 64704 | NM_019752 | 146-1522 encoding SEQ ID NO.: 112 | proteolysis |
| SEQ ID NO. 20 | Mm.2271/ Ccl9/ 20308 | NM_011338 | 154-522 encoding SEQ ID NO.: 113 | chemokine activity |
| SEQ ID NO. 21 | Mm.24684/ Fosl2/ 14284 | NM_008037 | 171-1151 encoding SEQ ID NO.: 114 | regulation of transcription, DNA-dependent |
| SEQ ID NO. 22 | Mm.251199/ Arrdc4/ 66412 | NM_025549 | 139-1029 encoding SEQ ID NO.: 115 | molecular function unknown |
| SEQ ID NO. 23 | Mm.2534/ Pstpip1/ 19200 | NM_011193 | 242-1489 encoding SEQ ID NO.: 116 | cell adhesion |
| SEQ ID NO. 24 | Mm.266592/ C030034I22Rik/ 77533 | XM_488832 | 1-987 encoding SEQ ID NO.: 117 | molecular function unknown |
| SEQ ID NO. 25 | Mm.268165/ Cflar/ 12633 | BC029223 | 475-1920 encoding SEQ ID NO.: 118 | caspase activity |
| SEQ ID NO. 26 | Mm.272047/ Helz/ 78455 | BC060114 | 246-1286 encoding SEQ ID NO.: 119 | helicase activity |
| SEQ ID NO. 27 | Mm.278726/ Mak3/ 72117 | NM_028108 | 296-802 encoding SEQ ID NO.: 120 | N-acetyltransferase activity |
| SEQ ID NO. 28 | Mm.279861/ Polr2f/ 69833 | BC024419 | 49-432 encoding SEQ ID NO.: 121 | regulation of transcription |
| SEQ ID NO. 29 | Mm.280895/ Uck2; AI481316/ 80914; 98383 | BC0237897 AI481316 | 218-1003 encoding SEQ ID NO.: 122 | kinase activity/ hypothetical protein LOC98383 |
| SEQ ID NO. 30 | Mm.217216/ Magi1/ 14924 | BC095943 | 574-3920 encoding SEQ ID NO.: 123 | intracellular signaling cascade |
| SEQ ID NO. 31 | Mm.286536/ Fblim1/ 74202 | NM_133754 | 137-1264 encoding SEQ ID NO.: 124 | cell adhesion |
| SEQ ID NO. 32 | Mm.286753/ Rgs3/ 50780 | NM_019492 | 236-2068 encoding SEQ ID NO.: 125 | signal transducer activity |
| SEQ ID NO. 33 | Mm.298728/ Nisch/ 64652 | NM_022656 | 335-4399 encoding SEQ ID NO.: 126 | receptor activity; integrin binding |
| SEQ ID NO. 34 | Mm.129840/ 9430063L05Rik/ 229622 | BC050783 | 371-3727 encoding SEQ ID. NO.: 127 | hypothetical protein LOC229622; function unknown |
| SEQ ID NO. 35 | Mm.31672/ Cdk6/ 12571 | NM_009873 | 56-1036 encoding SEQ ID NO.: 128 | cyclin-dependent protein kinase activity |
| SEQ ID NO. 36 | Mm.331198 Tdrkh/ 72634 | BC057030 | 94-1776 encoding SEQ ID NO.: 129 | transcription factor |
| SEQ ID NO. 37 | Mm.44901/ 2610510H03Rik/ 68215 | NM_026620 | 30-1319 encoding SEQ ID NO.: 130 | function unknown |
| SEQ ID NO. 38 | Mm.348047/ Usmg4/ 83679 | BC046620 | 329-610 encoding SEQ ID NO.: 131 | function unknown |
| SEQ ID NO. 39 | Mm.37803/ Specc1/ 432572 | BC030438 | | No significant predicted ORF at present/ function unknown |
| SEQ ID NO. 40 | Mm.295306/ BC025076/ 216829 | BC025076 | 123-494 encoding SEQ ID NO.: 132 | hypothetical protein LOC216829; function unknown |

TABLE 2-continued

Differentially expressed sequences found in osteoclasts with putative roles in bone remodeling.

| Nucleotide Sequence No. | NCBI Unigene #/Gene Symbol/Gene ID | Accession Number | ORF Nucleotide Positions/ Polypeptide sequence No. | Function |
| --- | --- | --- | --- | --- |
| SEQ ID NO. 41 | Mm.45815/ Bcar3/ 29815 | BC023930 | 405-2867 encoding SEQ ID NO.: 133 | guanyl-nucleotide exchange factor activity |
| SEQ ID NO. 42 | Mm.4615/ Dlgh3/ 53310 | NM_016747 | 325-2874 encoding SEQ ID NO.: 134 | function unknown |
| SEQ ID NO. 43 | Mm.86572/ BC017612/ 170748 | BC017612 | 192-371 encoding SEQ ID NO.: 135 | function unknown |
| SEQ ID NO. 44 | Mm.354736/ Gas2l3/ 237436 | XM_137276 | 730-2781 encoding SEQ ID NO.: 136 | function unknown |
| SEQ ID NO. 45 | Mm.240265/ 5830415L20Rik/ 68152 | BC027051 | 81-428 encoding SEQ ID NO.: 137 | hypothetical protein LOC68152; function unknown |
| SEQ ID NO. 46 | Mm.27545/ Hrmt1l2/ 15469 | BC002249 | 25-1056 encoding SEQ ID NO.: 138 | S-adenosylmethionine-dependent methyltransferase activity |
| SEQ ID NO. 47 | Mm.28071/ 1810030N24Rik/ 66291 | BC027508 | 65-358 encoding SEQ ID NO.: 139 | integral to membrane; function unknown |
| SEQ ID NO. 48 | Mm.293761/ Pofut1/ 140484 | BC046295 | 56-1237 encoding SEQ ID NO.: 140 | transferase activity, transferring glycosyl groups |
| SEQ ID NO. 49 | Mm.341204/ Itsn2/ 20403 | NM_011365 | 258-5234 encoding SEQ ID NO.: 141 | calcium ion binding |
| SEQ ID NO. 50 | Mm.347964/ Fahd1/ 68636 | BC026949 | 189-872 encoding SEQ ID NO.: 142 | hydrolase activity; calcium ion binding activity |
| SEQ ID NO. 51 | Mm.46513/ 2610200G18Rik/ 67149 | NM_025998 | 87-710 encoding SEQ ID NO.: 143 | hypothetical protein LOC67149; integral to membrane; function unknown |
| SEQ ID NO. 52 | Mm.6743/ Nfe2l1/ 18023 | NM_008686 | 249-2474 encoding SEQ ID NO.: 144 | regulation of transcription, DNA-dependent |
| SEQ ID NO. 53 | Mm.78861/ Nolc1/ 70769 | NM_053086 | 30-1229 encoding SEQ ID NO.: 145 | nucleolus organization and biogenesis |
| SEQ ID NO. 54 | Mm.86437/ Spcs3/ 76687 | BC054817 | 59-601 encoding SEQ ID NO.: 146 | hydrolase activity; receptor activity |
| SEQ ID NO. 55 | Mm.296902/ Tapbpl/ 213233 | BC017613 | 264-1619 encoding SEQ ID NO.: 147 | function unknown |
| SEQ ID NO. 56 | Mm.159563/ Tm7sf4/ 75766 | XM_128030 | 50-1294 encoding SEQ ID NO.: 148 | transmembrane 7 superfamily member 4; function unknown |

TABLE 3

List of mRNA spliced variants for some Sequence IDs isolated thus far from mouse and human osteoclast RNA samples

| Nucleotide Sequence No. | Spliced Variant Identification | ORF Nucleotide Postitions | Polypeptide sequence No. |
| --- | --- | --- | --- |
| SEQ ID NO. 83 | 0440-TO4-22-mFL_15 | 21-1259 | SEQ ID NO. 149 |
| SEQ ID NO. 84 | 0179-SL22-hFL_36 (human orthologue variant #1) | 40-1092 | SEQ ID NO.: 150 |
| SEQ ID NO. 85 | 0179-SL22-hFL_1 (human orthologue variant #2) | 40-978 | SEQ ID NO.: 155 |
| SEQ ID NO. 86 | 0799-SL22-mFL_3_(TAG1-3'UTR) | 40-978 | SEQ ID NO.: 151 |

TABLE 3-continued

List of mRNA spliced variants for some Sequence IDs isolated thus far from mouse and human osteoclast RNA samples

| Nucleotide Sequence No. | Spliced Variant Identification | ORF Nucleotide Postitions | Polypeptide sequence No. |
|---|---|---|---|
| SEQ ID NO. 87 | 0799-SL22-mFL_4_(TAG1-3'UTR) | 124-750 | SEQ ID NO.: 152 |

TABLE 4

List of some human orthologue

| Sequence Identification | NCBI Unigene Cluster | Accession Number | ORF Nucleotide Positions | Polypeptide sequence No. |
|---|---|---|---|---|
| SEQ ID NO. 88 | Hs.120365 | NM_013270 | 51-1208 | SEQ ID NO.: 153 |
| SEQ ID NO. 89 | Hs.436360 | NM_152565 | 70-1122 | SEQ ID NO.: 154 |

TABLE 5 list of additional sequences identification of plasmids and siRNA oligonucleotides

| Sequence Identification | name | Description |
|---|---|---|
| SEQ. ID. NO. 58 | p14 | Vector for STAR |
| SEQ. ID. NO. 59 | p17+ | Vector for STAR |
| SEQ. ID. NO. 60 | pCATRMAN | Vector for STAR |
| SEQ. ID. NO. 61 | p20 | Vector for STAR |
| SEQ. ID. NO. 62 | OGS 77 | Primer used for STAR p14 vector |
| SEQ. ID. NO. 63 | OGS 302 | Primer used for STAR p17+ vector |
| SEQ. ID. NO: 64 | 0440.1 | siRNA sequence for SEQ. ID. NO. 1 |
| SEQ. ID. NO: 65 | 0440.2 | siRNA sequence for SEQ. ID. NO. 1 |
| SEQ. ID. NO: 66 | 0440.3 | siRNA sequence for SEQ. ID. NO. 1 |
| SEQ. ID. NO: 67 | 0.179.1 | siRNA sequence for SEQ ID NO.: 2 |
| SEQ. ID. NO: 68 | 0.179.2 | siRNA sequence for SEQ ID NO.: 2 |
| SEQ. ID. NO: 69 | 0.179.3 | siRNA sequence for SEQ ID NO.: 2 |
| SEQ. ID. NO: 70 | 0799.1 | siRNA sequence for SEQ ID NO.: 3 |
| SEQ. ID. NO: 71 | 0799.2 | siRNA sequence for SEQ ID NO.: 3 |
| SEQ. ID. NO: 72 | 0799.3 | siRNA sequence for SEQ ID NO.: 3 |
| SEQ. ID. NO: 73 | 0351.1 | siRNA sequence for SEQ ID NO.: 4 |
| SEQ. ID. NO: 74 | 0351.2 | siRNA sequence for SEQ ID NO.: 4 |
| SEQ. ID. NO: 75 | 1035.1 | siRNA sequence for SEQ ID NO.: 5 |
| SEQ. ID. NO: 76 | 1035.2 | siRNA sequence for SEQ ID NO.: 5 |
| SEQ. ID. NO: 77 | 1200.1 | siRNA sequence for SEQ ID NO.: 6 |
| SEQ. ID. NO: 78 | 1200.2 | siRNA sequence for SEQ ID NO.: 6 |
| SEQ. ID. NO: 79 | 0233A.1 | siRNA sequence for SEQ ID NO.: 7 |
| SEQ. ID. NO: 80 | 0233A.2 | siRNA sequence for SEQ ID NO.: 7 |
| SEQ. ID. NO: 81 | 0682.1 | siRNA sequence for SEQ ID NO.: 57 |
| SEQ. ID. NO: 82 | 0682.2 | siRNA sequence for SEQ ID NO.: 57 |
| SEQ. ID. NO. 90 | | siRNA sequence for SEQ. ID. NO. 88 |
| SEQ. ID. NO. 91 | | Ip200 expression vector |
| SEQ. ID. NO. 92 | | pCMX-HA expression vector |

REFERENCES

Patents:

U.S. Pat. No. 5,712,127 Malek et al., Jan. 27, 1998
U.S. Pat. No. 6,498,024, Malek et al., Dec. 24, 2002
(U.S. patent application Ser. No. 11/000,958 field on Dec. 2, 2003 published under No. US 2005/0153333A1 on Jul. 14, 2005 and entitled "Selective Terminal Tagging of Nucleic Acids"
U.S. Pat. No. 6,617,434 Duffy, Sep. 9, 2003
U.S. Pat. No. 6,451,555 Duffy, Sep. 17, 2002

OTHER REFERENCES

1. Frost H. M., 1964 Dynamics of Bone Remodeling. In: Bone Biodynamics, Little and Brown, Boston, Mass., USA pp. 315;
2. Baron, R., Anatomy and Biology of Bone Matrix and Cellular Elements, In: Primer on the Metabolic Bone Diseases and Disorders of Mineral Metabolism, Fifth Edition 2003, American Society for Bone and Mineral Research, Washington D.C., pp. 1-8;
3. Jilka, R. L. et al., "Increased Osteoclast Development After Estrogen Loss: Mediation by Interleukin-6", Science 257: 88-91 (1992).
4. Poli, V. et al., "Interleukin-6 deficient mice are protected from bone loss caused by estrogen depletion", EMBO J 13: 1189-1196 (1994).
5. Srivastava, S. et al., "Estrogen Blocks M-CSF Gene Expression and Osteoclast Formation by Regulating Phosphorylation of Egr-1 and Its Interaction with Sp-1", J Clin Invest 102: 1850-1859 (1998).
6. de Vernejoul, M. C., "Dynamics of Bone Remodeling: Biochemical and Pathophysiological Basis", Eur J Clin Chem Clin Biochem 34: 729-734 (1996).
7. Netzel-Arnett, S., J. D. Hooper, et al. (2003). "Membrane anchored serine proteases: a rapidly expanding group of cell surface proteolytic enzymes with potential roles in cancer." Cancer Metastasis Rev 22(2-3): 237-58.
8. Shan, J., L. Yuan, et al. (2002). "TSP50, a possible protease in human testes, is activated in breast cancer epithelial cells." CancerRes 62(1): 290-4.
9. Yuan, L., J. Shan, et al. (1999). "Isolation of a novel gene, TSP50, by a hypomethylated DNA fragment in human breast cancer." Cancer Res 59(13): 3215-21.
10. Nishi, T. and M. Forgac (2002). "The vacuolar (H+)-ATPases—nature's most versatile proton pumps." Nat Rev Mol Cell Biol 3(2): 94-103.
11. Nishi, T., S. Kawasaki-Nishi, et al. (2003). "Expression and function of the mouse V-ATPase d subunit isoforms." J Biol Chem 278(47): 46396-402.

12. Morello, R., L. Tonachini, et al. (1999). "cDNA cloning, characterization and chromosome mapping of Crtap encoding the mouse cartilage associated protein." Matrix Biol 18(3): 319-24.
13. Tonachini, L., R. Morello, et al. (1999). "cDNA cloning, characterization and chromosome mapping of the gene encoding human cartilage associated protein (CRTAP)." Cytogenet Cell Genet 87(3-4): 191-4.
14. Kawai, J., A. Shinagawa, et al. (2001). "Functional annotation of a full-length mouse cDNA collection." Nature 409(6821): 685-90.
15. Strausberg, R. L., E. A. Feingold, et al. (2002). "Generation and initial analysis of more than 15,000 full-length human and mouse cDNA sequences." Proc Natl Acad Sci USA 99(26): 16899-903.
16. Janssen, E., M. Zhu, et al. (2003). "LAB: a new membrane-associated adaptor molecule in B cell activation." Natl Immunol 4(2): 117-23.
17. Kawaida, R., T. Ohtsuka, et al. (2003). "Jun dimerization protein 2 (JDP2), a member of the AP-1 family of transcription factor, mediates osteoclast differentiation induced by RANKL." J Exp Med 197(8): 1029-35.
18. Agrawal, N., P. V. Dasaradhi, et al. (2003). "RNA interference: biology, mechanism, and applications." Microbiol Mol Biol Rev 67(4): 657-85.
19. Hannon, G. J. (2002). "RNA interference." Nature 418 (6894): 244-51.
20. Brummelkamp, T. R., R. Bernards, et al. (2002). "A system for stable expression of short interfering RNAs in mammalian cells." Science 296(5567): 550-3.
21. Elbashir, et al. (2001). "Duplexes of 21-nucleotide RNAs mediate RNA interference in cultured mammalian cells." Nature 411(6836): 494-8.
22. Lee, J. S., Z. Hmama, et al. (2004). "Stable gene silencing in human monocytic cell lines using lentiviral-delivered small interference RNA. Silencing of the p110alpha isoform of phosphoinositide 3-kinase reveals differential regulation of adherence induced by 1alpha,25-dihydroxycholecalciferol and bacterial lipopolysaccharide." J Biol Chem 279(10): 9379-88.
23. Rubinson, D. A., C. P. Dillon, et al. (2003). "A lentivirus-based system to functionally silence genes in primary mammalian cells, stem cells and transgenic mice by RNA interference." Nat Genet 33(3): 401-6.
24. Boyle, W. J., W. S. Simonet, et al. (2003). "Osteoclast differentiation and activation." Nature 423(6937): 337-42.
25. Gee et al. In: Huber and Carr (1994) Molecular and Immunologic Approaches, Futura Publishing Co., Mt. Kisco N.Y., pp. 163-177.
26. Smith, A. N., F. Jouret, et al. (2005). "Vacuolar H+-ATPase d2 subunit: molecular characterization, developmental regulation, and localization to specialized proton pumps in kidney and bone." J Am Soc Nephrol 16(5): 1245-56
27. Smith, A. N., J. Skaug, et al. (2000). "Mutations in ATP6N1B, encoding a new kidney vacuolar proton pump 116-kD subunit, cause recessive distal renal tubular acidosis with preserved hearing." Nat Genet 26(1): 71-5.
28. Stehberger, P. A., N. Schulz, et al. (2003). "Localization and regulation of the ATP6VOA4 (a4) vacuolar H+-ATPase subunit defective in an inherited form of distal renal tubular acidosis." J Am Soc Nephrol 14(12): 3027-38.

What is claimed is:

1. A method for identifying an inhibitory compound able to impair the activity of a polypeptide comprising SEQ ID NO: 153 or of an analog having at least 67% similarity with SEQ ID NO: 153, wherein said analog has a sequence of a naturally occurring mammalian protein and wherein said polypeptide or analog is capable of inducing differentiation of osteoclasts, the method comprising contacting said polypeptide, said analog or a cell expressing said polypeptide or analog with a candidate compound and measuring the activity of said polypeptide or analog, whereby a reduction in the activity of said polypeptide or analog positively identifies a suitable inhibitory compound.

2. The method of claim 1, wherein said activity is associated with a reduced ability of said polypeptide or analog to promote osteoclast differentiation.

3. The method of claim 2, comprising inducing osteoclast differentiation when contacting said polypeptide, analog or cell with a candidate compound.

4. The method of claim 1, wherein said analog comprises SEQ ID NO: 93, wherein the activity of the analog comprising SEQ ID NO: 93 is impaired and wherein said cell is a mouse osteoclast cell.

5. The method of claim 1, wherein said analog is SEQ ID NO: 93.

6. A method for identifying a compound able to inhibit osteoclast differentiation, the method comprising
providing to an osteoclast precursor cell a compound able to bind to a polypeptide consisting of SEQ ID NO: 153 or to an analog having at least 67% similarity with SEQ ID NO: 153, wherein said analog has a sequence of a naturally occurring mammalian protein and wherein said polypeptide or analog is capable of inducing differentiation of osteoclast, and
inducing osteoclast differentiation,
whereby reduced osteoclast differentiation positively identifies a suitable compound.

7. The method of claim 6, wherein the osteoclast precursor cell is capable of expressing SEQ ID NO: 153.

8. The method of claim 6, wherein said analog is SEQ ID NO: 93.

9. The method of claim 1, wherein said polypeptide consists of SEQ ID NO: 153.

10. A method for identifying an inhibitory compound able to impair the expression of a polypeptide comprising SEQ ID NO: 153 or of an analog having at least 67% similarity with SEQ ID NO: 153, wherein said analog has a sequence of a naturally occurring mammalian protein and wherein said polypeptide or analog is capable of inducing differentiation of osteoclasts, the method comprising contacting a cell expressing said polypeptide or analog with a candidate compound and measuring the expression of said polypeptide or analog, whereby a reduction in the expression of said polypeptide or analog positively identifies a suitable inhibitory compound.

11. The method of claim 10, wherein said impaired expression is associated with a reduced ability of said polypeptide or analog to promote osteoclast differentiation.

12. The method of claim 11, comprising inducing osteoclast differentiation when contacting said polypeptide, analog or cell with a candidate compound.

13. The method of claim 10, wherein said analog comprises SEQ ID NO: 93, wherein expression of the analog comprising SEQ ID NO: 93 is impaired and wherein said cell is a mouse osteoclast cell.

14. The method of claim 10, wherein said analog is SEQ ID NO: 93.

15. The method of claim 10, wherein said polypeptide consists of SEQ ID NO: 153.

16. The method of claim 1, wherein the candidate compound is an antibody or an antigen-binding fragment.

17. The method of claim 10, wherein the candidate compound is an siRNA or a shRNA.

18. A method for identifying a compound able to inhibit osteoclast differentiation, the method comprising
contacting a candidate compound with a polypeptide having a sequence at least 95% identical to SEQ ID NO:153 or SEQ ID NO:93, or a cell expressing the polypeptide, wherein said polypeptide is capable of inducing osteoclast differentiation;
measuring activity of the polypeptide,
wherein a reduction in the activity of the polypeptide positively identifies a suitable inhibitory compound.

19. The method of claim 18, wherein the polypeptide has a sequence identical to SEQ ID NO:153 or SEQ ID NO:93.

20. The method of claim 18, wherein the step of measuring the activity of the polypeptide comprises determining osteoclast differentiation.

21. The method of claim 18, wherein said candidate compound is an antibody or an antigen binding fragment thereof.

22. The method of claim 18, wherein said candidate compound is an siRNA or a shRNA.

23. The method of claim 18, wherein the method further comprises a step of inducing osteoclast differentiation.

24. The method of claim 18, wherein the reduction of the activity is associated with a reduction of osteoclast differentiation.

25. A method for identifying a compound for inhibiting osteoclast differentiation, the method comprising
contacting a candidate compound with a cell expressing a polypeptide having a sequence at least 95% identical to SEQ ID NO: 153 or SEQ ID NO:93, wherein said polypeptide is capable of inducing osteoclast differentiation;
measuring expression of the polypeptide,
wherein a reduction in the expression of the polypeptide positively identifies a suitable inhibitory compound.

26. The method of claim 25, wherein the polypeptide has a sequence identical to SEQ ID NO:153 or SEQ ID NO:93.

27. The method of claim 25, wherein the method further comprises determining osteoclast differentiation.

28. The method of claim 25, wherein said candidate compound is an antibody or an antigen binding fragment thereof.

29. The method of claim 25, wherein said candidate compound is an siRNA or a shRNA.

30. The method of claim 25, wherein the method further comprises a step of inducing osteoclast differentiation.

31. The method of claim 25, wherein the reduction of the expression is associated with a reduction of osteoclast differentiation.

* * * * *